US011197933B2

(12) United States Patent
Jenkins et al.

(10) Patent No.: US 11,197,933 B2
(45) Date of Patent: Dec. 14, 2021

(54) POLYSUBUNIT OPIOID PRODRUGS RESISTANT TO OVERDOSE AND ABUSE

(71) Applicant: Elysium Therapeutics, Inc., Akron, OH (US)

(72) Inventors: Thomas E. Jenkins, Half Moon Bay, CA (US); Craig O. Husfeld, San Mateo, CA (US)

(73) Assignee: Elysium Therapeutics, Inc., Akron, OH (US)

( * ) Notice: Subject to any disclaimer, the term of this patent is extended or adjusted under 35 U.S.C. 154(b) by 0 days.

(21) Appl. No.: 16/572,408

(22) Filed: Sep. 16, 2019

(65) Prior Publication Data

US 2020/0101166 A1 Apr. 2, 2020

Related U.S. Application Data

(63) Continuation of application No. PCT/US2018/022986, filed on Mar. 16, 2018.

(60) Provisional application No. 62/479,014, filed on Mar. 30, 2017, provisional application No. 62/473,153, filed on Mar. 17, 2017.

(51) Int. Cl.
*A61K 47/64* (2017.01)
*A61K 47/55* (2017.01)
*A61K 31/485* (2006.01)

(52) U.S. Cl.
CPC ............ *A61K 47/64* (2017.08); *A61K 31/485* (2013.01); *A61K 47/55* (2017.08)

(58) Field of Classification Search
None
See application file for complete search history.

(56) References Cited

U.S. PATENT DOCUMENTS

| 2,996,431 | A | 8/1961 | Barry |
| 3,139,383 | A | 6/1964 | Nelville, Jr. |
| 3,402,240 | A | 9/1968 | Cain et al. |
| 3,811,444 | A | 5/1974 | Heller et al. |
| 3,845,770 | A | 11/1974 | Theeuwes et al. |
| 3,916,899 | A | 11/1975 | Theeuwes et al. |
| 3,962,414 | A | 6/1976 | Michaels |
| 3,992,518 | A | 11/1976 | Chien et al. |
| 4,063,064 | A | 12/1977 | Saunders |
| 4,066,747 | A | 1/1978 | Capozza |
| 4,070,347 | A | 1/1978 | Schmitt |
| 4,079,038 | A | 3/1978 | Choi et al. |
| 4,083,949 | A | 4/1978 | Benedikt |
| 4,088,864 | A | 5/1978 | Theeuwes et al. |
| 4,093,709 | A | 6/1978 | Choi et al. |
| 4,200,098 | A | 4/1980 | Ayer et al. |
| 4,285,987 | A | 8/1981 | Ayer et al. |
| 4,421,736 | A | 12/1983 | Walters |
| 4,434,153 | A | 2/1984 | Urquhart et al. |
| 4,507,466 | A | 3/1985 | Tomalia et al. |
| 4,631,337 | A | 12/1986 | Tomalia et al. |
| 4,721,613 | A | 1/1988 | Urquhart et al. |
| 4,752,470 | A | 6/1988 | Mehta |
| 4,765,539 | A | 8/1988 | Noakes et al. |
| 4,816,263 | A | 3/1989 | Ayer et al. |
| 4,820,523 | A | 4/1989 | Shtohryn et al. |
| 4,853,229 | A | 8/1989 | Theeuwes |
| 4,962,885 | A | 10/1990 | Coffee |
| 5,041,516 | A | 8/1991 | Frechet et al. |
| 5,112,598 | A | 5/1992 | Biesalski |
| 5,159,081 | A | 10/1992 | Cantrell et al. |
| 5,177,059 | A | 1/1993 | Handley et al. |
| 5,250,542 | A | 10/1993 | Cantrell et al. |
| 5,270,328 | A | 12/1993 | Cantrell et al. |
| 5,434,171 | A | 7/1995 | Frank et al. |
| 5,468,574 | A | 11/1995 | Ehrenberg et al. |
| 5,530,092 | A | 6/1996 | Meijer et al. |
| 5,556,611 | A | 9/1996 | Biesalski |
| 5,698,155 | A | 12/1997 | Grosswald et al. |
| 5,824,701 | A | 10/1998 | Greenwald et al. |
| 5,840,387 | A | 11/1998 | Berlowitz-Tarrant et al. |
| 5,880,131 | A | 3/1999 | Greenwald et al. |
| 5,932,462 | A | 8/1999 | Harris et al. |
| 5,950,619 | A | 9/1999 | Van et al. |
| 5,954,047 | A | 9/1999 | Armer et al. |
| 5,970,974 | A | 10/1999 | Van et al. |

(Continued)

FOREIGN PATENT DOCUMENTS

| WO | WO-9412285 A2 | 6/1994 |
| WO | WO-9414543 A2 | 7/1994 |

(Continued)

OTHER PUBLICATIONS

Worthington Enzyme Manual, Trypsin Inhibitors—Worthington Enzyme Manual, available online at http://worthington-biochem.com/TI/default.html, accessed on Jun. 8, 2020. (Year: 2020).*
Kitayama et al., Polym. Chem., 2016, 7, 2573. (Year: 2016).*
Alderman, et al. A review of cellulose ethers in hydrophilic matrices for oral controlled-release dosage forms. Int. J. Pharm. Tech. Prod. Mfr 5.3 (1984): 1-9.
Aoyama, et al. Synthesis and structure-activity study of protease inhibitors. IV. Amidinonaphthols and related acyl derivatives. Chem Pharm Bull (Tokyo). Apr. 1985;33(4):1458-71.
Bak, et al. Acyloxyalkoxy-based Cyclic Prodrugs of Opioid Peptides: Evaluation of the Chemical and Enzymatic Stability as well as Their Transport Properties Across Caco-2 Cell Monolayers. Pharmaceutical Research, 1999, vol. 16, pp. 24-29.

(Continued)

*Primary Examiner* — Thomas S Heard
(74) *Attorney, Agent, or Firm* — Wilson Sonsini Goodrich & Rosati

(57) ABSTRACT

The invention provides compositions and methods for the treatment or prevention of pain. Compositions provided are resistant to overdose and abuse. Compositions provided comprise two or more different molecules, where each molecule comprises at least one GI enzyme-labile opioid agonist releasing subunit comprising an opioid agonist that is covalently linked to at least one GI enzyme inhibitor subunit.

35 Claims, 18 Drawing Sheets

(56) References Cited

U.S. PATENT DOCUMENTS

| | | |
|---|---|---|
| 6,171,615 B1 | 1/2001 | Roussin et al. |
| 6,375,987 B1 | 4/2002 | Farah et al. |
| 6,379,700 B2 | 4/2002 | Joachim et al. |
| 6,545,097 B2 | 4/2003 | Pinchuk et al. |
| 6,664,331 B2 | 12/2003 | Harris et al. |
| 6,716,821 B2 | 4/2004 | Zhao et al. |
| 7,060,290 B1 | 6/2006 | Morimoto et al. |
| 7,338,939 B2 | 3/2008 | Mickle et al. |
| 7,375,082 B2 | 5/2008 | Mickle et al. |
| 8,101,661 B2 | 1/2012 | Mickle |
| 8,133,881 B2 | 3/2012 | Mickle et al. |
| 8,163,701 B2 | 4/2012 | Jenkins |
| 8,217,005 B2 | 7/2012 | Jenkins et al. |
| 8,497,237 B2 | 7/2013 | Jenkins et al. |
| 8,569,228 B2 | 10/2013 | Jenkins et al. |
| 8,685,916 B2 | 4/2014 | Jenkins et al. |
| 8,802,681 B2 | 8/2014 | Jenkins et al. |
| 9,040,032 B2 | 5/2015 | Jenkins et al. |
| 9,095,627 B2 | 8/2015 | Jenkins et al. |
| 9,139,612 B2 | 9/2015 | Jenkins et al. |
| 9,217,005 B2 | 12/2015 | Touge et al. |
| 9,499,581 B2 | 11/2016 | Jenkins et al. |
| 9,808,452 B2 | 11/2017 | Jenkins |
| 10,251,878 B2 | 4/2019 | Jenkins |
| 10,335,406 B2 | 7/2019 | Jenkins |
| 2004/0043030 A1 | 3/2004 | Griffiths et al. |
| 2005/0037059 A1 | 2/2005 | Miller et al. |
| 2005/0176644 A1 | 8/2005 | Mickle et al. |
| 2009/0136980 A1 | 5/2009 | Bebbington et al. |
| 2009/0137618 A1 | 5/2009 | Jenkins |
| 2009/0209569 A1 | 8/2009 | Arnelle et al. |
| 2010/0080797 A1 | 4/2010 | Yeomans et al. |
| 2011/0262359 A1 | 10/2011 | Jenkins et al. |
| 2011/0262360 A1 | 10/2011 | Jenkins et al. |
| 2011/0281886 A1 | 11/2011 | Jenkins et al. |
| 2012/0142718 A1 | 6/2012 | Jenkins et al. |
| 2012/0178773 A1 | 7/2012 | Jenkins et al. |
| 2017/0100390 A1 | 4/2017 | Jenkins |
| 2018/0085366 A1 | 3/2018 | Jenkins |
| 2019/0183884 A1 | 6/2019 | Jenkins |

FOREIGN PATENT DOCUMENTS

| | | |
|---|---|---|
| WO | WO-9526234 A1 | 10/1995 |
| WO | WO-9526235 A1 | 10/1995 |
| WO | WO-9532807 A1 | 12/1995 |
| WO | WO-2004041324 A2 | 5/2004 |
| WO | WO-2004062614 A2 | 7/2004 |
| WO | WO-2004082620 A2 | 9/2004 |
| WO | WO-2006073396 A1 | 7/2006 |
| WO | WO-2007120864 A2 | 10/2007 |
| WO | WO-2007140272 A2 | 12/2007 |
| WO | WO-2008101187 A2 | 8/2008 |
| WO | WO-2009092073 A2 | 7/2009 |
| WO | WO-2010045599 A1 | 4/2010 |
| WO | WO-2011002991 A1 | 1/2011 |
| WO | WO-2011002995 A1 | 1/2011 |
| WO | WO-2011133150 A1 | 10/2011 |
| WO | WO-2012109445 A1 | 8/2012 |
| WO | WO-2012122420 A2 | 9/2012 |
| WO | WO-2017059459 A1 | 4/2017 |
| WO | WO-2018170465 A1 | 9/2018 |

OTHER PUBLICATIONS

Bamba, et al. Release mechanisms in gelforming sustained release preparations. International Journal of Pharmaceutics. vol. 2, Issues 5-6, Jun. 1979, pp. 307-315.

Birk, Y. Trypsin and chymotrypsin inhibitors from soybeans. Methods Enzymol. 1976;45:700-7.

Coleman, et al. Polymer Reviews: A Practical Guide to Polymer Miscibility. 1990, 31, 1187-1231.

Co-pending U.S. Appl. No. 16/386,671, filed Apr. 17, 2019.

Definition of "ex vivo" from thefreedictionary.com, accessed Oct. 7, 2014.

During, et al. Controlled release of dopamine from a polymeric brain implant: in vivo characterization. Ann Neurol. Apr. 1989;25(4):351-6.

EP16852850.3 The Extended European Search report dated Mar. 21, 2019.

FDA Center for Drug Evaluation and Research, Joint Meeting of the Anesthetic and Life Support Drugs Advisory Committee and the Drug Safety and Risk Management Advisory Committee, Meeting Transcript, Jul. 23-24, 2010.

Fincher, JH. Particle size of drugs and its relationship to absorption and activity. J Pharm Sci. Nov. 1968;57(11):1825-35.

Geratz, et al. Novel Bis(benzamidine) Compounds with an Aromatic Central Link. Inhibitors of Thrombin, Pancreatic Kallkrein, I Trypsin, and Compliment. J. Medicinal Chemistry, 1976, vol. 19, pp. 634-639.

Goodson. Medical Applications of Controlled Release. vol. 2, pp. 115-138, 1984.

Gotoh, et al. The Advantages of the Ussing Chamber in Drug Absorption Studies. Journal of Biomolecular Screening 10(5), pp. 517-523, 2005.

Gunatillake, et al. Thermal polymerization of a 2-(carboxyalkyl)-2-oxazoline. Macromolecules, 1988, 21 (6), pp. 1556-1562.

Hawker, et al. One-step synthesis of hyperbranched dendritic polyesters. J. Am. Chem. Soc., 1991, 113 (12), pp. 4583-4588.

Howard, et al. Intracerebral drug delivery in rats with lesion-induced memory deficits. J Neurosurg. Jul. 1989;71(1):105-12.

International Search Report with Opinion dated Dec. 23, 2016 for PCT/US16/55231.

Ito, et al. A medium-term rat liver bioassay for rapid in vivo detection of carcinogenic potential of chemicals. Cancer Sci. Jan. 2003;94(1):3-8.

Kaneda, et al. The use of PVP as a polymeric carrier to improve the plasma half-life of drugs. Biomaterials. Jul. 2004;25(16):3259-66.

Langer, et al. Chemical and Physical Structure of Polymers as Carriers for Controlled Release of Bioactive Agents: A Review. J Macromol. Sci. Rev. Macromol. Chem. 1983, 23:61-126.

Langer, R. New methods of drug delivery. Science. Sep. 28, 1990;249(4976):1527-33.

Leong, et al. Polymeric controlled drug delivery. Advanced Drug Delivery Reviews, vol. 1, Issue 3, Sep. 1988, pp. 199-233.

Levy, et al. Inhibition of calcification of bioprosthetic heart valves by local controlled-release diphosphonate. Science. Apr. 12, 1985;228(4696):190-2.

Lin, et al. The 0.25-nm X-ray structure of the Bowman-Birk-type inhibitor from mun gean in ternary complex with porcine trypsin. Eur. J. Biochem, 1993, vol. 212, pp. 549-555.

Lu, et al. Dimensionless presentation for drug release from a coated pure drug bead: 2. Experiment. Int. J. Pharm. 1994, 112, 117-124.

Markwardt, et al. Comparative Studies on the Inhibition of Trypsin, Plasmin, and Thrombin, by Derivatives of Benzylamine and Benzylamidine. Eur. J. Biochem, 1968, vol. 6, pp. 502-506.

Notice of allowance dated Aug. 17, 2017 for U.S. Appl. No. 15/284,269.

Ozawa, et al. The reactive site of trypsin inhibitors. J Biol Chem. Sep. 10, 1966;241(17):3955-61.

PCT/US2018/022986 International Search Report dated May 31, 2018.

Raleigh, et al. American Association for Cancer Research Anuual Meeting. 1999, 40, 397.

Roerdink, et al. Drug Carrier Systems 1989, vol. 9, chapter 3, pp. 57-109.

Rosoff. Controlled Release of Drugs. Chapter 2, pp. 53-95, 1989.

Saudek, et al. A preliminary trial of the programmable implantable medication system for insulin delivery. N Engl J Med. Aug. 31, 1989;321 (9):574-9.

Schanker, et al. Absorption of drugs from the rat small intestine. Journal of Pharmacology and Experimental Therapeutics 123.1 (1958): 81-88.

Sefton, MV. Implantable pumps. Crit Rev Biomed Eng. 1987;14(3):201-40.

(56) References Cited

OTHER PUBLICATIONS

Sekizaki et al. "The Structural Requirements for an Inverse Substrate for Enzymatic Peptide Synthesis: Position Isomers of Guanidononaphthyl Esters as the Acyl Donor Component", Chem. Pharm. Bull. 1999. vol. 47(1), pp. 104-110.
Sekizaki, et al. Synthesis and tryptic hydrolysis of p-guanidinophenyl esters derived from amino acids and peptides. Chem Pharm Bull (Tokyo). Aug. 1996;44(8):1577-9.
Sekizaki, et al. Trypsin-catalyzed peptide synthesis and various p-guanidinophenyl esters as acyl donors. Chem Pharm Bull (Tokyo). Aug. 1996;44(8):1585-7.
Thanou, et al. Polymer-protein and polymer-drug conjugates in cancer therapy. Curr Opin Investig Drugs. Jun. 2003;4(6):701-9.
Thormann, et al. Protease-catalyzed hydrolysis of substrate mimetics (inverse substrates): A new approach reveals a new mechanism. Biochemistry. May 11, 1999;38(19):6056-62.
Tomalia, et al. Discovery of dendrimers and dendritic polymers: A brief historical perspective. Journal of Polymer Science Part A: Polymer Chemistry. vol. 40, Issue 16, pp. 2719-2728, Aug. 15, 2002.
U.S. Appl. No. 15/683,356 Notice of Allowance dated Feb. 8, 2019.
U.S. Appl. No. 15/683,356 Notice of Allowance dated Jan. 3, 2019.
U.S. Appl. No. 15/683,356 Notice of Allowance dated Jan. 9, 2019.
U.S. Appl. No. 15/683,356 Notice of Allowance dated Nov. 26, 2018.
U.S. Appl. No. 15/683,356 Office Action dated Aug. 16, 2018.
U.S. Appl. No. 15/795,126 Notice of Allowance dated Jan. 17, 2019.
U.S. Appl. No. 15/795,126 Office Action dated Jun. 22, 2018.
Umezawa, H. Structures and activities of protease inhibitors of microbial origin. Methods Enzymol. 1976;45:678-95.
Van Gelder, et al. Drug Metabolism and Disposition 30 (8) p. 924-930, 2002.
Verma, et al. Osmotically controlled oral drug delivery. Drug Dev Ind Pharm. Jul. 2000;26(7):695-708.
Veronese, et al. Bioconjugation in pharmaceutical chemistry. Farmaco. Aug. 30, 1999;54(8):497-516.
Verschoyle, et al. British J. Cancer, 1999, 80, Suppl. 2, 96. Poster Presentations.
U.S. Appl. No. 16/286,096 Office Action dated Aug. 18, 2020.
U.S. Appl. No. 16/386,671 Office Action dated Sep. 4, 2020.
EP18766937.9 The Extended European Search Report dated Dec. 14, 2020.
U.S. Appl. No. 16/286,096 Notice of Allowance dated Feb. 11, 2021.
U.S. Appl. No. 16/386,671 Notice of Allowance dated Mar. 4, 2021.

* cited by examiner

POLYSUBUNIT OPIOID PRODRUGS RESISTANT TO OVERDOSE AND ABUSE

CROSS-REFERENCE

This application is a continuation of PCT Application No. PCT/US18/22986, filed Mar. 16, 2018; which claims priority to U.S. Provisional Application Nos. 62/479,014, filed Mar. 30, 2017, and 62/473,153, filed Mar. 17, 2017; which are incorporated herein by reference in their entirety and to which applications we claim priority under 35 USC § 120.

STATEMENT AS TO FEDERALLY SPONSORED RESEARCH

This invention was made with the support of the United States government under SBIR Grant numbers 1R44DA037900 and 1R43DA046302-01 by the National Institute on Drug Abuse (NIDA), one of the National Institutes of Health (NIH) in the U.S. Department of Health and Human Services.

TECHNICAL FIELD

The present invention relates to compounds, methods and formulations for the prevention and/or treatment of pain. More particularly, the invention relates to pharmaceutical agents that interact with analgesic receptors, methods of preparing these agents, and their use for analgesia, pain, and other conditions, while protecting against overdose and abuse.

BACKGROUND

Pharmacologically, opioid agonists represent an important class of agents for the management of pain. The high abuse liability of opioid agonists often limits their use in the treatment of patients, and results in the under-treatment of pain, and severe social and financial costs. The U.S. Food and Drug Administration has recently described prescription opioid analgesics as being at the center of a major public health crisis of addiction, misuse, abuse, overdose, and death (FDA/Center for Drug Evaluation and Research, Joint Meeting of the Anesthetic and Life Support Drugs Advisory Committee and the Drug Safety and Risk Management Advisory Committee, Meeting Transcript, Jul. 23-4, 2010).

The class of drugs exhibiting opium or morphine-like properties are referred to as opioid agonists, or opioids, and they interact with opioid receptors in the brain, the peripheral nervous system and other tissues. The three major opioid receptor subtypes are mu, delta, and kappa. Each of these receptors has a unique anatomical distribution in the central nervous system, the peripheral nervous system and the gastrointestinal tract. Most of the clinically used opioids exert their desired therapeutic action (i.e. analgesia) at the mu receptor subtype.

Opioids include morphine, codeine, oxycodone, hydrocodone, hydromorphone, and the like. Examples of marketed opioid products in the United States include OxyContin® (comprising oxycodone), Vicodin® (comprising hydrocodone and acetaminophen), and Percocet® (comprising oxycodone and acetaminophen). Opioids have diverse effects, including analgesia, euphoria, drowsiness, changes in mood and alterations of the endocrine and autonomic nervous systems. Opioid analgesics comprise the major class of drugs used in the management of moderate to severe pain. As a class, opioids are among the most prescribed drugs in the US. Data provided by IMS Health, Inc. show that about 9 billion hydrocodone containing pills are prescribed annually. However, several concerns exist regarding the nonmedical use and abuse of opioids. There exists a need for pharmaceutical products which provide the therapeutic benefits of opioids to a subject but are not susceptible to abuse.

SUMMARY

Provided herein are compositions comprising two or more different polysubunit molecules, wherein each different polysubunit molecule comprises at least one gastrointestinal (GI) enzyme labile opioid agonist releasing subunit covalently linked to at least one gastrointestinal enzyme inhibitor subunit. The two or more different polysubunit molecules can comprise a first strong GI enzyme inhibitor subunit and a first weak GI enzyme inhibitor subunit. The compositions described herein can provide a plasma profile that is distinct from compositions comprising one similar polysubunit molecule.

In one aspect is a composition comprising two or more different molecules, wherein each different molecule comprises at least one GI enzyme-labile opioid agonist releasing subunit comprising an opioid agonist, wherein the at least one GI enzyme-labile opioid agonist releasing subunit is covalently linked to at least one GI enzyme inhibitor subunit.

In some instances, the disclosure provides a composition comprising two or more different polysubunit molecules, wherein each different polysubunit molecule comprises at least one GI enzyme-labile opioid agonist releasing subunit, wherein the at least one GI enzyme-labile opioid agonist releasing subunit is covalently linked to at least one GI enzyme inhibitor subunit, wherein an opioid agonist in the GI enzyme-labile opioid agonist releasing subunit is hydrolyzable by a GI enzyme. The two or more different polysubunit molecules can have different GI enzyme inhibitor subunits. The different GI enzyme inhibitor subunits can have different inhibitory potencies. In some instances, at least one of the different GI enzyme inhibitor subunits has an $IC_{50}$ that is from about 1 pM to about 100 uM, and at least another different GI enzyme inhibitor subunit has an $IC_{50}$ that is from about 100 uM to about 10 mM.

In some instances, the two or more different polysubunit molecules described herein can have the same or different GI enzyme-labile opioid agonist releasing subunits and the same or different GI enzyme-labile opioid agonist releasing subunits can release the same or different opioid agonists. In some embodiments, the opioid agonists are selected from the group consisting of morphine, hydromorphone, hydrocodone, oxycodone, codeine, levorphanol, meperidine, methadone, oxymorphone, dihydrocodeine, tramadol, tapentadol, buprenorphine, and pharmaceutically acceptable salts, prodrugs, and mixtures thereof. In some instances, the same or different opioid agonists are released in vivo or in vitro at different rates. As described herein, some of the aforementioned compositions comprise at least three, at least four, at least five, or at least six different polysubunit molecules. In some cases, at least one GI enzyme-labile opioid agonist releasing subunit and the at least one non-opioid agonist releasing GI enzyme subunit of each different polysubunit molecule are covalently linked via a scaffold moiety. In some cases, at least one GI enzyme-labile opioid agonist releasing subunit and the at least one GI enzyme inhibitor subunit of each different polysubunit molecule are covalently linked via a scaffold moiety. In some cases, the scaffold moiety comprises a natural or non-natural amino acid, a peptide, a polypeptide, or a polysaccharide.

In some cases, at least one GI enzyme inhibitor subunit is an inverse-substrate. The GI enzyme can be trypsin, chymotrypsin, or another GI enzyme present from the mouth to the anus including on and within the intestinal brush border. A polysubunit comprising a GI enzyme-labile opioid agonist releasing subunit can release the opioid agonist in the presence of the GI enzyme. A polysubunit comprising a GI enzyme inhibitor subunit of at least one different polysubunit molecule can saturate or inhibit the GI enzyme. A polysubunit comprising GI enzyme inhibitor subunit of at least one different polysbunit molecule inhibits the GI enzyme.

In some instances, the disclosure provides a composition comprising two or more different polysubunit molecules, wherein each different polysubunit molecule comprises at least one polysubunit molecule of formula (I):

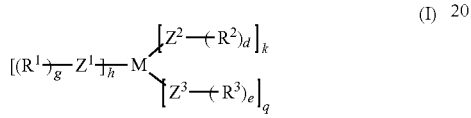

or a salt thereof, wherein:
each $R^1$ is independently a GI enzyme inhibitor subunit;
each $R^2$ is independently a GI enzyme-labile opioid agonist releasing subunit;
each $R^3$ is independently an opioid antagonist releasing subunit;
M is, an atom, or a scaffold moiety;
each $Z^1$, $Z^2$, and $Z^3$ is independently absent or a linking moiety;
each h, k, g, d, and e is independently an integer ranging from 1 to 10, 1 to 100, 1 to 1,000, 1 to 100,000, 1 to 1,000,000, or 1 to 1,000,000,000; and q is an integer ranging from 0 to 10, 0 to 100, 0 to 1,000, 0 to 100,000, 0 to 1,000,000, or 0 to 1,000,000,000.

In some instances, g=1 and $(R^1)_g$—$Z^1$— is selected from the group consisting of:

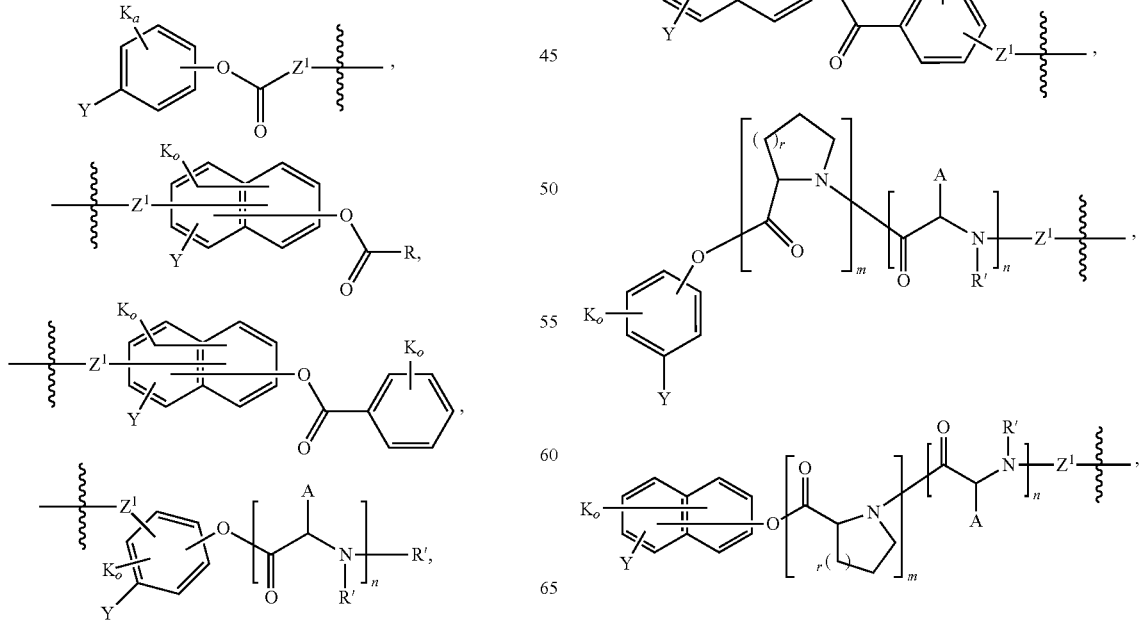

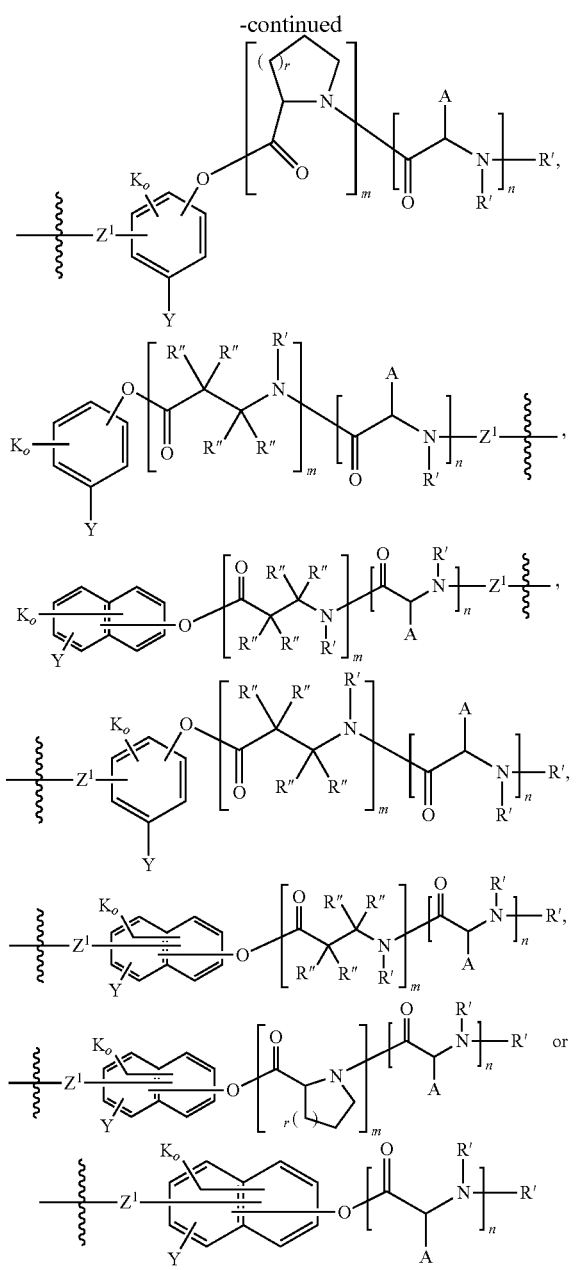

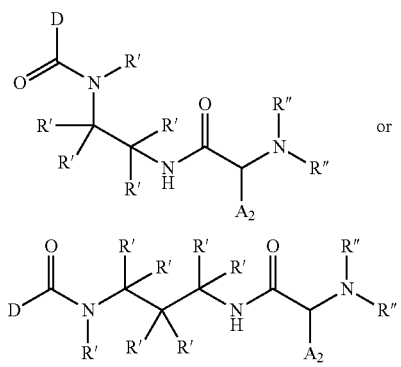

wherein:
Y is amidine, guanidine, aminomethyl, substituted amidine, substituted guanidine, substituted aminomethyl, amidinomethyl, guanidinomethyl, substituted amidinomethyl, or substituted guanidinomethyl;
$Z^1$ is absent or a linking moiety;
each $K_o$ is independently hydrogen or methyl;
A is an amino acid side chain;
r is an integer from 0-10;
m is an integer from 1-10;
p is an integer from 1-10;
n is an integer from 0-10;
each R is independently alkyl, alkylene, alkynyl, aryl, substituted alkyl, substituted alkylene, substituted alkynyl, or substituted aryl;
each R' is independently alkyl, aryl, substituted alkyl, substituted aryl, acyl, substituted acyl, polyethylene glycol containing an acyl, aryl, or alkyl group; and each R" is independently hydrogen, methyl, alkyl, aryl.

In some instances, at least one of $Z^1$, comprises an electron donating or electron withdrawing group. The electron donating group can be alkyl, substituted alkyl, —OH, —OR, —NH$_2$, —NR$_2$, —SH, —SR, or —NHC(O)R. The electron withdrawing group can be —C(O)OH, —C(O)OR, —C(O)NH$_2$, —C(O)NR$_2$, —NO$_2$, —NR$_3$+, —C(O)CF$_3$, —CF$_3$, halogen, —CCl$_3$, cyano, —SO$_3$H, —SO$_3$R, —CHO, —COR, —C(NH)NH$_2$, or —NHC(NH)NH$_2$.

In some instances, $R^2$— is selected from the group consisting of:

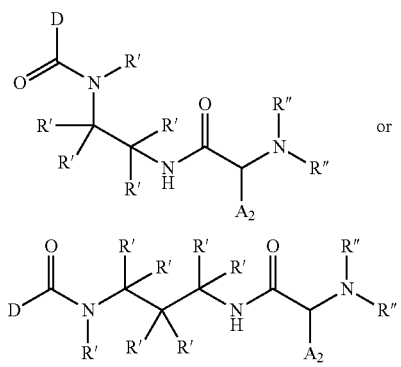

wherein:
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond;
R' optionally forms a spirocyclic or fused aliphatic ring with a geminal or vicinal R' group;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a bond;
each $A_2$ is independently an amino acid side chain or an amino acid side-chain functional or structural mimic that is recognized by a digestive enzyme.

In other instances, $R^2$— is selected from the group consisting of:

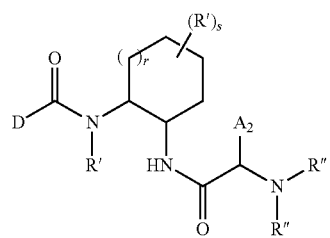

-continued

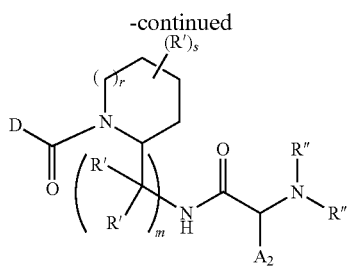

wherein:
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a linking moiety $Z^2$;
each $A_2$ is independently an amino acid side chain or an amino acid side-chain mimic that is recognized by a digestive enzyme;
m is an integer from 0-10
r is an integer from 0-10
s is an integer from 0-27.
In yet other instances, $R^2$— is:

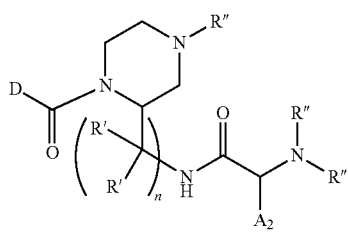

wherein:
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a bond;
each $A_2$ is independently an amino acid side chain or an amino acid side-chain mimic that is recognized by a digestive enzyme; and
n is an integer from 0 to 10.
In some of the structures described herein $R^2$— has the structure:

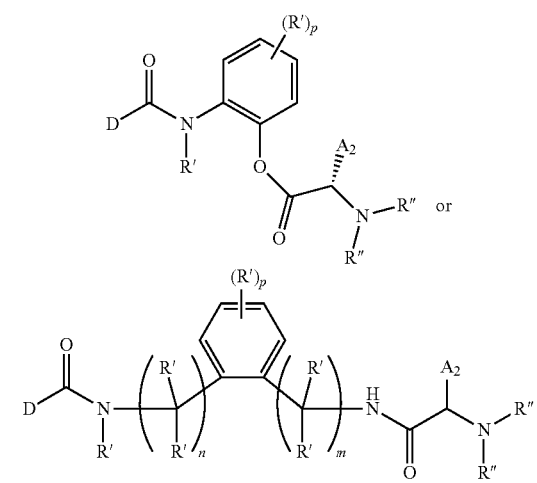

wherein
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a bond; and
each $A_2$ is independently an amino acid side chain or an amino acid side-chain mimic that is recognized by a digestive enzyme.
In some of the structures described herein $A_2$ is:

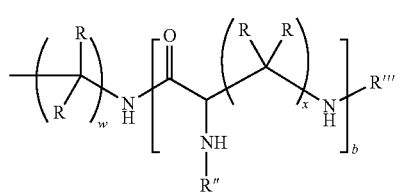

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, or a polyethylene glycol containing moiety; w and x are each or independently an integer from 1 to 6; b is an integer from 0 to 10; R'" is hydrogen, methyl, —C(=NR)—NR$_2$ wherein R is each or independently hydrogen or methyl; or

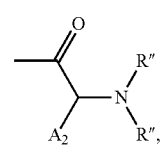

wherein $A_2$ is a natural or unnatural amino acid side chain, or an amino acid side-chain mimic that is recognized by a digestive enzyme, wherein the digestive enzyme effects the regiospecific hydrolysis of R''' prior to the release of the appended opioid agonist from the $R^2$ subunit, and wherein $A^2$ is optionally selected from the amino acid side chain of arginine, homoarginine, lysine, homolysine, ε-N-methyl lysine, omithine, or structural/functional mimics thereof; and w is an integer from 0 to 10
x is an integer from 0 to 10
b is an integer from 0 to 4.

Some of the structures described herein comprise a polysubunit molecule wherein e=1 and the $(R^3)_e$—$Z^3$— subunit is selected from the group consisting of:

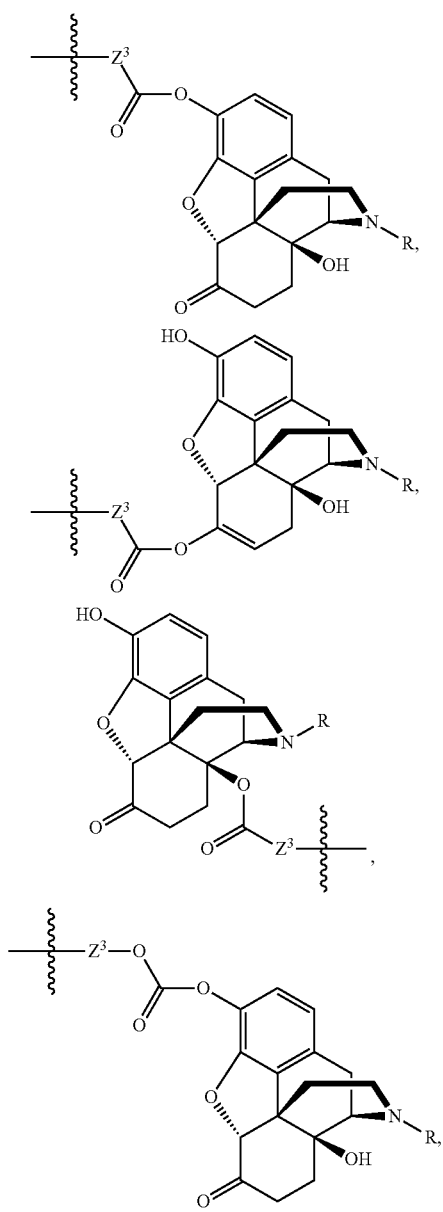

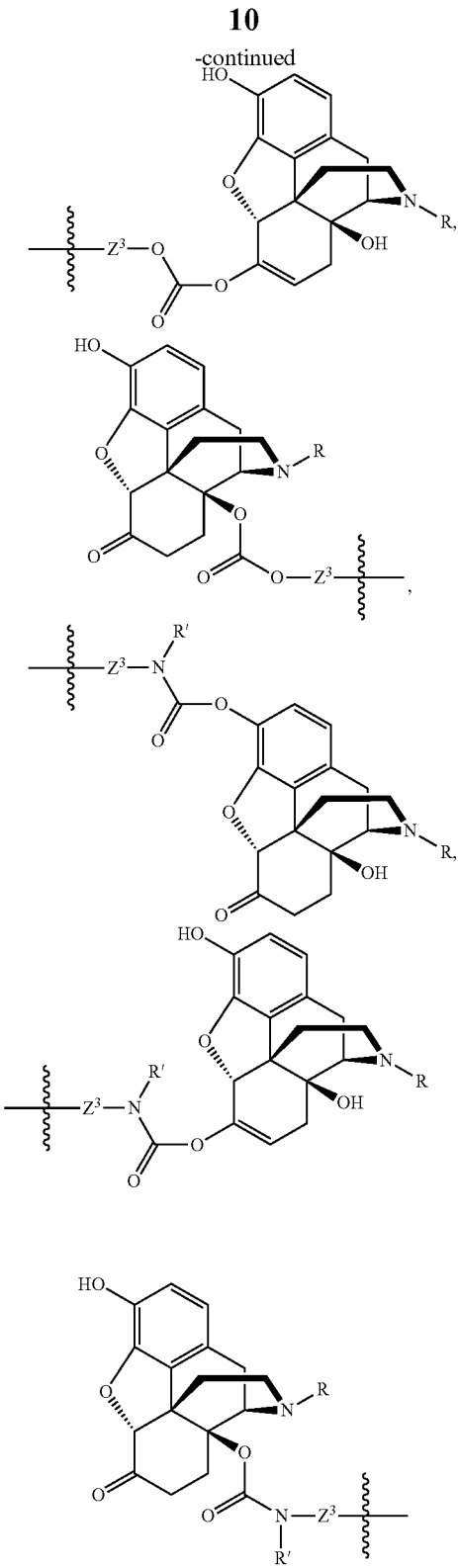

wherein:
R is cyclopropylmethyl or allyl; and
R' is hydrogen, methyl, alkyl, aryl, substituted alkyl, or substituted aryl.

For some of the structures described herein the opioid antagonist is naltrexone, naloxone, or a combination of both.

In some of the structures described herein $Z^1$, $Z^2$, and $Z^3$ are independently represented by the formula:

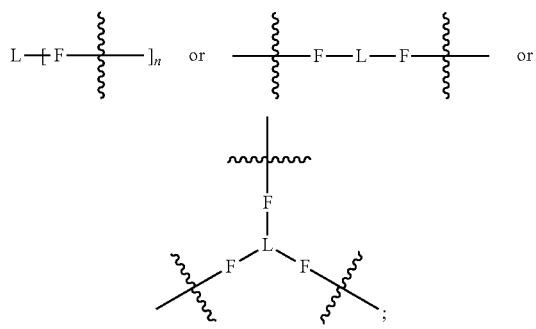

wherein:
each F is independently:

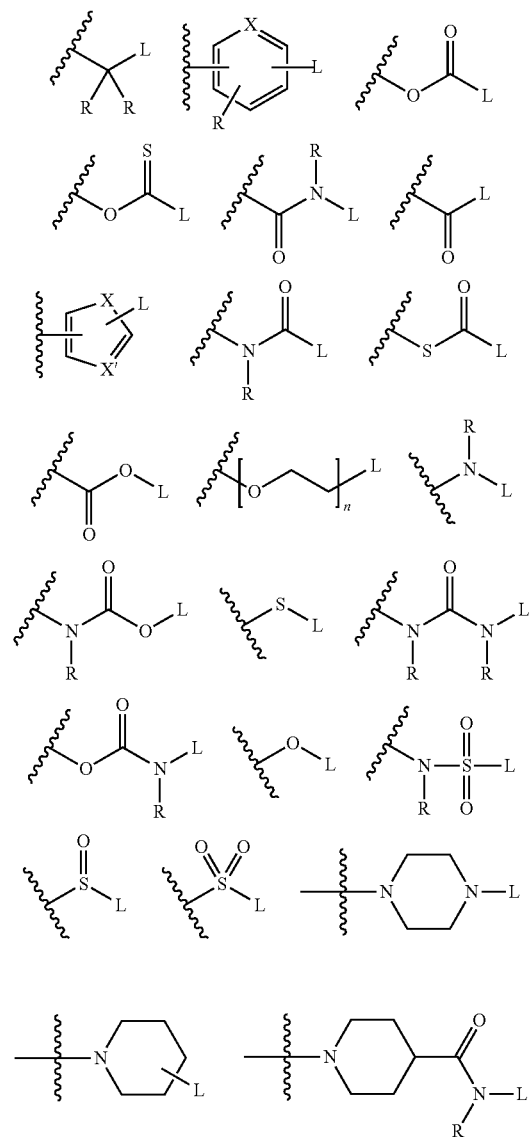

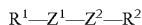

each R is independently hydrogen, lower alkyl, aryl, or arylalkyl;
X is carbon or nitrogen;
L is linear, branched, or a multivalent scaffold comprising an alkyl, an aryl, a substituted alkyl, a substituted aryl, a heteroalkyl, a substituted heteroalkyl, a polyalkylene glycol, a polypeptide, a polyamide, a polycarbamate, a polyurea, a polycarbonate, or a combination thereof.

In some instances, for some of the structures described herein each linking moiety $Z^1$, $Z^2$, $Z^3$ independently is a covalent bond, an atom, or forms an ester or a substituted ester, an amide or a substituted amide, an amine or a substituted amine, a carbamate or a substituted carbamate, an ether, an alkylane or a substituted alkylane, an arene or a substituted arene, or a urea or a substituted urea; and M is an atom, or a linear, a branched, or a multivalent scaffold moiety comprising an alkyl, an aryl, a substituted alkyl, a substituted aryl, a heteroalkyl, a polyalkylene glycol, a natural or a non-natural amino acid, a polyester, a polysaccharide, a polypeptide, or polyamide.

In some instances, for some of the structures described herein D is a morphone, a codone, morphine, or a combination thereof. The scaffold moiety M can be an oligomeric or polymeric scaffold, a polyalkylene oxide, a polypeptide, a polysaccharide or a biopolymer. The scaffold moiety M can also be a linear, a branched, a brush, or a comb polymer. In some instances, the scaffold moiety M is polycationic. In some instances, compositions of the invention comprise at least three, at least four, at least five, or at least six distinct polysubunit molecules. The scaffold moiety M can be an optionally substituted heteroalkyl group or an optionally substituted peptide. The optionally substituted peptide can range from 1 to 500 amino acids, from 1 to 50 amino acids, from 1 to 10 amino acids, or from 1 to 3 amino acids.

In some embodiments, is at least one of the two or more different molecules a molecule of formula (I), above, where h=k=1, q=0, and M is a bond. In some embodiments, is at least one of the two or more different molecules a molecule of formula (I), above, where g=h=d=k=1, q=0, and M is a bond. In some embodiments, is at least one of the two or more different molecules a molecule of formula (I), above, where formula (I) is the structure:

$$R^1—Z^1—Z^2—R^2$$

In some instances, a molecule of formula (I), above, is a structure of Formula (IA), (IB), (IC), (ID), or (IE):

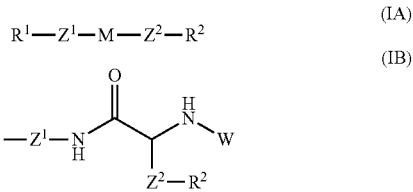

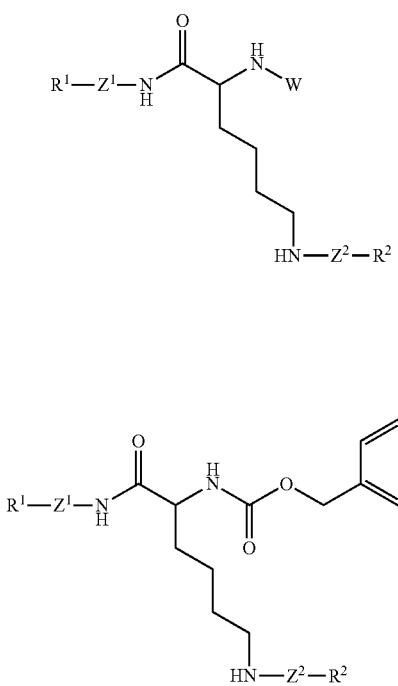

(IC)

(ID)

wherein W is selected from hydrogen, optionally substituted alkyl, optionally substituted acyl, and optionally substituted alkoxycarbonyl, or

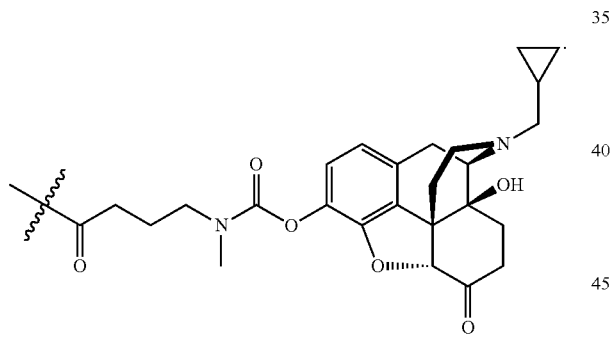

In other instances, a molecule of formula (I) is represented by a structure of Formula (IF), (IG), (IH), or (II):

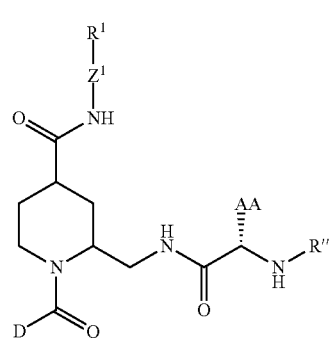

(IF)

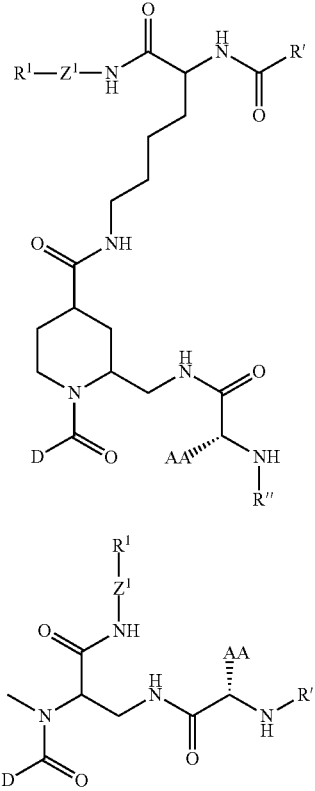

(IG)

(IH)

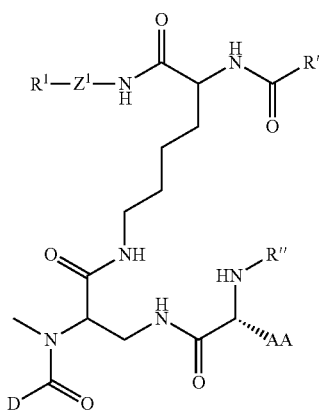

(II)

wherein:

D is an opioid agonist, each $R^1$ is independently a non-opioid agonist releasing GI enzyme subunit or GI enzyme inhibitor;

R' is selected from the group consisting of a methyl, a lower alkyl, a substituted alkyl, an aryl, a substituted aryl, a heteroalkyl, a natural or a non-natural amino acid, a polypeptide chain comprising natural or non-natural amino acids up to 10 amino acids in length, a linear or a branched polyethylene glycol chain up to 5 kDa, benzyloxy, and

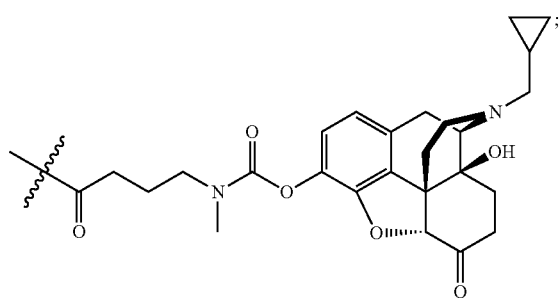

R" is selected from the group consisting of an acetyl, a substituted acyl, a natural or a non-natural amino acid, a polypeptide chain comprising natural or non-natural amino acids up to 10 amino acids in length;

AA is a natural or a non-natural amino acid side chain that is recognized by a GI enzyme; wherein $Z^1$ is a linker.

In such instances, at least one distinct polysubunit molecule can have an R' that is a GI enzyme inhibitor, a serine protease inhibitor or a trypsin inhibitor. In some instances, R' is independently selected from the group consisting of:

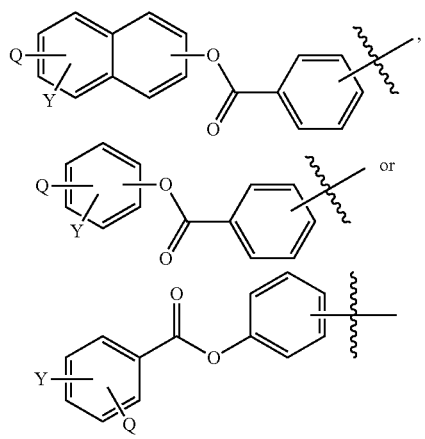

wherein:
Y is amidine, guanidine, aminomethyl, substituted amidine, substituted guanidine, substituted aminomethyl, amidinomethyl, guanidinomethyl, substituted amidinomethyl, or substituted guanidinomethyl; and
Q is independently selected from hydrogen, cyano, nitro, halogen, alkyl and alkoxy.

In some of the structures disclosed herein that describe a Y, the Y can be amidine, aminomethyl or guanidine. In some such structures, $R^1$—$Z^1$ can be selected from the group consisting of:

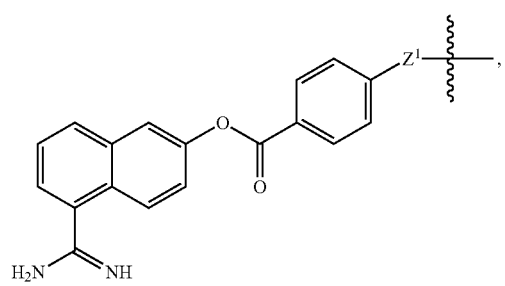

-continued

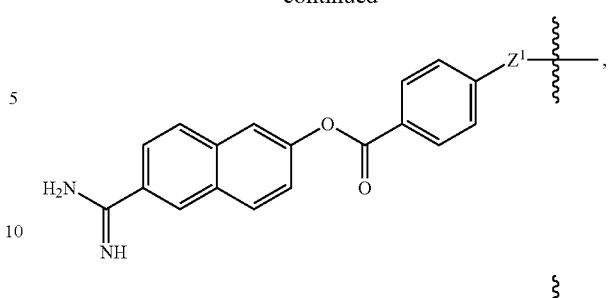

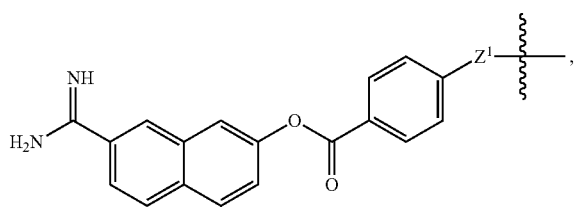

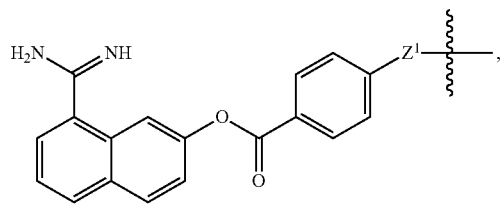

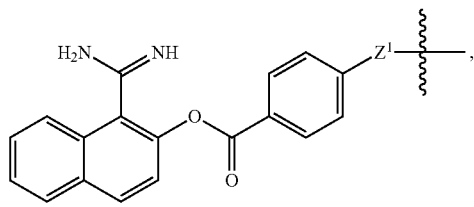

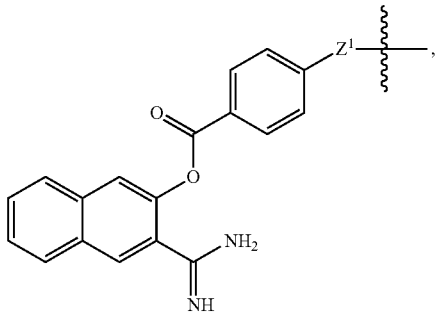

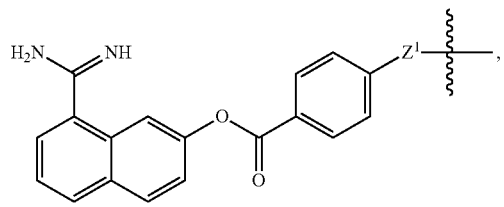

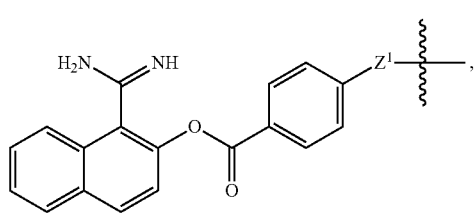

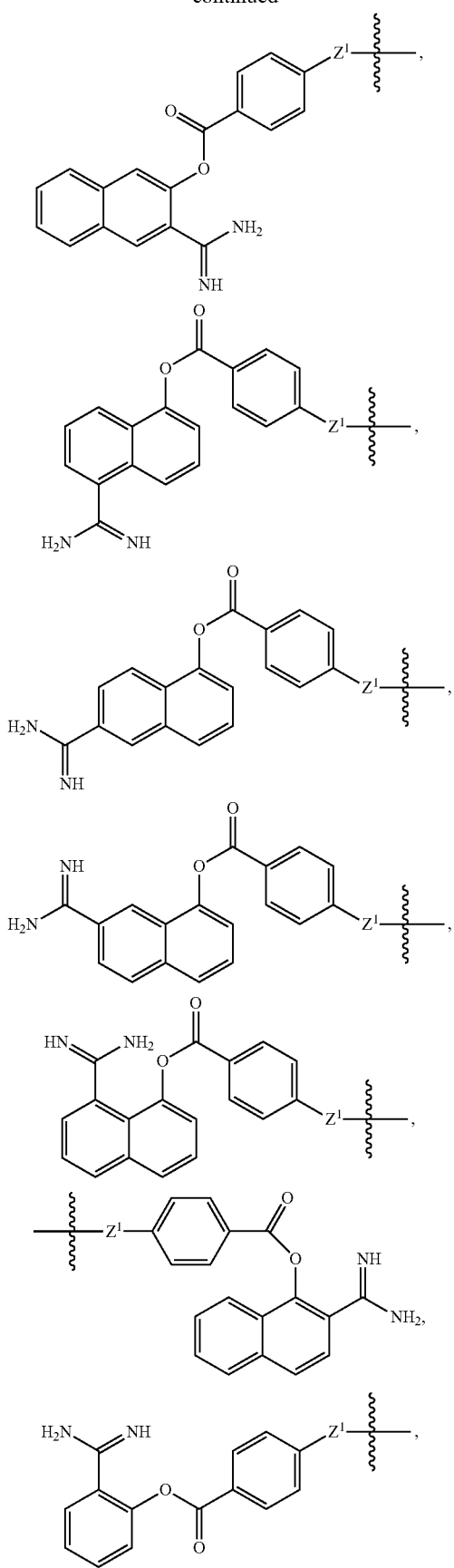
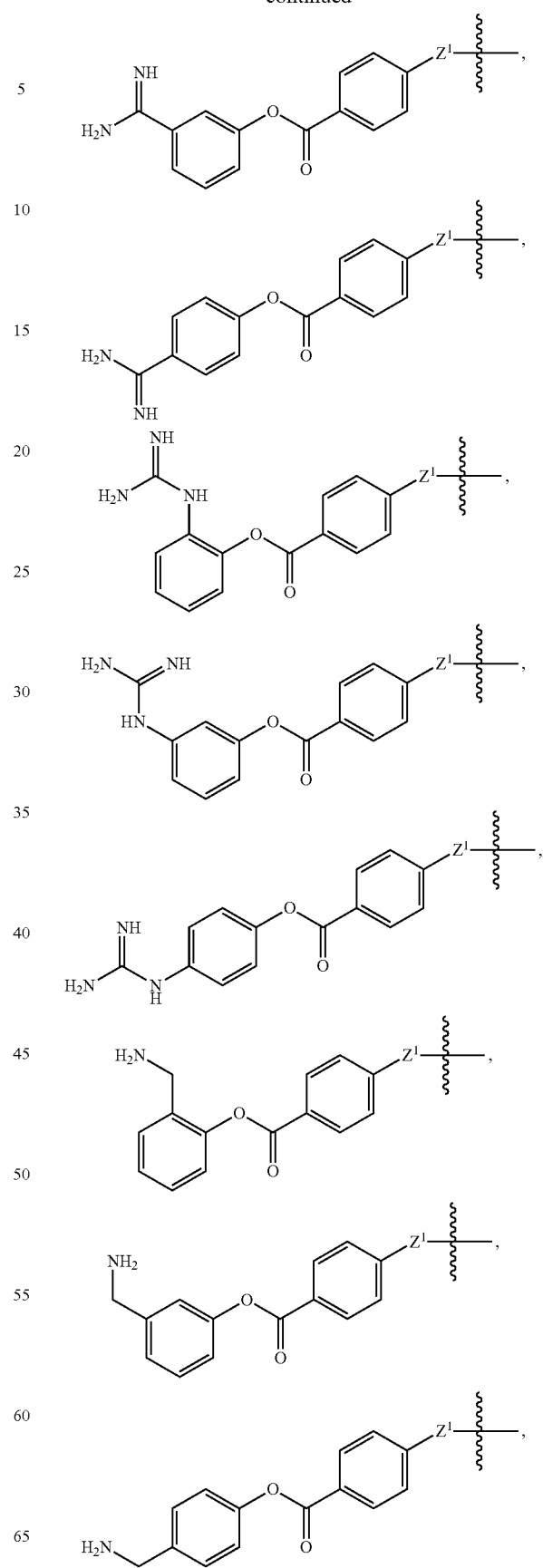

-continued
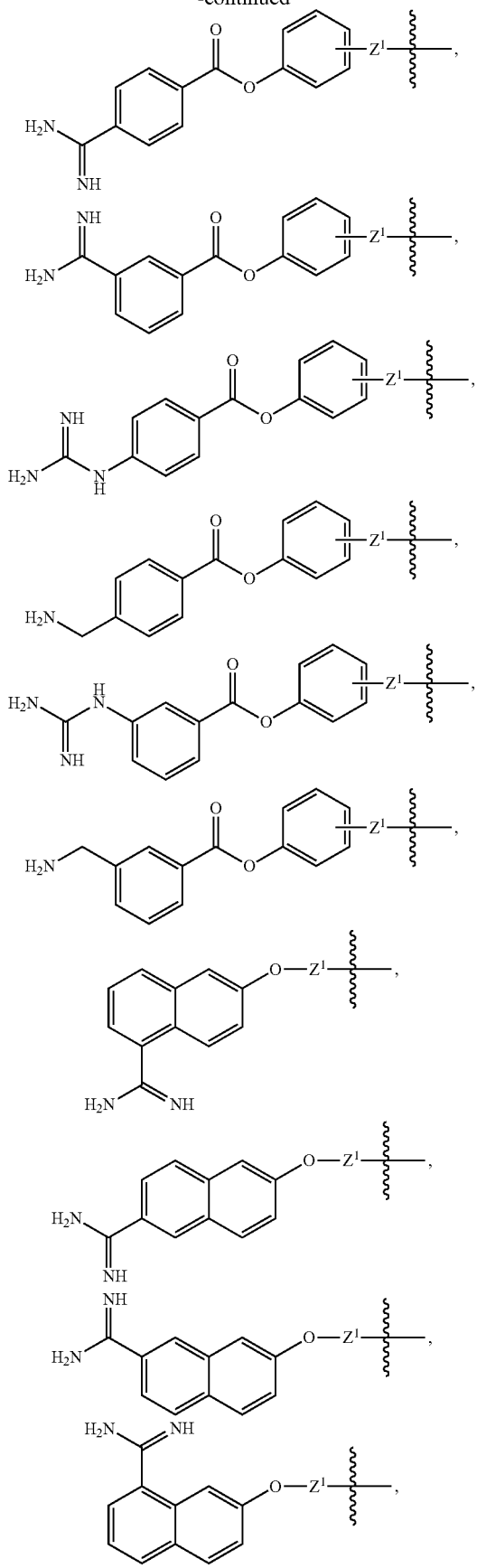
-continued
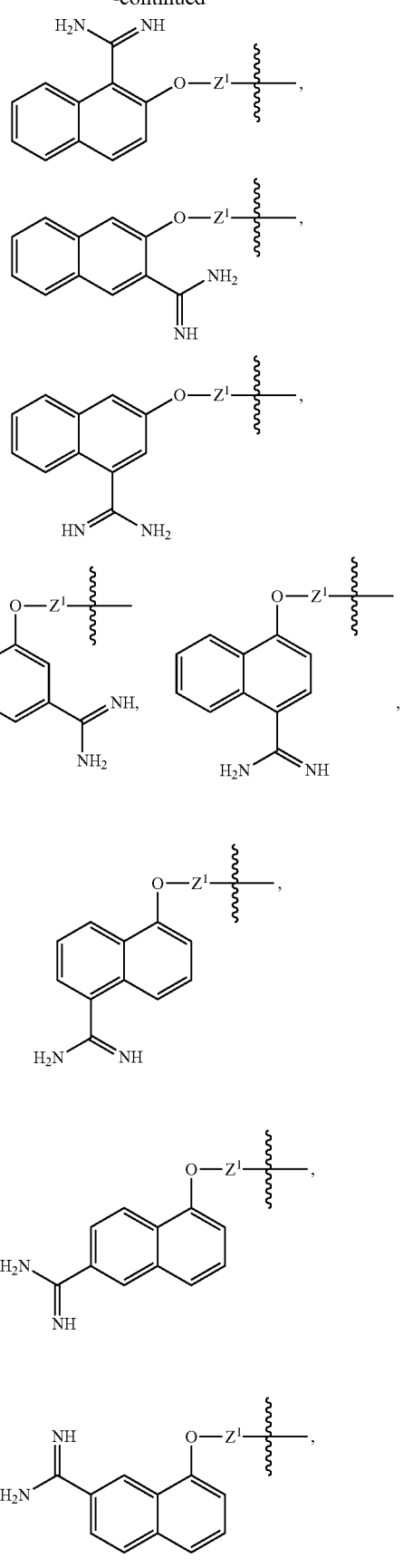

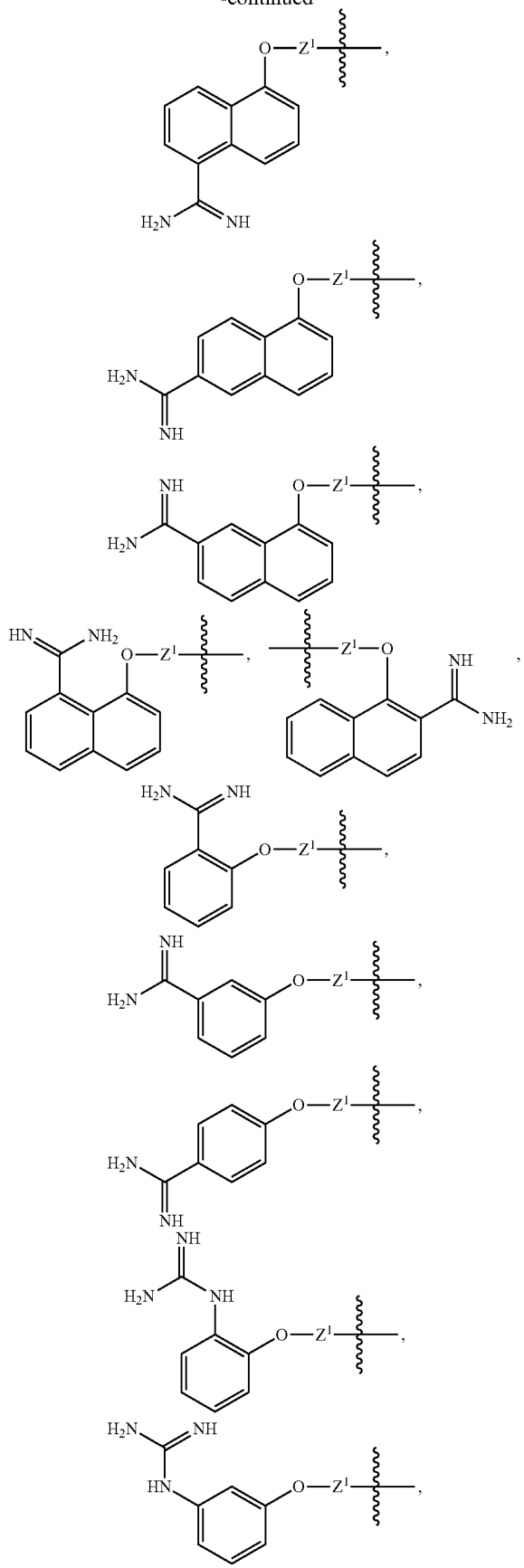

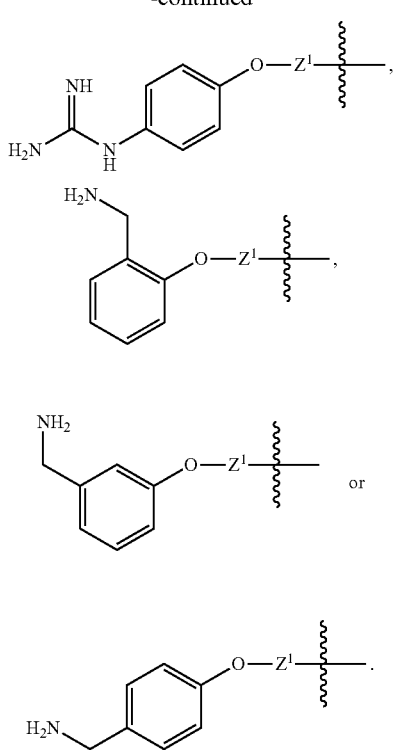

In some instances, the disclosure provides a polysubunit molecule wherein each $Z^1$ and $Z^2$ are selected from a linker comprising from 1 to 15 atoms.

In some instances, the polysubunit molecules described herein comprise a compound of represented by a structure of Formula (II-A), (II-B), (II-C), (II-D), (II-E), (II-F), (II-G), (II-H), (II-I), (II-J), (II-K), (II-L), (II-M), (II-N), (II-O), (II-P), (II-Q), (II-R), (II-S), (II-T), (II-U), (II-V), (II-W), and (II-X):

II-A

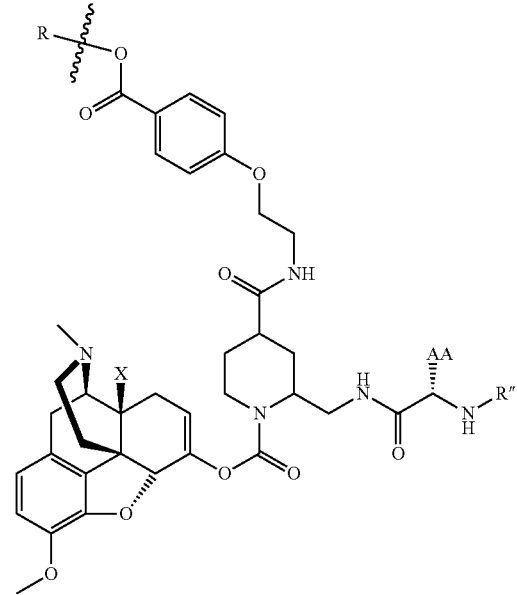

II-B
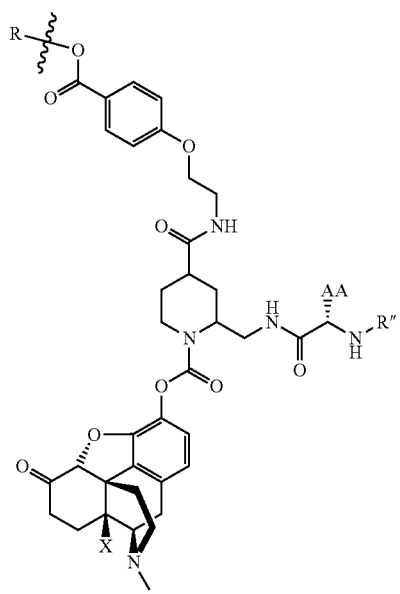
II-D
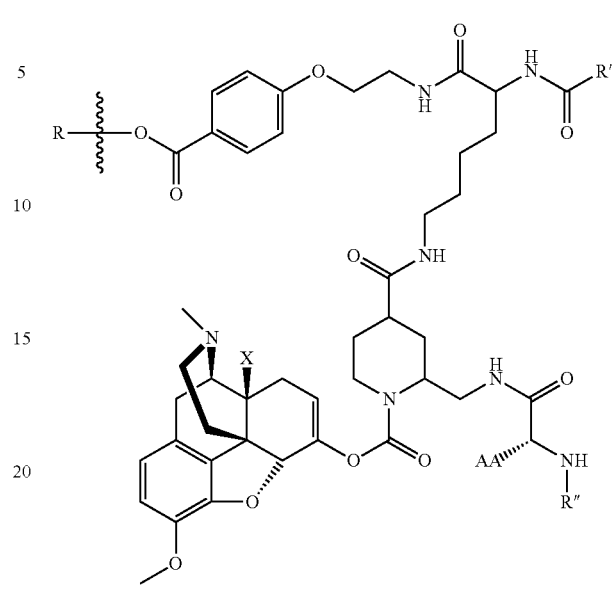
II-C
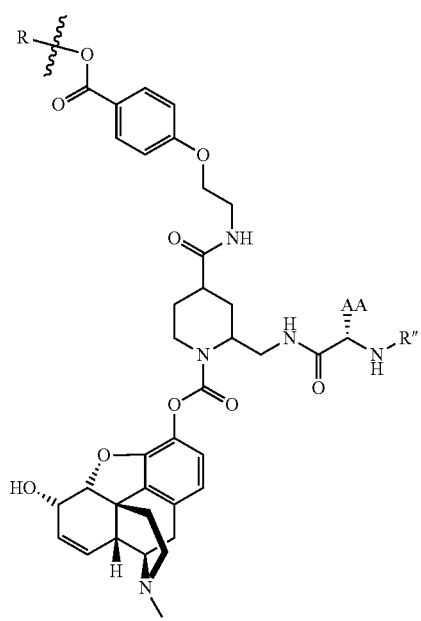
II-E
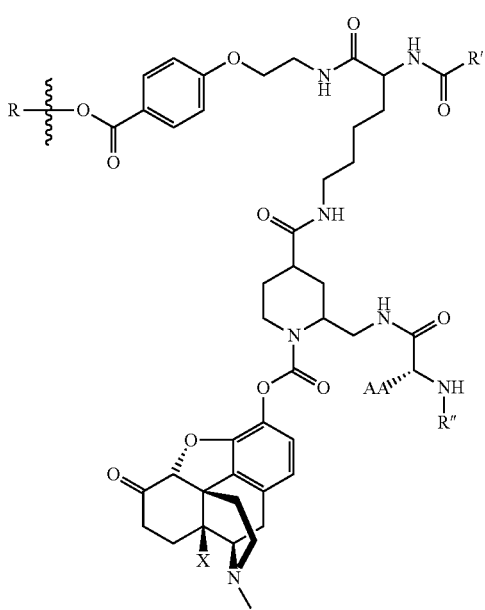

II-F
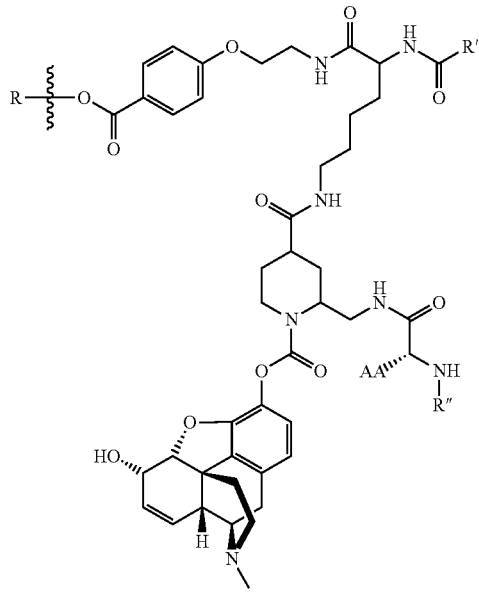
II-G
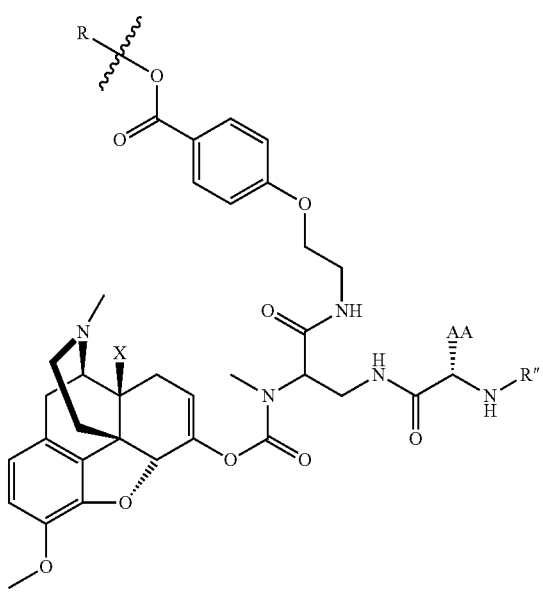
II-H
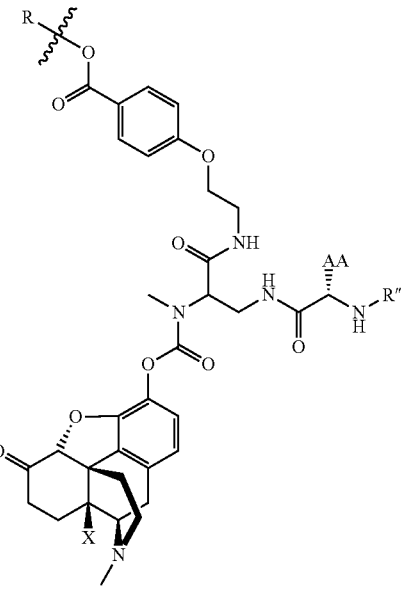
II-I
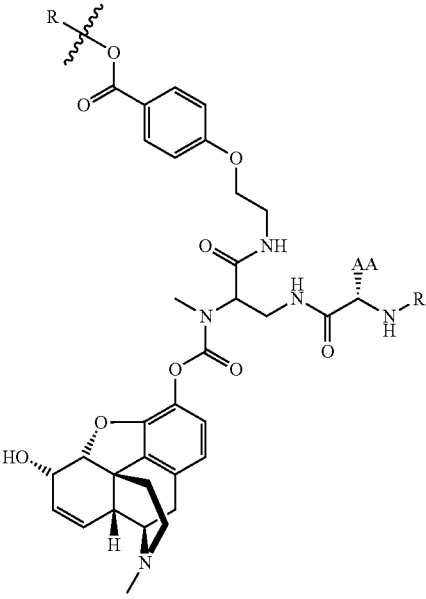

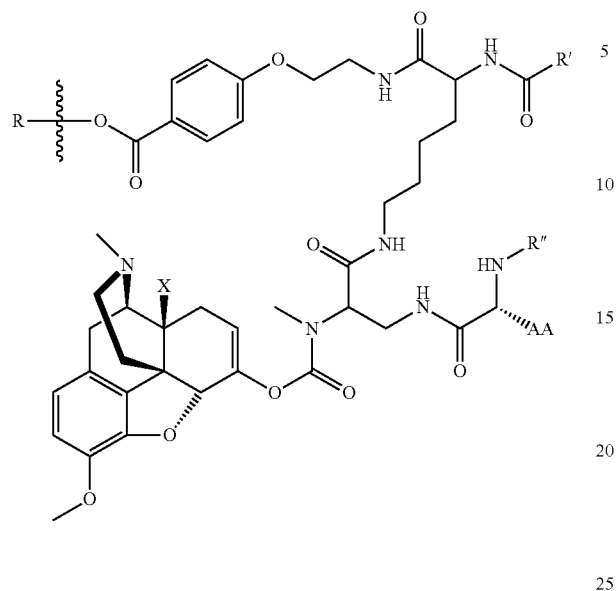
II-J
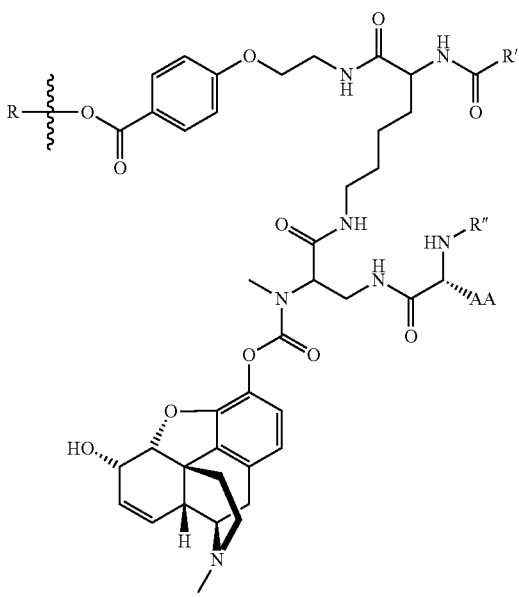
II-L
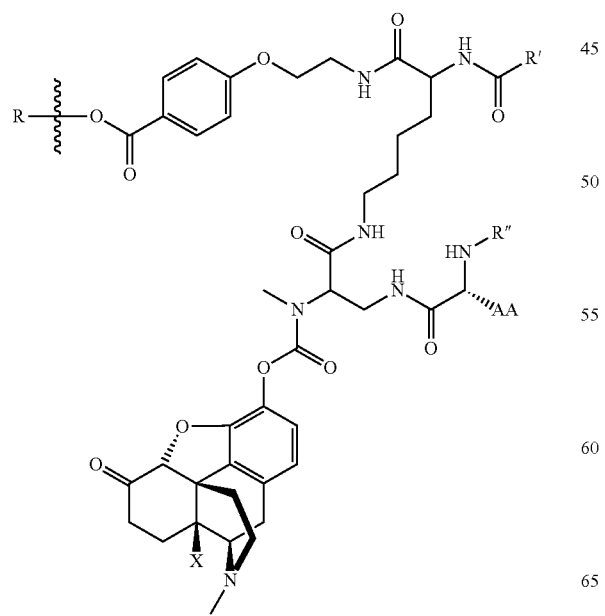
II-K
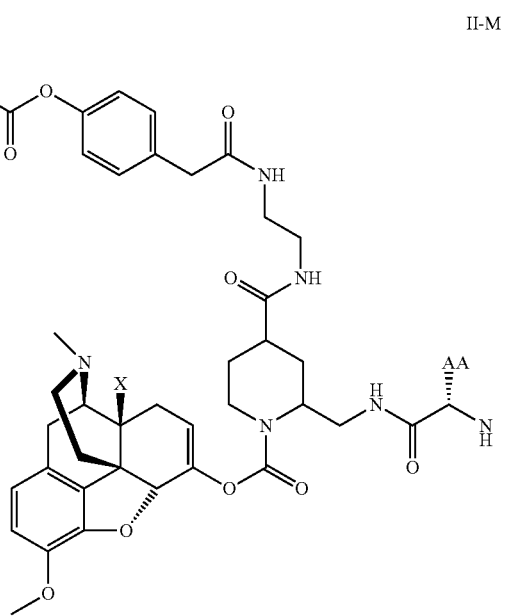
II-M

29
-continued
II-N
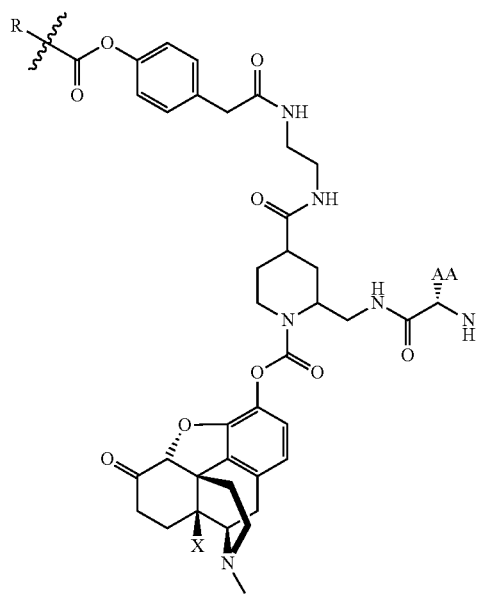
30
-continued
II-P
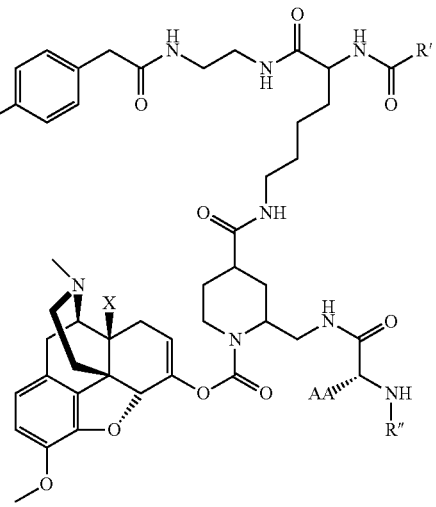
II-O
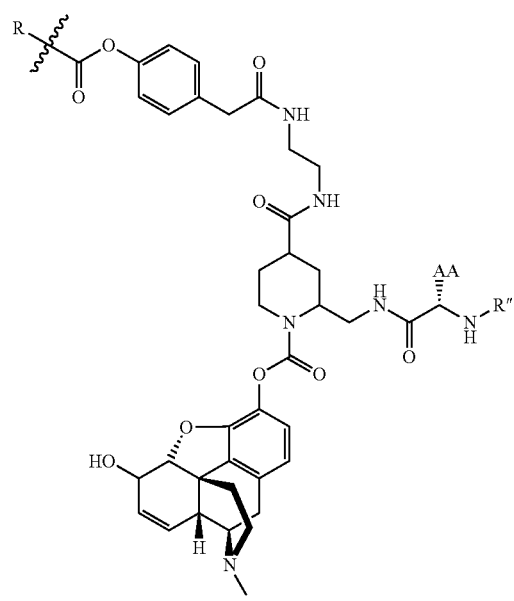
II-Q
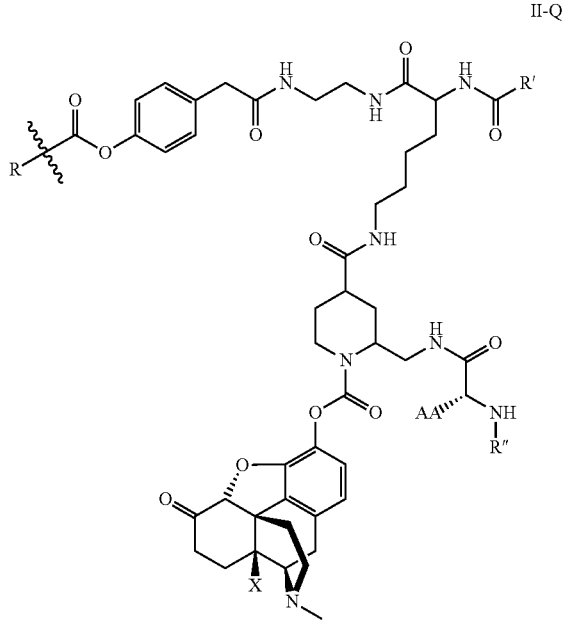

II-R
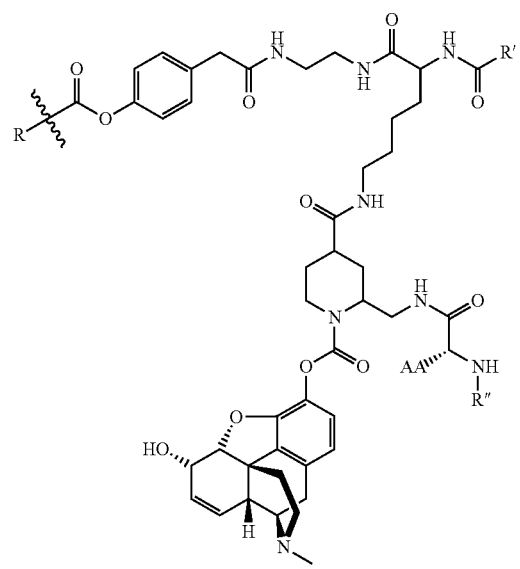
II-S
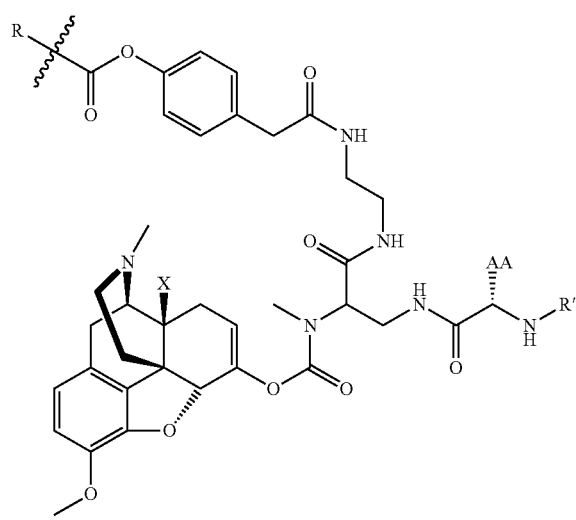
II-T
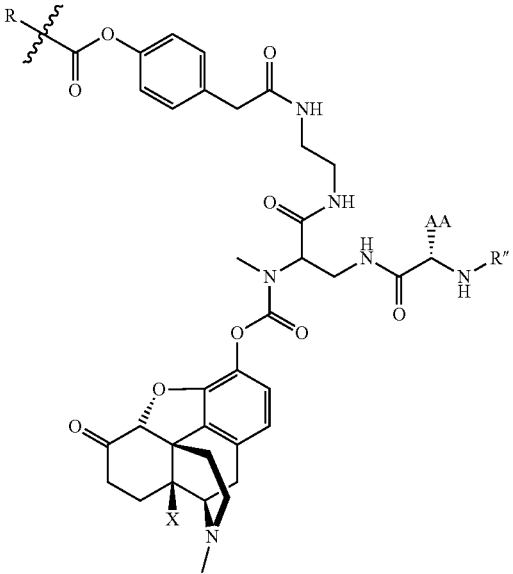
II-U
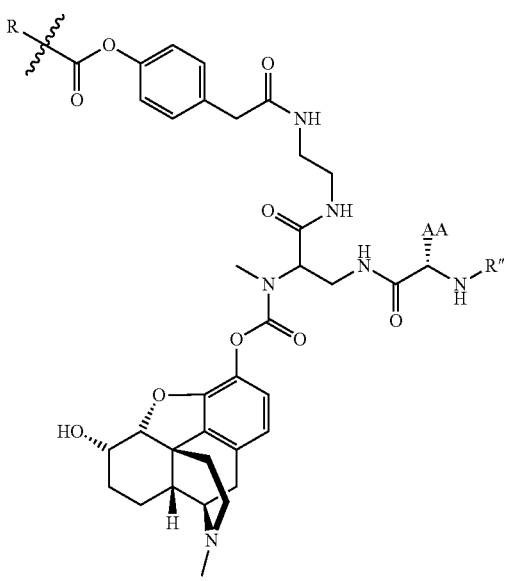
II-V
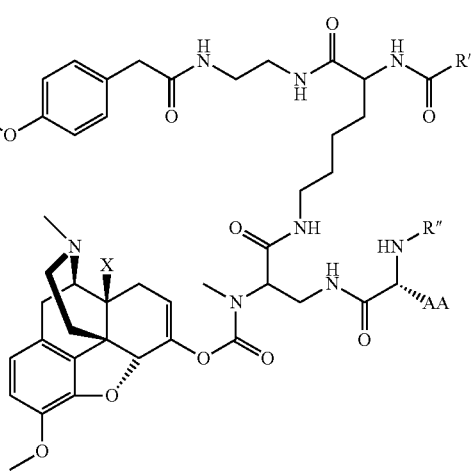

-continued

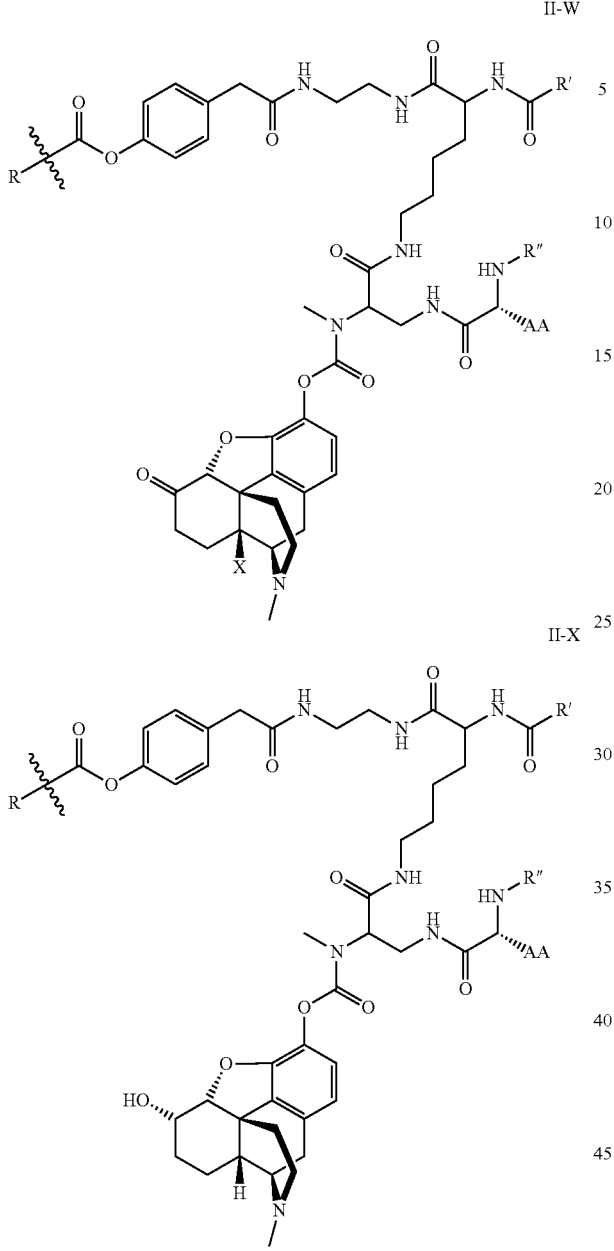

wherein:
R is selected from the group consisting of

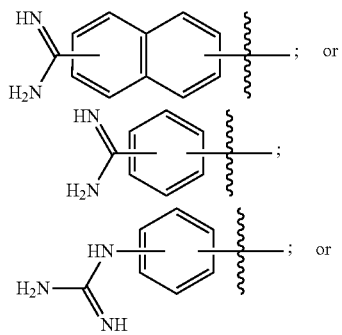

-continued

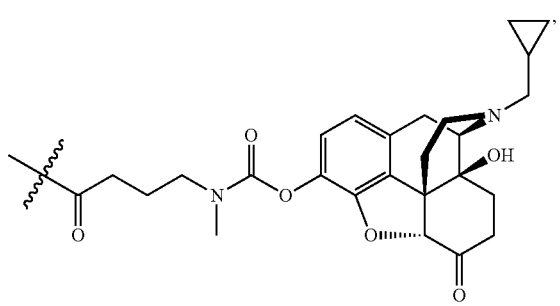

R' is selected from the group consisting of methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear or branched polyethylene glycol chain up to 5 kDa, benzyloxy,

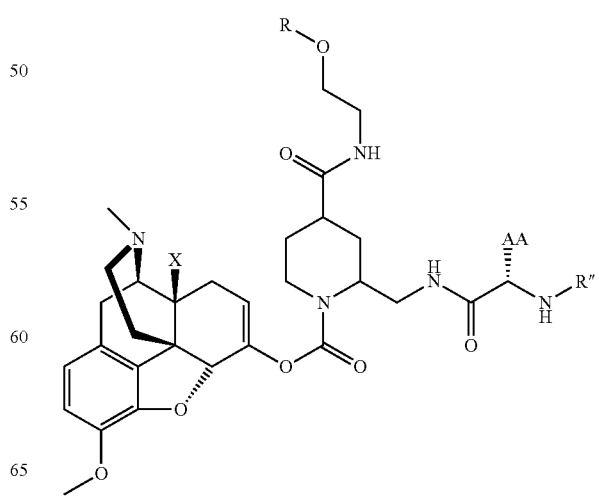

and the like;

R" is selected from the group consisting of an acetyl, substituted acyl, a natural or non-natural amino acid, or a polypeptide chain comprising natural and/or non-natural amino acids up to 10 amino acids in length;

AA is a natural or non-natural amino acid side chain recognized by trypsin;

X is hydrogen or OH.

In some the disclosure provides a composition comprising two or more polysubunit molecules selected from the group consisting of III-A, III-B, III-G, III-H, III-I, III-L, and salts thereof:

III-B
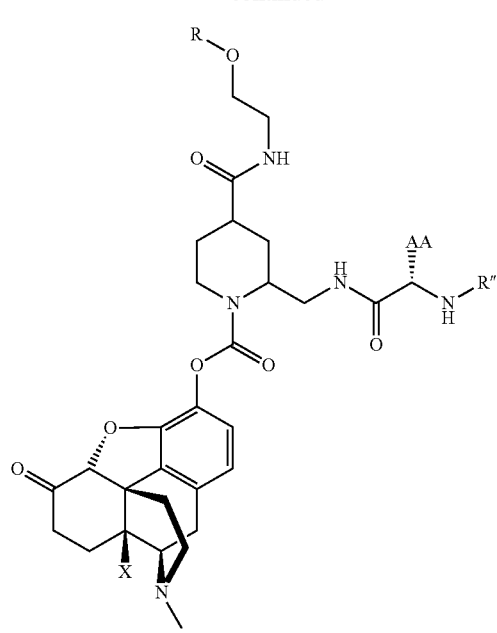
III-D
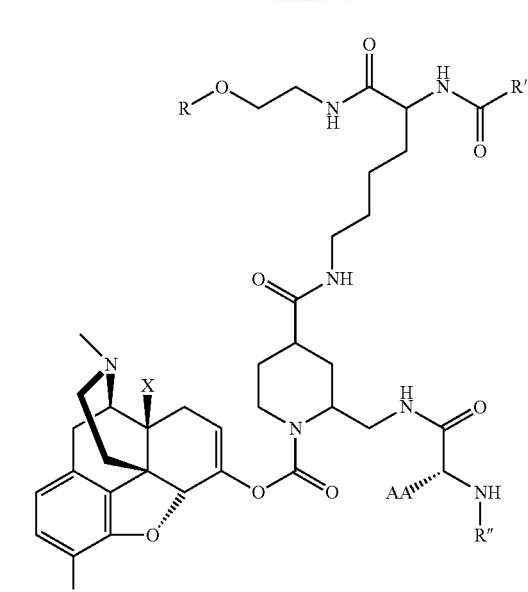
III-C
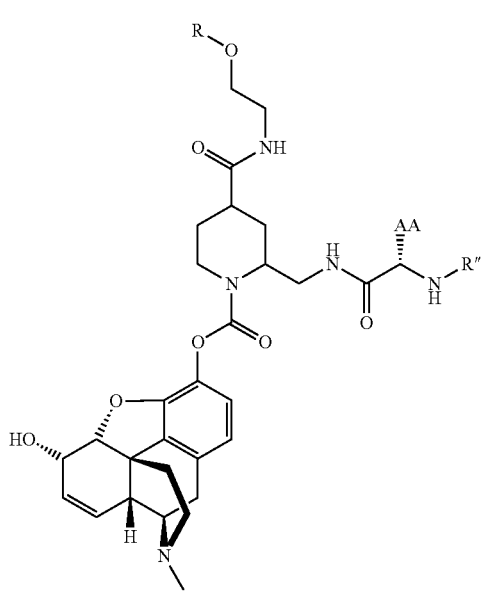
III-E
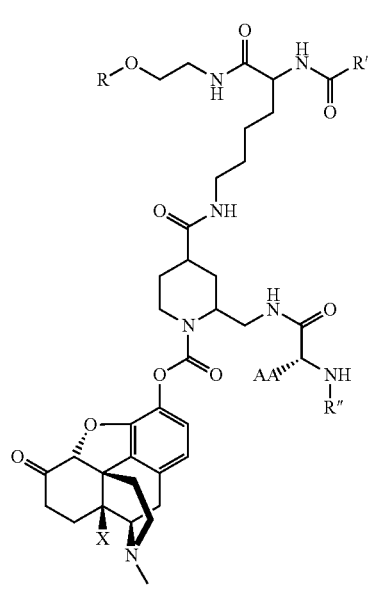

III-F
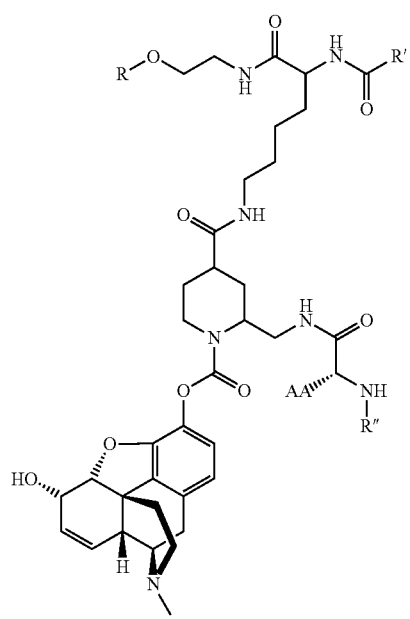
III-G
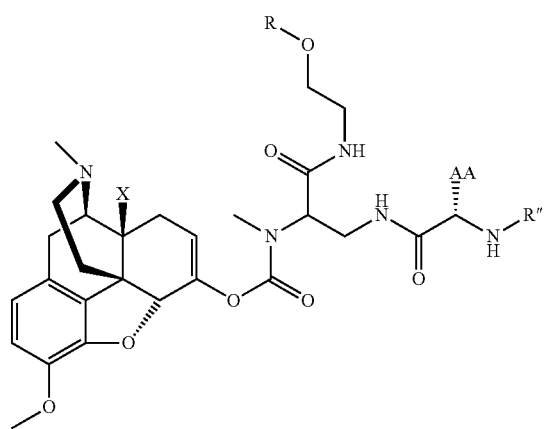
III-H
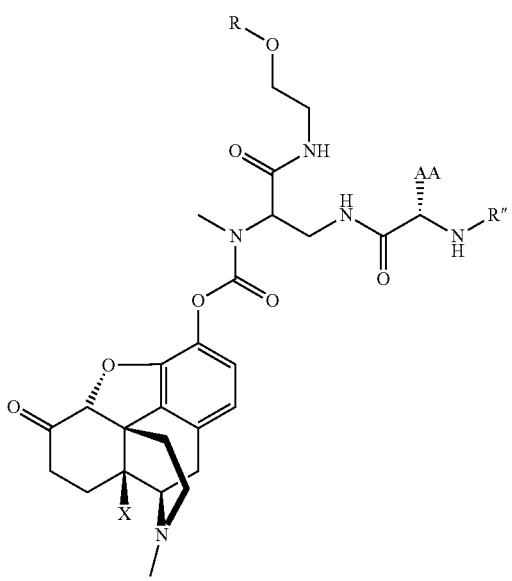
III-I
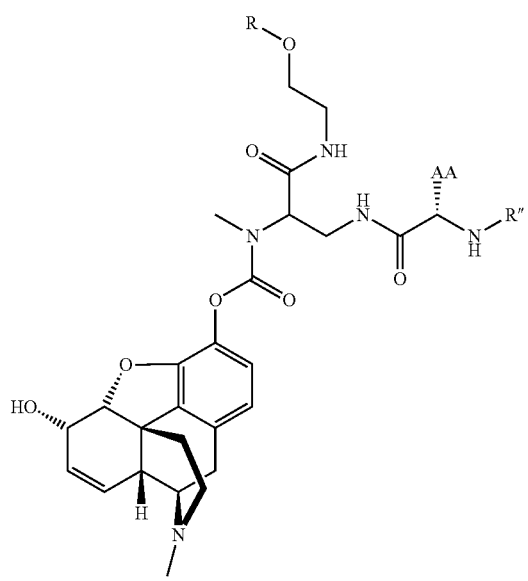
III-J
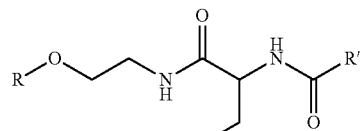
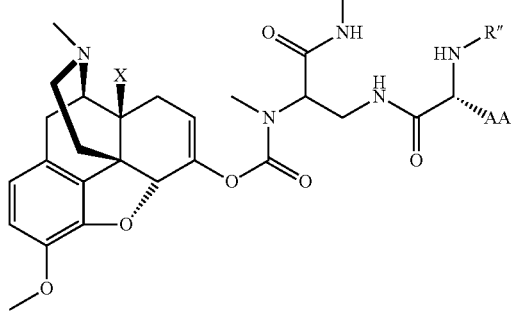

III-K

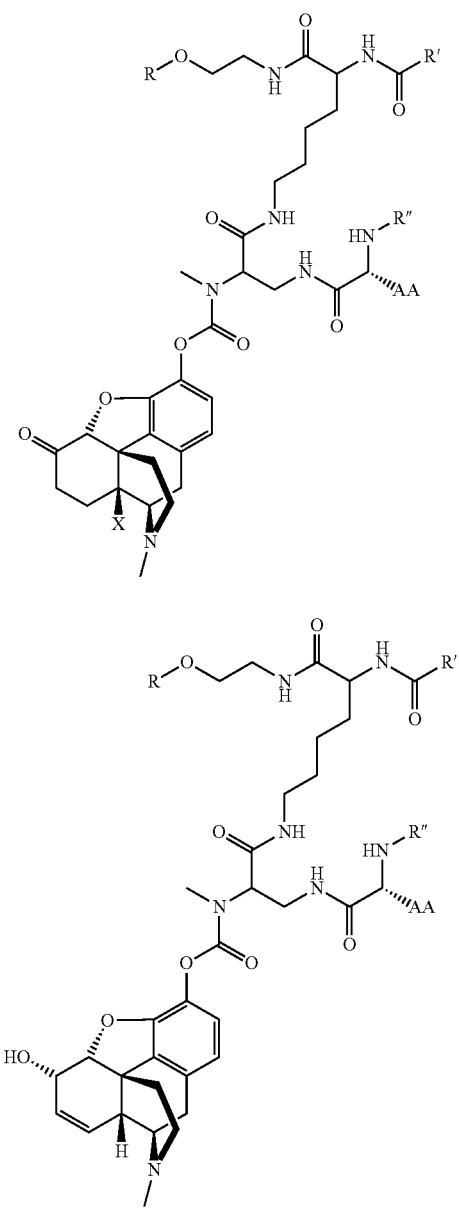

R is selected from the group consisting of

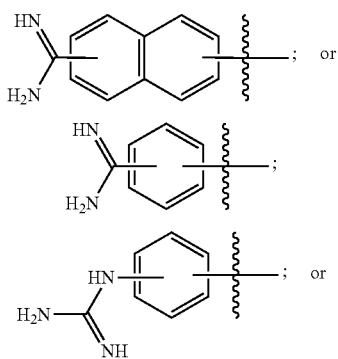

III-L

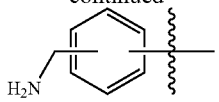

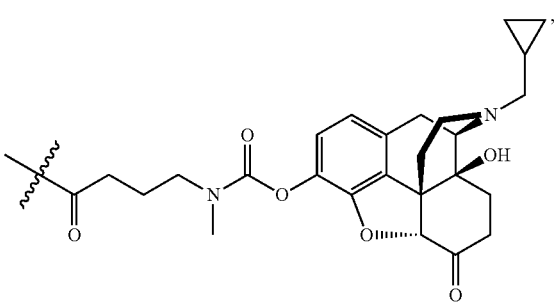

and the like;

R' is selected from the group consisting of methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear or branched polyethylene glycol chain up to 5 kDa, benzyloxy, R" is selected from the group consisting of an acetyl, substituted acyl, a natural or non-natural amino acid, or a polypeptide chain comprising natural and/or non-natural amino acids up to 10 amino acids in length;

AA is a natural or non-natural amino acid side chain recognized by trypsin;

X is hydrogen or OH. The compositions of claim 64 wherein AA is the side chain of lysine or arginine and X is hydrogen or OH.

In some instances, R' is methyl or benzyloxy, in other instances R" is acetyl, -Gly-NAc, or -Ala-NAc.

In some instances, the disclosure provides a method of treating pain in a subject in need thereof, the method comprising administrating to the subject a therapeutically effective amount of a composition comprising one or more polysubunit molecules.

In some instances, the disclosure provides a pharmaceutical formulation comprising a composition containing any of the polysubunits described herein and a pharmaceutically acceptable excipient.

In some instances, the disclosure provides a pharmaceutical formulation comprising two or more polysubunit molecules, wherein each polysubunit molecule comprises:
an opioid prodrug;
a gastrointestinal enzyme inhibitor; and
a scaffold moiety, wherein the opioid prodrug and the inhibitor are covalently linked via a covalent bond, an atom, or a scaffold moiety.

In some instances, the disclosure provides a pharmaceutical composition comprising two or more polysubunit molecules, wherein each polysubunit molecule comprises:
an opioid prodrug comprising an opioid covalently bonded to a promoiety comprising a gastrointestinal enzyme-cleavable moiety; and
a gastrointestinal enzyme inhibitor wherein the opioid prodrug and the enzyme inhibitor are covalently linked via a covalent bond, an atom, or a scaffold moiety.

In some instances, the disclosure provides a pharmaceutical composition comprising:

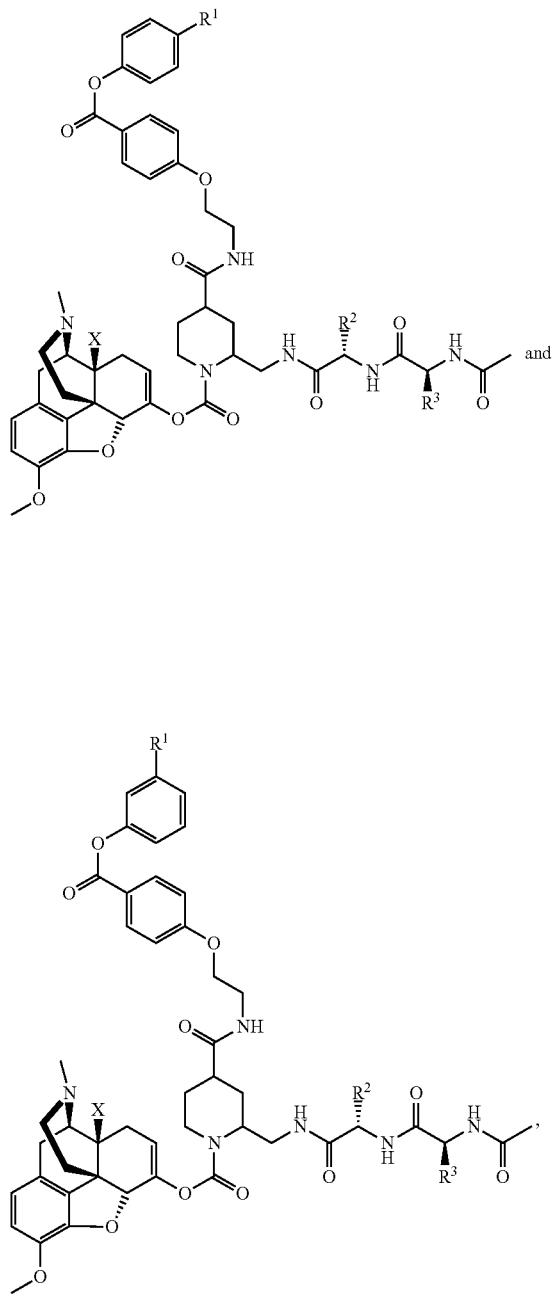

or salts thereof,
wherein:
R[1] is independently, amidine, aminomethyl or guanidine;
R[2] is independently, the side chain of lysine or arginine;
R[3] is independently, hydrogen or methyl; and
X is independently, hydrogen or —OH.

In some instances, the disclosure provides a pharmaceutical composition comprising:

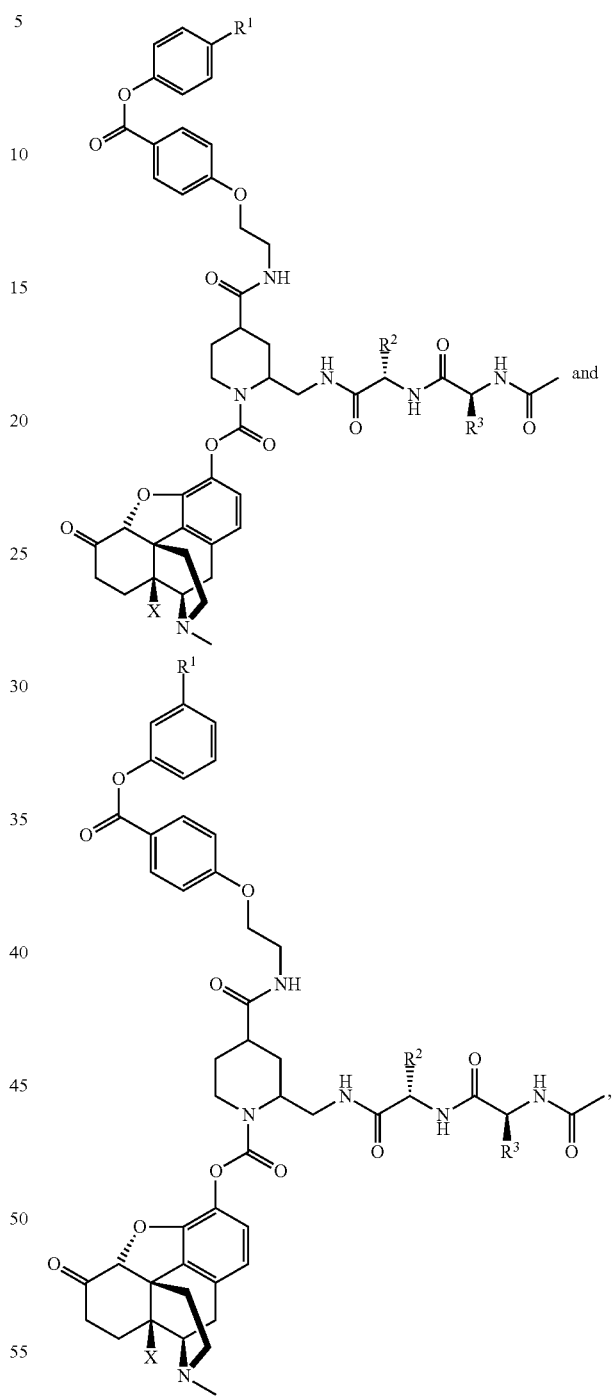

or salts thereof,
wherein:
R[1] is independently, amidine, aminomethyl or guanidine;
R[2] is independently, the side chain of lysine or arginine;
R[3] is independently, hydrogen or methyl; and
X is independently, hydrogen or —OH.

In some instances, the disclosure provides a pharmaceutical composition comprising:

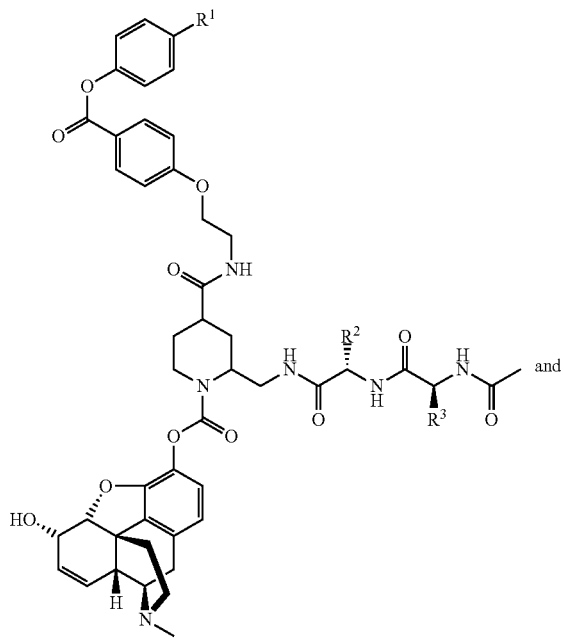

and

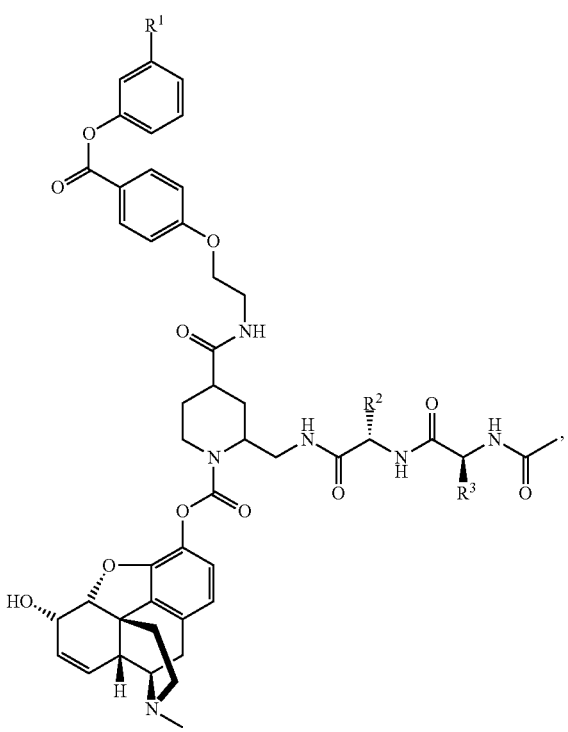

or salts thereof,
wherein:
R¹ is independently, amidine, aminomethyl or guanidine;
R² is independently, the side chain of lysine or arginine; and
R³ is independently, hydrogen or methyl.

In some instances, the disclosure provides a pharmaceutical composition comprising:

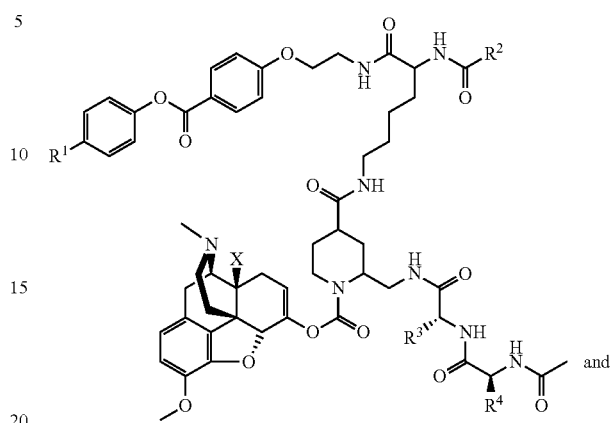

and

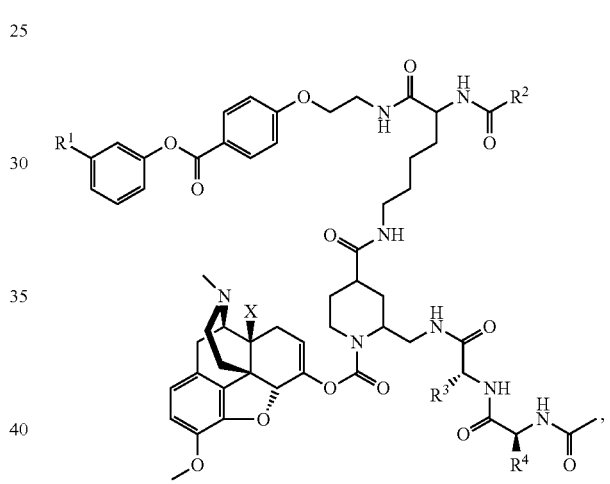

or salts thereof,
wherein:
R¹ is independently, amidine, aminomethyl or guanidine;
R² is independently, methyl, benzyloxy, or

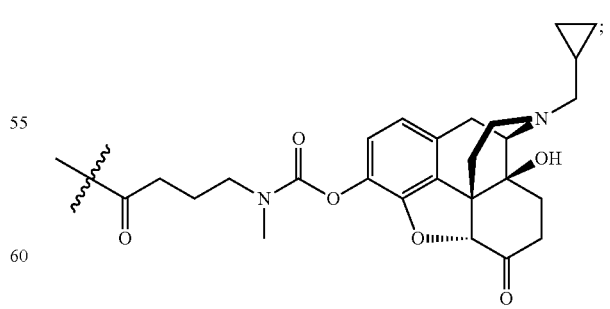

R³ is independently, the side chain of lysine or arginine;
R⁴ is independently, hydrogen or methyl; and
X is independently, hydrogen or —OH.

In some instances, the disclosure provides a pharmaceutical composition comprising:

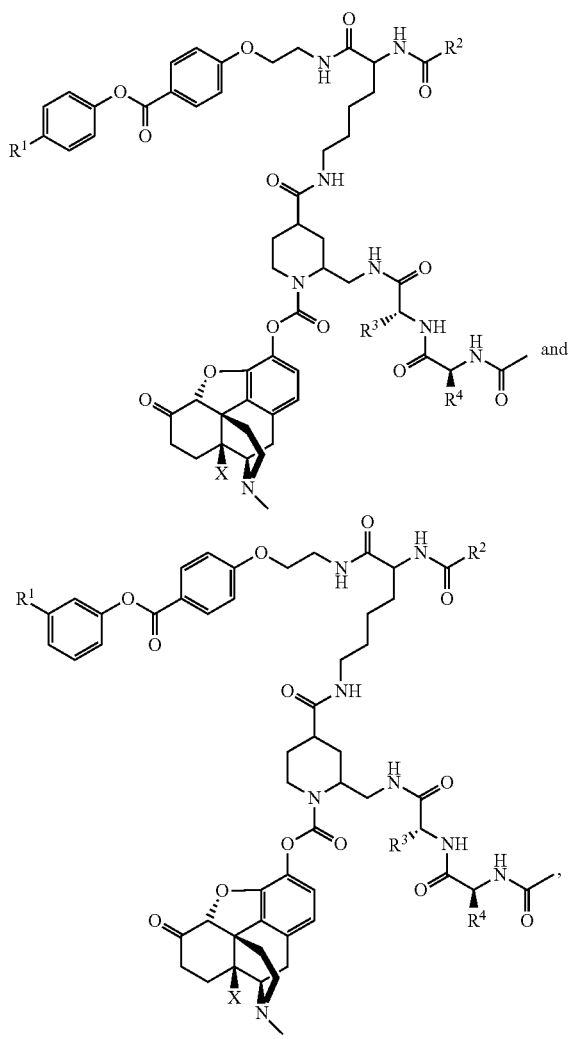

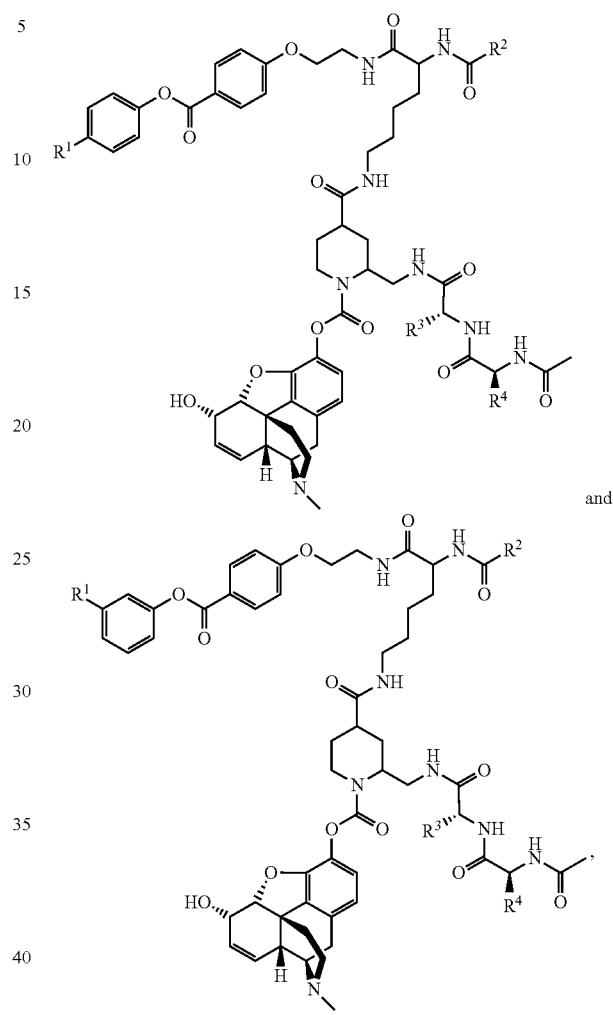

or salts thereof,
wherein:
$R^1$ is independently, amidine, aminomethyl or guanidine;
$R^2$ is independently, methyl, benzyloxy, or

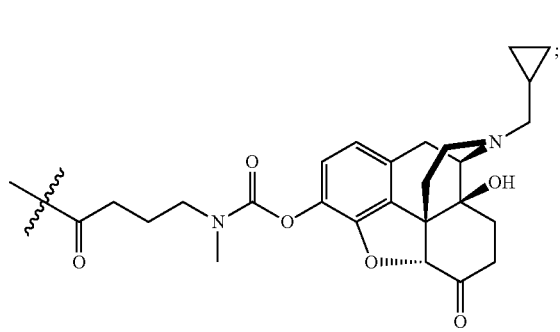

$R^3$ is independently, the side chain of lysine or arginine;
$R^4$ is independently, hydrogen or methyl; and
X is independently, hydrogen or —OH.

In some instances, the disclosure provides a pharmaceutical composition comprising:

or salts thereof,
wherein:
$R^1$ is independently, amidine, aminomethyl or guanidine;
$R^2$ is independently, methyl, benzyloxy, or

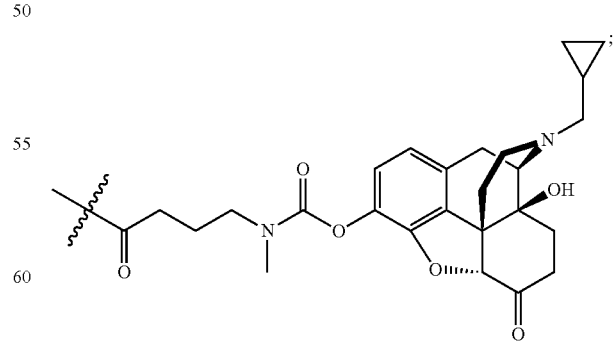

$R^3$ is independently, the side chain of lysine or arginine; and
$R^4$ is independently, hydrogen or methyl.

In some instances, the disclosure provides a pharmaceutical composition comprising:

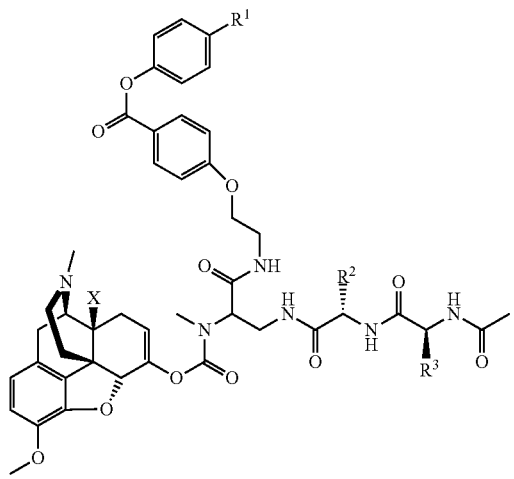

and

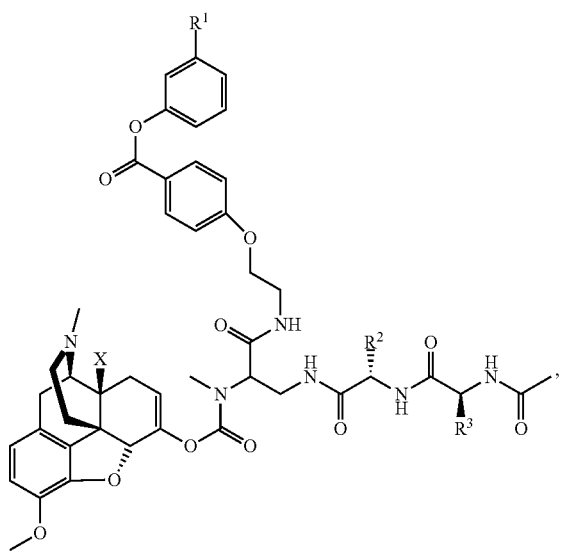

or salts thereof,
wherein:
R[1] is independently, amidine, aminomethyl or guanidine;
R[2] is independently, the side chain of lysine or arginine;
R[3] is independently, hydrogen or methyl; and
X is independently, hydrogen or —OH.

In some instances, the disclosure provides a pharmaceutical composition, comprising:

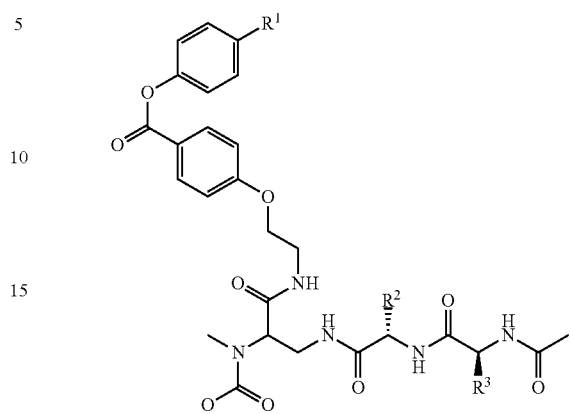

and

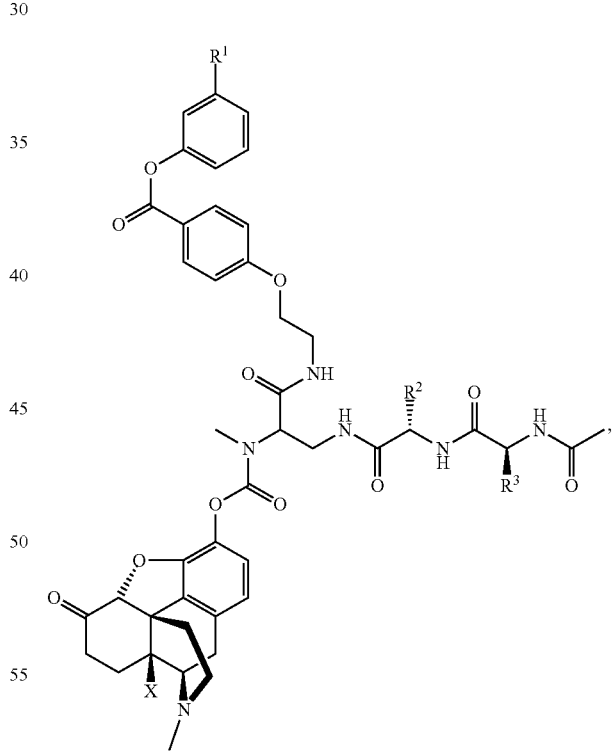

or salts thereof,
wherein:
R[1] is independently, amidine, aminomethyl or guanidine;
R[2] is independently, the side chain of lysine or arginine;
R[3] is independently, hydrogen or methyl; and
X is independently, hydrogen or —OH.

In some instances, the disclosure provides a pharmaceutical formulation composition comprising:

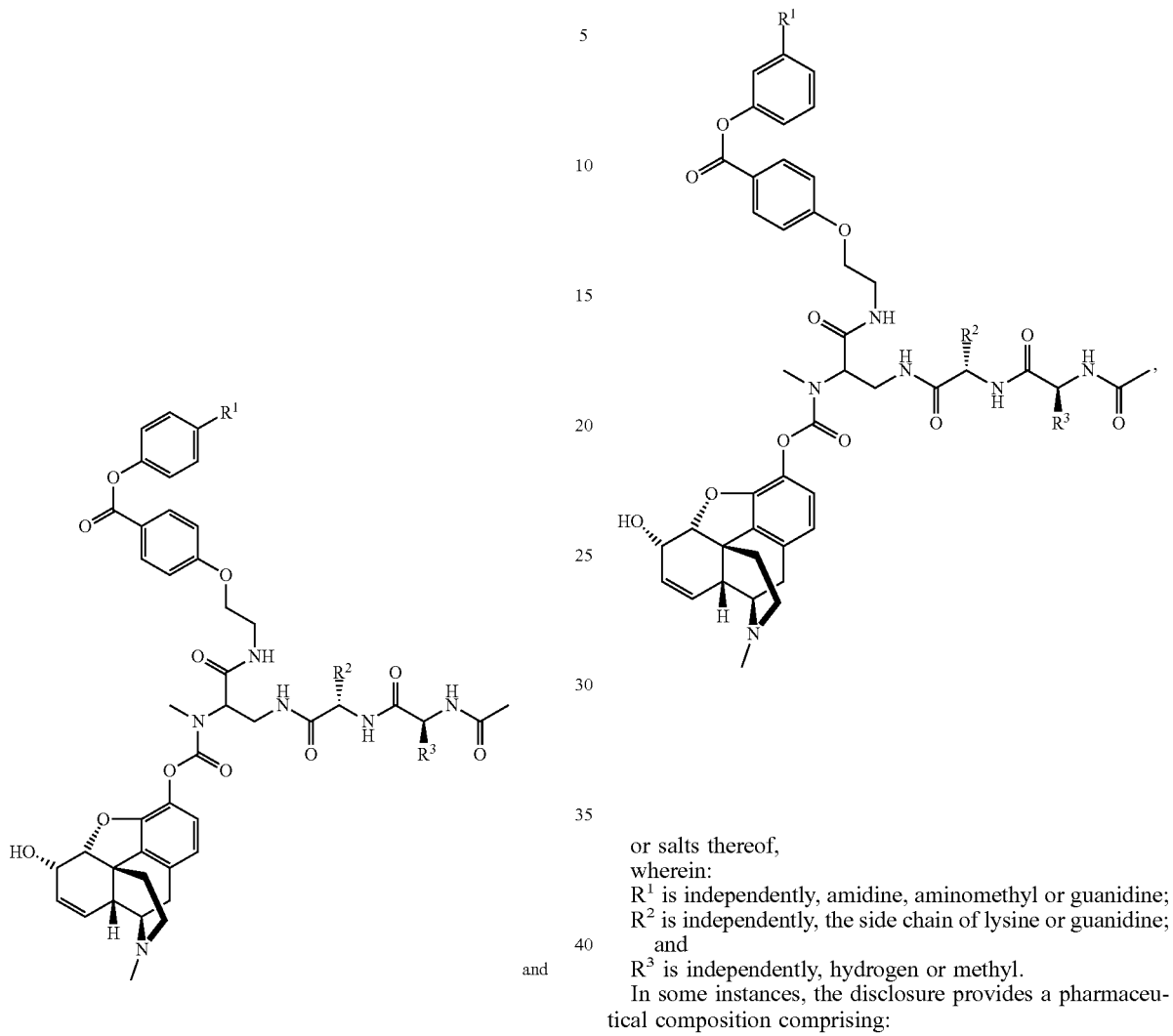

or salts thereof,
wherein:
R[1] is independently, amidine, aminomethyl or guanidine;
R[2] is independently, the side chain of lysine or guanidine; and
R[3] is independently, hydrogen or methyl.

In some instances, the disclosure provides a pharmaceutical composition comprising:

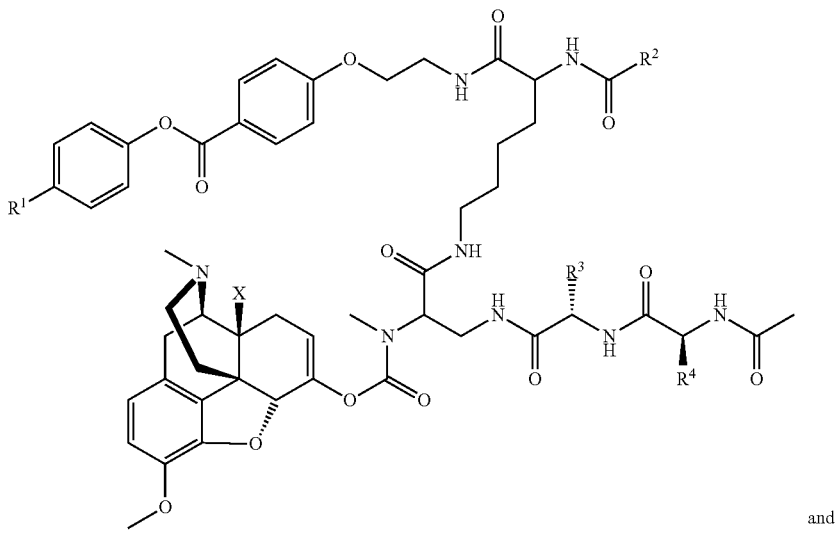

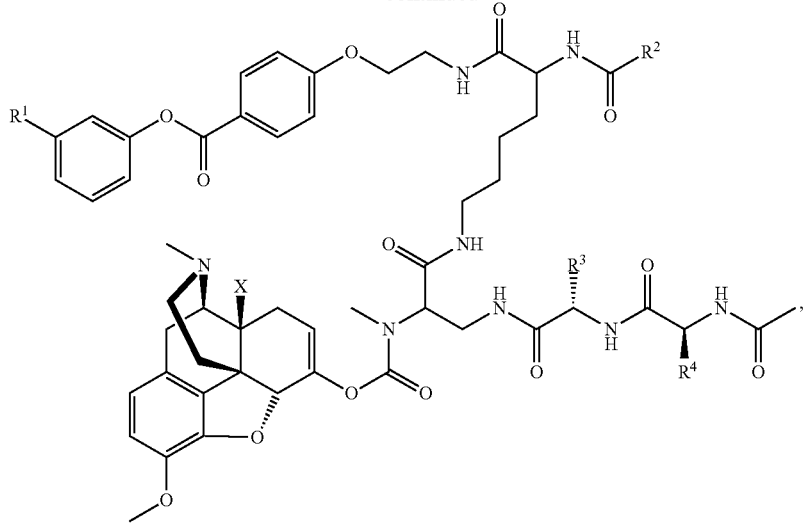

or salts thereof,
wherein:
R¹ is independently, amidine, aminomethyl or guanidine;
R² is independently, methyl, benzyloxy, or

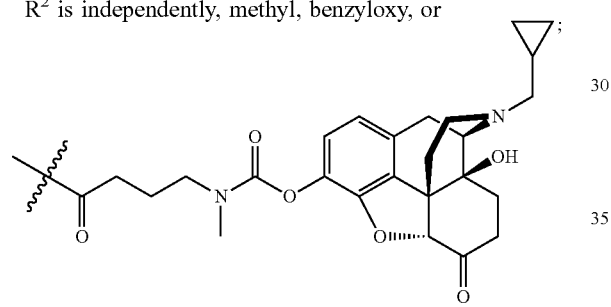

R³ is independently, the side chain of lysine or arginine;
R⁴ is independently, hydrogen or methyl; and
X is independently, hydrogen or —OH.

In some instances, the disclosure provides a pharmaceutical composition, comprising:

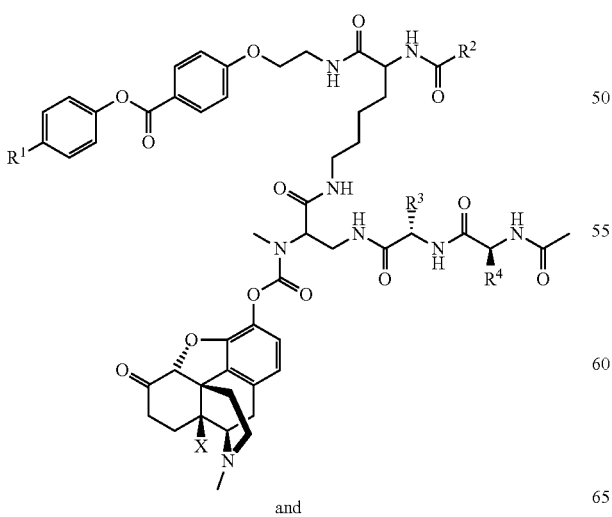

and

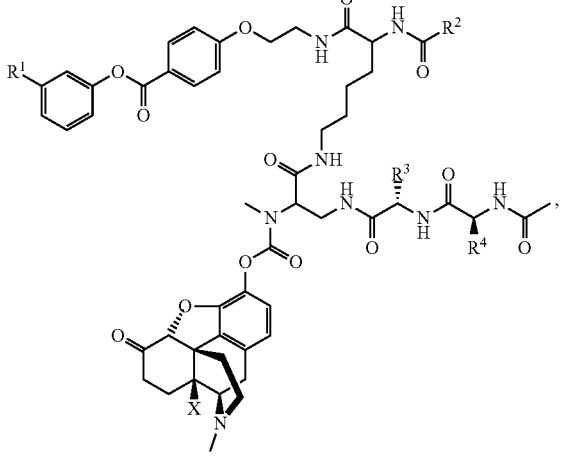

or salts thereof,
wherein:
R¹ is independently, amidine, aminomethyl or guanidine;
R² is independently, methyl, benzyloxy, or

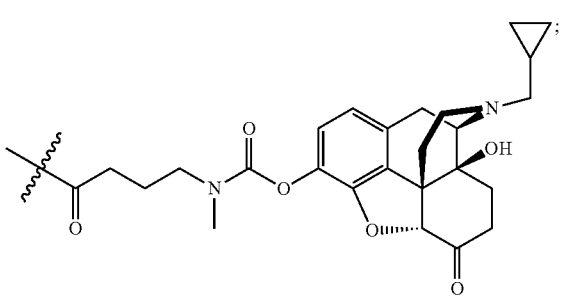

R³ is independently, the side chain of lysine or arginine;
R⁴ is independently, hydrogen or methyl; and
X is independently, hydrogen or —OH.

In some instances, the disclosure provides a pharmaceutical composition comprising:

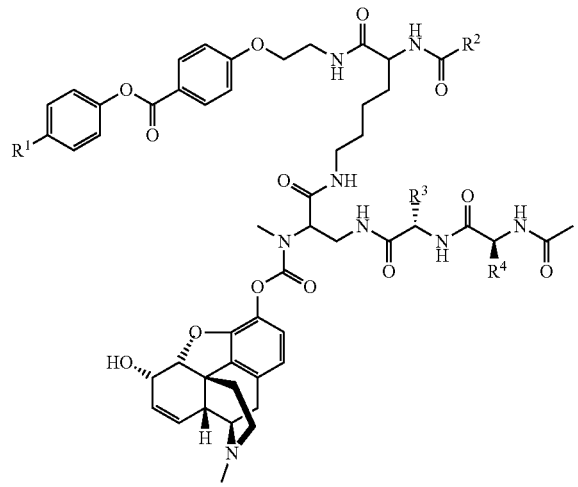

and

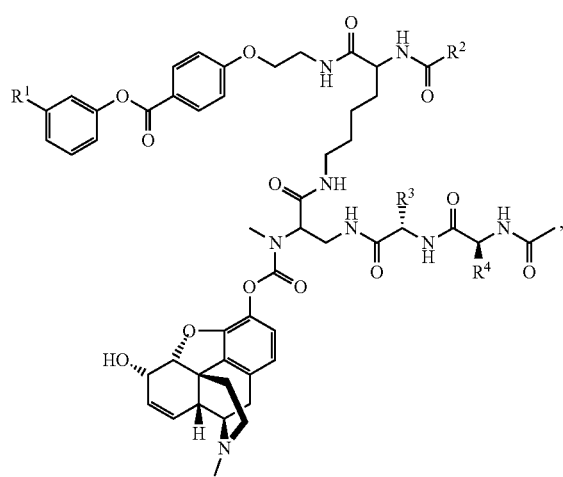

or salts thereof;
wherein:
$R^1$ is independently, amidine, aminomethyl or guanidine;

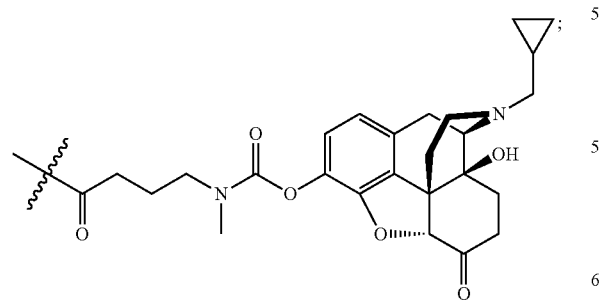

$R^2$ is independently, methyl, benzyloxy, or
$R^3$ is independently, the side chain of lysine or arginine; and
$R^4$ is independently, hydrogen or methyl.

In some instances, the disclosure provides a pharmaceutical composition comprising one of the following compounds:

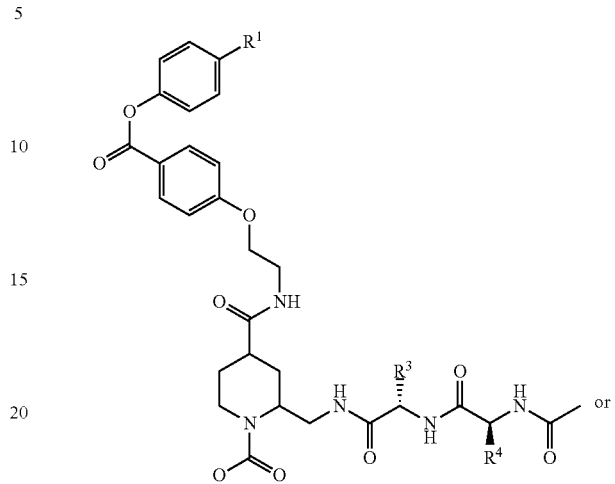

or

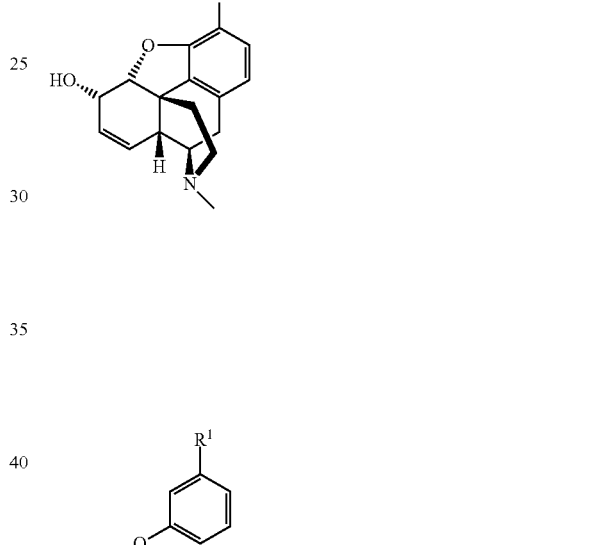

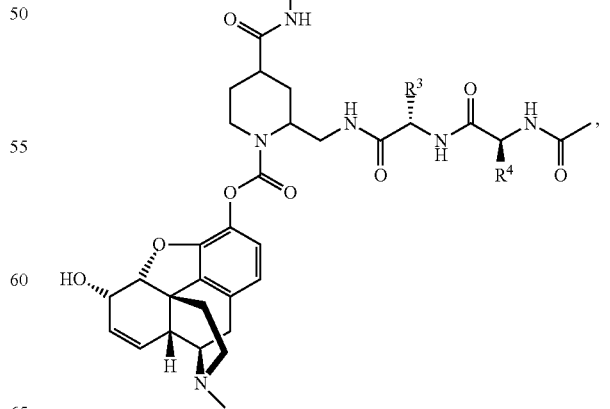

or a salt thereof, and one of the following compounds:

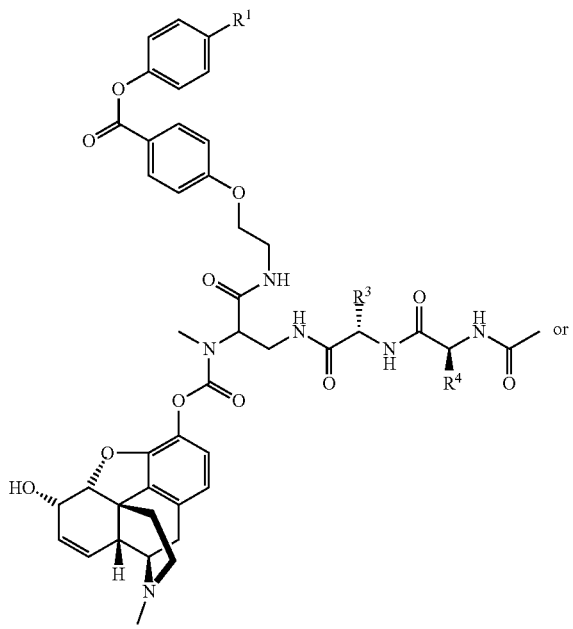

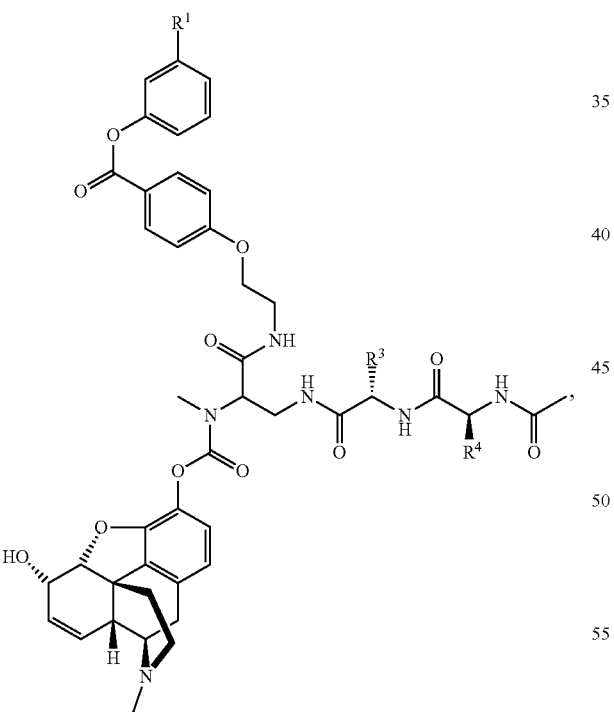

or salt thereof,
wherein:
R¹ is independently, amidine, aminomethyl or guanidine;
R³ is independently, the side chain of lysine or arginine; and
R⁴ is independently, hydrogen or methyl.

In some instances, the disclosure provides a pharmaceutical composition comprising one of the following compounds:

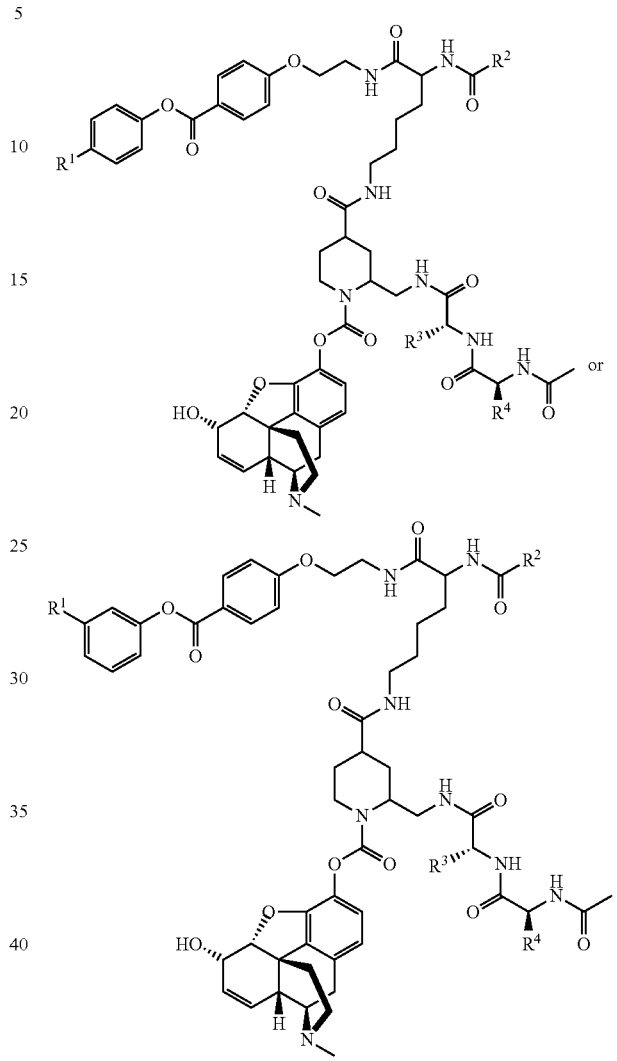

and one of the following compounds:

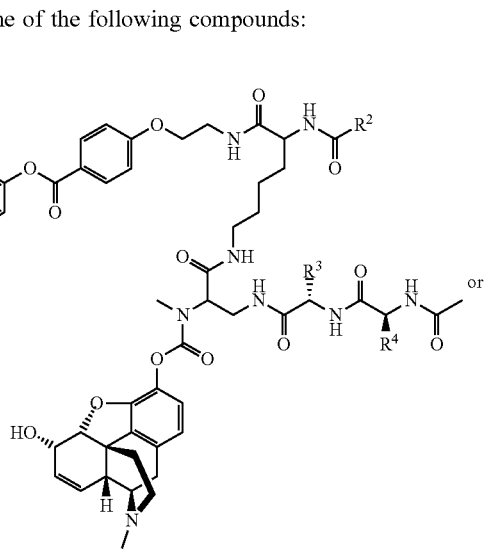

57
-continued
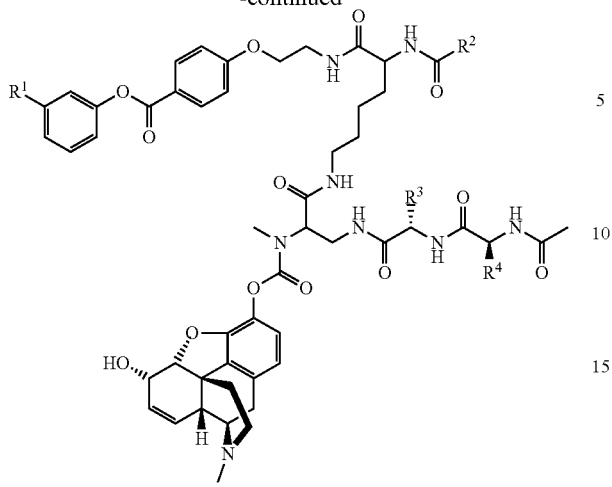
wherein:
R¹ is amidine, aminomethyl or guanidine;
R² is methyl.
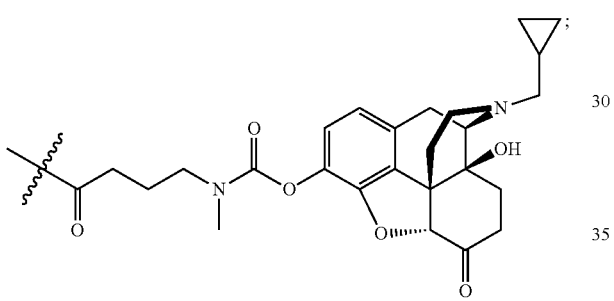
R³ is the side chain of lysine or arginine; and
R⁴ is hydrogen or methyl.
In some instances, the disclosure provides a pharmaceutical composition comprising one of the following compounds:
58
-continued
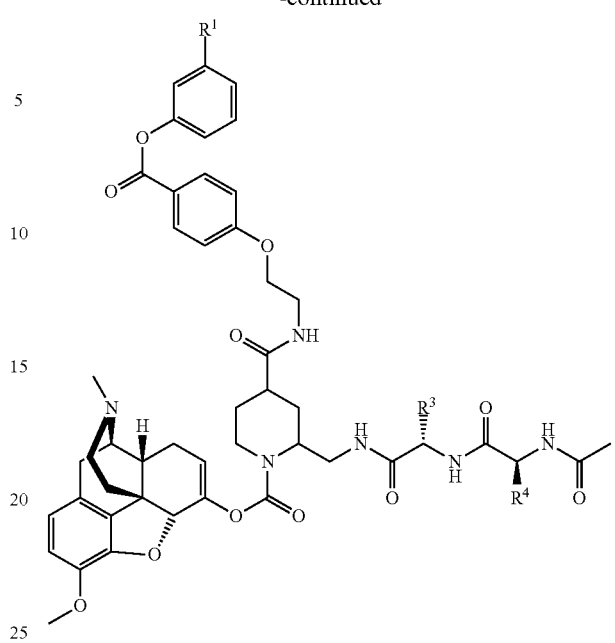
and one of the following compounds:
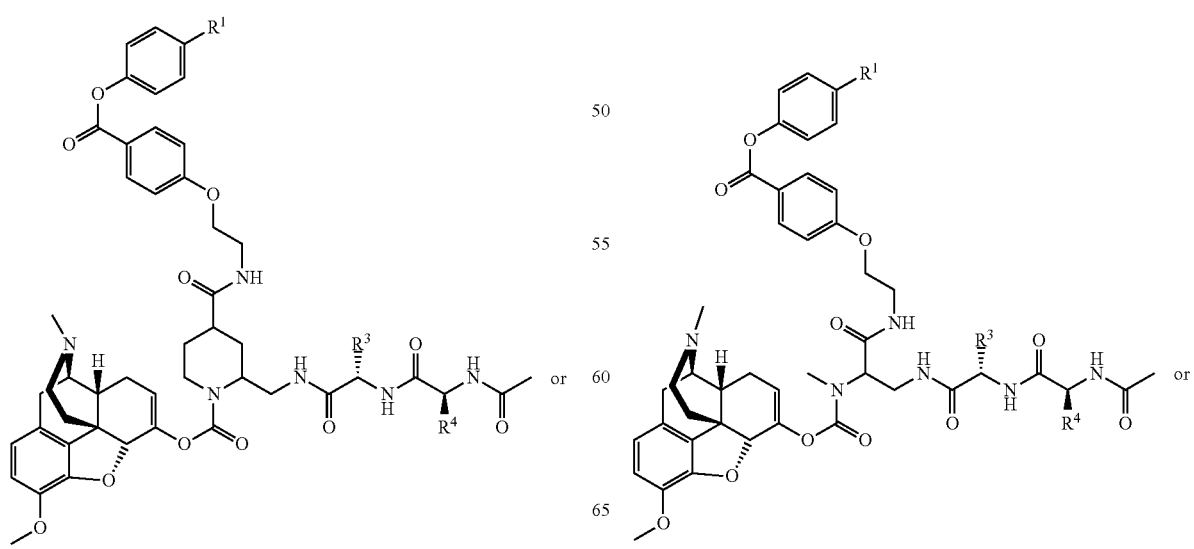

59
-continued

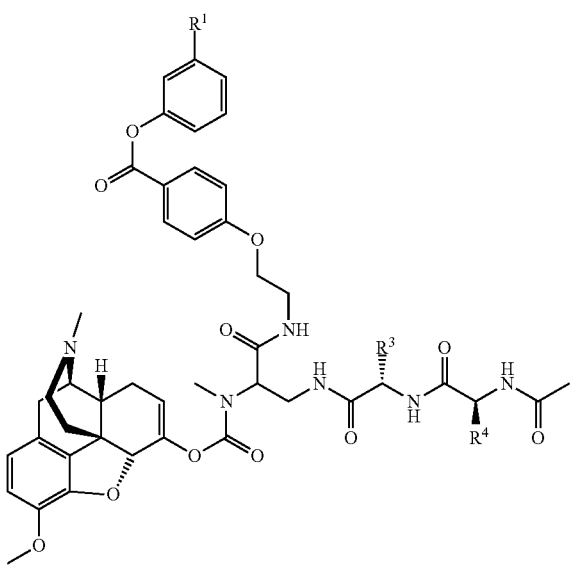

wherein:

R[1] is amidine, aminomethyl or guanidine;

R[3] is the side chain of lysine or arginine; and

R[4] is hydrogen or methyl.

In some instances, the disclosure provides a pharmaceutical composition comprising one of the following compounds:

![compound structure]

or

60
-continued

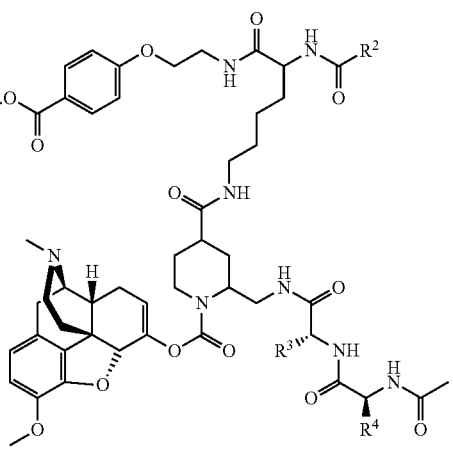

and one of the following compounds:

![compound structure]

or

![compound structure]

wherein:

R[1] is amidine, aminomethyl or guanidine;

R[2] is methyl, or benzyloxy, or

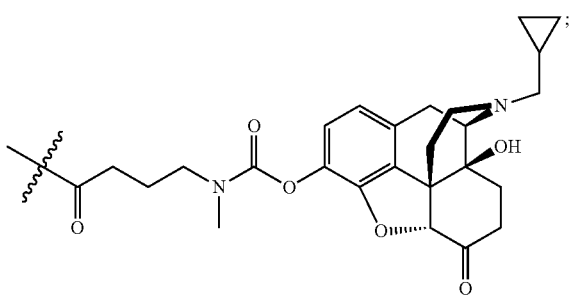
$R^3$ is the side chain of lysine or arginine; and
$R^4$ is hydrogen or methyl.
In some instances, the disclosure provides a pharmaceutical composition comprising one of the following compounds:
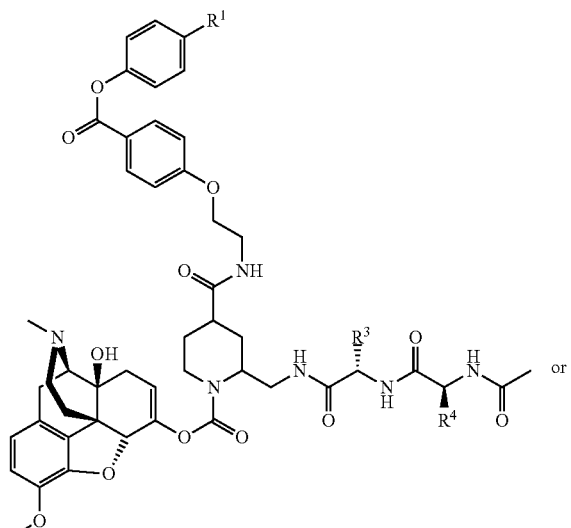
or
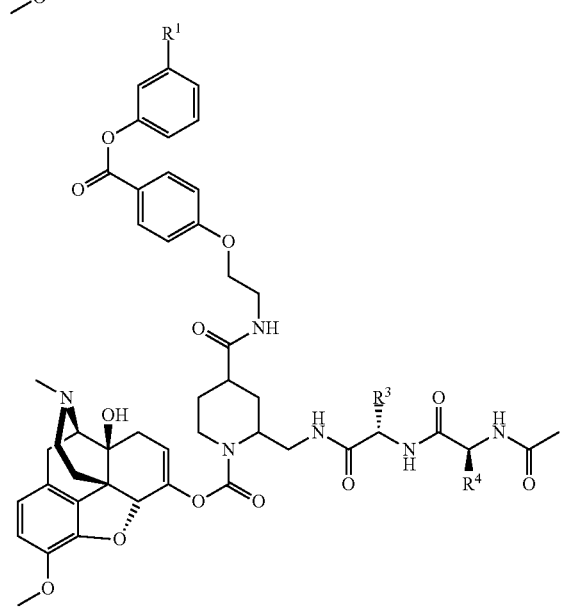
and one of the following compounds:
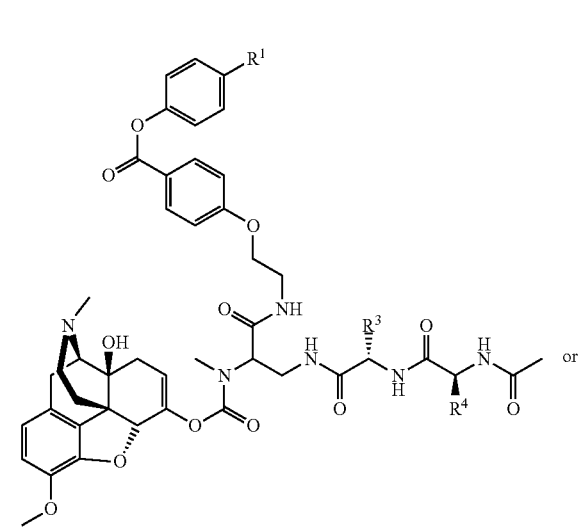
wherein:
$R^1$ is amidine, aminomethyl or guanidine;
$R^3$ is the side chain of lysine or arginine; and
$R^4$ is hydrogen or methyl.

In some instances, the disclosure provides a pharmaceutical composition comprising one of the following compounds:

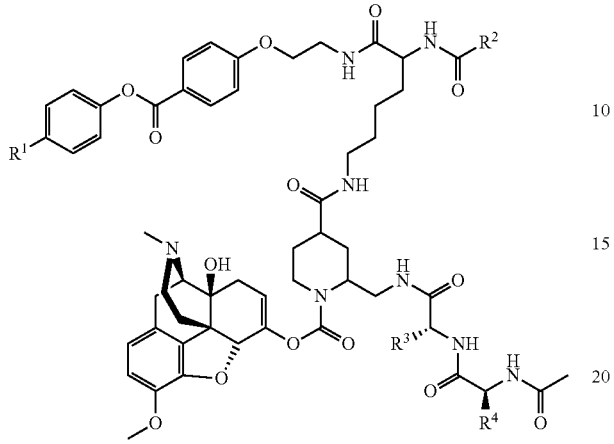

or

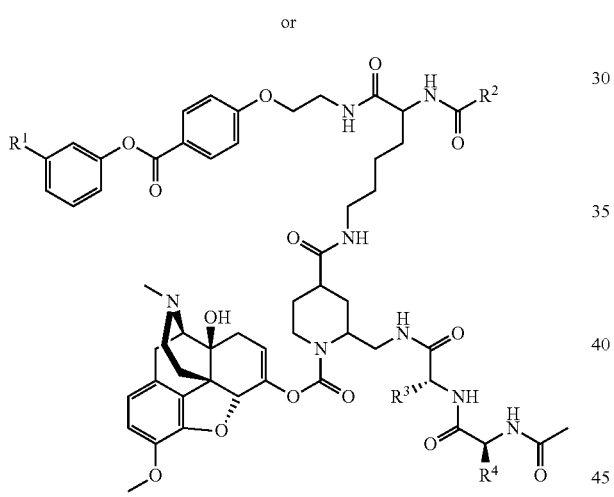

and one of the following compounds:

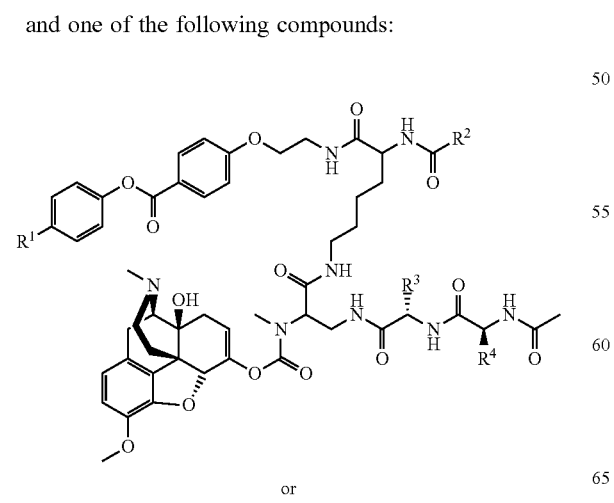

or

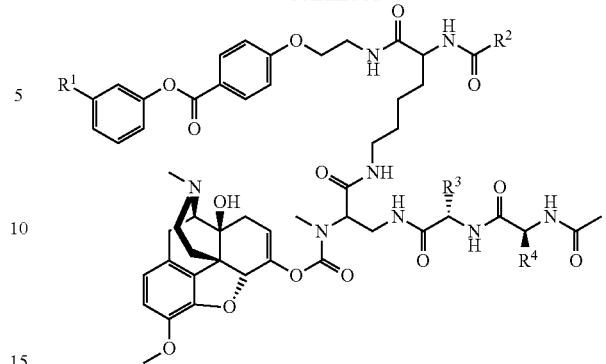

wherein:

$R^1$ is amidine, aminomethyl or guanidine;

$R^2$ is methyl or benzyloxy, or

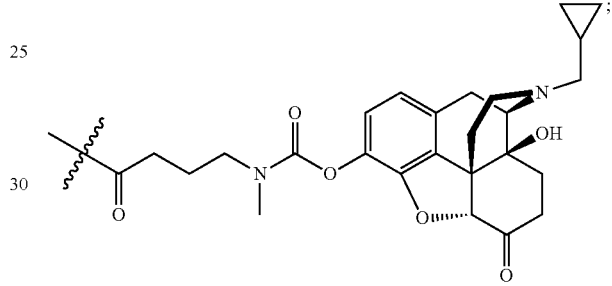

$R^3$ is the side chain of lysine or arginine; and $R^4$ is hydrogen or methyl.

In some instances, the disclosure provides a pharmaceutical composition comprising one of the following compounds:

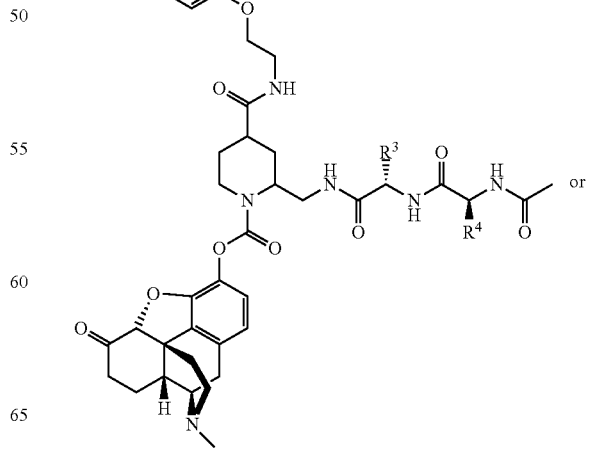

65
-continued
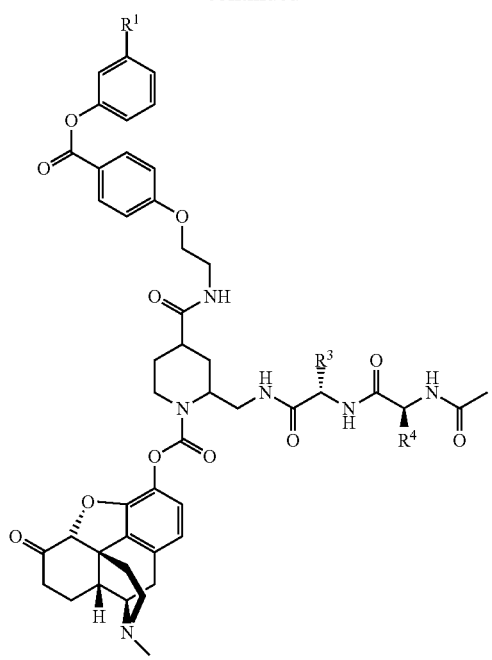
and one of the following compounds:
66
-continued
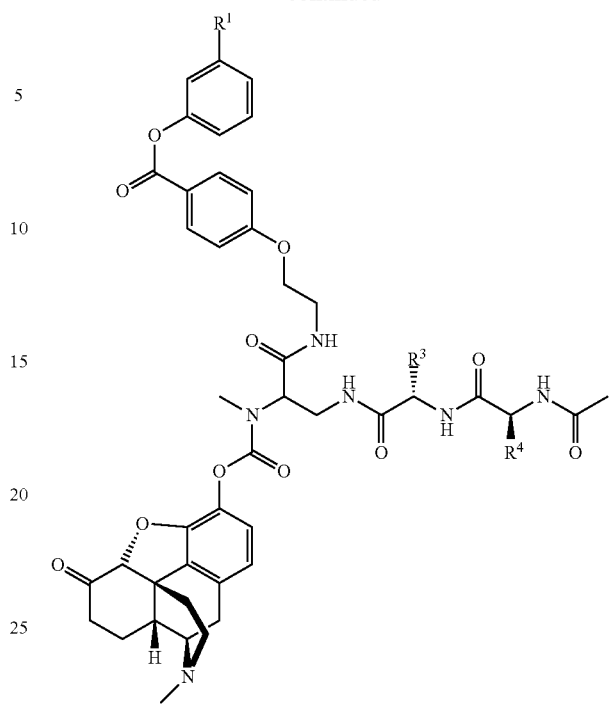
wherein:
R¹ is amidine, aminomethyl or guanidine;
R³ is the side chain of lysine or arginine; and
R⁴ is hydrogen or methyl.
In some instances, the disclosure provides a pharmaceutical composition comprising one of the following compounds:
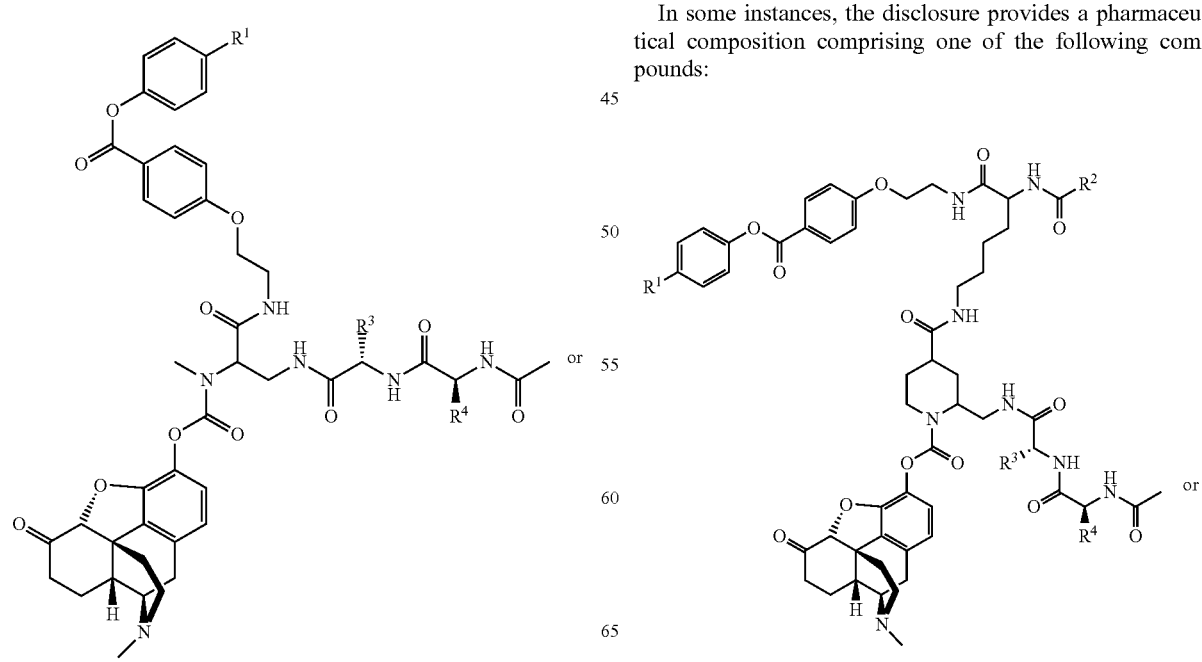

-continued
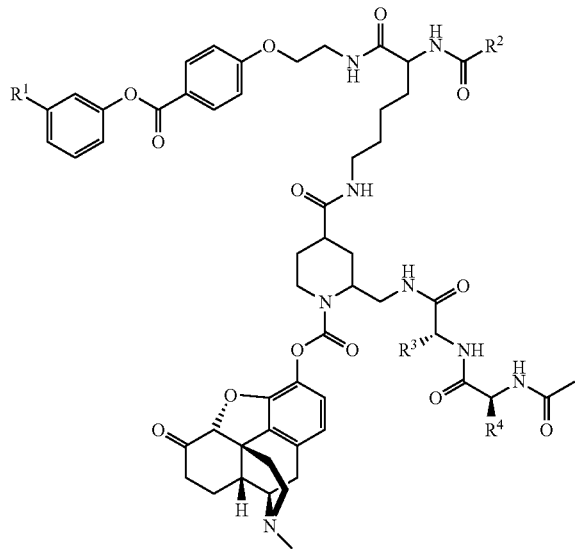
and one of the following compounds:
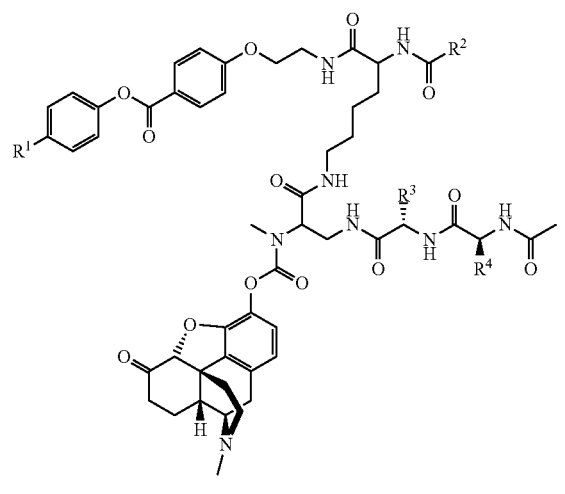
or
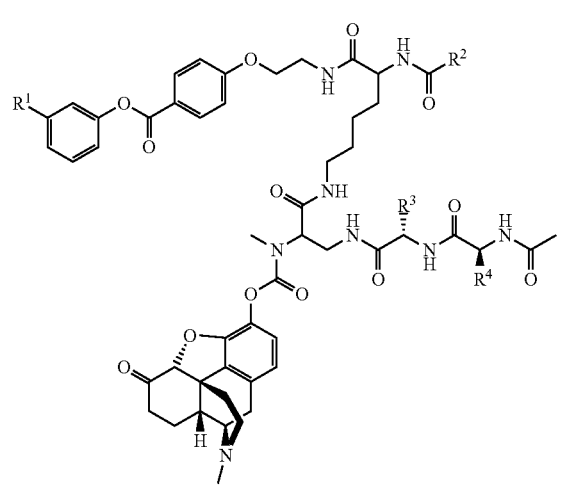
wherein:
R[1] is amidine, aminomethyl or guanidine;
R[2] is methyl, or benzyloxy, or
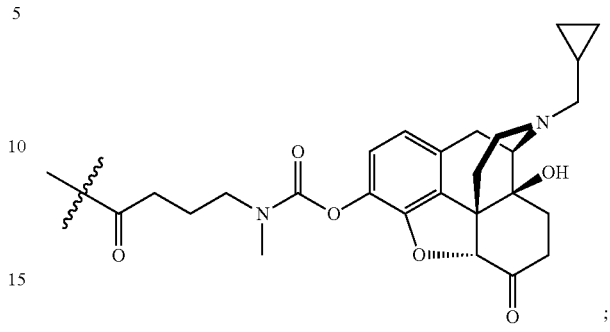
R[3] is the side chain of lysine or arginine; and
R[4] is hydrogen or methyl.
In some instances, the disclosure provides a pharmaceutical composition comprising one of the following compounds:
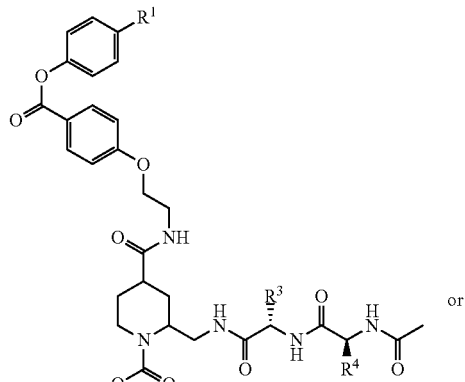
or
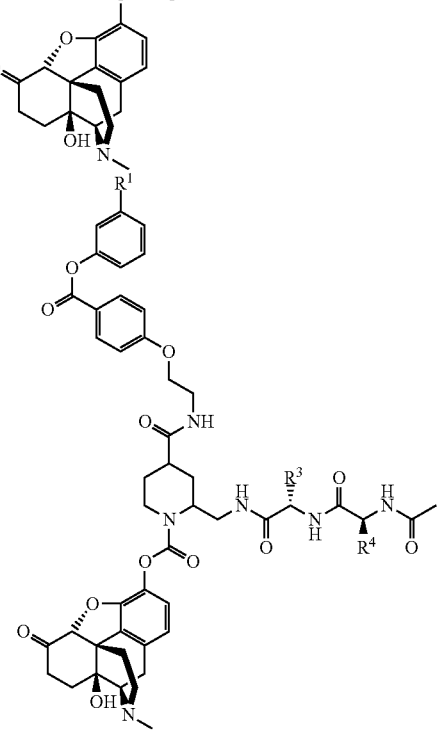

and one of the following compounds:
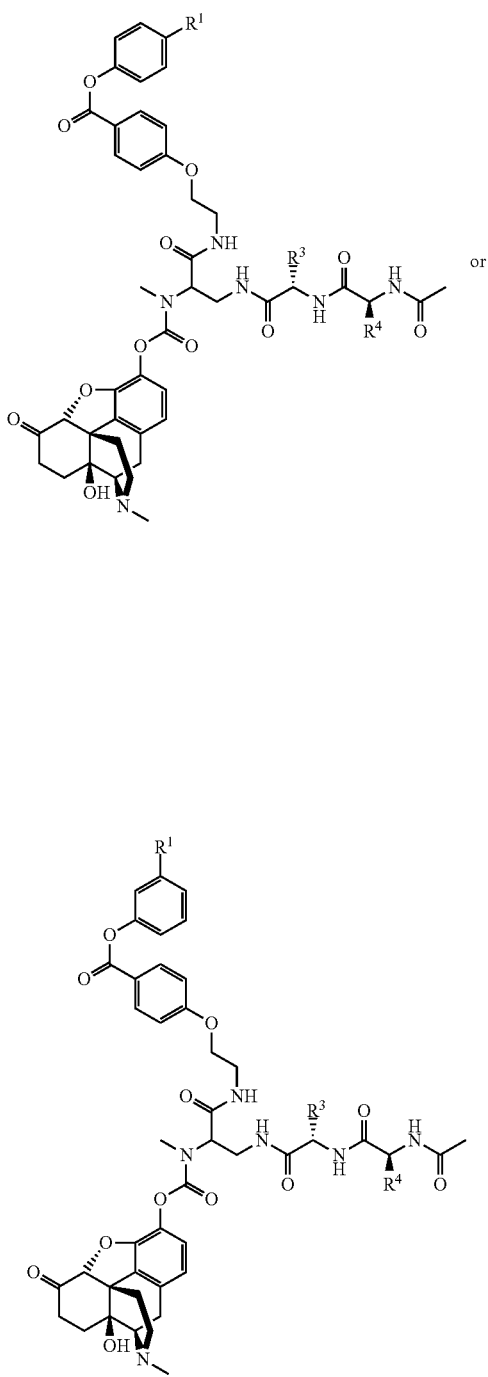
wherein:
R[1] is amidine, aminomethyl or guanidine;
R[3] is the side chain of lysine or arginine; and
R[4] is hydrogen or methyl.
In some instances, the disclosure provides a pharmaceutical composition comprising one of the following compounds:
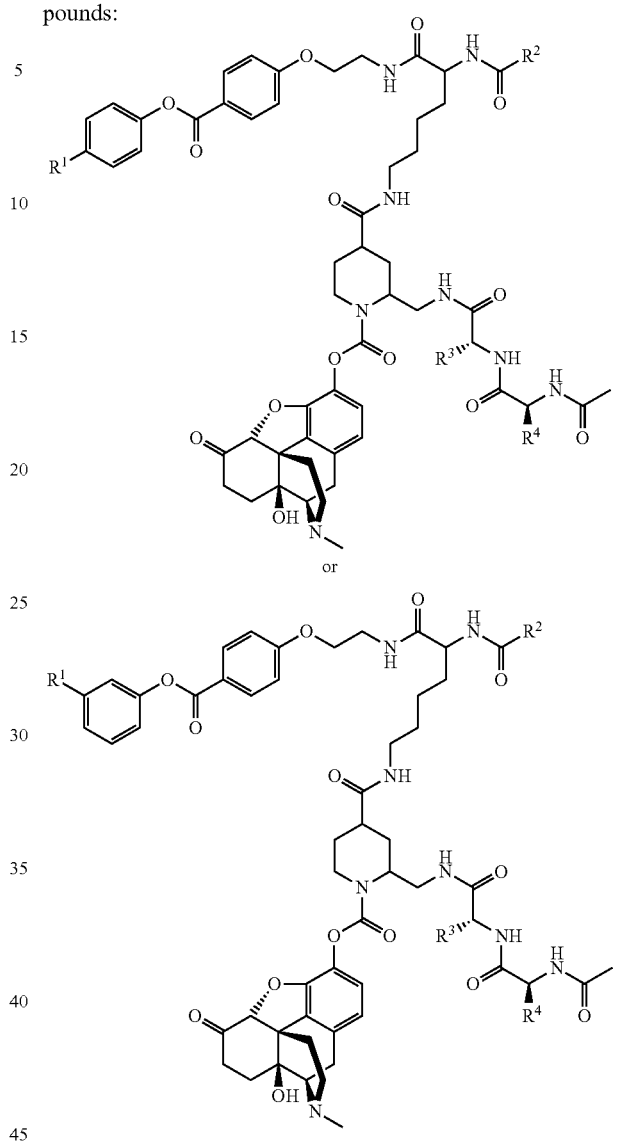
and one of the following compounds:
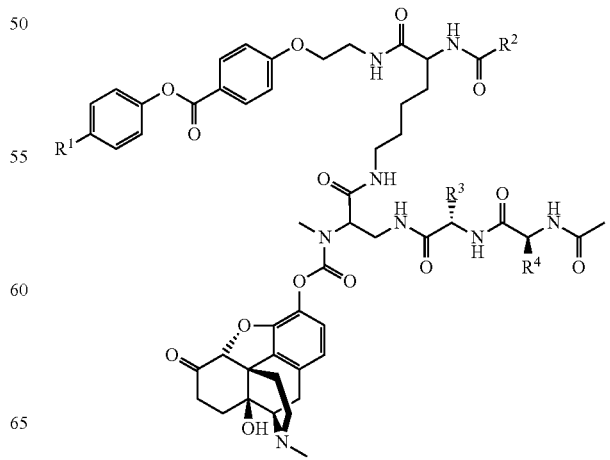

-continued
or

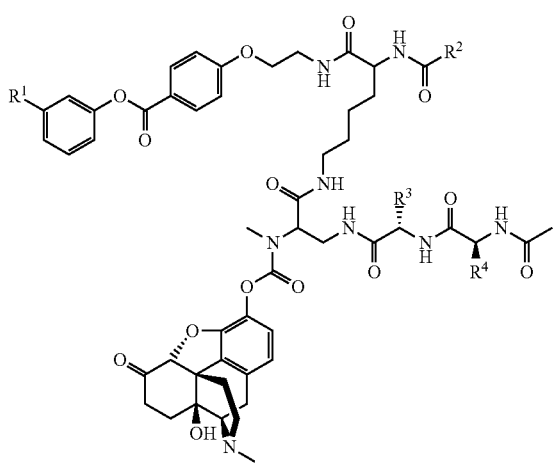

wherein:
R¹ is amidine, aminomethyl or guanidine;
R² is methyl, or benzyloxy, or

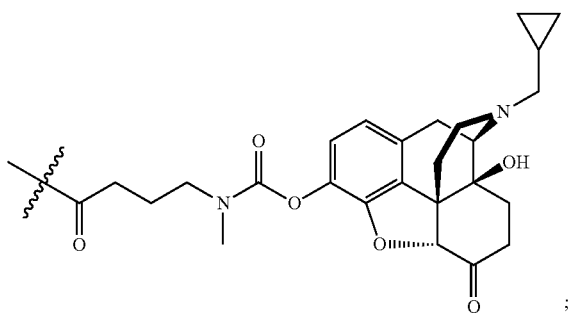

R³ is the side chain of lysine or arginine; and
R⁴ is hydrogen or methyl.

In some instances, the disclosure provides a pharmaceutical composition comprising one of the compounds described herein, wherein the composition has a ratio of a first polysubunit molecule to a second polysubunit molecule that is 20:1. 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.75:1, 1.5:1, 1.25:1, 1.2:1, 1.15:1, 1.1:1, or 1:1.

In some embodiments is a composition comprising two different molecules, each different molecule comprises at least one GI enzyme-labile opioid agonist releasing subunit comprising an opioid agonist, the at least one GI enzyme-labile opioid agonist releasing subunit is covalently linked to at least one GI enzyme inhibitor subunit, and the molecules are in a weight ratio of 20:1. 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.75:1, 1.5:1, 1.25:1, 1.2:1, 1.15:1, 1.1:1, 1:1, 1:1.1, 1:1.15, 1:1.2, 1:1.25, 1:1.5, 1:1.75, 1:2, 1:2.5, 1:3, 1:3.5, 1:4, 1:4.5, 1:5, 1:5.5, 1:6, 1:6.5; 1:7, 1:7.5, 1:8, 1:8.5, 1:9, 1:9.5, 1:10, 1:11, 1:12, 1:13, 1:14, 1:15, 1:16, 1:17, 1:18, 1:19, or 1:20.

In some embodiments is a composition comprising two different molecules, each different molecule comprises at least one GI enzyme-labile opioid agonist releasing subunit comprising an opioid agonist, the at least one GI enzyme-labile opioid agonist releasing subunit is covalently linked to at least one GI enzyme inhibitor subunit, and the molecules are in a molar ratio of 20:1. 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.75:1, 1.5:1, 1.25:1, 1.2:1, 1.15:1, 1.1:1, 1:1, 1:1.1, 1:1.15, 1:1.2, 1:1.25, 1:1.5, 1:1.75, 1:2, 1:2.5, 1:3, 1:3.5, 1:4, 1:4.5, 1:5, 1:5.5, 1:6, 1:6.5; 1:7, 1:7.5, 1:8, 1:8.5, 1:9, 1:9.5, 1:10, 1:11, 1:12, 1:13, 1:14, 1:15, 1:16, 1:17, 1:18, 1:19, or 1:20.

In some embodiments is a composition comprising two different molecules, each different molecule comprises at least one GI enzyme-labile opioid agonist releasing subunit comprising an opioid agonist, the at least one GI enzyme-labile opioid agonist releasing subunit is covalently linked to at least one GI enzyme inhibitor subunit, and the molecules are in a weight ratio from about 10:1 to 1:10, In some embodiments is a composition comprising two different molecules, each different molecule comprises at least one GI enzyme-labile opioid agonist releasing subunit comprising an opioid agonist, the at least one GI enzyme-labile opioid agonist releasing subunit is covalently linked to at least one GI enzyme inhibitor subunit, and the molecules are in a molar ratio from about 10:1 to 1:10.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
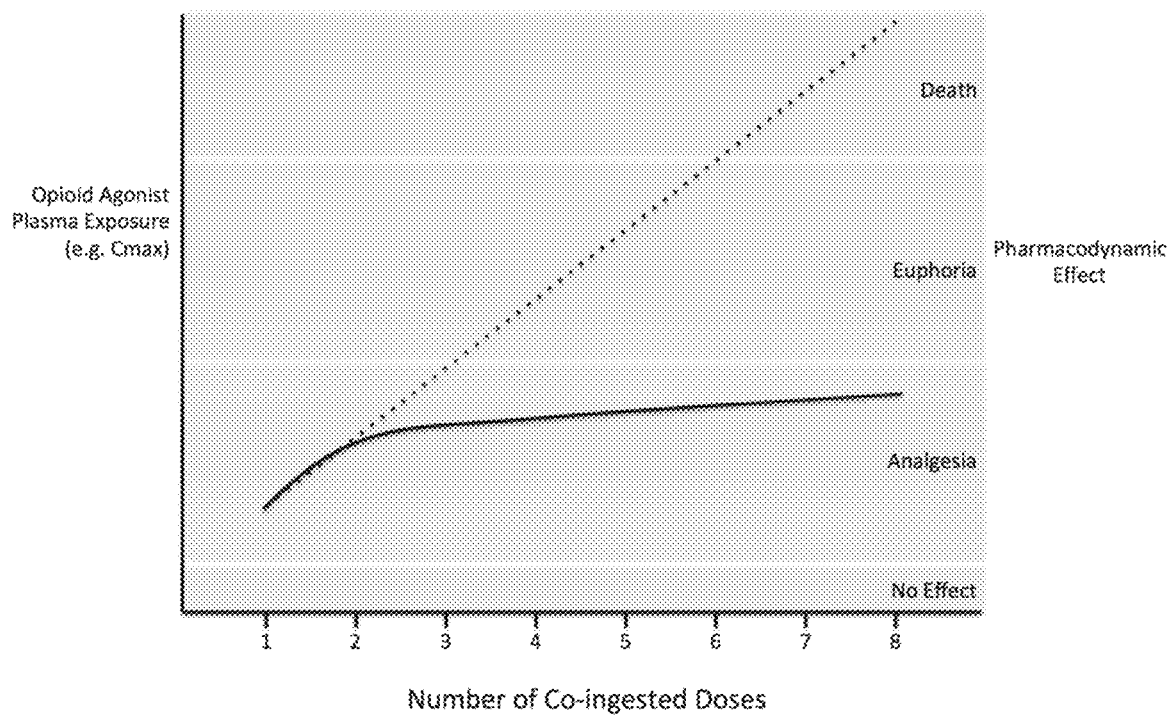
FIG. 1 is a graph illustrating representative examples of the predicted pharmacodynamic and pharmacokinetic parameters of (i) a dose proportional opioid agonist (dotted line), and (ii) an opioid agonist delivered by a composition of the disclosure (solid line).

Typically, opioids pass rapidly through the blood-brain-barrier (BBB) and rapidly reach peak concentrations that produce the euphoria or "high" experienced by opioid abusers. Strategies to reduce opioid abuse have focused on formulation or alternative delivery strategies; such as orally administered delayed release tablets and transdermal patches. Abusers can easily defeat these formulations by crushing, chewing, or dissolving these formulations in commonly available household solvents, thereby enabling them to achieve the desired pharmacokinetic profile, and/or enable non-oral routes of administration, useful for achieving a "high". None of these technologies address oral overdose via the co-ingestion of multiple pills in excess of the recommended dosage, which is the primary mode of prescription opioid abuse. Thus, there exists a need for opioid drug products with lower abuse potential than currently available opioid products used in analgesia. In particular, there exists a need for new opioid drugs that (i) offer safe and effective pain relief to patients when taken as prescribed and (ii) prevent high plasma concentrations resulting from the co-ingestion of multiple pills, while (iii) effectively deterring non-oral abuse.

The present disclosure seeks to address these and other needs by providing compositions comprising two or more novel polysubunit opioid releasing molecules that provide unique pharmacokinetic profiles of the delivered opioid agonist. These novel polysubunit molecules are designed to (i) release effective levels of the covalently attached opioid agonist for the treatment of pain when ingested by compliant patients at the prescribed dose, (ii) prevent oral overdose or abuse of the composition via novel enzyme saturation or inhibition processes when multiple pills containing the composition are co-ingested by potential abusers (or accidentally by children), (iii) produce a safe, non-abusable mixture of opioid agonist and opioid antagonist when potential abusers tamper with pills containing the composition, (iv) yield an optimum pharmacokinetics profile.

In some instances, a composition of the disclosure comprises at least two different GI enzyme inhibiting subunits, wherein one GI enzyme inhibiting subunit has an $IC_{50}$ that is from about 1 pM to about 100 uM, 10 pM to about 100 uM, 100 pM to about 100 uM, 1 uM to about 100 uM, or 10 uM to about 100 uM; and a second GI enzyme inhibiting subunit has an $IC_{50}$ that is from about 100 uM to about 10 mM or from about 1 mM to about 10 mM. In some embodiments, a composition of the disclosure comprises at least two different GI enzyme inhibiting subunits, wherein one GI enzyme inhibiting subunit has an $IC_{50}$ that is from about 1 pM to about 100 uM, and a second GI enzyme inhibiting subunit has an $IC_{50}$ that is from about 100 uM to about 10 mM. In some embodiments, a composition of the disclosure comprises at least two different GI enzyme inhibiting subunits, wherein one GI enzyme inhibiting subunit has an $IC_{50}$ that is from about 10 pM to about 100 uM, and a second GI enzyme inhibiting subunit has an $IC_{50}$ that is from about 100 uM to about 10 mM. In some embodiments, a composition of the disclosure comprises at least two different GI enzyme inhibiting subunits, wherein one GI enzyme inhibiting subunit has an $IC_{50}$ that is from about 100 pM to about 100 uM, and a second GI enzyme inhibiting subunit has an $IC_{50}$ that is from about 100 uM to about 10 mM. In some embodiments, a composition of the disclosure comprises at least two different GI enzyme inhibiting subunits, wherein one GI enzyme inhibiting subunit has an $IC_{50}$ that is from about 1 uM to about 100 uM, and a second GI enzyme inhibiting subunit has an $IC_{50}$ that is from about 100 uM to about 10 mM. In some embodiments, a composition of the disclosure comprises at least two different GI enzyme inhibiting subunits, wherein one GI enzyme inhibiting subunit has an $IC_{50}$ that is from about 10 uM to about 100 uM, and a second GI enzyme inhibiting subunit has an $IC_{50}$ that is from about 100 uM to about 10 mM. In some embodiments, a composition of the disclosure comprises at least two different GI enzyme inhibiting subunits, wherein one GI enzyme inhibiting subunit has an $IC_{50}$ that is from about 1 pM to about 100 uM, and a second GI enzyme inhibiting subunit has an $IC_{50}$ that is from about 1 mM to about 10 mM. In some embodiments, a composition of the disclosure comprises at least two different GI enzyme inhibiting subunits, wherein one GI enzyme inhibiting subunit has an $IC_{50}$ that is from about 10 pM to about 100 uM, and a second GI enzyme inhibiting subunit has an $IC_{50}$ that is from about 1 mM to about 10 mM. In some embodiments, a composition of the disclosure comprises at least two different GI enzyme inhibiting subunits, wherein one GI enzyme inhibiting subunit has an $IC_{50}$ that is from about 100 pM to about 100 uM, and a second GI enzyme inhibiting subunit has an $IC_{50}$ that is from about 1 mM to about 10 mM. In some embodiments, a composition of the disclosure comprises at least two different GI enzyme inhibiting subunits, wherein one GI enzyme inhibiting subunit has an $IC_{50}$ that is from about 1 uM to about 100 uM, and a second GI enzyme inhibiting subunit has an $IC_{50}$ that is from about 1 mM to about 10 mM. In some embodiments, a composition of the disclosure comprises at least two different GI enzyme inhibiting subunits, wherein one GI enzyme inhibiting subunit has an $IC_{50}$ that is from about 10 uM to about 100 uM, and a second GI enzyme inhibiting subunit has an $IC_{50}$ that is from about 1 mM to about 10 mM.

These polysubunit opioid analogs can be further designed to have a high molecular weight and/or possess a highly charged state at physiological pH ranges to prevent or minimize absorption from the GI tract, thereby (i) reducing their systemic exposures (and resulting safety risks) to the subject, and (ii) maximizing the efficiency of both the opioid delivery and overdose protection mechanisms.

In one aspect, the invention provides a pharmaceutical composition comprising two or more molecules whereby each molecule comprises one, two, or more GI enzyme-labile opioid releasing subunits, and one, two or more GI enzyme inhibitor subunits, wherein the GI enzyme-labile opioid releasing subunit(s), and the GI enzyme inhibiting subunit(s) are covalently attached directly to each other or to a molecular scaffold.

When patients ingest the pharmaceutical compositions defined herein, endogenous GI enzymes release targeted therapeutic levels of the opioid agonist. When excessive doses of pharmaceutical compositions defined herein are ingested, the GI enzyme that releases the opioid agonist becomes saturated or inhibited so that increases in the number of co-ingested doses do not lead to dose proportional increases in the amount of opioid agonist released. The opioid agonist can be selected from the group consisting of morphine, hydromorphone, hydrocodone, oxycodone, codeine, levorphanol, meperidine, methadone, oxymorphone, dihydrocodeine, tramadol, tapentadol, and pharmaceutically acceptable salts, prodrugs, and mixtures thereof. When present, the opioid antagonist subunit contains an opioid antagonist selected from naltrexone and naloxone. In some embodiments, the scaffold moiety is an amino acid or an oligomeric scaffold. In other embodiments, the scaffold moiety is a polymeric scaffold.

Definitions

Unless otherwise stated, the following terms used in this application, including the specification and claims, have the definitions given below. Definition of standard chemistry terms may be found in reference works, including Carey and Sundberg (2004) "Advanced Organic Chemistry 4rd Ed." Vols. A and B, Springer, New York. The practice of the present invention will employ, unless otherwise indicated, conventional methods of mass spectroscopy, protein chemistry, biochemistry, synthetic organic chemistry, and pharmacology, within the skill of the art.

The term "alkyl" or "lower alkyl" means the monovalent branched or unbranched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, butyl, isobutyl, sec-butyl, tert-butyl, pentyl, n-hexyl, octyl, dodecyl, and the like.

The term "alkylene" as used herein means the divalent linear or branched saturated hydrocarbon radical, consisting solely of carbon and hydrogen atoms, having from one to eight carbon atoms inclusive, unless otherwise indicated. Examples of alkylene radicals include, but are not limited to, methylene, ethylene, trimethylene, propylene, tetramethylene, pentamethylene, ethylethylene, and the like.

The term "alkenylene" means the divalent linear or branched unsaturated hydrocarbon radical, containing at least one double bond and having from two to eight carbon atoms inclusive, unless otherwise indicated. The alkenylene radical includes the cis or trans ((E) or (Z)) isomeric groups or mixtures thereof generated by the asymmetric carbons. Examples of alkenylene radicals include, but are not limited to ethenylene, 2-propenylene, 1-propenylene, 2-butenyl, 2-pentenylene, and the like.

The term "aryl" means the monovalent monocyclic aromatic hydrocarbon radical consisting of one or more fused rings in which at least one ring is aromatic in nature, which can optionally be substituted with hydroxy, cyano, lower alkyl, lower alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like.

The term "agonist" means a molecule such as a compound, a drug, an enzyme activator or a hormone that enhances the activity of another molecule at a target receptor, or directly or indirectly enhances the activity of the target receptor.

The term "amino acid" refers to either natural and/or unnatural or synthetic amino acids, and both the D- or L-optical isomers, the N-acyl and N-methyl derivatives thereof, and amino acid analogs, isosteres, and peptidomimetics. The natural amino acids include alanine, arginine, asparagine, cysteine, glutamic acid, glutamine, glycine, histidine, isoleucine, leucine, methionine, phenylalanine, proline, serine, threonine, tryptophan, tyrosine, valine, selenocysteine, and pyrrolysine.

Naturally occurring amino acids are those encoded by the genetic code, as well as those amino acids that are later modified, e.g., hydroxyproline, carboxyglutamate, and 0-phosphoserine. The terms "non-natural amino acids" or "amino acid mimics" refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine, and methyl sulfonium. Such analogs have modified side-chain groups, such as norleucine, homoarginine, homolysine, s-N-methyl lysine, ε,ε-N,N-dimethyl lysine, ε,ε,ε-N,N,N-trimethyl lysine, ornithine, and the like, or modified peptide backbones, but retain the same basic chemical structure and/or function as a naturally occurring amino acid. For example, amino acid mimetics (or mimics) refers to chemical compounds that have a structure that is different from the general chemical structure of an amino acid, but functions in a manner similar to a naturally occurring amino acid. For example, the unnatural amino acid L-(7-hydroxycoumarin-4-yl)ethylglycine (or 7-hydroxycoumarin-ethylglycine) finds use with the invention.

The terms "enzymatically degradable" or "enzyme-labile" refer to a molecular entity that is subject to degradation by one or more enzymes under ordinary physiological conditions.

The term "recognized" refers to the requisite initial molecular process whereby a specific amino acid substrate is bound to a specific complementary recognition site or pocket on an enzyme prior to the ensuing hydrolysis of the substrate. Recognition is usually (i) highly specific, (ii) occurs via a recognition site or pocket that is usually adjacent to the active site of the enzyme which effects the catalytic chemical hydrolysis of the substrate, and (iii) results in the ensuing hydrolysis of the substrate by the enzyme.

The term GI refers to "gastrointestinal." The term "gastrointestinal enzyme" or "GI enzyme" refers to an enzyme located in, derived from, or on, the gastrointestinal tract (GI tract) from the mouth to the anus, such as trypsin, chymotrypsin, elastase, tryptase, and the like.

The term "polysubunit" refers to a multi-functional compound of the invention designed to (i) release an opioid agonist when administered to a subject and prescribed therapeutic doses, and (ii) inhibit the release of the appended opioid agonist when doses in excess of the prescribed therapeutic doses are co-ingested. The release of the opioid agonist from a polysubstrate or polysubunit can be auto-attenuated in vivo when overdoses are ingested via a built in enzyme saturation or inhibition mechanism. In addition, polysubunits of the invention may also release an opioid antagonist when subjected to chemical tampering by, or when administered via non-oral routes to, potential abusers.

The term "two or more polysubunit molecules" is used herein to describe a composition containing two or more different polysubunit molecules. For example, different polysubunit molecules contained in a composition may differ with regard to one or more of the following aspects: (i) the specific opioid agonists delivered, (ii) the rates at which the opioid agonist is delivered in vivo (i.e. to modify the oral pharmacokinetic profile of the delivered opioid), and (iii) the inhibitory potency of the GI enzyme inhibiting subunits (i.e. to modify the overdose protection profile and/or the prescribed dose strengths of the delivered opioid agonist).

"Gastrointestinal enzyme substrate" or "GI enzyme substrate" refers to a group comprising a site susceptible to cleavage by a GI enzyme. For example, a "trypsin-substrate" refers to a group comprising a site susceptible to hydrolysis by trypsin.

The term "opioid-releasing gastrointestinal enzyme substrate subunit" or "opioid-releasing GI enzyme substrate subunit" refers to a group comprising an opioid and a site susceptible to cleavage by a GI enzyme. For example, an "opioid releasing trypsin-substrate" refers to a group comprising a site susceptible to cleavage by trypsin that directly, or indirectly, releases an opioid after being hydrolyzed by trypsin.

The term "halogen" as used herein refers to fluorine, bromine, chlorine and/or iodine.

The term "inhibitor" refers to any agent capable of inhibiting the action of an enzyme on a substrate. For example, a trypsin inhibitor refers to any agent capable of inhibiting the action of trypsin on a substrate.

The term "gastrointestinal enzyme inhibitor" or "GI enzyme inhibitor" refers to a group that inhibits the action of the GI enzyme on the opioid-releasing GI enzyme substrate subunit, or opioid-releasing GI enzyme substrate subunits to which it is covalently linked to, and/or co-administered with. For example, a trypsin inhibitor subunit, or subunits, are covalently linked to, and/or co-administered with, a compound, or compounds of the invention, that comprise an opioid-releasing gastrointestinal enzyme substrate subunit, or subunits, that is/are hydrolyzed by trypsin.

The term "modulator" means a molecule that interacts with a target. The interactions include, but are not limited to, agonist, antagonist, and the like, as defined herein.

"PEG" or "polyethylene glycol," as used herein, is meant to encompass any water-soluble poly(akylene oxide). Typically, PEG oligomers for use in the present invention contain —$(CH_2CH_2O)_n$— or —$(CH_2CH_2O)_n$—$CH_2CH_2$—, but can also include polyalkylene glycols including, but not limited to polypropylene- or polybutylene glycols where the number of monomer units can be from about 2 to 1000, or from about 2 to about 200.

As used herein, the terms "treat" and "treatment" are used interchangeably and are meant to indicate a postponement of development of diseases and/or a reduction in the severity of such symptoms that will or are expected to develop. The terms further include ameliorating existing symptoms, preventing additional symptoms, and ameliorating or preventing the underlying symptoms (e.g. pain in a subject).

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

In one aspect of the invention, compositions comprising polysubunit molecules with one or more, two, three, four, five, six, seven, eight, nine, ten or more GI enzyme-labile opioid agonist releasing substrates covalently linked to one two, three, four, five, six, seven, eight, nine, ten or more GI enzyme inhibitors, and an optional opioid antagonist releasing moiety, or optional opioid antagonist releasing moieties, are administered to a patient for the prevention and/or treatment of pain. The GI enzyme-labile opioid agonist releasing, and the gastrointestinal (GI) enzyme inhibiting, and the optional opioid antagonist releasing subunits can be covalently linked to each other via an atom or via suitable linkers (Z), or assembled onto, or independently attached to, a suitably functionalized scaffold moiety such as an oligomer, macromolecule, or polymer via covalent linkages. In preferred embodiments, the release of the opioid agonist is mediated by a specific GI enzyme, whereby the opioid agonist is released concomitant with, or subsequent to, the action of a specific GI enzyme on a specific portion of the polysubstrate molecules.

The opioid agonist releasing GI enzyme substrate can release alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, so-called "biased" opioid agonists including, but not limited to PZMO21 and structurally or functionally similar analogs thereof, TRV130 and structurally or functionally similar analogs thereof, BU08028 and structurally or functionally similar analogs thereof, as well as salts, prodrugs, mixtures, derivatives, analogs, homologues, and polymorphs of any of the foregoing. The opioid agonist releasing substrates and the GI enzyme inhibitors can be targeted by trypsin, and can be an alkylguanidine, alkylamidine, alkylamine, arylguanidine, arylamidine, benzylamine, alkyl substituted benzylamine, or alkyl amine substrate, and salts thereof. The GI enzyme labile opioid releasing opioid agonist releasing substrates and the GI enzyme inhibitors are preferably covalently linked to each other directly, or linked to each other indirectly via a covalent bond or to the same atom, or linker, or molecular scaffold in a suitable ratio, or co-assembled via covalent attachment to the same oligomer or polymer, such as polyamino acid, poly-D-amino acid, poly N-methyl (D-, or L-) amino acid, a "biopolymer", or polyalkylene glycol (e.g. PEG).

Linking moieties "Z", or linkers "Z", are utilized for purposes of the invention for covalently conjoining one or more of the components are intended to be of wide scope and not specifically limited to the scope specifically defined herein. Based on their intended functionality of conjoining the different functional subunits defined herein, the scope of useful linkers for the present invention is intended to be broad. In an effort to define the broad scope of useful linkers, and provide non-limiting specific examples of linkers of use for the in the present invention, an array of the terminal functionalities that may be present on representative linkers, and their chemical composition are presented below. The specific choice of linker unit, or units, incorporated into particular embodiments of the invention will vary based on the molecular structures of the entities that they conjoin, with specific regard to the available atoms or functional groups present on the specific elements that they covalently conjoin. Thus, it is intended that the specific composition of linking moieties useful for the invention can vary widely with regard to composition, size (i.e. length), geometry, valency, and functional groups present on their termini. Linking moieties can be divalent—covalently adjoining two polysubstrate components, or trivalent—adjoining several polysubstrate components, or can be multivalent—adjoining a multiplicity of polysubstrate components.

In some embodiments, linking moieties $Z^1$, $Z^2$, or $Z^3$ are each independently represented by the general formulae:

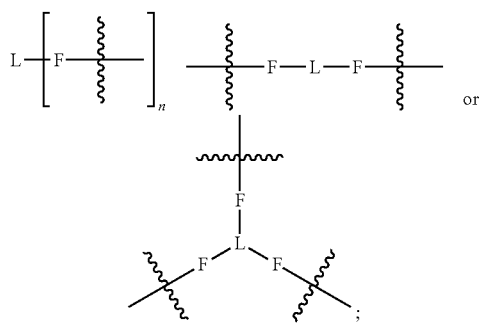

and can also be defined by

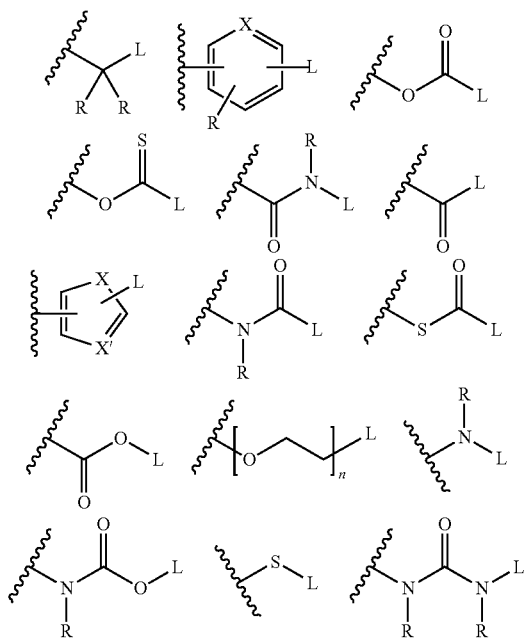

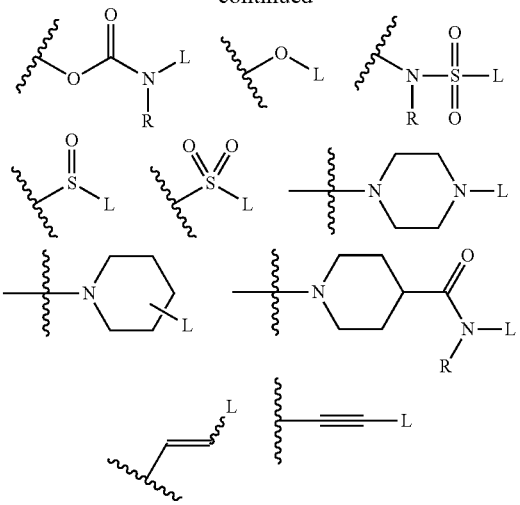

Exemplary terminal linker functionalities "F" can each or independently be as shown below:

wherein:
each R is independently hydrogen, methyl, lower alkyl, aryl, or arylalkyl;
X is carbon, oxygen, or nitrogen;
L is a linear, branched, or multivalent scaffold moiety which is alkyl, aryl, substituted alkyl, substituted aryl, heteroalkyl, substituted heteroalkyl, polyalkylene glycol, polypeptide, polyamide, polycarbamate, polyurea, or polycarbonate.

In some embodiments, the linking moiety defined as "Z" is formed of 0-100 atoms. In some embodiments, the linking moieties defined as "Z" is formed of 1-50 non-hydrogen atoms as well as additional hydrogen atoms. Such atoms may be, for example, C, N, O, P or S. In other embodiments, the linking moieties defined as "Z" may connect two or more groups comprising 1 to 50 consecutive bonds between the groups. The linking moieties defined as "Z" may have 1 to 40, 1 to 30, 1 to 20, 1 to 10, 1 to 5, 5 to 25, or 5 to 20 such consecutive bonds.

In some embodiments, compounds or compositions of the invention may have the advantages that they and their post-enzyme hydrolysis products are minimally or not absorbed by the subject, and the expected enzymatic hydrolysis of compounds of the invention can be designed to produce systemic exposures of only the opioid analgesic, and generally regarded as safe (GRAS) metabolites following oral ingestion.

Further, the compositions of the invention prevent overdose via the oral route. If multiple pharmaceutical oral dosage forms of the invention are co-ingested, such as co-ingestion of tablets or capsules containing compositions of the invention, the resulting concentration reaches a high enough level in the small intestine to effectively saturate or inhibit the digestive enzyme that mediates the release of the opioid. This saturation or inhibition of the digestive enzyme that mediates opioid release results from careful tuning of the enzyme kinetics and equilibrium constants attending the interactions of (i) the enzyme inhibiting subunits, and (ii) the opioid releasing substrate subunits with the targeted GI enzyme. In some preferred embodiments of the invention, the digestive enzyme (e.g. trypsin) recognizes and interacts with, the GI enzyme inhibiting subunits much more rapidly and avidly than it recognizes and interacts with the opioid releasing substrate moieties. Importantly, the resulting saturation or inhibition of the digestive enzyme that mediates release of the opioid agonist under overdose conditions can be extensive and sustained due to the very low absorbability of the opioid releasing polysubstrate analogs, and the fact that the covalently assembled non-opioid releasing substrate subunits and the opioid-releasing substrate subunits cannot partition away from each other during transit through the GI tract. Thus, intentional ingestion of multiple pills of the invention will not enable abusers to achieve the desired pharmacokinetic profile for achieving a "high" or euphoric state. Furthermore, accidental co-ingestion of multiple pills by young children, the elderly, or the subjects will be less likely to produce toxic or lethal effects.

Without being limited by theory, the current invention provides opioid releasing compositions that can protect individuals from opioid overdoses via an enzyme saturation or inhibition mechanism. Enzyme inhibition and enzyme saturation are highly distinct processes that have been described in detail, for example, in: "Enzymes: A Practical Introduction to Structure, Mechanism, and Data Analysis by Robert A. Copeland, 2000, Wiley-VCH, Inc"; incorporated herein by reference in its entirety.

By design, the rate, and thereby the extent, of opioid agonist release will not be proportional to the number of doses (aka pills) co-ingested. FIG. 1 graphically compares the representative dose-proportional opioid agonist plasma exposures (Cmax) and pharmacodynamic effect profiles common to all current generic and emerging abuse-resistant opioid drug products (dotted line) that exhibit essentially linear pharmacokinetics, vs. a representative composition of the invention that provides oral overdose protection (solid line) that exhibits non-linear pharmacokinetics as multiple doses are co-ingested.

Advantages of the subject invention include:
(i) The ability to readily tune the overdose protection profile by modifying the nature, and/or number and ratio of polysubunit molecules administered to a subject.
(ii) Compounds of the invention are unimolecular and thereby prevent partitioning of the covalently linked opioid-releasing and enzyme inhibiting subunits in vivo. Consequently, the overdose protection afforded by compositions of the invention will be persistent during the time required for transport through the gastrointestinal tract where the digestive enzymes capable of effecting opioid agonist release are present.
(iii) By design, the enzymatic pathway for hydrolysis of the polysubunit molecules is chemoselective, and mediated primarily by the action of the digestive enzyme they are designed to target/saturate within the gastrointestinal tract.
(iv) Compositions of the invention comprise high molecular weight, and/or poly-charged polysubunit molecules. In such embodiments, absorption of polysubunits molecules, or their resulting post-hydrolysis products, from the gastrointestinal tract into the systemic circulation is minimized. This serves to maximize drug delivery efficiency as effective opioid agonist delivery requires that the polysubstrate or polysubunit be exposed to digestive enzymes accessed primarily in the lumen of the gastrointestinal tract. Further, minimizing the systemic exposure of polysubunit molecules can provide important benefits from both safety and clinical development perspectives.
(v) Compositions of the invention can be designed to release opioid antagonist molecules when subjected to chemical tampering methods by potential abusers, or when exposed to enzymes found in the plasma, blood, liver, or other systemically accessible tissues.
(vi) A targeted oral pharmacokinetic profile can be achieved by administering pharmaceutical compositions containing specific combinations of different polysubunit molecules to subjects. For example, the different polysubunit molecules contained in the composition may differ with regard to (i) the specific opioid agonists delivered, (ii) the rates at which the opioid agonist(s) is(are) delivered in vivo (i.e. oral pharmacokinetic profile), and (iii) the inhibitory potency of the non-opioid releasing subunits (i.e. overdose protection profile).

Opioid Agonists

Any opioid agonist known in the art may be used. The terms "opioid agonist" and "opioid" are used interchangeably herein to refer to any drug, whether natural and synthetic, which has morphine-like mechanism of action. Opioid agonists useful in the present invention include, but are not limited to, alfentanil, allylprodine, alphaprodine, anileridine, benzyl morphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, so-called "biased" opioid agonists including, but not limited to PZM021 and structurally or functionally similar analogs thereof, TRV130 and structurally or functionally similar analogs thereof, BU08028 and structurally or functionally similar analogs thereof, as well as salts, prodrugs, mixtures, derivatives, analogs, homologues, and polymorphs of any of the foregoing. In certain embodiments, the amount of the opioid agonist released can be from about 0.25 nmols to about 2.5 mmols. The specified amount of opioid released by polysubstrate compositions of the invention will likely vary as a function of the potency and bioavailability of the specific opioid agonist released.

In some embodiments, a pharmaceutical composition of the present invention includes one or more opioids such as hydrocodone, hydromorphone, morphine, oxycodone, oxymorphone, and/or salts or prodrugs thereof, as the therapeutically active ingredient.

In some embodiments, a unit dose form includes an amount of opioid agonist that is about 0.0001, about 0.001, about 0.003 mmols, about 0.015 mmols, about 0.03 mmols, about 0.045 mmols, about 0.075 mmols, about 1.50 mmols, about 0.225 mmols, about 0.3 mmols, about 0.375 mmols, about 0.45 mmols, about 0.525 mmols or about 0.6 mmols. More typically, the drug can be present in an amount from about 0.003 mmols to about 1.66 mmols, preferably about 0.015 mmols to 0.6 mmols. As will be understood by one of skill in the art, a dosage form preferably contains an appropriate amount of drug to provide a therapeutic effect. Dose units of the invention may also include co-formulations with additional therapeutically active drugs such as acetaminophen, ibuprofen, naltrexone, promethazine, etc.

Opioid Antagonists

The term "opioid antagonist", as used herein, refers to any molecule that blocks the action of an opioid agonist at one or more opioid receptor types. Opioid antagonists include so-called "agonist-antagonist" molecules that act as an antagonist for one opioid receptor type and an agonist for another receptor type, such as, for example, naloxone, naltrexone, nalorphine or pentazocine.

When co-administered with opioid agonists, opioid antagonists are capable of blocking the effects of the opioid agonist. Antagonists such as naltrexone, naloxone or buprenorphine are often used to combat the abuse and the overdose effects of an opioid agonist. For example, naltrexone is commonly prescribed to help fight addiction to either alcohol or opioid drugs.

Suitable opioid antagonists include, but are not limited to, buprenorphine, cyclazocine, cyclorphan, naloxone, N-methylnaloxone, naltrexone, N-methylnaltrexone, nalmephene, 6-amino-6-desoxo-naloxone, levallorphan, nalbuphine, naltrendol, naltrindole, nalorphine, nor-binaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

In one aspect of the invention, the opioid antagonist includes naltrexone, naloxone, nalmefene, cyclazacine, levallorphan and mixtures thereof. In another aspect of the invention, the opioid antagonist is naltrexone or naloxone.

In one aspect of the invention, the antagonist is naloxone. Naloxone is almost devoid of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously, in man, prevent or reverse the effects of morphine-like opioid agonists. One mg of naloxone administered intravenously has been reported to completely block the effects of 25 mg of heroin. The effects of naloxone are seen almost immediately after intravenous administration. The drug is absorbed after oral administration but has been reported to be rapidly and extensively metabolized into an inactive form via first-pass metabolism. Therefore, it has been demonstrated to have significantly lower potency when delivered orally than when parenterally administered.

Other exemplary opioid antagonists include cyclazocine and naltrexone, both of which have cyclopropylmethyl substitutions on the nitrogen, retain much of their efficacy by the oral route and their durations of action are much longer, approaching 24 hours after oral doses.

In another aspect of the invention, the antagonist is naltrexone. Naltrexone works by blocking the opioid receptors in the brain and blocking the feeling of euphoria felt when alcohol or an opioid agonist is ingested. This in turn decreases the craving for the substance, according to the National Institute of Health. Naltrexone can be delivered both orally and by intravenous injection.

Naltrexone is known as a synthetic congener of oxymorphone with no opioid agonist properties, and differs in structure from oxymorphone by replacement of the methyl group located on the nitrogen atom of oxymorphone with a cyclopropylmethyl group. As a result, the physicochemical properties of naltrexone (and chemically related antagonists) are nearly identical to those inherent to structurally related opioid agonists. This renders the physical separation of naltrexone-opioid agonist mixtures essentially impossible without the employment of highly sophisticated chemical separation techniques (e.g. high-performance liquid chromatography—HPLC). The hydrochloride salt of naltrexone is soluble in water up to about 100 mg/mL. Following oral administration, naltrexone is rapidly absorbed (within 1 hour) and has an oral bioavailability ranging from 5-40% in man.

It is known that when co-administered with morphine, heroin or other opioid agonists, naltrexone blocks the development of physical dependence to opioid agonists, reduces "drug liking" by recreational abusers, can precipitate withdrawal symptoms in opioid dependent subjects, and can completely block the effects of the co-delivered opioid agonist. In the treatment of patients previously addicted to opioids, naltrexone has been used to prevent the euphorigenic effects of opioid agonists. Naltrexone is commercially available in oral tablet form (Revia®) for the treatment of alcohol dependence and for the blockade of exogenously administered opioids. An oral dosage of 50 mg Revia blocks the pharmacological effects of 25 mg of IV administered heroin for up to 24 hours.

When present, the molar ratio of the opioid antagonist to the opioid agonist in compositions of the invention can be from about 0.001:1 to about 10:1, preferably about 0.01:1 to about 5:1. As will be understood by one of skill in the art, compositions of the invention preferably contain an appropriate amount of opioid antagonist to provide the desired abuse-deterrent effects when released.

GI Enzyme Inhibiting Subunits

An example of a GI enzyme inhibiting subunit is a protease inhibitor, such as a trypsin inhibitor, or a chymotrypsin inhibitor.

As used herein, the term "trypsin inhibitor" refers to any agent capable of inhibiting trypsin, and includes salts of trypsin inhibitors. The ability of an agent to be an inhibitor or substrate for trypsin can be measured using assays well known in the art. For example, in a typical assay, one can directly measure the rate and extent of expected hydrolysis products formed in incubations containing specified concentrations of digestive enzymes with known concentrations of inhibitors or substrates using common HPLC or spectrophotometric detection methods.

Compositions of the invention comprise two or more separate compounds with each compound comprising a covalently linked digestive enzyme inhibitor subunit, or multiple enzyme inhibitor subunits. In some embodiments, the enzyme substrate inhibiting subunit comprises a GI enzyme inverse substrate ester. For example, the enzyme inhibiting subunit can be attached with a linking moiety "$Z^1$" attached via the carboxylate-containing component of the ester and can be represented by one of the following moieties shown below:

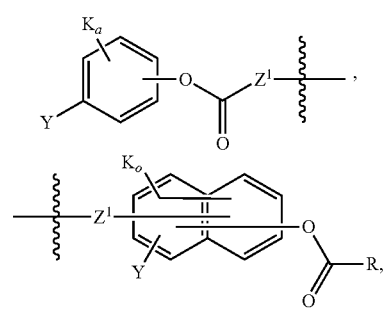

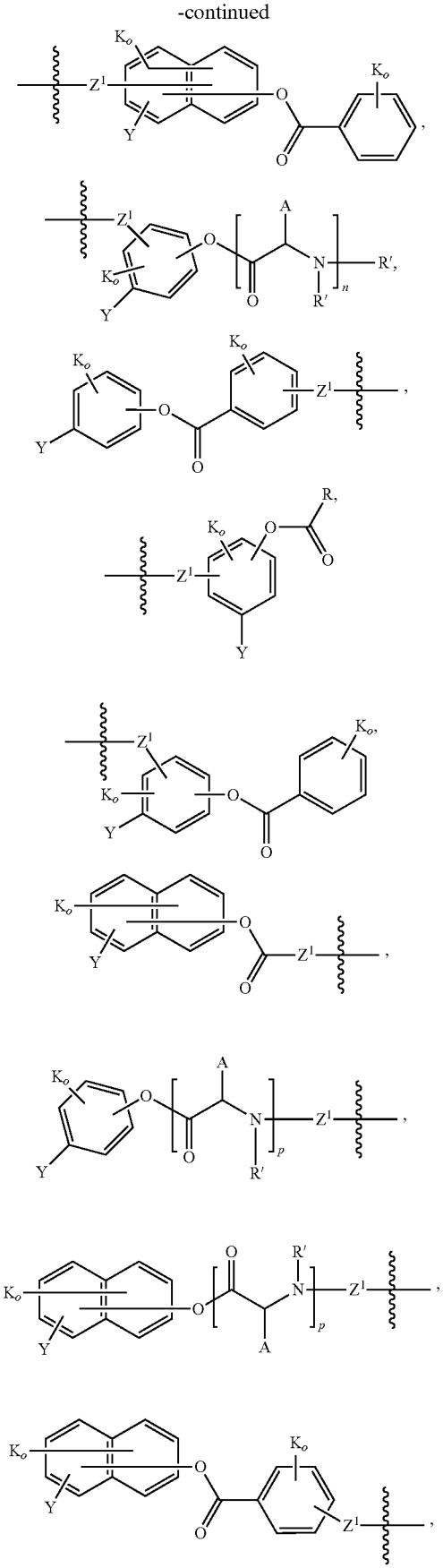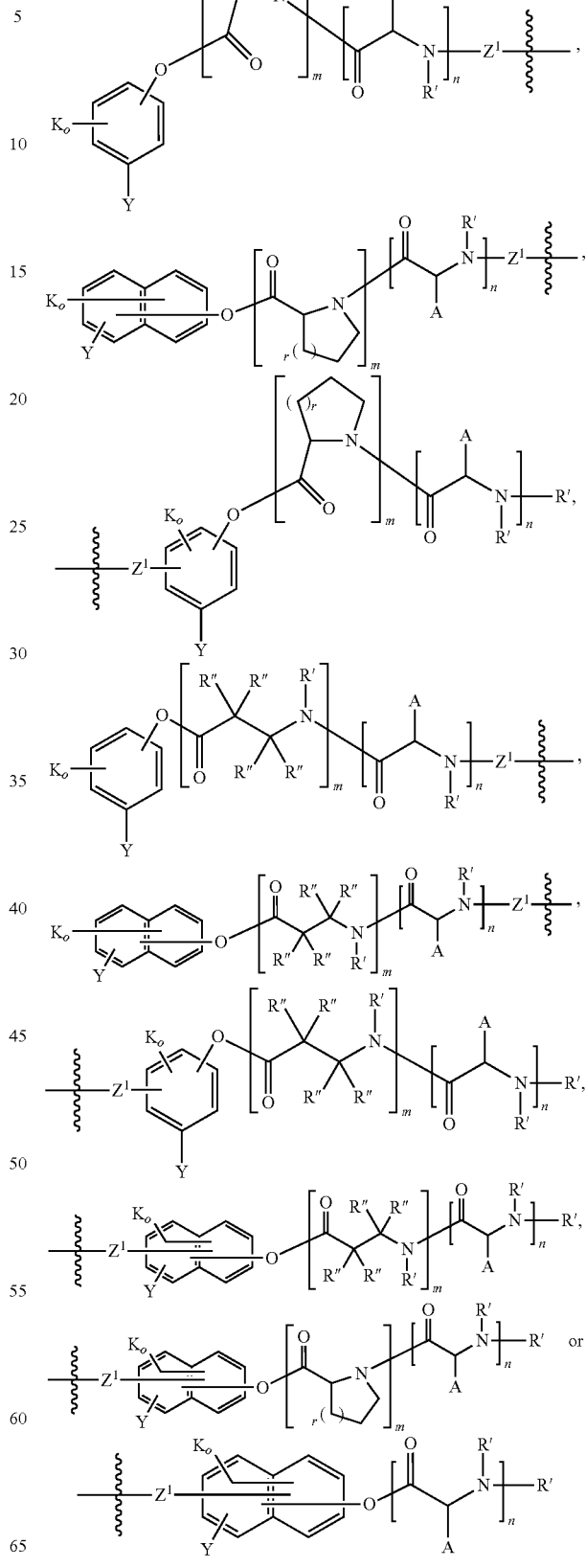

wherein:
Y is an amidine, guanidine, aminomethyl, alkyl substituted amidine, alkyl substituted guanidine, alkyl substituted aminomethyl, benzylamidine, benzylguanidine, alkyl substituted benzylamidine, or alkyl substituted benzylguanidine;
Z is a linking moiety;
each $K_o$ is independently hydrogen or methyl;
A is an amino acid side chain;
r is an integer from 0-10;
m is an integer from 1-10;
p is an integer from 1-10;
n is an integer from 0-10;
each R' is independently alkyl, aryl, substituted alkyl, substituted aryl, acyl, substituted acyl group, or polyethylene glycol containing acyl, aryl, or alkyl group; and each R" is independently a hydrogen, methyl, alkyl, or aryl group.

In some embodiments, at least one of Z' and $K_o$ comprises an electron donating, or electron withdrawing, atom or functionality that influences the formation, or the hydrolysis, of the acyl enzyme intermediate resulting from interaction with the targeted digestive enzyme. For example, electron donating groups include alkyl, substituted alkyl, —OH, —OR, —NH$_2$, —NR$_2$, —SH, —SR, and —NHC(O)R. For example, electron withdrawing groups include —C(O)OH, —C(O)OR, —C(O)NH$_2$, —C(O)NR$_2$, —NO$_2$, —NR$_3$+, —C(O)CF$_3$, halogen, —CCl$_3$, cyano, —SO$_3$H, —SO$_3$R, —CHO, —COR, —C(NH)NH$_2$, and —NHC(NH)NH$_2$.

In other embodiments, the enzyme inhibiting subunit is connected to a scaffold or linking moiety via the phenol component of the ester. Examples include, but are not limited to those described below:

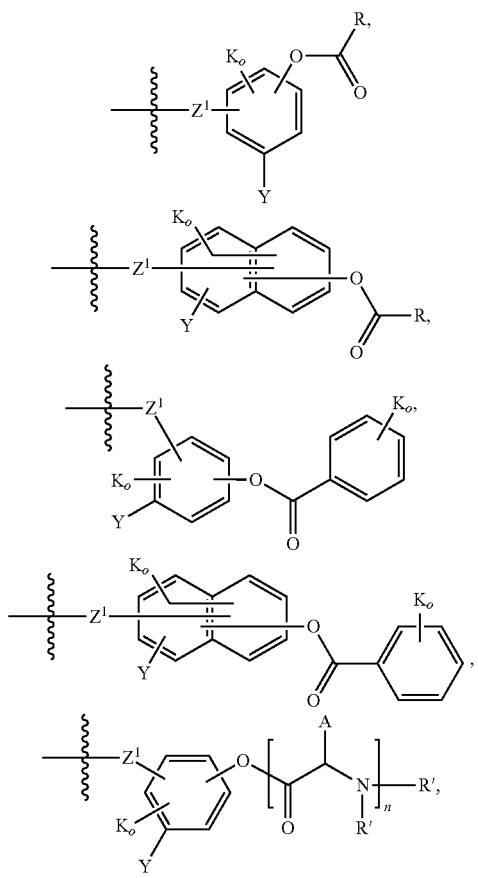

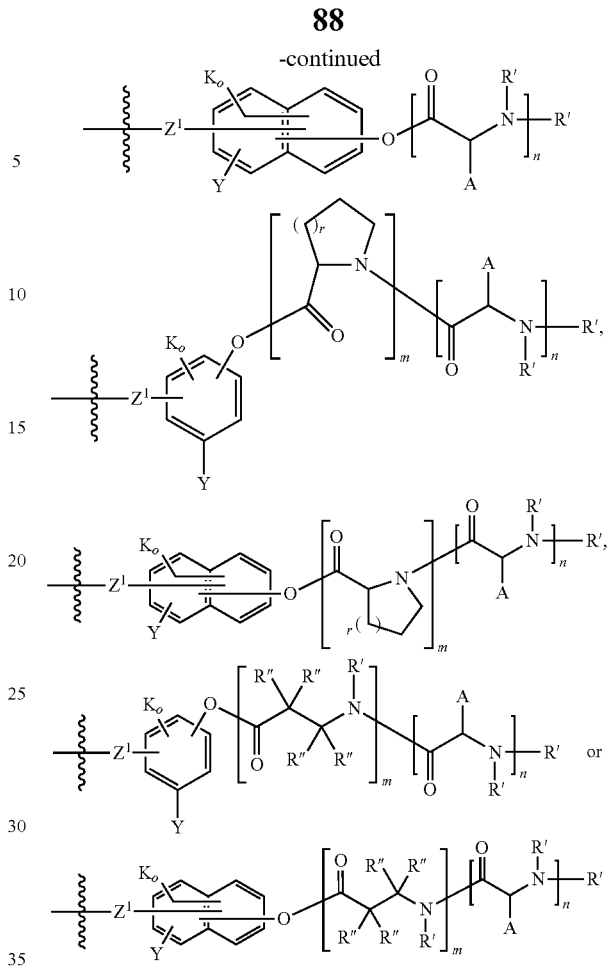

wherein:
Y is an amidine, guanidine, aminomethyl, alkyl substituted amidine, alkyl substituted guanidine, alkyl substituted aminomethyl, benzylamidine, benzylguanidine, alkyl substituted benzylamidine, or alkyl substituted benzylguanidine;
Z is a linking moiety;
each $K_o$ is independently hydrogen or methyl;
A is an amino acid side chain;
r is an integer from 0-10;
m is an integer from 1-10;
p is an integer from 1-10;
n is an integer from 0-10;
each R is alkyl, alkylene, alkynyl, or aryl, or substituted alkyl, substituted alkylene, substituted alkynyl, substituted aryl group;
each R' is independently alkyl, aryl, substituted alkyl, substituted aryl, acyl, substituted acyl group, or polyethylene glycol containing acyl, aryl, or alkyl group; and
each R" is independently a hydrogen, methyl, alkyl, or aryl group.

In some embodiments, at least one of $Z^1$ and $K_o$ can comprises an electron donating, or electron withdrawing, atom or functionality that influences the formation, or the hydrolysis, of the acyl enzyme intermediate resulting from the interaction of the subunit by the targeted digestive enzyme. For example, electron donating groups include alkyl, substituted alkyl, —OH, —OR, —NH$_2$, —NR$_2$, —SH, —SR, and —NHC(O)R. For example, electron withdrawing groups include: —C(O)OH, —C(O)OR, —C(O)NH$_2$, —C(O)NR$_2$, —NO$_2$, —C(O)CF$_3$, halogen, —CCl$_3$, cyano, —SO$_3$H, —SO$_3$R, —CHO, —COR, —C(NH)NH$_2$, and —NHC(NH)NH$_2$.

GI enzyme hydrolysis (e.g. by trypsin) of the ester inhibitor subunits listed above results in the formation of a carboxylic acid, amino acid, or benzoic acid metabolites. In some embodiments, GI enzyme hydrolysis (e.g. by trypsin) of ester inhibitor subunits may be designed to produce an acid metabolite that is generally regarded as safe (GRAS). The hydrolysis of a representative ester inhibitor subunit by a GI enzyme resulting in the release of a GRAS acid metabolite is illustrated by the general mechanism below:

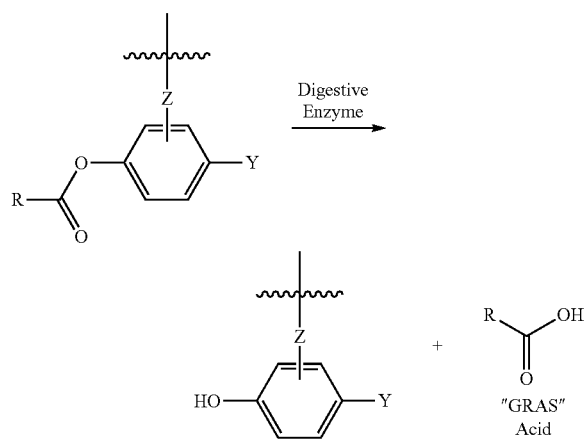

"GRAS" stands for "generally recognized as safe" and refers to a compound as defined by sections 201(s) and 409 of the Federal Food, Drug, and Cosmetic Act. Exemplary GRAS acid metabolites include, but are not limited to: benzoic acid, salicylic acid, aspirin, 3-hydroxybenzoic acid, 4-hydroxybenzoic acid, gallic acid, 2,3,4-trihydroxybenzoic acid, 2,3,6-trihydroxybenzoic acid, 2,4,5-trihydroxy benzoic acid, 6-methylsalicylic acid, o-cresotinic acid, (alkyl)-anacardic acids, o-thymotic acid, 3-O-methylgallic acid, 4-O-methylgallic acid, syringic acid, 3,4,5-trimethoxybenzoic acid, diflusinal, p-anisic acid, 2,3-dihydroxybenzoic acid, alpha-resorcylic acid, anthranilic acid, 3-aminobenzoic acid, 4,5-dimethylanthranilic acid, N-methylanthranilic acid, protocatechuic acid, gentisic acid, piperonylic acid, 3-methoxysalicylic acid, fenamic acid, toifenamic acid, mefenamic acid, flufenamic acid, vanillic acid, isovanillic acid, veratric acid, 3,5-dimethoxybenzoic acid, 2,4-diaminobenzoic acid, N-acetylanthranilic acid, 2-acetylamino-4-aminobenzoic acid, 2,4-diacetylaminobenzoic acid, 4-aminosalicylic acid, 3-hydroxyanthranilic acid, 3-methoxyanthranilic acid, nicotinic acid, isonicotinic acids, and cinnamic acids.

In one aspect of the invention, the compositions, pharmaceutical formulations, and methods disclosed herein comprise inverse-ester inhibitor subunits for GI enzymes, such as trypsin, chymotrypsin, or tryptase. Thus, when trypsin is an exemplary GI enzyme, trypsin preferentially cleaves C-terminal peptide bonds of arginine and lysine, both of which are positively charged amino acids. The specificity pocket of trypsin has an aspartic acid residue (Asp-189), which has a negative charge, resulting in a negative electrostatic field in the substrate binding pocket, thereby selectively recognizing the positively charged arginine and lysine substrate side chains. The negative electrostatic field in the substrate binding pocket also helps stabilize the positive charge in the enzyme-substrate complex.

Mechanistically, the GI enzyme catalyzed hydrolysis of inverse-ester based inhibitor subunits can be described using the following scheme:

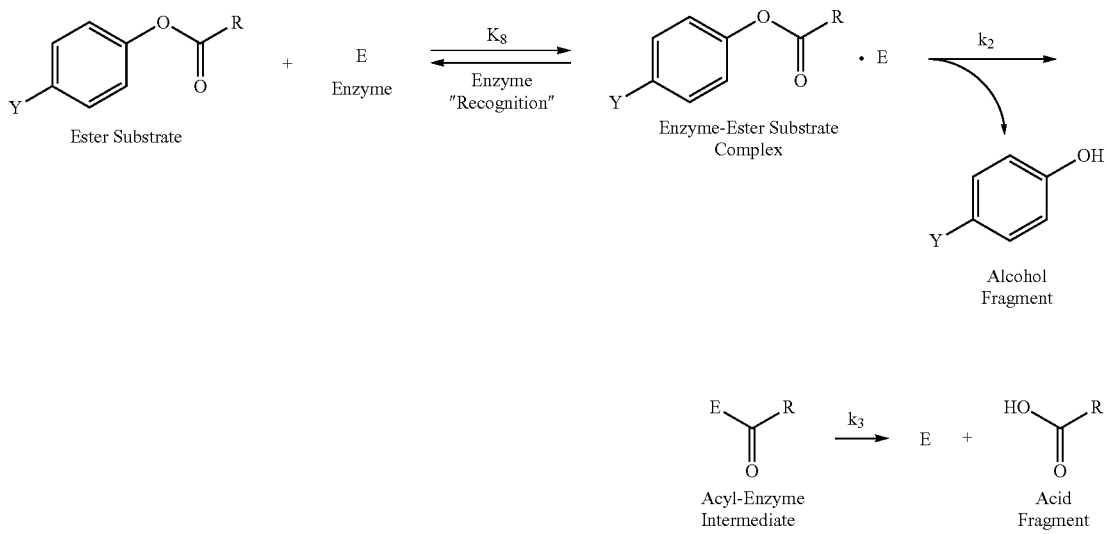

Where E is a GI enzyme. $K_s$ is the association constant for the formation of the enzyme-substrate complex, $k_2$ is the rate constant of the acylation step, and $k_3$ is the rate constant of the deacylation step. In the initial enzyme recognition step, the inverse-ester substrate and the enzyme bind to form an enzyme-substrate complex. The inverse-ester subunit is then irreversibly hydrolyzed to produce an alcohol (or phenol) fragment and an active-site acyl-enzyme intermediate. The acyl-enzyme intermediate subsequently dissociates to a free enzyme (E) and an acid fragment with a rate constant of $k_3$. The rate at which the deacylation step occurs, $k_3$, determines the lifetime of the acyl-enzyme intermediate and the proclivity of specific subunits to saturate trypsin.

Thus, in one aspect of the invention, the compositions, pharmaceutical formulations, and methods disclosed herein comprise an inverse-ester substrate inhibitor, where the inverse-ester substrate inhibitor has an enzyme recognition moiety covalently linked to a carbonyl group that is capable of acylating the active site of the enzyme.

Thus, in one aspect of the invention, the products produced by the hydrolysis of inverse-ester inhibitors are an acid and an alcohol, such as a substituted phenol, where the phenol can remain covalently attached to a polysubstrate of the invention and as a result will generally not be systemically absorbed, but rather pass through the gastrointestinal system and are excreted. Such inverse-ester containing polysubunits of the invention can be designed to release GRAS acids and thereby have the advantage that GRAS acids have well-characterized safety profiles. In addition, these ester substrates are chemically stable in vivo and are not easily hydrolyzed by acid in the stomach, nor hydrolyzed non-specifically by digestive enzymes, of the patient.

Representative non-limiting inverse-ester enzyme inhibitor $R^1$—$Z^1$— subunit examples include:

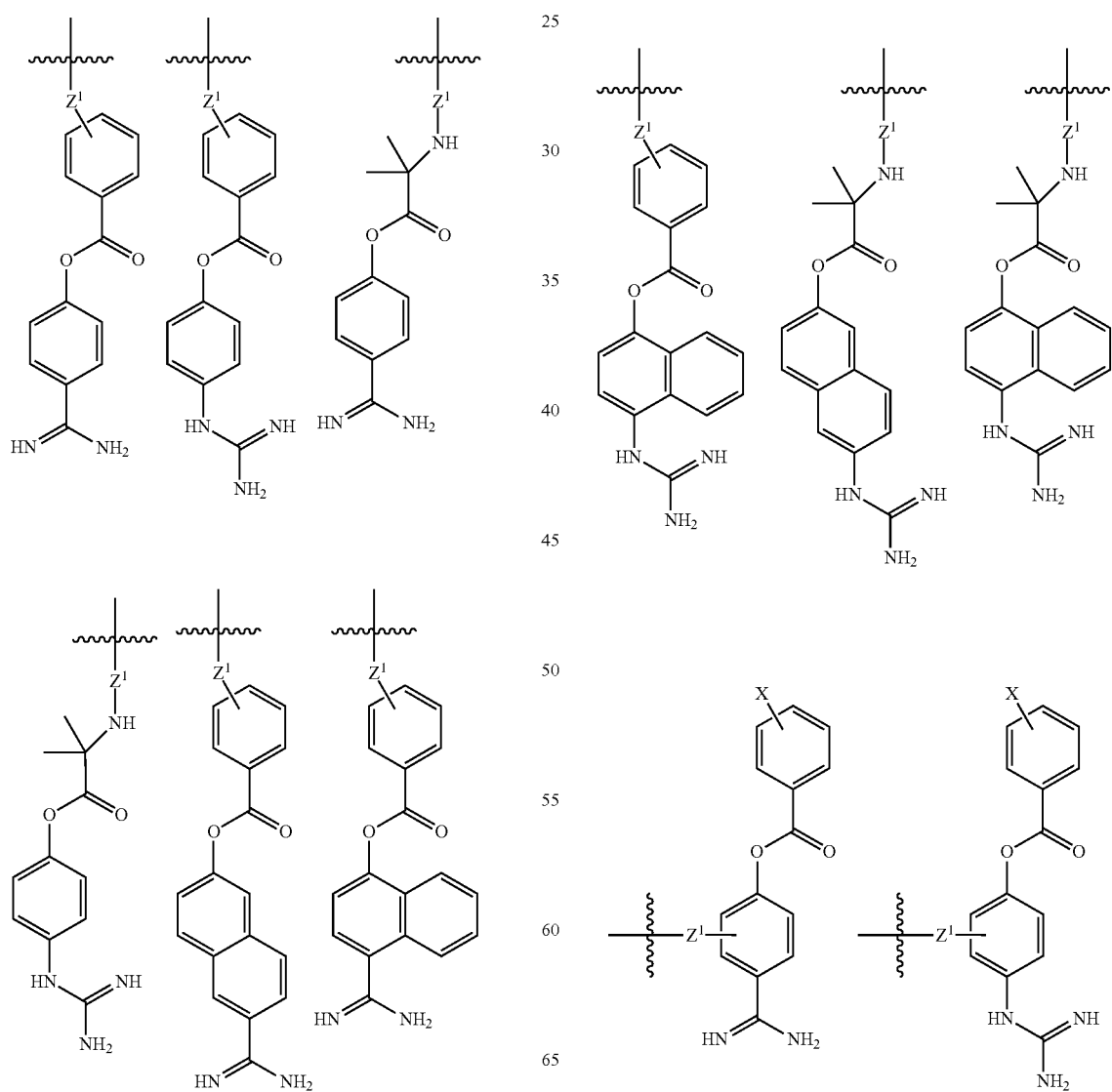

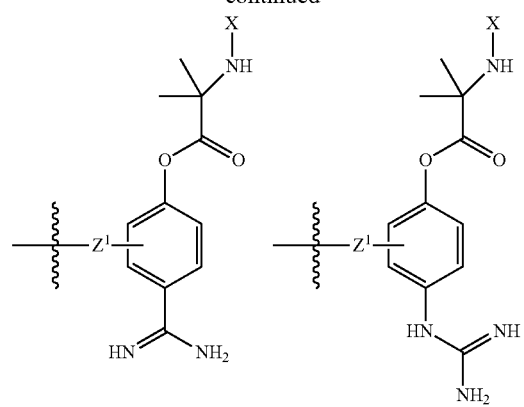

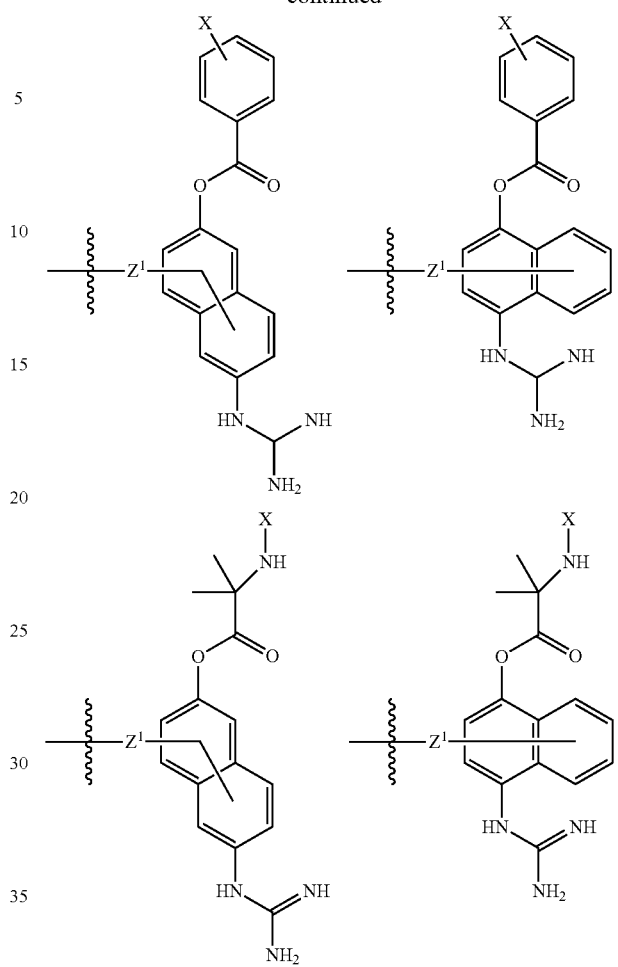

wherein $Z^1$ is a linking moiety as described herein; and

X can be hydrogen, an amino acid, alkyl, heteroalkyl, aryl, substituted aryl, acyl, substituted acyl, terminally functionalized polyethylene glycol chain, or X is a substituent (or substituents) on a GRAS carboxylic acid as described above.

In some embodiments, the non-opioid releasing digestive enzyme subunit is a GI enzyme inhibitor. The non-opioid releasing GI enzyme inhibitor subunit is attached to a linking moiety Z as represented by any one of the following non-limiting examples described below.

The GI enzyme inhibitor subunit can be derived from amidinophenylpyruvate (APPA) including, but not limited to:

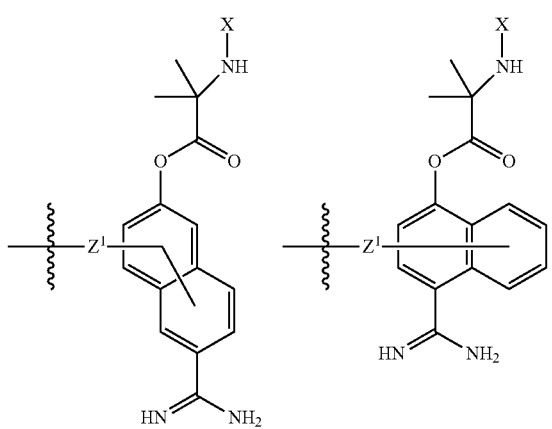

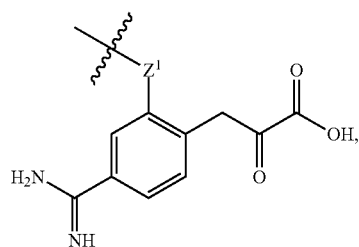

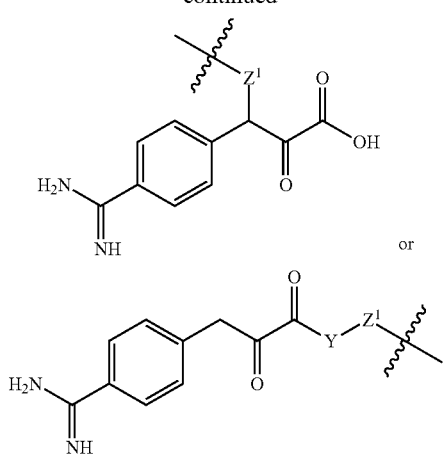

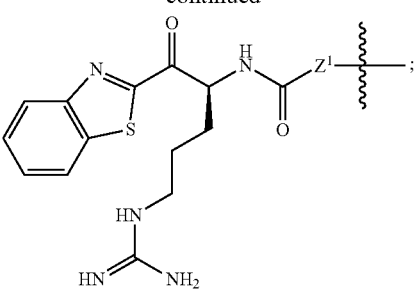

Wherein Y can be O, NH, NR or S; $Z^1$ is a linker as defined above.

In another aspect of the invention, the GI enzyme inhibitor subunit can be derived from an activated ketone derivative, including, but not limited to the following:

where Y is N, O, N—R, or carbon, and R is methyl, ethyl, alkyl, substituted alkyl, acyl, substituted acyl, aryl, substitutes aryl, a natural or non-natural amino acid, or a polypeptide chain comprising natural or non-natural amino acids. The arginine side chain in the above structure can be substituted for a lysine side chain, or a natural or non-natural lysine or arginine side chain mimic.

In another aspect of the invention, the GI enzyme inhibitor subunit can be derived from chloroketone or aldehyde analogs as shown below:

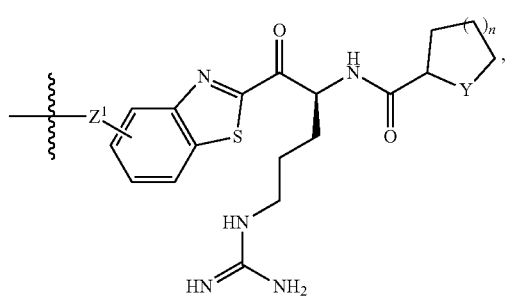

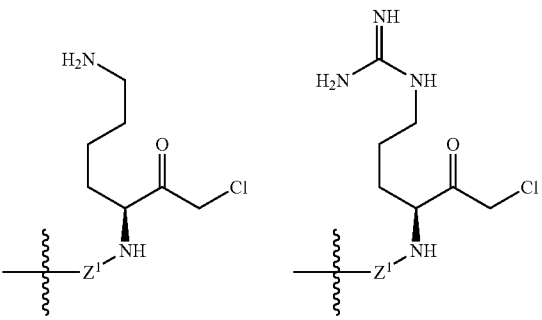

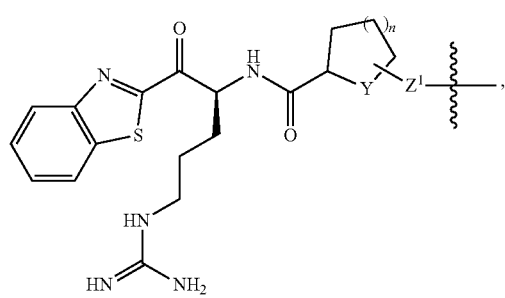

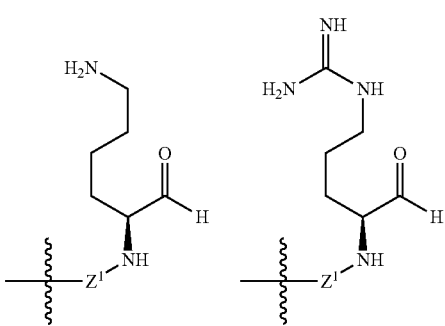

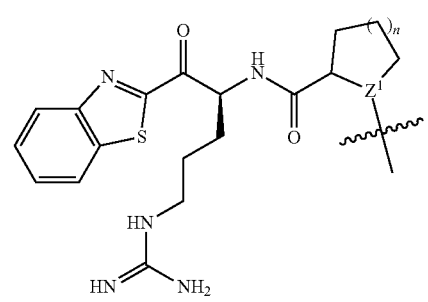

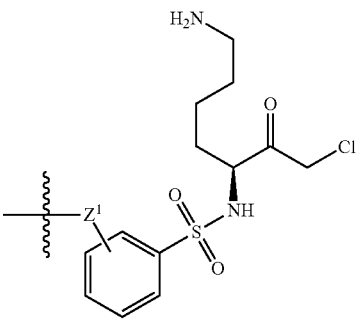

97

-continued

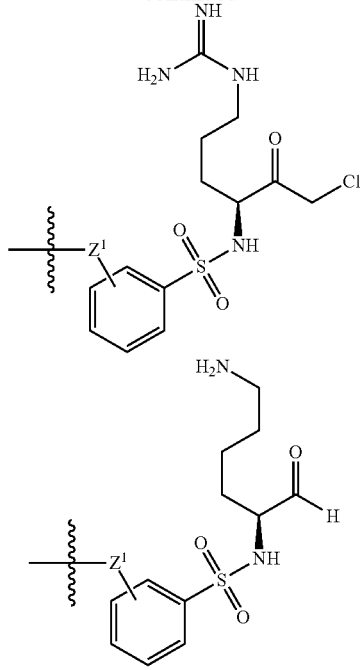

98

-continued

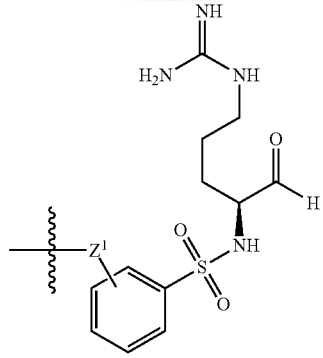

The chloroketone and aldehyde analogs illustrated above can also comprise natural or non-natural lysine-mimic or arginine-mimic side-chain variants.

In another non-limiting aspect of the invention, the GI enzyme inhibitor subunit inhibitor can have cycloheteroalkyl groups, naphthylamidines, arylguanidines, arylamidines, benzylamines, 4-guanidinopiperazines, and peptide based structures, as illustrated below:

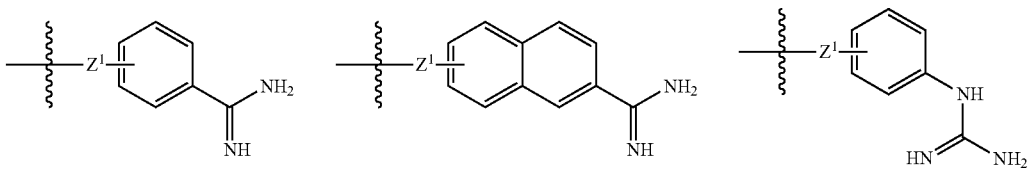

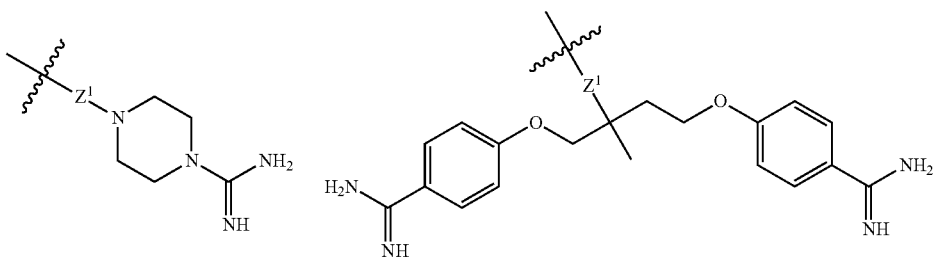

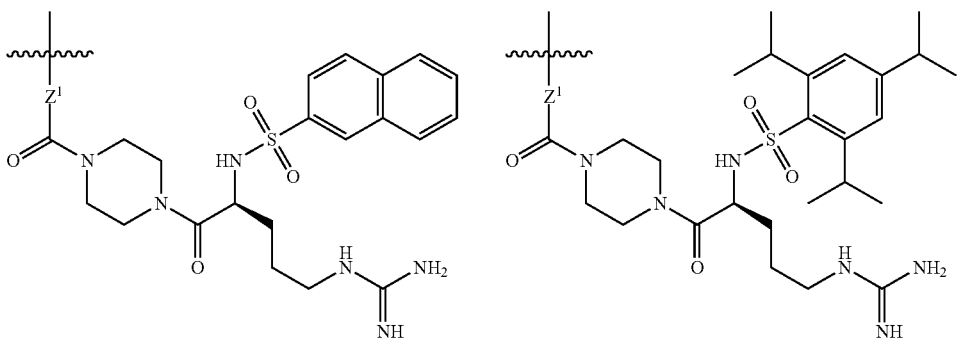

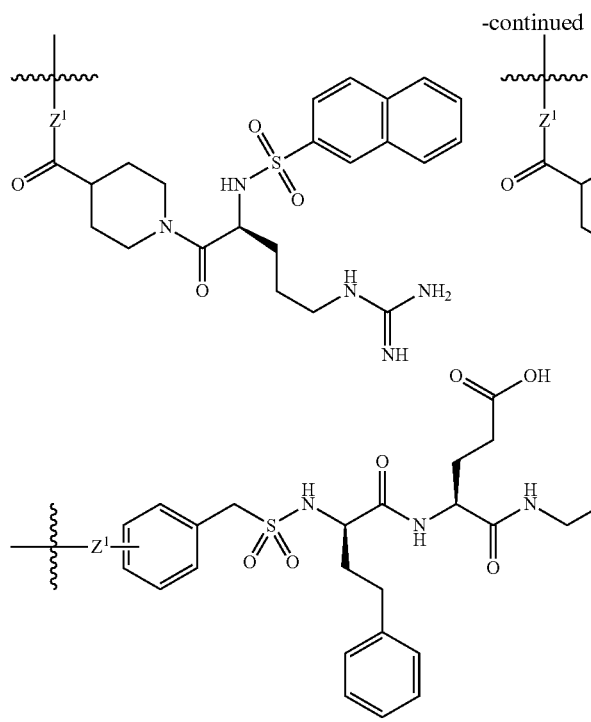

In some cases, the GI enzyme inhibitor subunits illustrated above can also comprise natural or non-natural lysine-mimic or arginine-mimic side-chain variants capable of being recognized by a GI enzyme.

Preparation of GI Enzyme Inhibiting Subunits

Multiple synthetic procedures useful for the preparation of non-opioid releasing subunits have been reported in the literature (see for example: Tanizawa, K., et al, Chem. Pharm. Bull. 1999, 47(1), 104-110, Aoyama, T., et al, Chem. Pharm. Bull. 1985, 33(4), 1458-1471, Bordusa, F., et al, Biochemistry, 1999, 38, 6056-6062, Tanizawa. K., et al, Chem. Pharm. Bull. 1996, 44, 1577-1579, 1585-1587, Lal, B., et al, Tetrahedron Lett. 1996, 37, 2483-2486, Sekizaki, H., et al, Bioorganic & Medicinal Chemistry Letters, 2003, 13, 3809-3812, Tanizawa, K., et al, Acc. Chem. Res. 1987, 20, 337-343) and commonly involve the coupling between an alcohol (or phenol) synthon and a carboxylic acid (e.g. benzoic acid) moieties that is pre-activated for coupling by first conversion to an acid chloride, or the like; or activated for coupling in situ with an appropriate coupling reagent (e.g. DCC) to form the desired ester functionality. Amidine substituted phenol synthons are commonly used in an unprotected salt form, while guanidine and benzylamine containing esters are often prepared via similar coupling reactions using a protected form (e.g. the Cbz or Boc protected forms) of the aryl guanidine and benzylamine synthons. Purification of the resulting esters can be accomplished using standard purification procedures involving normal or reverse phase HPLC, crystallization, trituration, etc. The chemical identity of the esters can be readily established by LC/MS and/or NMR analysis.

Some representative synthetic routes useful for the preparation of inverse ester enzyme inhibitor subunits are depicted below.

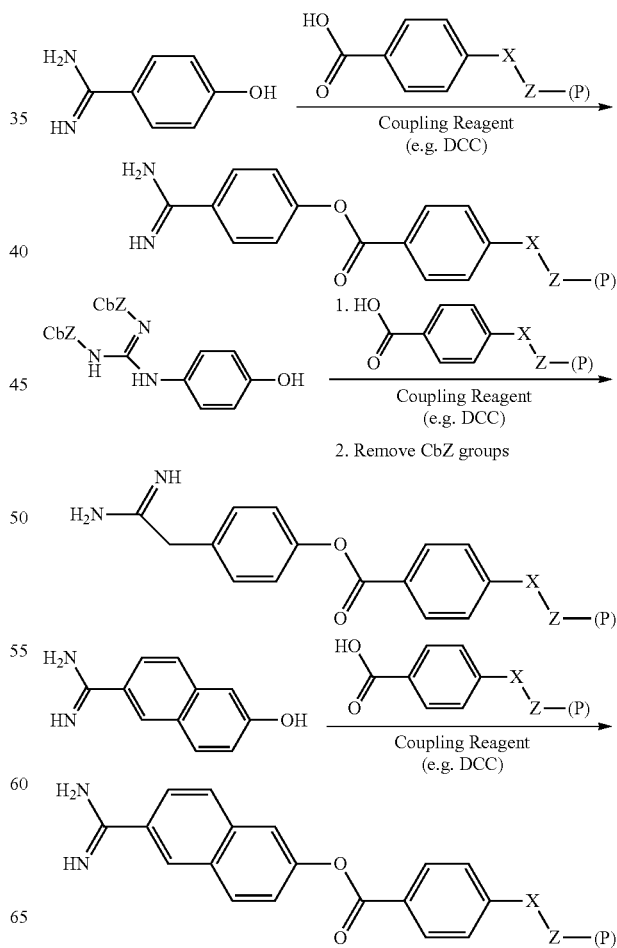

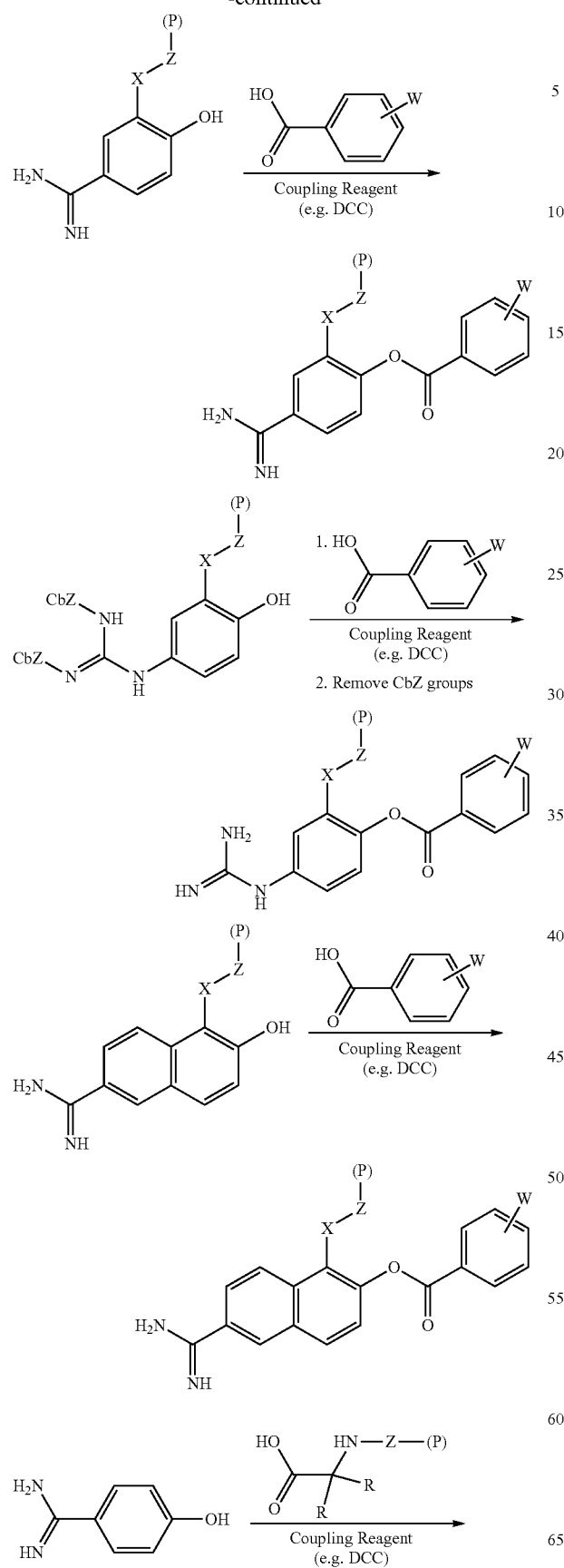
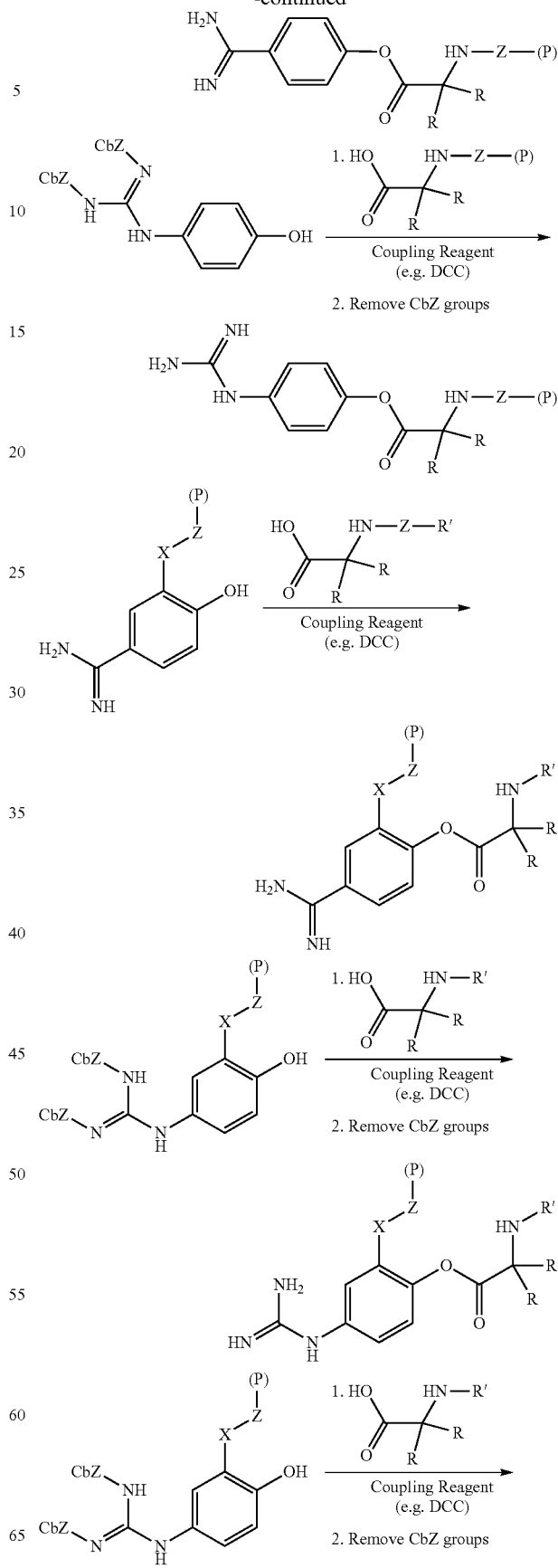

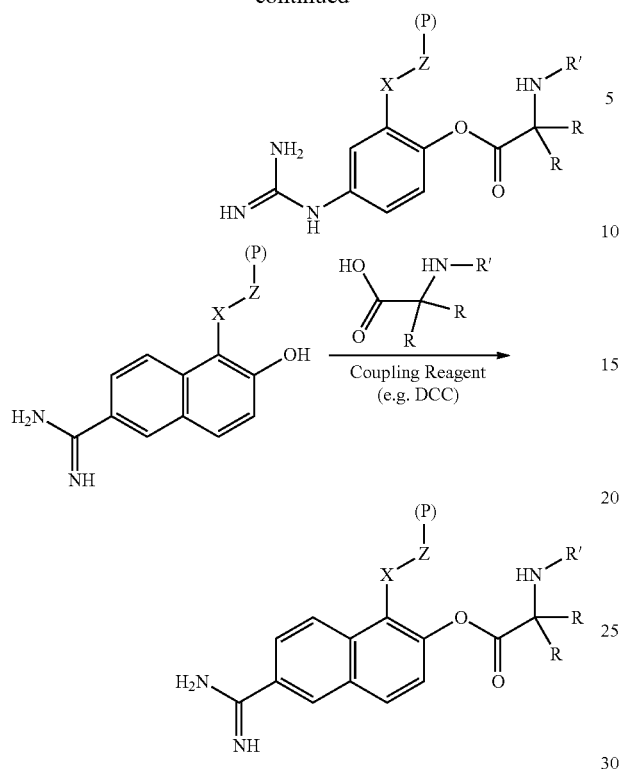

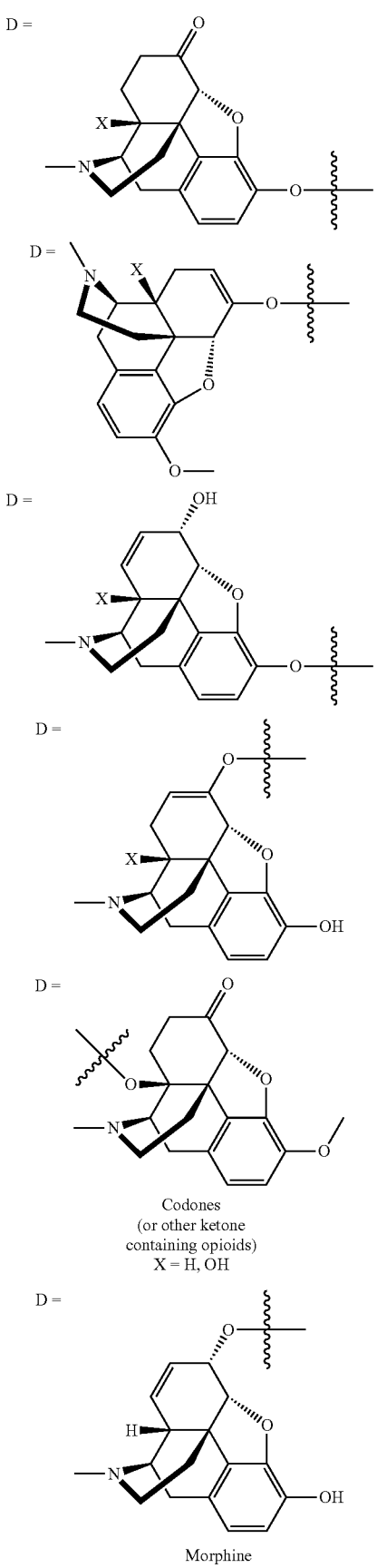

wherein:

each R' is independently alkyl, aryl, substituted alkyl, substituted aryl, acyl, substituted acyl group, or polyethylene glycol containing acyl, aryl, or alkyl group;

each R is independently a hydrogen, methyl, alkyl, or aryl group;

W is hydrogen or an atom or substituent that renders the benzoic acid metabolite of the inverse ester subunit a GRAS compound, or W is an electron donating or withdrawing atom or functionality that influences the formation, or the hydrolysis, of the acyl enzyme intermediate resulting from the interaction of the inverse ester subunit by the targeted digestive enzyme.

Z is a linking moiety $Z^1$;

X is a covalent bond or an atom such as oxygen or nitrogen, or a functional group suitable for the attachment of, or incorporated by, the linker group Z; and (P) is an optional protecting group present on the terminus of the linker Z distal to the inverse ester subunit that may be employed to enhance the chemical efficiency of the desired ester forming coupling reaction.

GI Enzyme Labile Opioid Agonist Releasing Subunits

Compositions of the invention comprise two or more molecules with covalently linked opioid agonist releasing digestive enzyme substrate subunits. The released opioid agonist can be morphine, a morphone or other phenol containing opioid agonist, or a codone or other ketone containing opioid agonist, such as illustrated by the non-limiting formulae below. The opioid agonist releasing substrates may be linked via phenol, alcohol, or ketone (e.g. enol) functionalities present on the opioid agonist as shown below.

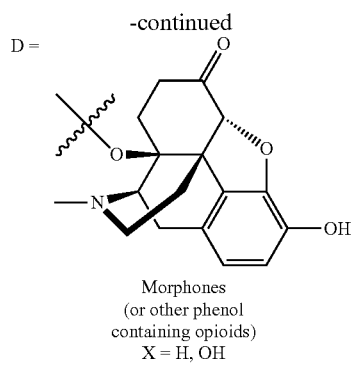

D =

Morphones
(or other phenol
containing opioids)
X = H, OH

In some embodiments, D is a phenol-linked opioid agonist. For example, D is selected from buprenorphine, dihydroetorphine, diprenorphine, etorphine, hydromorphone, levorphanol, morphine, oxymorphone, tapentadol, and the like.

In some embodiments, D is an enol-linked opioid agonist. For example, D is selected from acetylmorphone, hydrocodone, hydromorphone, oxycodone, oxymorphone, pentamorphone, ketobemidone, methadone, and the like.

According to one aspect, the invention provides pharmaceutical compositions that comprise two or more molecules that contain opioid agonist releasing digestive enzyme substrates or subunits. The disclosure provides novel digestive enzyme substrate moieties attached to an opioid agonist through a functional group present on the opioid agonist, where the functional group present on the opioid agonist comprises a reactive group. Any type of reactive group on an opioid agonist can provide a handle for a point of attachment to the opioid agonist releasing substrate moiety. Examples of reactive groups on an opioid agonist include, but are not limited to, alcohol, phenol, ketone, amino, and amide. An alcohol or phenol on an opioid agonist can provide a point of attachment by reaction to form a linkage, such as a carbamate. A ketone on an opioid agonist can provide a point of attachment via reaction to form a linkage, such as an enol carbamate. An amino group on an opioid agonist can provide a point of attachment by reaction to form an amino linkage, including quaternary salts, or an amide. An amide on an opioid agonist can provide a point of attachment by reaction to form a linkage, such as an O-acylated or O-alkylated amide enol, or an N-alkylated or N-acylated amide.

A opioid agonist releasing subunit can be linked via an alcoholic or phenolic opioid agonist via modification of the alcohol or phenol moiety, through the enolic oxygen atom of the ketone moiety, to an amino-containing opioid agonist through the amino moiety, to an amide-containing opioid agonist through the enolic oxygen of the amide moiety or its imine tautomer. In each case, the opioid agonist releasing digestive enzyme substrate comprises an enzyme-cleavable moiety that is susceptible to cleavage by a GI enzyme. Release of the opioid agonist is mediated by enzymatic cleavage by a digestive enzyme. Such cleavage can initiate, contribute to, or immediately effect release of the opioid agonist.

Examples of opioid agonist releasing digestive enzyme substrate moieties comprising releasable opioid agonists designated as D are shown below.

In some embodiments, the opioid agonist releasing subunit has one of the formulas:

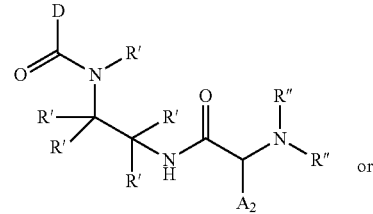

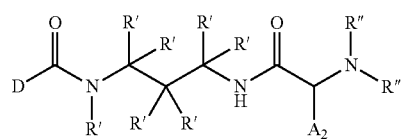

wherein:

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond; In some embodiments, R' can also form a spirocyclic or fused aliphatic ring with a geminal or vicinal R' group;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a bond;

each $A_2$ is independently an amino acid side chain or an amino acid side-chain functional or structural mimic that is capable of being recognized by a digestive enzyme.

In some embodiments, the amino acid side-chain or amino acid side-chain functional or structural mimic $A_2$ directs the regiospecific digestive enzyme mediated hydrolysis of the opioid agonist releasing substrate prior to the release of the appended opioid agonist from the opioid agonist releasing subunit. In some embodiments, the amino acid side chain can be, but is not limited to, the side chain of arginine, homoarginine, lysine, homolysine, s-N-methyl lysine, ornithine, or structural/functional mimics thereof.

In some embodiments, the opioid agonist releasing subunit has one of the formulas:

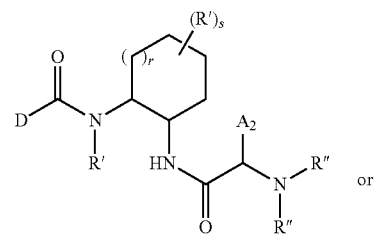

-continued

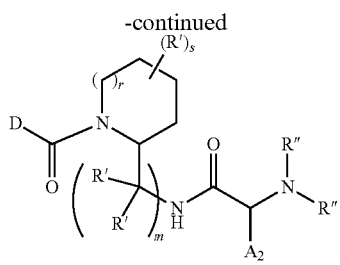

wherein:
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety ($Z^2$);
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a bond;
each $A_2$ is independently an amino acid side chain or an amino acid side-chain mimic that is capable of being recognized by a digestive enzyme;
In some of the structures described herein $A_2$ is:

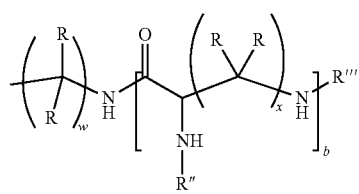

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, or a polyethylene glycol containing moiety; w and x are each or independently an integer from 1 to 6; b is an integer from 0 to 10; R''' is hydrogen, methyl, —C(=NR)—NR$_2$ wherein R is each or independently hydrogen or methyl; or

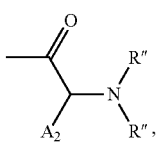

wherein $A_2$ is a natural or unnatural amino acid side chain, or an amino acid side-chain mimic that is recognized by a digestive enzyme, wherein the digestive enzyme effects the regiospecific hydrolysis of R" prior to the release of the appended opioid agonist from the $R^2$ subunit, and wherein $A^2$ is optionally selected from the amino acid side chain of arginine, homoarginine, lysine, homolysine, ε-N-methyl lysine, ornithine, or structural/functional mimics thereof; and w is an integer from 0 to 10
x is an integer from 0 to 10
b is an integer from 0 to 4.

In some embodiments, the amino acid side-chain or amino acid side-chain mimic $A_2$ directs the regiospecific hydrolysis of the opioid agonist releasing substrate prior to the release of the appended opioid agonist from the opioid agonist releasing subunit. In some embodiments, the amino acid side chain can be, but is not limited to, the side chain of arginine, homoarginine, lysine, homolysine, ε-N-methyl lysine, ornithine, or structural/functional mimics thereof.

In some embodiments, the opioid agonist releasing subunit has the formula:

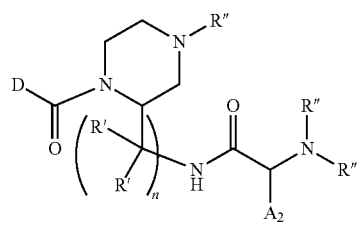

wherein:

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond; each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a bond;

each $A_2$ is independently an amino acid side chain or an amino acid side-chain mimic that is capable of being recognized by a digestive enzyme; and In some of the structures described herein $A_2$ is:

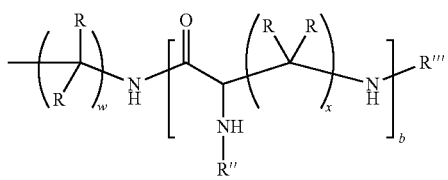

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, or a polyethylene glycol containing moiety; w and x are each or independently an integer from 1 to 6; b is an integer from 0 to 10; R''' is hydrogen, methyl, —C(=NR)—NR$_2$ wherein R is each or independently hydrogen or methyl; or

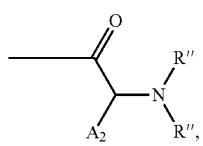

wherein A$_2$ is a natural or unnatural amino acid side chain, or an amino acid side-chain mimic that is recognized by a digestive enzyme, wherein the digestive enzyme effects the regiospecific hydrolysis of R" prior to the release of the appended opioid agonist from the R$^2$ subunit, and wherein A$^2$ is optionally selected from the amino acid side chain of arginine, homoarginine, lysine, homolysine, ε-N-methyl lysine, ornithine, or structural/functional mimics thereof; and w is an integer from 0 to 10
x is an integer from 0 to 10
b is an integer from 0 to 4.

In some embodiments, the amino acid side chain or amino acid side-chain mimic A$_2$ directs the regiospecific hydrolysis of the opioid agonist releasing substrate prior to the release of the appended opioid agonist from the opioid agonist releasing subunit. In some embodiments, the amino acid side chain can be, but is not limited to, the side chain of arginine, homoarginine, lysine, homolysine, ε-N-methyl lysine, ornithine, or structural/functional mimics thereof.

In some embodiments, the opioid agonist releasing subunit has the formula:

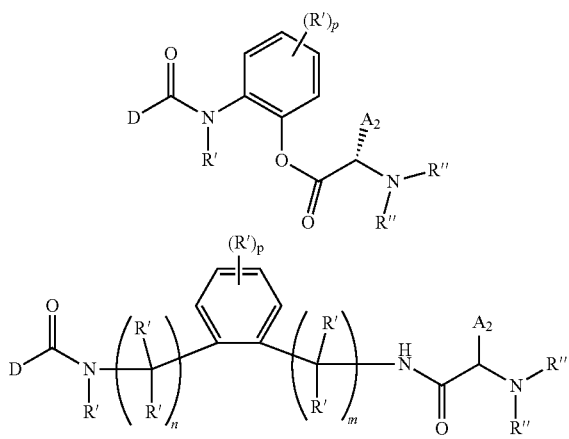

wherein
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond as previously defined;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a bond as previously defined; and
each A$_2$ is independently an amino acid side chain or an amino acid side-chain mimic that is capable of being recognized by a digestive enzyme.

In some of the structures described herein A$_2$ is:

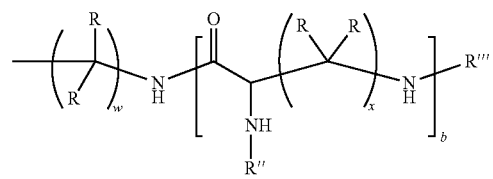

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, or a polyethylene glycol containing moiety; w and x are each or independently an integer from 1 to 6; b is an integer from 0 to 10; R'" is hydrogen, methyl, —C(=NR)—NR$_2$ wherein R is each or independently hydrogen or methyl; or

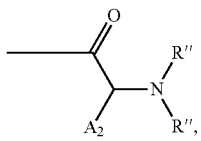

wherein A$_2$ is a natural or unnatural amino acid side chain, or an amino acid side-chain mimic that is recognized by a digestive enzyme, wherein the digestive enzyme effects the regiospecific hydrolysis of R'" prior to the release of the appended opioid agonist from the R$^2$ subunit, and wherein A$^2$ is optionally selected from the amino acid side chain of arginine, homoarginine, lysine, homolysine, ε-N-methyl lysine, ornithine, or structural/functional mimics thereof; and w is an integer from 0 to 10
x is an integer from 0 to 10
b is an integer from 0 to 4.

In some embodiments, the amino acid side chain or amino acid side-chain mimic A$_2$ directs the regiospecific hydrolysis of the opioid agonist releasing substrate prior to the release of the appended opioid agonist from the opioid agonist releasing subunit. In some embodiments, the amino acid side chain can be, but is not limited to, the side chain of arginine, homoarginine, lysine, homolysine, ε-N-methyl lysine, ornithine, or structural/functional mimics thereof.

As will be evident to one of skill in the art, the opioid agonist releasing subunits can be covalently attached to form a polysubunit molecule of the invention via one or more linking moieties Z$^2$ at any substitution point on the opioid agonist releasing subunit as long as the attachment(s) do(es) not preclude either the requisite recognition or hydrolytic action of the digestive enzyme on, or the subsequent release of opioid agonist from, the opioid agonist releasing substrate subunit.

In one aspect of the invention, the opioid agonist is an alcohol, phenol or ketone containing opioid agonist. Accordingly, an alcohol, phenol, or ketone containing opioid agonist is attached through a hydroxylic, phenolic, or enolic oxygen to a linker, which is further attached to an enzyme cleavable moiety. A single enzymatic hydrolysis of a cleavable moiety, or a cascade of enzymatic hydrolyses of cleavable moieties, may release the opioid agonist by (i) directly cleaving the bond between the enzyme cleavable moiety and the opioid agonist, or (ii) revealing a latent nucleophile, such as an amine or carboxylate, that subsequently undergoes an intramolecular cyclization-release reaction, or (iii) revealing an additional enzyme substrate, or substrates, that are further cleaved by the digestive enzyme ultimately resulting in release of an additional enzyme substrate, or the release of the appended opioid agonist.

The mechanisms of enzyme-mediated opioid agonist release from the representative opioid agonist releasing substrates subunits are presented below:

General Mechanism of Enzyme-Mediated Opioid Agonist Release from Representative Cyclic Urea Forming Opioid Agonist Releasing Subunit Example:

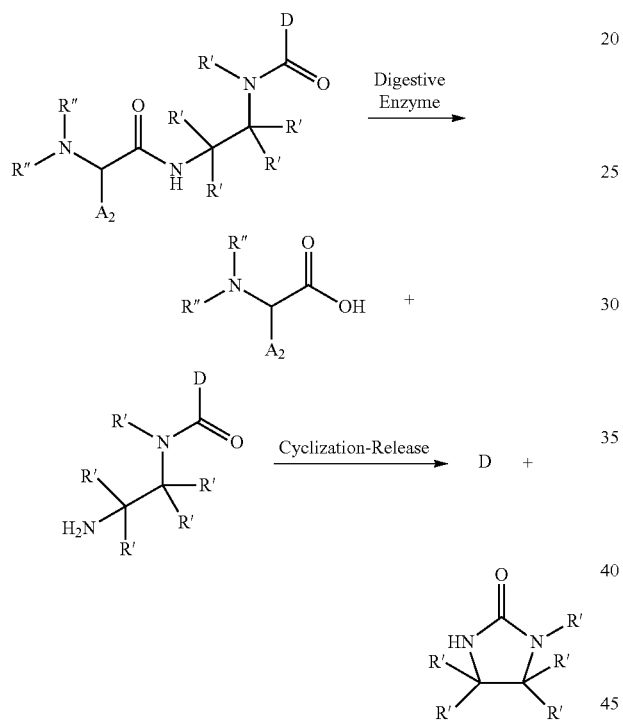

General Mechanism of Enzyme-Mediated Opioid Agonist Release from Representative Aliphatic Fused-Ring Cyclic Urea Forming Opioid Agonist Releasing Subunit Example:

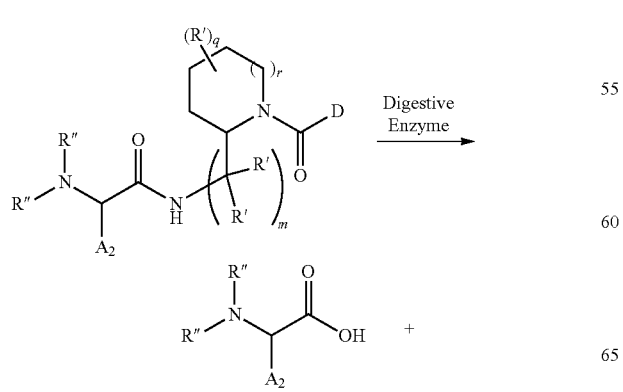

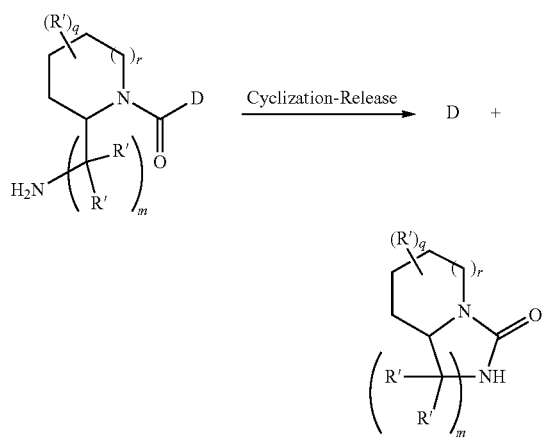

General Mechanism of Enzyme-Mediated Opioid Agonist Release from Representative Heterocyclic Fused-Ring Cyclic Urea Forming Opioid Agonist Releasing Subunit Example:

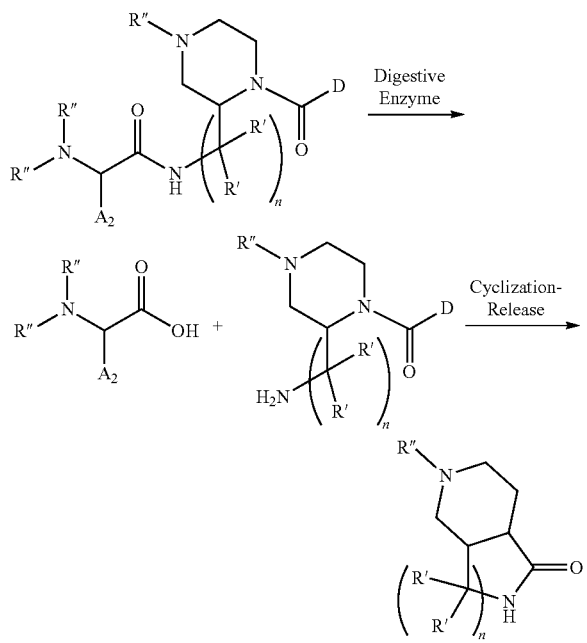

General Mechanism of Enzyme-Mediated Opioid Agonist Release from Representative Aromatic Fused-Ring Cyclic Urea Forming Opioid Agonist Releasing Subunit Examples:

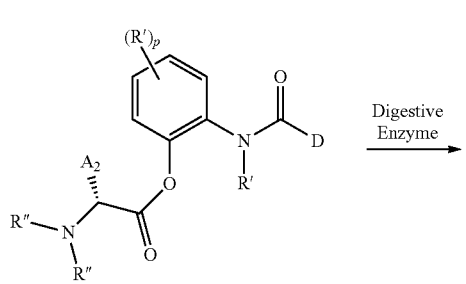

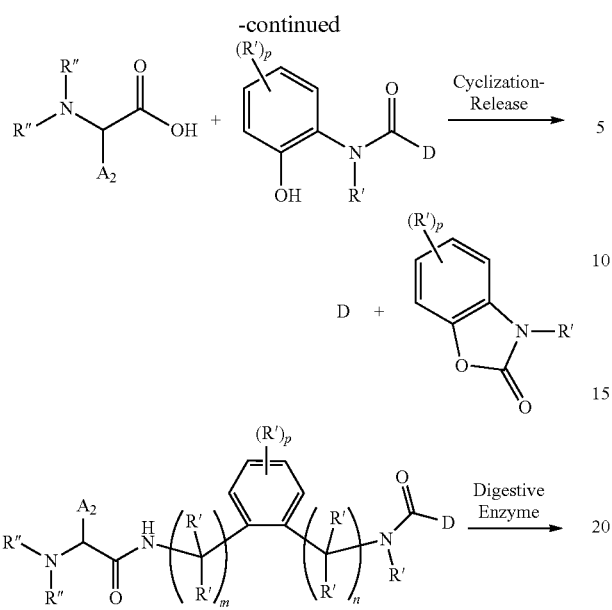
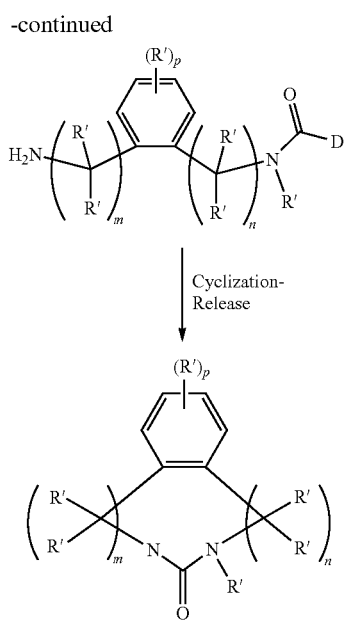
Representative Non-Limiting Opioid Agonist Releasing Subunit Examples Include, but are not Limited to:
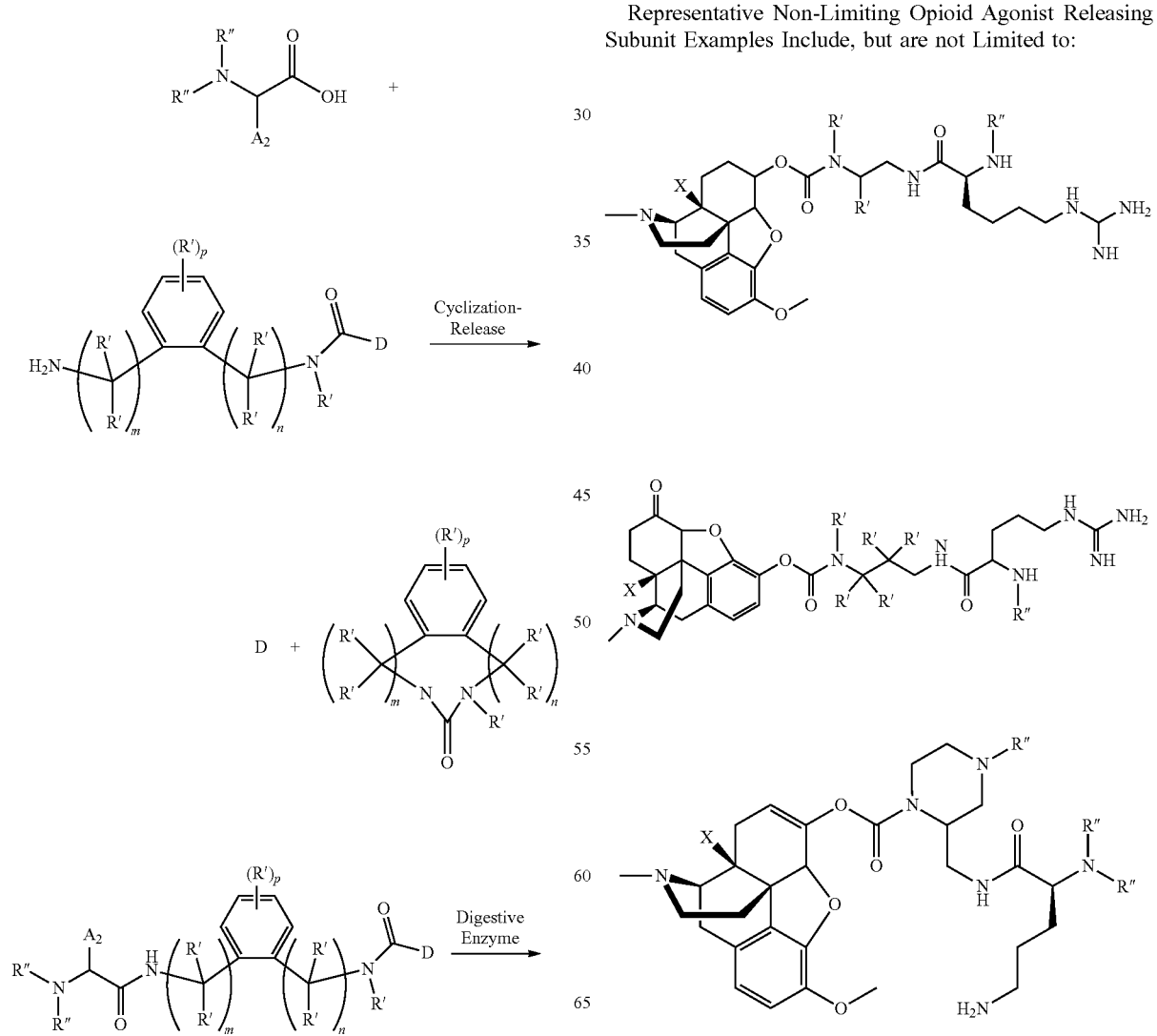

115
-continued

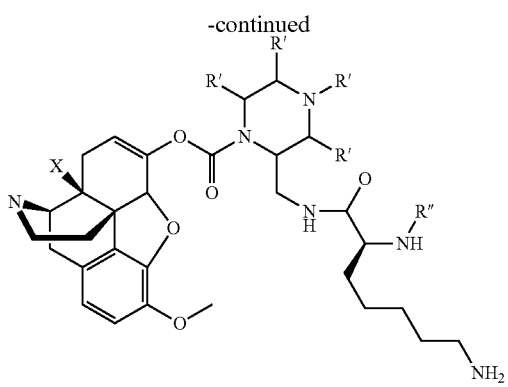

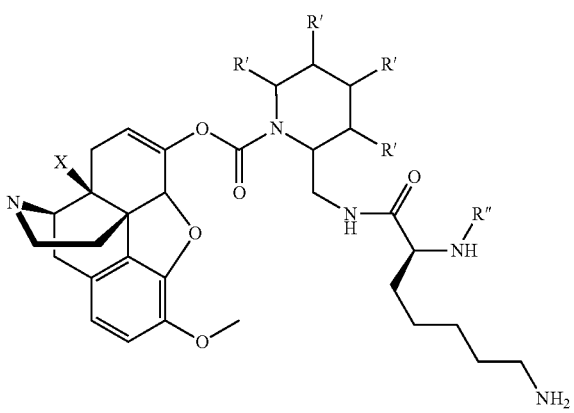

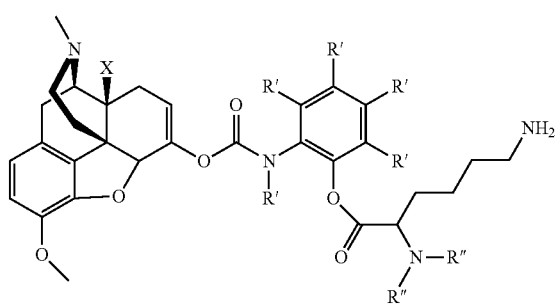

116
-continued

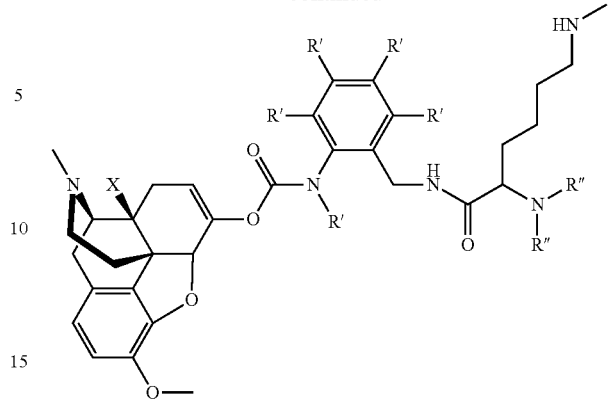

wherein:

X is hydrogen or hydroxyl;

each R' is independently hydrogen, methyl, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a bond; each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a bond.

Representative synthetic routes useful for the preparation of opioid agonist releasing substrate subunits are depicted below. The syntheses utilize readily obtained peptide-derived synthons, well-established peptide-based couplings, and known protecting group strategies.

Phenol- and enol-carbamate forming opioid attachment strategies published in the art are also employed (see, for example: U.S. Pat. Nos. 8,802,681, 8,685,916, 8,217,005, and 8,163,701, 8,685,916, 8,569,228, 8,497,237 and U.S. Patent Application Nos. 2014016935). (P) is an optional protecting group present on the terminus of the linker $Z^2$ distal to the opioid agonist releasing subunit that may be employed to enhance chemical efficiency. Purification of the resulting opioid agonist releasing subunits can be accomplished using standard purification procedures involving normal or reverse phase chromatography, crystallization, trituration, etc. The chemical identity of the opioid agonist releasing subunits can be established by LC/MS and/or NMR analyses, Relevant chemical protocols for the synthesis of opioid releasing subunits are presented below:

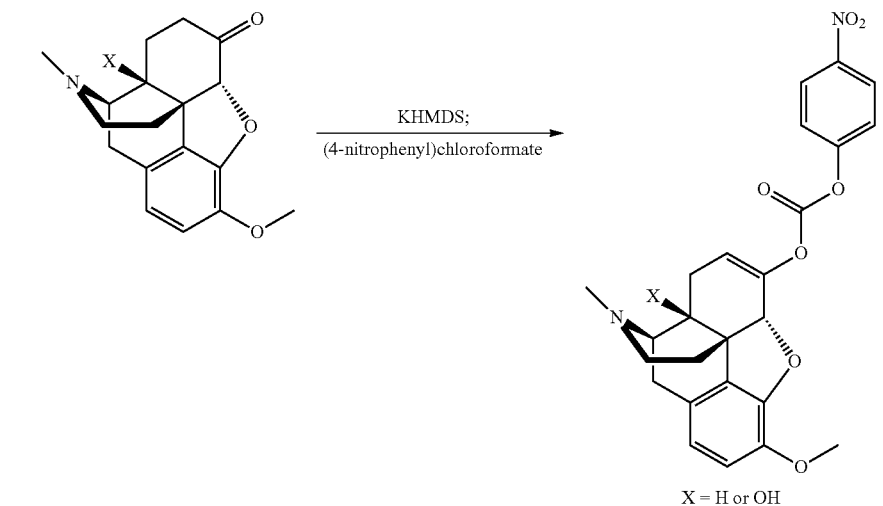
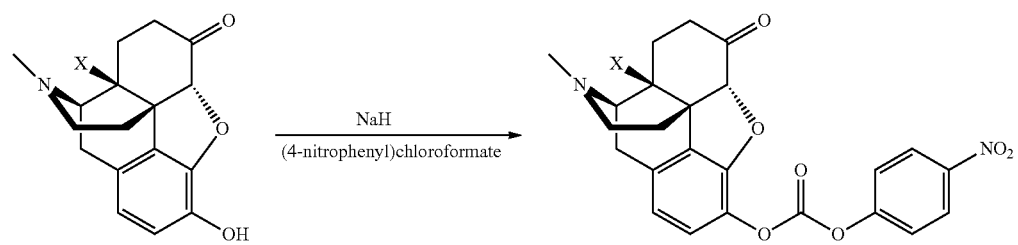
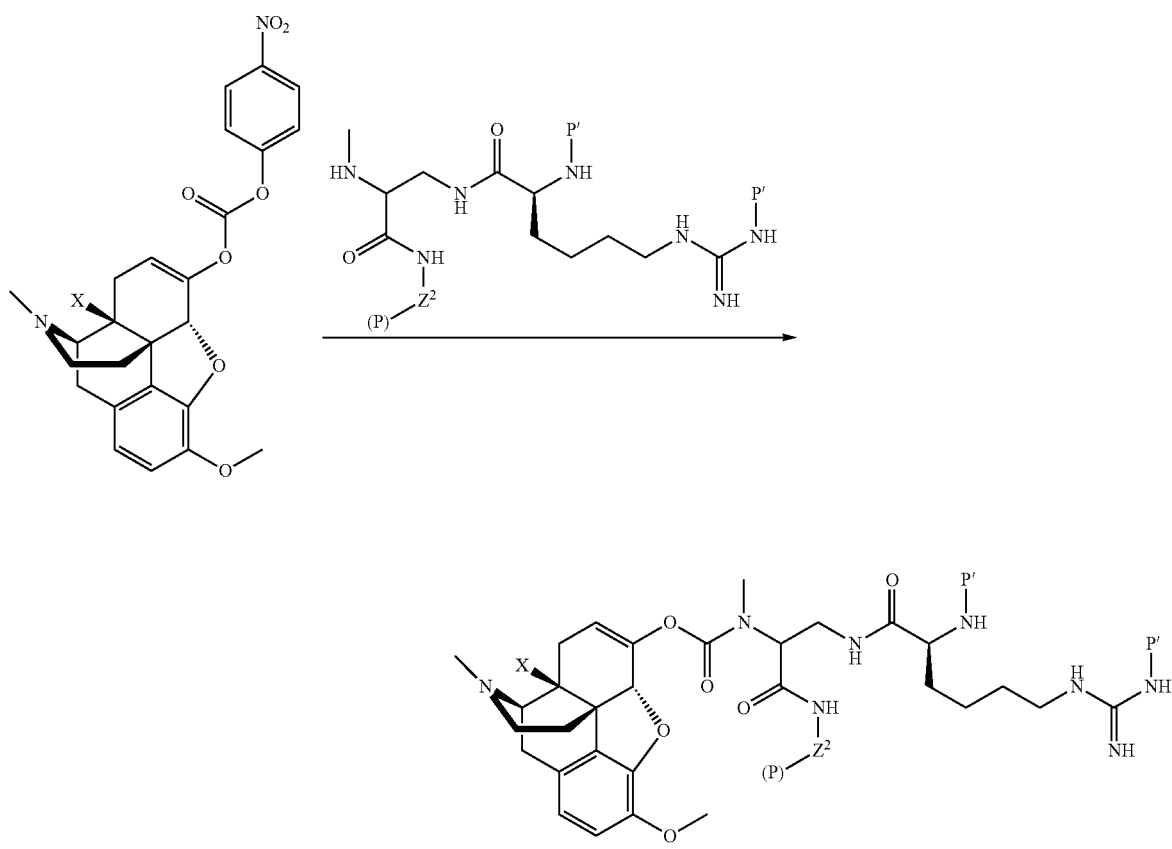

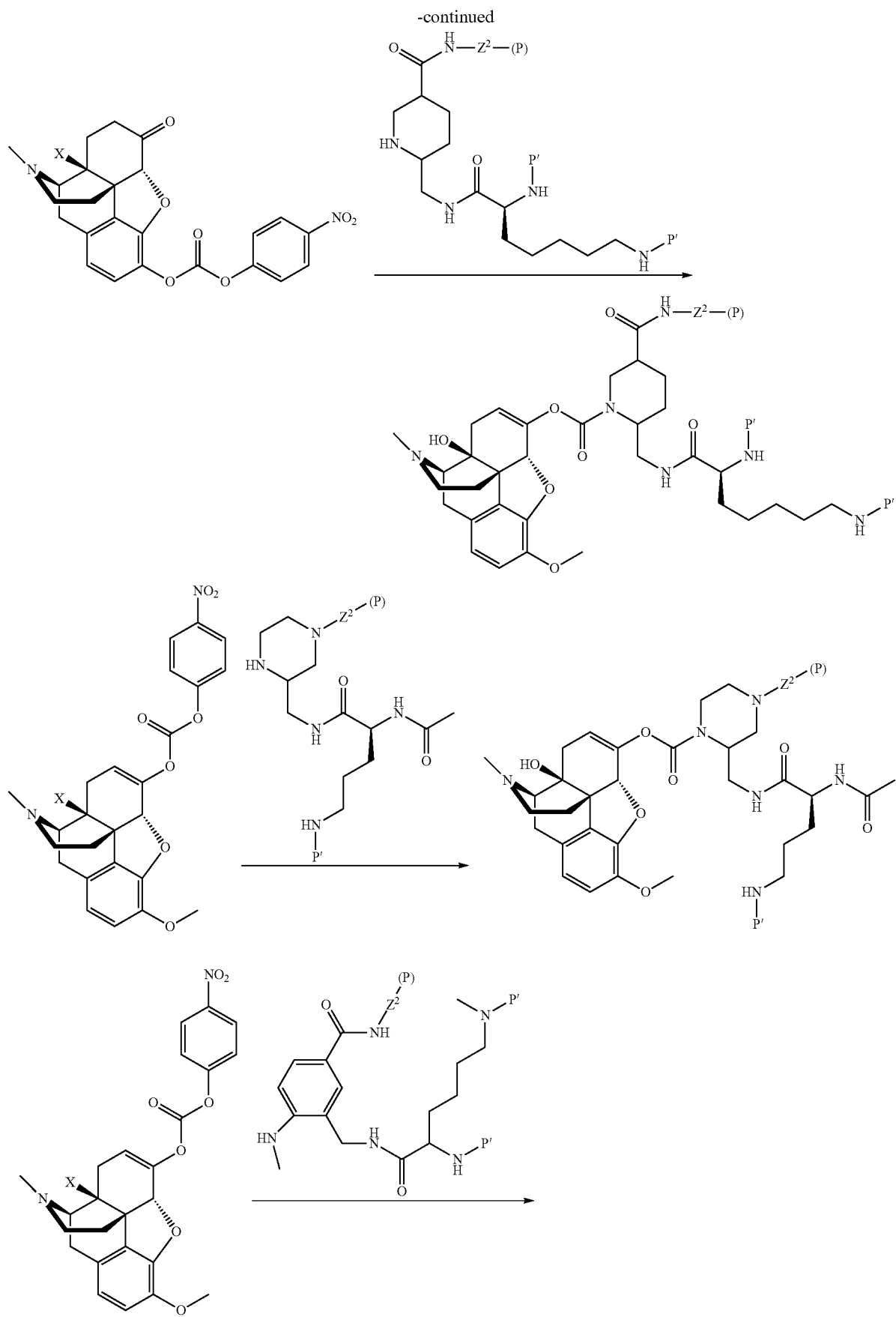

-continued

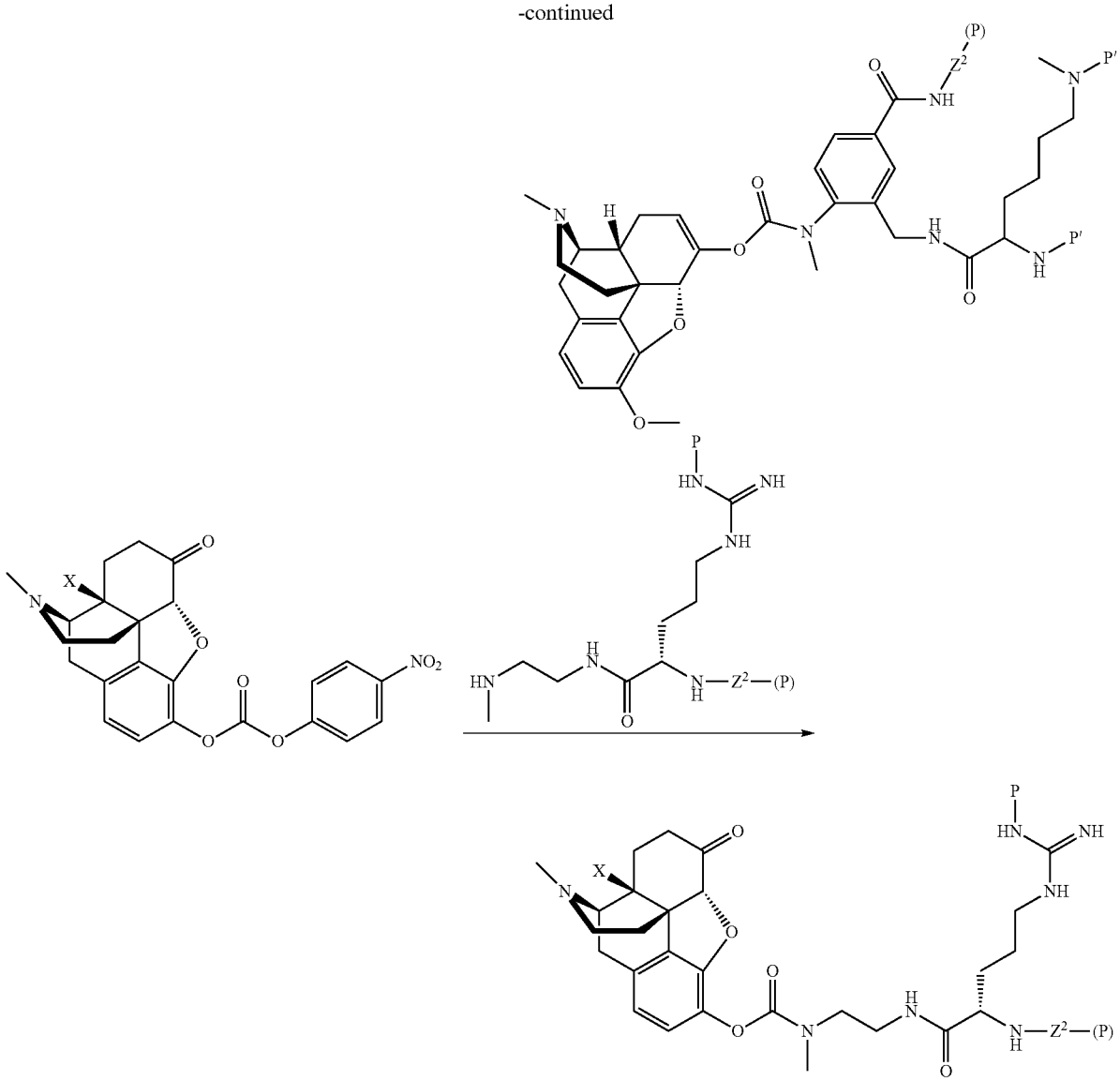

Opioid Antagonist Releasing Subunits

Polysubstrates of the invention may optionally contain none, one, or more covalently linked opioid antagonist releasing subunits. The opioid antagonist releasing subunits preferably do not substantially release the appended opioid antagonist upon oral ingestion by a subject. By design, opioid antagonist releasing subunits preferably are not digestive enzyme substrates, but may be substrates for enzymes found in blood, plasma, liver, or other systemically accessible tissues. The opioid antagonist releasing GI enzyme substrates can be designed to efficiently release the appended opioid antagonist in the systemic circulation (i.e. upon exposure to enzymes found in the plasma, liver, red blood cells, or other tissues located outside the gastrointestinal tract), and/or when potential abusers attempt to abuse polysubstrates of the invention via unintended non-oral routes (e.g. intravenous injection and/or snorting).

Further, the opioid antagonist releasing substrates can also be designed to release the appended opioid antagonist upon chemical tampering by potential abusers. Chemical tampering methods capable of hydrolyzing the opioid releasing subunits in polysubstrates of the invention to release the opioid agonist, will also efficiently liberate the opioid antagonist from the opioid antagonist releasing subunits. As a result, tampering methods aimed at liberating the opioid agonist or defeating the oral overdose protection can be effectively thwarted by the presence of opioid antagonist releasing subunits in polysubstrates of the invention. Suitable opioid antagonists include, but are not limited to, buprenorphine, cyclazocine, cyclorphan, naloxone, naltrexone, nalmephene, 6-amino-6-desoxo-naloxone, levallorphan, nalbuphine, naltrendol, naltrindole, nalorphine, norbinaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

The opioid antagonist-releasing substrates may be linked via an ester, or an alternative chemically labile functionality, to the phenol, alcohol, or ketone (e.g. enol) functionalities found in naltrexone or naloxone as illustrated below.

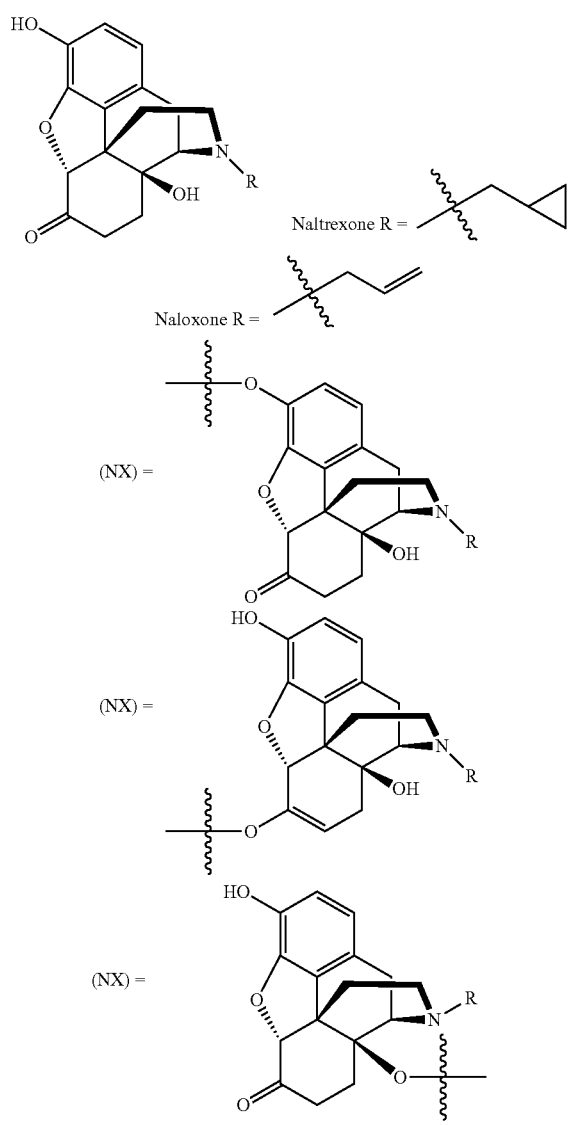

Non-limiting generic examples of opioid antagonist releasing subunits comprising chemically releasable opioid antagonists designated as NX and a linking moiety $Z^3$ are shown below:

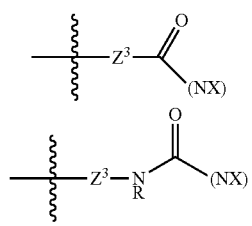

wherein:
NX is an opioid antagonist as defined above and can preferably be naltrexone or naloxone;
R is hydrogen or alkyl; and
$Z^3$ is a linking moiety as described herein.

General mechanisms of chemically-mediated opioid antagonist release from generic opioid antagonist releasing subunits are shown below:

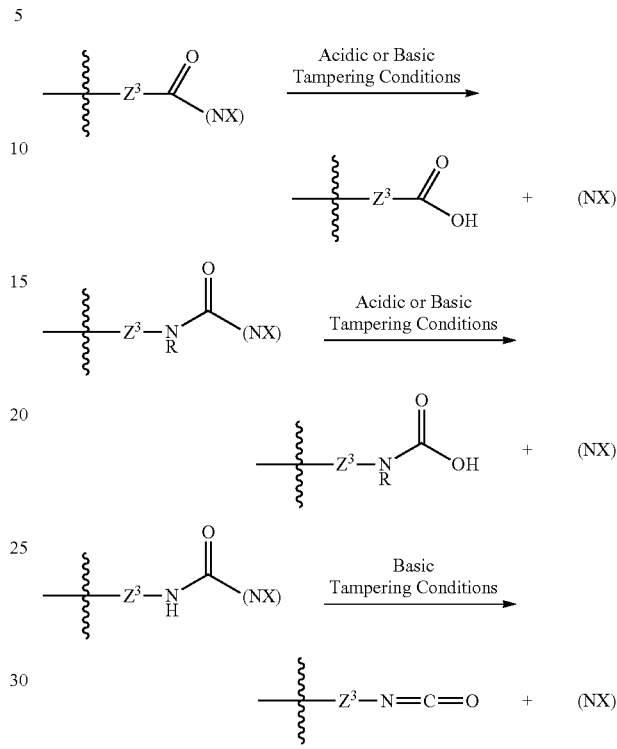

In some embodiments, the opioid antagonist releasing subunit is selected from the group consisting of:

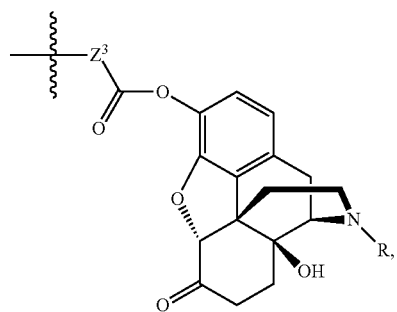

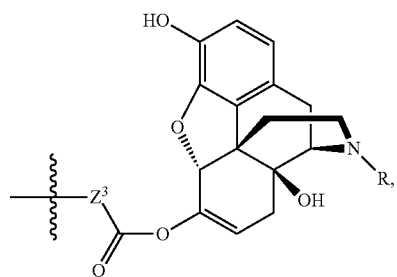

-continued

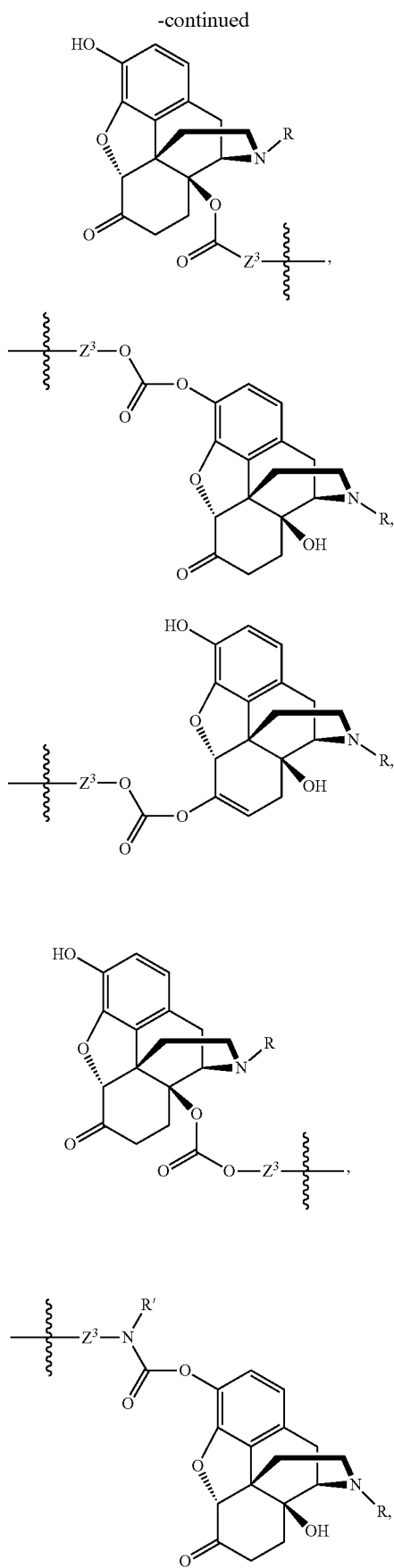

-continued

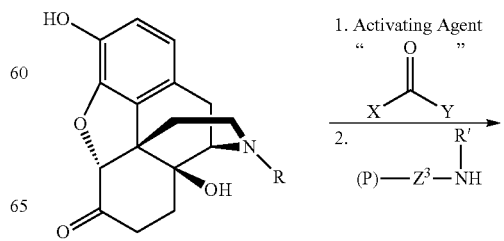

wherein:

R is cyclopropylmethyl or ally; R' is hydrogen, methyl, alkyl, aryl, substituted alkyl, or substituted aryl, acyl or substituted acyl; and $Z^3$ is a linking moiety as defined herein.

In some embodiments, the opioid antagonist is naltrexone or naloxone.

Representative synthetic routes useful for the preparation of opioid antagonist releasing subunits are depicted below. The syntheses utilize readily obtained synthons, well-established chemistry, and known protecting group strategies. Reported enol-carbamate forming opioid attachment strategies are also employed (see: U.S. Pat. Nos. 8,802,681, 8,685,916, 8,217,005, and 8,163,701, 8,685,916, 8,569,228, 8,497,237 and U.S. Patent Application Nos. 2014016935). P', a phenol protecting group used to enhance chemical efficiency, can be easily removed during the course of subsequent polysubstrate synthesis. (P) is an optional protecting group present on the terminus of the linker $Z^3$ distal to the opioid antagonist releasing subunit that may be employed to enhance chemical efficiency. Purification of the resulting opioid antagonist releasing subunits can be accomplished using standard purification procedures involving normal or reverse phase chromatography, crystallization, trituration, etc. The chemical identity of the opioid antagonist releasing subunits can be established by LC/MS and/or NMR analysis.

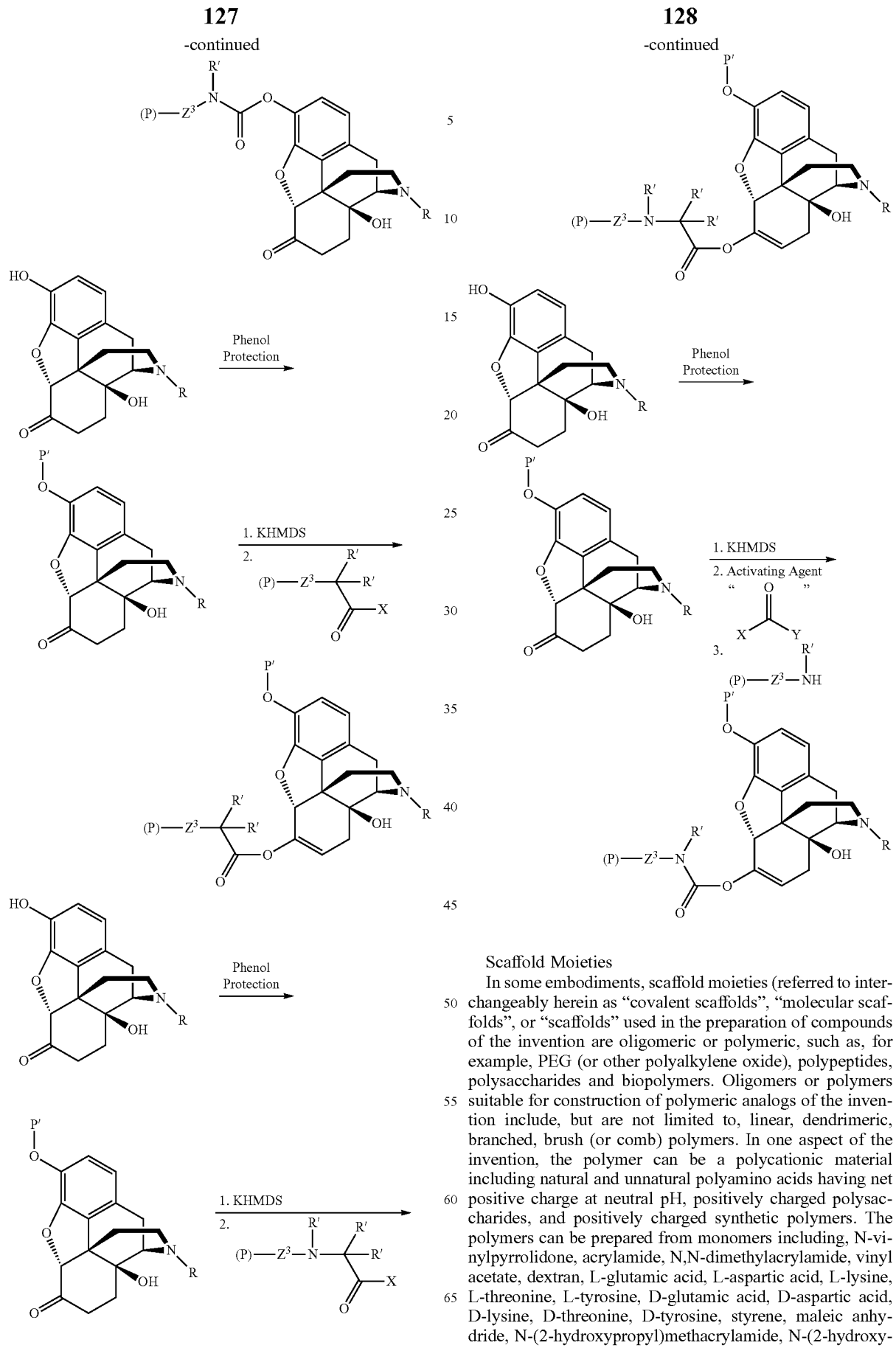

Scaffold Moieties

In some embodiments, scaffold moieties (referred to interchangeably herein as "covalent scaffolds", "molecular scaffolds", or "scaffolds" used in the preparation of compounds of the invention are oligomeric or polymeric, such as, for example, PEG (or other polyalkylene oxide), polypeptides, polysaccharides and biopolymers. Oligomers or polymers suitable for construction of polymeric analogs of the invention include, but are not limited to, linear, dendrimeric, branched, brush (or comb) polymers. In one aspect of the invention, the polymer can be a polycationic material including natural and unnatural polyamino acids having net positive charge at neutral pH, positively charged polysaccharides, and positively charged synthetic polymers. The polymers can be prepared from monomers including, N-vinylpyrrolidone, acrylamide, N,N-dimethylacrylamide, vinyl acetate, dextran, L-glutamic acid, L-aspartic acid, L-lysine, L-threonine, L-tyrosine, D-glutamic acid, D-aspartic acid, D-lysine, D-threonine, D-tyrosine, styrene, maleic anhydride, N-(2-hydroxypropyl)methacrylamide, N-(2-hydroxyethyl)methacryalte, N-(2-hydroxyethyl)methacrylamide, ethylene glycol, ethylene oxide, propylene glycol, propylene oxide, tetrahydrofuran, butylene glycol, tetrahydropyran, ethyl vinyl ether, nonpeptide polyamines such as poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly (N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan, and copolymers of the previous, including random, alternating, block, multi-block linear copolymers, and star polymers. The polymers may be isotactic, syndiotactic, or atactic as appropriate. Methods for synthesis of biopolymers and for conjugating them to biological materials are well known in the art (see, for example, published U.S. Patent Application 20040043030; U.S. Pat. Nos. 5,177,059; 6,716,821; 5,824,701; 6,664,331; 5,880,131; Kameda, Y. et al., Biomaterials 25: 3259-3266, 2004; Thanou, M. et al, Current Opinion in Investigational Drugs 4(6): 701-709, 2003; Veronese, F. M., et al., Il Farmaco 54: 497-516, 1999).

In addition, dendritic polymers may be used for preparation of compounds of the invention. Appropriate dendrimers include, but are not limited to, polyamido amine (PAMAM) (Gunatillake et al., Macromolecules, 1988, 21, 1556; U.S. Pat. No. 4,507,466), polyethyleneimine (U.S. Pat. No. 4,631,337), polypropyleneimine (U.S. Pat. No. 5,530,092), and Frechet-type dendrimers (U.S. Pat. No. 5,041,516; Hawker et al., J. Am. Chem. Soc., 1991, 113, 4583) terminated with amines, alcohols, or carboxylic acid surface groups. A recent review on dendrimer synthesis is Tomalia et al., J. Polym. Sci., Part A: Polym. Chem., 2002, 40, 2719. The polymers can be prepared by methods known in the art, or they can be obtained from commercial sources.

In one aspect of the invention, the molecular weight of the scaffold polymer portion of a polymer conjugate of the invention is greater than about 500 Daltons (Da), and more preferably is greater than about 2,000 Da. In another aspect of the invention, the polymer has a molecular weight of about 10,000 Da to about 250,000 Da. Thus, the ranges of molecular weights for the polymer portion of the conjugate can be from about 2,000 Da to about 200,000 Da, preferably about 5,000 Da to about 50,000 Da, more preferably about 7,000 Da to about 50,000 Da, or from about 10,000 Da to about 50,000 Da. The polymer backbones having an average molecular weight of about 5,000 Da, about 7,000 Da, about 10,000, about 15,000 Da, about 17,500 Da, about 20,000 Da, about 30,000 Da, about 35,000 Da, about 40,000 Da, about 45,000 Da, and about 50,000 Da are particularly preferred.

Commercially available polymers suitable for use in the invention include, but are not limited to, mPEG-NH$_2$ ($M_w$ ~10 kDa, ~20 KDa), mPEG-OH ($M_w$ ~1 kDa, 2 KDa, ~3 KDa, ~5 KDa, ~10 KDa, ~12 kDa, ~20 KDa), 3-arm PEG-triol ($M_w$ ~10 kDa glycerol core, 15 kDa glycerol core, ~20 kDa glycerol core), 4-arm PEG-tetrol ($M_w$ ~2 kDa pentaerythritol core, ~10 kDa pentaerythritol core, ~15 kDa pentaerythritol core, ~20 kDa pentaerythritol core), 8-arm PEG-octol ($M_w$ ~2 kDa hexaglycerine, ~10 kDa hexaglycerine, ~15 kDa hexaglycerine, ~20 kDa hexaglycerine, ~40 kDa hexaglycerine); such as Poly(acrylic acid), $M_w$ ~50 kDa, Poly(l-glycerol methacrylate), Poly(acrylamide-co-acrylic acid), Poly(ethylene oxide-block-propylene oxide), Poly(L-lysine) hydrobromide, Poly(styrenesulfonic acid), Poly(vinyl alcohol), Poly(vinyl amine) hydrochloride, poly (caprolactone) diol; O,O'-bis(2-carboxyethyl)dodecaethylene glycol, Poly(allyl amine), Poly(antholesulfonic acid, sodium salt), Poly(caprolactone) triol 1,1,1-tris(hydroxymethyl)propane core, Poly(di(ethylene glycol) phthalate) diol, Poly(di(ethylene glycol)/trimethylolpropane-alt-adipic acid), polyol, PEG-bis(3-aminopropyl) terminated, PEG-bis (carboxymethyl) ether $M_w$ ~250 Da, PEG-bis(carboxymethyl) ether $M_w$ ~600 Da, PEG-block-PPG-block-PEG diol ($M_w$ ~1,100 Da, ~1,900 Da, ~2,000 Da, ~2,800 Da, ~2,900 Da, ~4,400 Da, ~5,800 Da, ~8,400 Da, ~14,600 Da), PEG-ran-PPG diol ($M_w$ ~2,500 Da, ~12,000 Da, ~970 Da, ~1,700 Da, ~3,900 Da), PEG-tetrahydrofurfuryl ether, Poly(2-hydroxyethyl methacrylate), Polyoxyethylene bis(amine) $M_w$ ~2,000 Da, Polyoxyethylene bis(amine) $M_w$ ~20,000 Da, PPG diol ($M_w$ ~425 Da, ~725 Da, ~1,000 Da, ~2,000 Da, ~2,700 Da, ~3,500 Da), Poly(DL-lysine) hydrobromide ($M_w$ ~1,000-4,000 Da, ~30,000-70,000 Da, ~500-2,000 Da, ~1,000-4,000 Da, ~4,000-15,000 Da, ~15,000-30,000 Da, ~30,000-70,000 Da), Poly(D-lysine) hydrobromide ($M_w$ ~1,000-4,000 Da, ~4,000-15,000 Da, ~15,000-30,000 Da, ~30,000-70,000 Da), Poly(L-tyrosine) $M_w$ ~10,000-40,000 Da, Poly-(L-serine) $M_w$ ~5,000-10,000 Da, Poly(L-threonine) $M_w$ ~5,000-15,000 Da, PAMAM Dendrimer G(0)-NH$_2$, ethylenediamine core (surface groups: 4, 8, 16, 32, or 64), PAMAM Dendrimer G(2)-OH, ethylenediamine core (surface groups: 16, 32, 64), DAB-AM-4, polypropyleneimine tetraamine dendrimer (surface groups: 4, 8, 16, 32, 64), PAMAM-tris(hydroxymethyl)amidomethane dendrimer, Generation 2, ethylenediamine core (surface groups: 48), PAMAM-tris(hydroxymethyl)amidomethane dendrimer, Generation 3, ethylenediamine core (surface groups: 96), PAMAM-succinamic acid dendrimer, ethylenediamine core, Generation 2 (surface groups: 16), Amino-dPEG$_2$™ t-butyl ester, Amino-dPEG$_4$™ t-butyl ester, Amino-dPEG$_8$™ t-butyl ester, Amino-dPEG$_{12}$™ t-butyl ester, Amino-dPEG$_{24}$™ t-butyl ester, m-dPEG$_4$™ amine, m-dPEG$_{12}$™ amine, m-dPEG$_{24}$™ amine, Hydroxy-dPEG$_4$™ t-butyl ester, Hydroxy-dPEG$_8$™ t-butyl ester, m-dPEG$_{11}$™ alcohol, dPEG$_{12}$™ diol, Mono-N-t-boc-amido-dPEG$_3$™-amine, Mono-N-t-boc-amido-dPEG$_{11}$™-amine, Mono-N-t-CBZ-amido-dPEG$_3$™-amine, N-t-boc-amido-dPEG$_4$™ alcohol, N-t-boc-amido-dPEG$_{12}$™ alcohol, Bis-dPEG$_5$™ acid, Bis-dPEG$_7$™ acid, Bis-dPEG$_5$™ half benzyl half acid, Bis-dPEG$_9$™ half benzyl half acid, N-Fmoc-amido-dPEG$_2$™ acid, N-Fmoc-amido-dPEG$_4$™ acid, N-Fmoc-amido-dPEG$_8$™ acid, N-Fmoc-amido-dPEG$_{12}$™ acid, N-Fmoc-amido-dPEG$_{24}$™ acid, N—CBZ-amido-dPEG$_4$™-acid, N—CBZ-amido-dPEG$_8$™-acid, N—CBZ-amido-dPEG$_{12}$™ M-acid, N—CBZ-amido-dPEG$_{24}$™-acid, N-t-boc-amido-dPEG$_4$™-acid, and the like.

Non-limiting examples of polymers for use in the present invention include: polyesters, polyethers, poly(orthoesters), poly(vinyl alcohols), polyamides, polycarbonates, polyacrylamides, polyalkylene glycols, polyalkylene oxides, polyalkylene terephthalates, polyolefins, polyvinyl ethers, polyvinyl esters, polyvinyl halides, polyvinylpyrrolidone, polyglycolides, polysiloxanes, polylactides, polyurethanes, polyethylenes, polyanhydrides, polyhydroxyacids, polypropylfumerates, polycaprolactones, polyacetals, polyurethanes, polyphosphazenes, polyacrylates, polymethacrylates, polycyanoacrylates, polyureas, polystyrenes, polyamines, olefinic polymers derived from metatheses reactions with functionalized monomers, and block- or co-polymers thereof.

Non-limiting examples of biopolymers for use in the present invention include: polyesters such as polyhydroxyalkanoates, polylactic acid and the like; proteins such as silks, collagens, gelatins, elastin, resilin, adhesives, polyamino acids, soy, zein, wheat gluten, casein, serum albumin and the like; polysaccharides such as xanthan, dextran, gellan, levan, curd ian, polygalactosamine, cellulose, pullulan, elsinan, yeast glucans, starch, agar, alginate, carrageenan, pectin, konjac, and various gums (e.g. guar), chitin, chitosan, hyaluronic acid, and the like; lipids/surfactants such as acetoglycerides, waxes, emulsions, and the like; polyphenols such as lignin, tannin, humic acid and the like; specialty polymers such as shellac, poly-gamma-glutamic acid, natural rubbers, synthetic rubbers from natural fats, and the like. Also included are chemically modified versions (to enhance solubility/functionality in the drug product formulation, resist digestion/degradation, facilitate chemical modification with antagonist synthons, etc.) of the above biopolymers.

In one aspect of the invention, the polymer is a "charged polymer" wherein the polymer can have one or more charged groups. Charged polymers can include a wide range of species, including polycations and their precursors (e.g., polybases, polysalts, etc.), polyanions and their precursors (e.g., polyacids, polysalts, etc.), polymers having multiple anionic and cationic groups (e.g., polymers having multiple acidic and basic groups such as are found in various proteins), ionomers (charged polymers in which a small but significant proportion of the constitutional units carry charges), and so forth. Typically, the number of charged groups is so large that the polymers are soluble in polar solvents (particularly water) when in ionically dissociated form (also called polyions). Some charged polymers have both anionic and cationic groups (e.g., proteins) and may have a net negative charge (e.g., because the anionic groups contribute more charge than the cationic groups—referred to herein as polyanions), a net positive charge (e.g., because the cationic groups contribute more charge than the anionic groups—referred to herein as polycations), or may have a neutral net charge (e.g., because the cationic groups and anionic groups contribute equal charge). In this regard, the net charge of a particular charged polymer may change with the pH of its surrounding environment. Charged polymers containing both cationic and anionic groups may be categorized herein as either polycations or polyanions, depending on which groups predominate.

Specific examples of suitable polycations may be selected, for instance, from the following: polyamines, including polyamidoamines, poly(amino methacrylates) including poly(dialkylaminoalkyl methacrylates) such as poly(dimethylaminoethyl methacrylate) and poly(diethylaminoethyl methacrylate), poly vinylamines, polyvinylpyridines including quaternary polyvinylpyridines such as poly (N-ethyl-4-vinylpyridine), poly (vinylbenzyltrimethylamines), polyallylamines such as poly (allylamine hydrochloride) (PAH) and poly (diallyidialklylamines) such as poly (diallyidimethylammonium chloride), spermine, spermidine, hexadimethrene bromide(polybrene), polyimines including polyalkyleneimines such as polyethyleneimines, polypropyleneimines and ethoxylated polyethyleneimines, basic peptides and proteins, including histone polypeptides and homopolymer and copolymers containing lysine, arginine, ornithine and combinations thereof including poly-L-lysine, poly-D-lysine, poly-L,D-lysine, poly-L-arginine, poly-D-arginine, poly-D,L-arginine, poly-L-ornithine, poly-D-ornithine, and poly-L,D-ornithine, gelatin, albumin, protamine and protamine sulfate, and polycationic polysaccharides such as cationic starch and chitosan, as well as copolymers, derivatives and combinations of the preceding, among various others. The preferred polymers for use in the invention include poly(d-glutamic acid), poly(dl-glutamic acid), poly(l-aspartic acid), poly(d-aspartic acid), poly (dl-aspartic acid), poly(l-lysine), poly(d-lysine), poly(dl-lysine), and copolymers of the polyamino acids, and the polymers of the N-methyl derivatives of the amino acids. Other preferred polymers include polyethylene glycol (PEG), as well as poly(2-hydroxyethyl 1-glutamine), chitosan, carboxymethyl dextran, hyaluronic acid, human serum albumin and alginic acid.

Specific examples of suitable polyanions may be selected, for instance, from the following: polysulfonates such as polyvinylsulfonates, poly(styrenesulfonates) such as poly (sodium styrenesulfonate) (PSS), sulfonated poly(tetrafluoroethylene), sulfonated polymers such as those described in U.S. Pat. No. 5,840,387, including sulfonated styrene-ethylene/butylene-styrene triblock copolymers, sulfonated styrenic homopolymers and copolymers such as a sulfonated versions of the polystyrene-polyolefin copolymers described in U.S. Pat. No. 6,545,097 to Pinchuk et al., which polymers may be sulfonated, for example, using the processes described in U.S. Pat. Nos. 5,840,387 and 5,468,574, as well as sulfonated versions of various other homopolymers and copolymers, polysulfates such as polyvinylsulfates, sulfated and non-sulfated glycosaminoglycans as well as certain proteoglycans, for example, heparin, heparin sulfate, chondroitin sulfate, keratan sulfate, dermatan sulfate, polycarboxylates such as acrylic acid polymers and salts thereof (e.g., ammonium, potassium, sodium, etc.), for instance, those available from Atofina and Polysciences Inc., methacrylic acid polymers and salts thereof (e.g., EUDRAGIT, a methacrylic acid and ethyl acrylate copolymer), carboxymethylcellulose, carboxymethylamylose and carboxylic acid derivatives of various other polymers, polyanionic peptides and proteins such as glutamic acid polymers and copolymers, aspartic acid polymers and copolymers, polymers and copolymers of uronic acids such as mannuronic acid, galatcuronic acid and guluronic acid, and their salts, alginic acid and sodium alginate, hyaluronic acid, gelatin, and carrageenan, polyphosphates such as phosphoric acid derivatives of various polymers, polyphosphonates such as polyvinylphosphonates, polysulfates such as polyvinylsulfates, as well as copolymers, derivatives and combinations of the preceding, among various others.

Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, silks, collagen, elastin, resilin, polyamino acids, soy, wheat gluten, and casein.

Non-limiting examples of polyesters include polylactic acid, polyglycolic acid, poly(lactide-co-glycolide), poly(e-caprolactone), polydioxanone, poly(ethylene terephthalate), poly(malic acid), poly(tartronic acid), polyphosphazenes, poly(orthoester), poly(valeric acid), poly(buteric acid), polyhydroxybutyrate, polyhydroxyvalerate, polyanhydride, and copolymers of the monomers used to synthesize any of the above-mentioned polymers, e.g., poly(lactic-co-glycolic acid) (PLGA) or the copolymer of polyhydroxy butyrate with hydroxyvaleric acid.

Non-limiting examples of polyesters include polylactic acid, polyglycolic acid, poly(lactide-co-glycolide), poly(ε-caprolactone), polydioxanone, poly(ethylene terephthalate), poly(malic acid), poly(tartronic acid), polyphosphazenes, poly(orthoester), poly(valeric acid), poly(buteric acid), polyhydroxybutyrate, polyhydroxyvalerate, polyanhydride, and copolymers of the monomers used to synthesize any of the above-mentioned polymers, e.g., poly(lactic-co-glycolic acid) (PLGA) or the copolymer of polyhydroxy butyrate with hydroxyvaleric acid.

Polyethers and poly(orthoesters) can also be used in preparing the polymer conjugate for use in the present invention. These polymers can be incorporated into multi-blocks resulting in block polymers having diverse degradation rates, mechanical strengths, porosities, diffusivities, and inherent viscosities. Examples of polyethers include polyethylene glycol and polypropylene glycol. An example of a multi-block copolymer is poly(ether ester amide). Additionally, triblock copolymers of poly(orthoesters) with various poly(ethylene glycol) contents are useful for their stability in water/oil (w/o) emulsions. Other useful block copolymers include diblock copolymers of poly (lactic-co-glycolic acid) and poly(ethylene glycol) (PEG), triblock copolymers of PEG-PLGA-PEG, copolymers of PLGA and polylysine, and poly (ester ether) block copolymers.

In one aspect of the invention, the polymer is poly (ethylene glycol) (PEG) or a related poly(alkylene glycol). The term PEG includes poly(ethylene glycol) in any its forms, including linear forms (e.g., alkoxy PEG or bifunctional PEG), branched or multi-arm forms (e.g., forked PEG or PEG attached to a polyol core), pendant PEG, and the like. The general formula of PEG is —$CH_2CH_2O$—($CH_2CH_2O)_n$—$CH_2CH_2$— wherein n is from about 0 to about 500, typically from about 2 to about 200. Similar polymers can also be derived from polypropylene glycol and related poly(alkylene) glycols.

Multi-armed or branched PEG molecules, such as those described in U.S. Pat. No. 5,932,462 can also be used as the PEG polymer. Generally speaking, a multi-armed, branched, or star or dendrimeric polymers possess two or more polymer arms extending from a central branch point that is covalently attached, either directly or indirectly via intervening connecting atoms, to one or more active moieties such as an opioid agonist, antagonist, or digestive enzyme inverse substrate. It is understood by those skilled in the art that the term poly(ethylene glycol) or PEG represents or includes all the above forms of PEG or poly(alkylene glycols).

Preferred scaffolds selected from those listed above most useful for the construction of polysubstrates of the invention (i) are readily commercially available, (ii) comprise a sufficient number and type of chemically accessible functionalities (e.g. carboxylate, amine, thiol, alcohol, isocyanate, etc.), (iii) efficiently undergo the requisite coupling chemistry to attach the desired numbers of non-opioid releasing, opioid agonist releasing, and optional opioid antagonist releasing subunits, and (iv) result in polysubstrate products with the desired physicochemical (e.g. solubility, stability, release of opioid antagonist upon chemical tampering in vitro, etc.) and biological (e.g. selective enzymatic release of opioid agonist in vivo, overdose protection via enzyme saturation, release of opioid antagonist in the systemic circulation, etc.) profiles.

Compounds of the Disclosure

The disclosure provides for compositions containing two or more polysubunit molecules that comprise subunits that interact with gastrointestinal (GI) or digestive enzymes. In some cases, such a composition can be specifically hydrolyzed by at least one of any of the GI enzymes disclosed herein. The GI enzyme can be, for example, pepsin, trypsin, chymotrypsin, colipase, elastase, aminopeptidases, dipeptidylaminopeptidase IV, tripeptidase, enteropeptidases, carboxypeptidases, dipeptidal aminopeptidases, pteroyl polyglutamate hydrolyase, gamma-glutamyl transferase, aminoaspartate aminopeptidases, amino-oligopeptidase, membrane Gly-Leu peptidase, and zinc stable Asp-Lys peptidase.

An example of a GI enzyme subunit is a protease substrate, such as a trypsin substrate, or a chymotrypsin substrate.

As used herein, the term "trypsin substrate" refers to any agent capable of being hydrolyzed by trypsin, and includes salts of trypsin substrates. The ability of an agent to be a substrate for trypsin can be measured using assays well known in the art. For example, in a typical assay, one can directly measure the rate and extent of expected hydrolysis products formed in incubations containing specified concentrations of digestive enzymes and enzyme substrates using common HPLC or spectrophotometric detection methods.

There are many trypsin substrates known in the art, and include substrates that are specific to trypsin and those that are specific to other proteases such as chymotrypsin. Trypsin substrates include natural, synthetic, and semi-synthetic compounds. The disclosure provides for trypsin substrates that are proteins, peptides, and small molecules. The disclosure also provides for trypsin substrates that are hydrolyzed via "normal" or "inverse" substrate mechanisms. A trypsin substrate can be an arginine mimic or lysine mimic. In certain embodiments, the trypsin substrate is an arginine mimic or a lysine mimic, wherein the arginine mimic or lysine mimic is a synthetic compound. As used herein, an arginine mimic or lysine mimic can include moieties capable of being recognized by, and binding to, the specificity pocket of trypsin and/or interacting with the trypsin active site functionalities. The arginine or lysine mimic can comprise a cleavable moiety. In some embodiments, cleavage of the cleavable moiety will directly, or indirectly result in release of an opioid agonist from the substrate moiety. In some cases, when supra-therapeutic doses (overdoses) are ingested, the presence of GI enzyme inhibitor subunits can saturate or inhibit the capacity of the enzyme to cleave the cleavable moieties that directly, or indirectly, release opioid agonists resulting in overdose protection.

Examples of trypsin substrates which are arginine mimics and/or lysine mimics include a cationic specificity pocket binding moiety designed to be recognized by, and bind to, the negatively charged specificity pocket of the enzyme, and a hydrolyzable functionality that is cleaved by the active site of the enzyme. Cationic specificity pocket binding moieties include, but are not limited to, alkyl-amines, alkylguanidines, alkylamidines, arylguanidines, benzamidines, benzylamines, naphthylamidines, naphthylguanidines, naphthylamines, and the like. Hydrolyzable functionalities include, but are not limited to, amide, ester, carbamate, thioester, carbonate, and the like.

In one aspect of the invention, the opioid agonist releasing GI enzyme substrate subunit(s) and the GI enzyme inhibitor subunit(s) are covalently linked via a covalent bond, an atom, or via a scaffold, for example a polymeric, oligomeric, or molecular scaffold. The opioid releasing and non-opioid releasing subunits can be linked directly, or indirectly, via a wide range of atoms or linkers as described herein. The particular linkages and linkage chemistries employed will depend upon the specific functional groups available on the opioid releasing and the enzyme inhibiting subunits, and the available complimentary functional groups present on the linker or scaffold moiety components. The presence of suitable functional groups within the opioid releasing and enzyme inhibiting subunits, and scaffold moiety components, and useful chemistry for linking strategies involving these suitable functional groups can be readily determined by one skilled in the art based upon the guidance presented herein. Particular examples of unimolecular compositions comprised of linkers (Z), opioid releasing subunits, enzyme inhibiting subunits, and opioid antagonist subunits, and atomic, molecular, oligomeric or polymeric scaffolds are disclosed herein.

In another aspect of the invention, compositions of the invention are not required to be, and preferably are not, orally bioavailable. Thus, in one aspect of the invention, a composition in accordance with the invention will demonstrate low (from about 0% to about 30%) oral bioavailability. Oral bioavailability can be assessed using suitable in-vivo or in-vitro assays. Thus, a polysubstrate of the invention will possess oral bioavailability of about or less than about 0%, 0.25%, 0.5%, 0.75%, 1%, 2%, 5%, 10%, 15%, 25%, or 30%, when measured in a suitable model.

Compositions of the invention are not required to have, and preferably do not have opioid agonist activity. Thus, in one aspect of the invention, a composition in accordance with the invention will retain from about 0% to about 30% of the specific agonist activity of the delivered opioid agonist compound. Such activity may be determined using suitable in-vivo, or in-vitro functional assays, depending upon the known activity of the particular opioid parent compound. For example, a functional opioid receptor based assay, or an in vivo hot-plate or tail-flick analgesia assay can be used to assess the level of agonist activity of the polymer conjugates of the invention. Thus, compositions of the invention will possess a specific activity of about 0% or less than about 0.25%, 0.5%, 0.75%, 1% 2%, 5%, 10%, 15%, 25%, 30% or 50% relative to that of the delivered opioid agonist, when measured in a suitable model, such as those well known in the art.

In another aspect of the invention, compositions of the invention are not required to be, and preferably are not, able to efficiently traverse the blood-brain barrier and gain access to the central nervous system (CNS). For example, compositions of the invention may not efficiently penetrate the central nervous system. Thus, in one aspect of the invention, a composition in accordance with the invention will retain from about 0% to about 30% of the CNS penetration of the delivered opioid agonist. CNS penetration can be determined using suitable in-vivo assays. Thus, a composition of the invention will possess CNS penetration of about 0% or less than about 0.25%, 0.5%, 0.75%, 1% 2%, 5%, 10%, 15%, 25%, or 30% relative to that of the unmodified parent opioid, when measured in a suitable model, such as those well known in the art.

In one aspect, the present disclosure provides a compound represented by the structure of Formula (I):

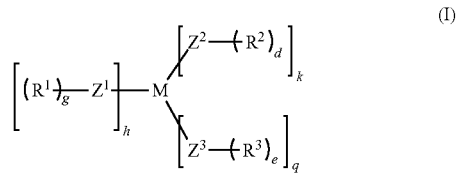

or a salt thereof, wherein:
each $R^1$ is independently a GI enzyme inhibitor subunit;
each $R^2$ is independently a GI enzyme-labile opioid agonist releasing subunit;
each $R^3$ is independently an opioid antagonist releasing subunit;
M is, an atom, or a scaffold moiety;
each $Z^1$, $Z^2$, and $Z^3$ is independently absent or a linking moiety;
each h, k, g, d, and e is independently an integer ranging from 1 to 10, 1 to 100, 1 to 1,000, 1 to 100,000, 1 to 1,000,000, or 1 to 1,000,000,000; and
q is an integer ranging from 0 to 10, 0 to 100, 0 to 1,000, 0 to 100,000, 0 to 1,000,000, or 0 to 1,000,000,000.

In some embodiments, for the compound or salt of Formula (I), M is an optionally substituted heteroalkyl group.

In some embodiments, for the compound or salt of Formula (I), M is an optionally substituted peptide.

In some embodiments, for the compound or salt of Formula (I), M is an optionally substituted peptide with from 1 to 500 amino acids. In some embodiments, for the compound or salt of Formula (I), M is an optionally substituted peptide with from 1 to 50 amino acids. In some embodiments, for the compound or salt of Formula (I), M is an optionally substituted peptide with from 1 to 10 amino acids. In some embodiments, for the compound or salt of Formula (I), M is an optionally substituted peptide with from 1 to 3 amino acids. In some embodiments, a compound or salt of Formula (I) is represented by a structure of Formula (IA), (IB), (IC), or (ID):

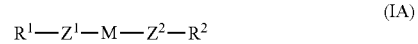

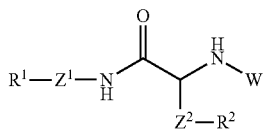

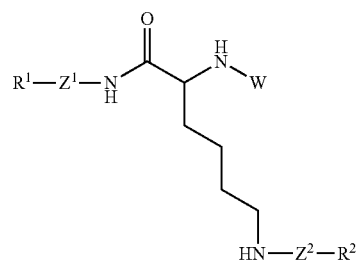

-continued (ID)

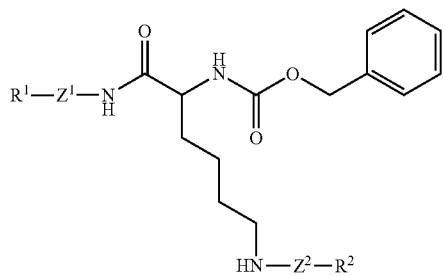

wherein M is an atom, a functional group, a substituted functional group, or a molecular scaffold, and W is selected from hydrogen, optionally substituted alkyl, optionally substituted acyl, and optionally substituted alkoxycarbonyl, or

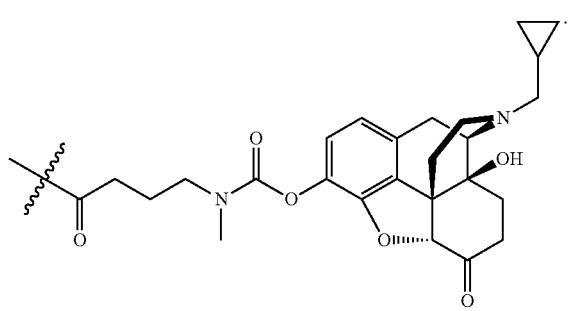

In some embodiments, the compound or salt, wherein R' is independently selected at each occurrence from a GI enzyme inhibitor. In some embodiments, for the compound or salt of Formula (I), R' at each occurrence is a serine protease inhibitor. In some embodiments, for the compound or salt of Formula (I), R' at each occurrence is a trypsin inhibitor. In some embodiments, for the compound or salt of Formula (I), each R' is independently selected from the group consisting of:

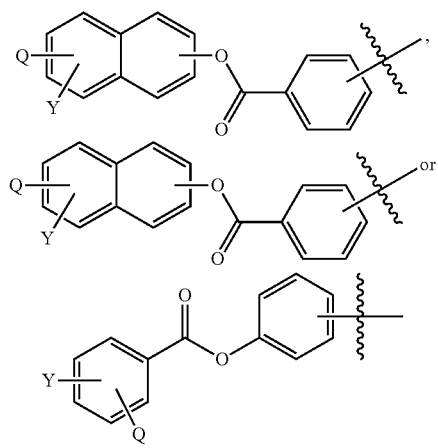

wherein:
Y is amidine, guanidine, aminomethyl, substituted amidine, substituted guanidine, substituted aminomethyl, amidinomethyl, guanidinomethyl, substituted amidinomethyl, or substituted guanidinomethyl; and Q is independently selected from hydrogen, cyano, nitro, halogen, alkyl and alkoxy.

In some embodiments, for the compound or salt of Formula (I), $R^1$—$Z^1$— is represented by the formula:

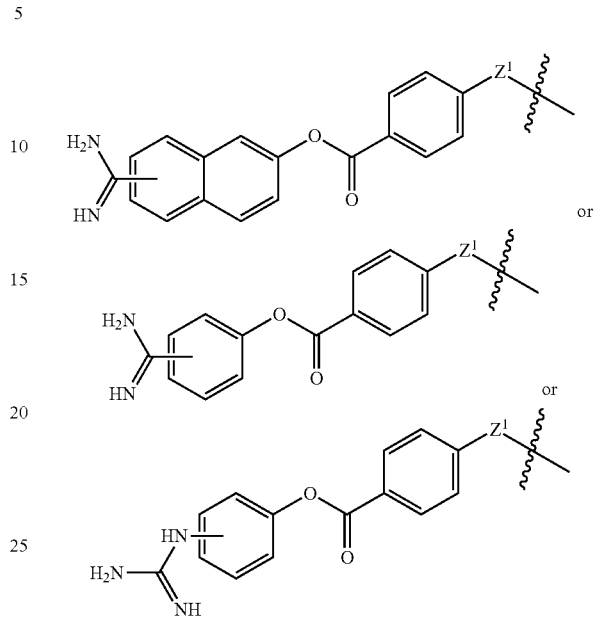

In some embodiments, for the compound or salt of Formula (I), Z' at each occurrence is selected from a cleavable or non-cleavable linker including from 2 to 15 atoms.

In some embodiments, for the compound or salt of Formula (I), $Z^1$ is —O—$CH_2$—$CH_2$—NH— or —O—$CH_2$—$CH_2$—O—.

In some embodiments, for the compound or salt of Formula (I), g, d, or e is independently selected from 1 to 20. In some embodiments, for the compound or salt of Formula (I), g, d, or e is independently selected from 1 to 10. In some embodiments, for the compound or salt of Formula (I), g, d, ore is independently selected from 1 to 3.

In some embodiments, for the compound or salt of Formula (I), $R^2$— is independently selected at each occurrence from:

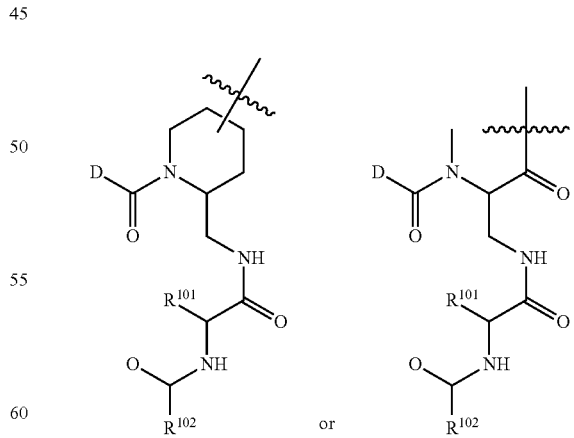

wherein:
D is an opioid agonist;
$R^{101}$ is independently selected from an amino acid side chain, or an amino acid side-chain mimic that is recognized by a GI enzyme.

$R^{102}$ is independently selected from hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic.

In some embodiments, for the compound or salt of Formula (I), $R^{101}$ is selected from an amino acid side chain and $R^{102}$ is optionally substituted alkyl. In some embodiments, for the compound or salt of Formula (I), $R^{101}$ is selected from an arginine or lysine side chain and $R^{102}$ is optionally substituted methyl. In some embodiments, for the compound or salt of Formula (I), $R^{102}$ is methyl substituted with —NH-acetyl, or dimethyl substituted with —NH-acetyl.

In some embodiments, linking moieties $Z^1$, $Z^2$, and $Z^3$ are independently represented by the general formulae:

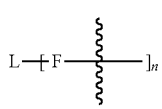

and can also be defined by

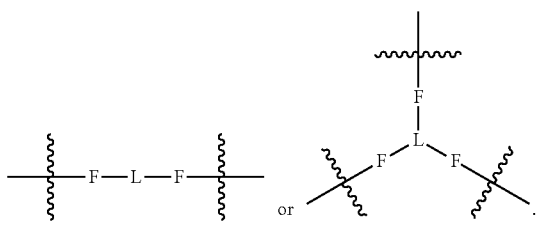

Exemplary terminal linker functionalities "F" can each or independently be as shown below:

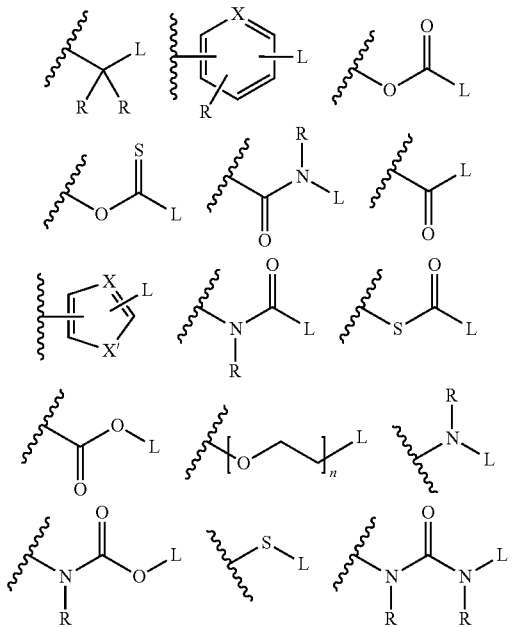

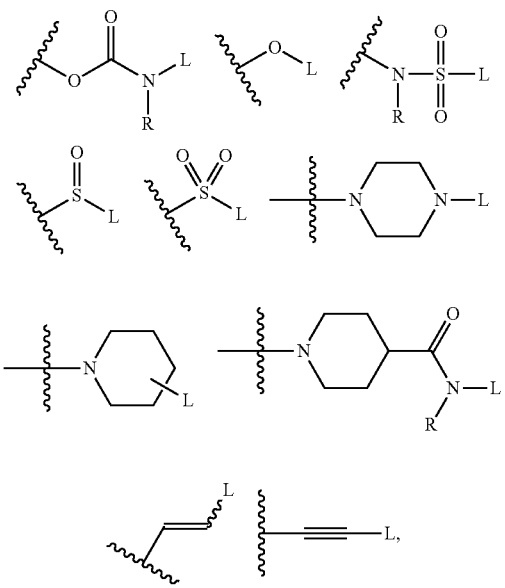

where "L" is shown in the structures of "F", illustrated above, to indicate the connectivity of F and L, and wherein:

each R is independently hydrogen, methyl, lower alkyl, aryl, or arylalkyl;

X is carbon, oxygen, or nitrogen;

L is a linear, branched, or multivalent scaffold which is alkyl, aryl, substituted alkyl, substituted aryl, heteroalkyl, substituted heteroalkyl, polyalkylene glycol, poly peptide, polyamide, polycarbamate, polyurea, or polycarbonate.

In some embodiments, L is formed of 0-100 atoms. In some embodiments, L is formed of 1-50 non-hydrogen atoms as well as additional hydrogen atoms. Such atoms may be, for example, C, N, O, P or S. In other embodiments, L may connect two or more groups comprising 1 to 50 consecutive bonds between the groups. L may have 1 to 40, 1 to 30, 1 to 20, 1 to 10, 1 to 5, 5 to 25, or 5 to 20 such consecutive bonds.

In some embodiments, for the compound or salt of Formula (I), D is selected from morphine, hydromorphone, hydrocodone, oxycodone, codeine, levorphanol, meperidine, methadone, oxymorphone, dihydrocodeine, tramadol, tapentadol, and buprenorphine. In some embodiments, for the compound or salt of Formula (I), D is represented by the formula:

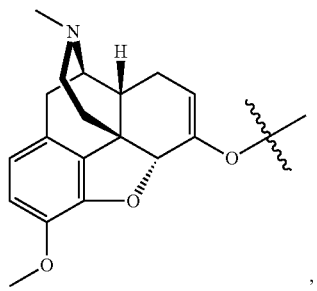

-continued

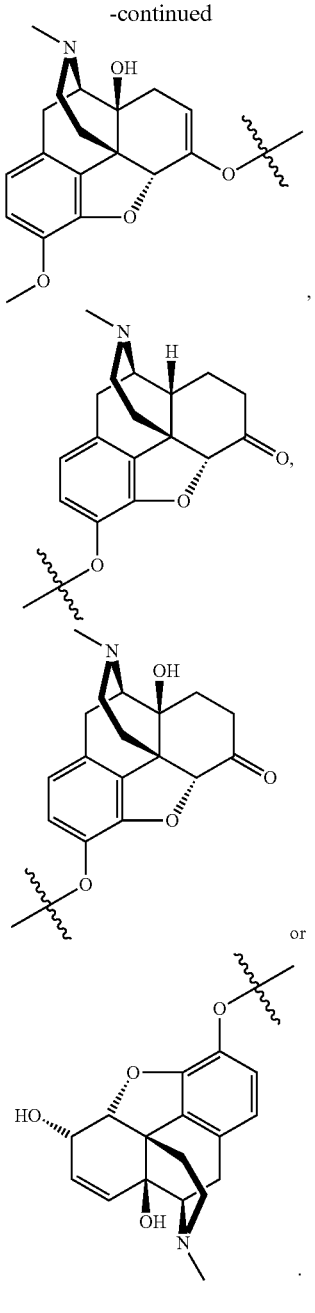

In some embodiments, for the compound or salt of Formula (I), k is selected from 1 to 20. In some embodiments, for the compound or salt of Formula (I), k is selected from 1 to 10. In some embodiments, for the compound or salt of Formula (I), k is 1 to 3.

In one aspect, the present disclosure provides a method of treating pain in a subject in need thereof, the method comprising administrating to the subject a therapeutically-effective amount of two or more compound(s) or salt(s) of Formula (I).

In one aspect, the present disclosure provides two or more compound(s) or salt(s) of Formula (I) and one or more pharmaceutically acceptable excipient(s).

In one aspect, the present disclosure provides a pharmaceutical formulation comprising two or more polysubunit molecules with each molecule comprising:
an opioid prodrug;
a gastrointestinal enzyme inhibitor; and
a scaffold moiety, wherein the opioid prodrug and the inhibitor are covalently attached to the scaffold moiety.

In one aspect, the present disclosure provides a pharmaceutical composition, the composition comprising:
Two or more polysubunit molecules each comprising GI enzyme labile opioid releasing subunit(s), and GI enzyme inhibitor subunit(s) wherein the GI enzyme labile opioid releasing subunit(s) and the GI enzyme inhibitor subunit(s) are covalently linked via a covalent bond, an atom, or a scaffold. In some embodiments the disclosure provides for polysubunit compounds comprising one GI enzyme labile opioid releasing subunit covalently linked to one GI enzyme inhibitor subunit represented by formulae II (A-X) below:

II-A

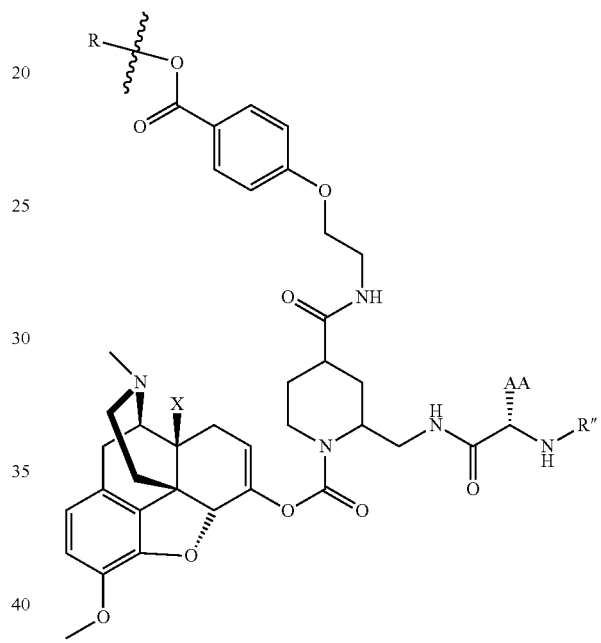

II-B

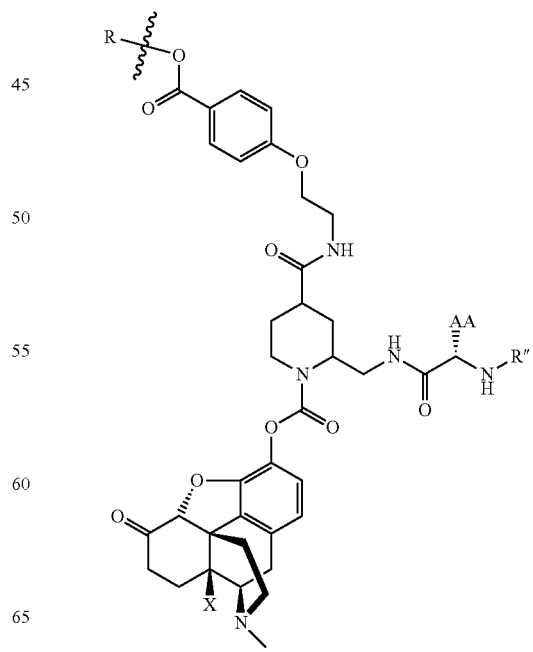

II-C
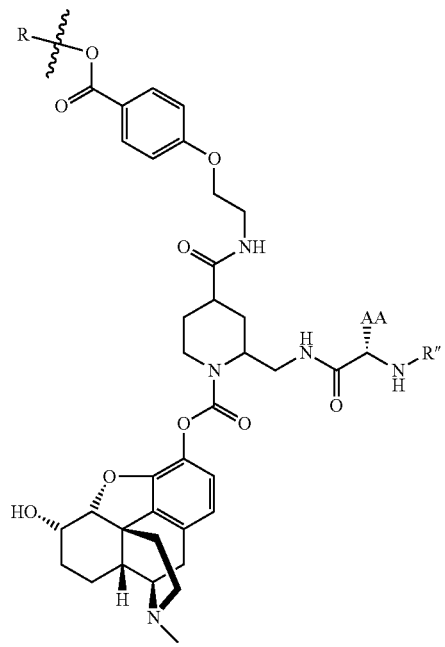
II-E
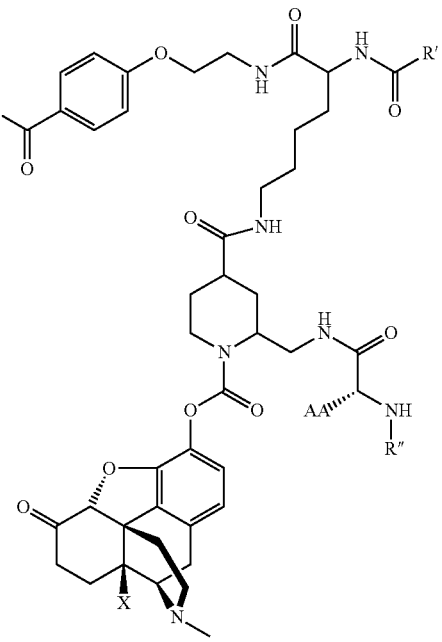
II-D
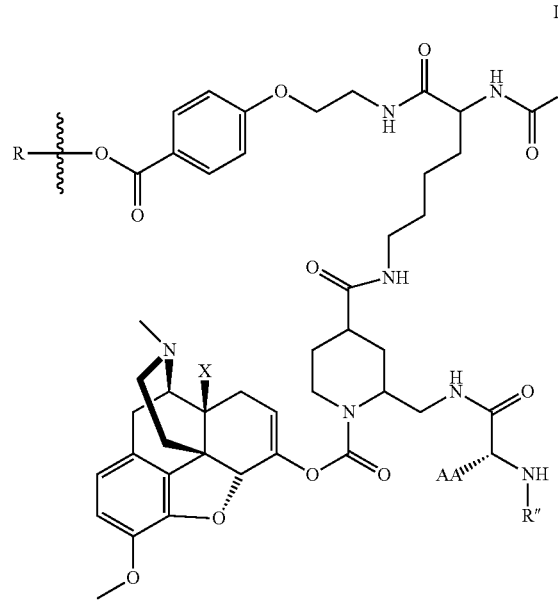
II-F

II-G
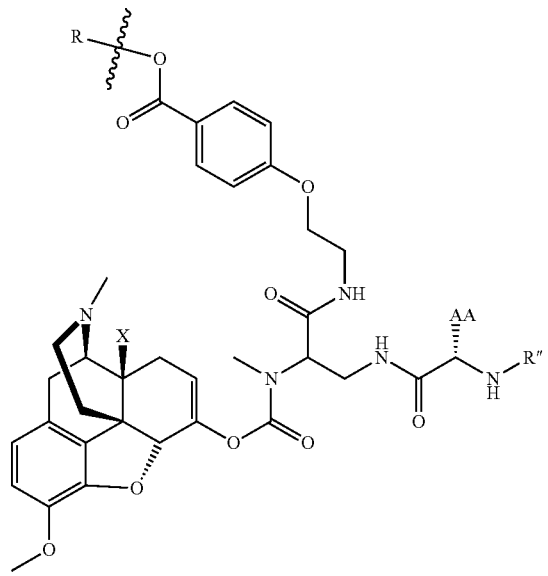
II-H
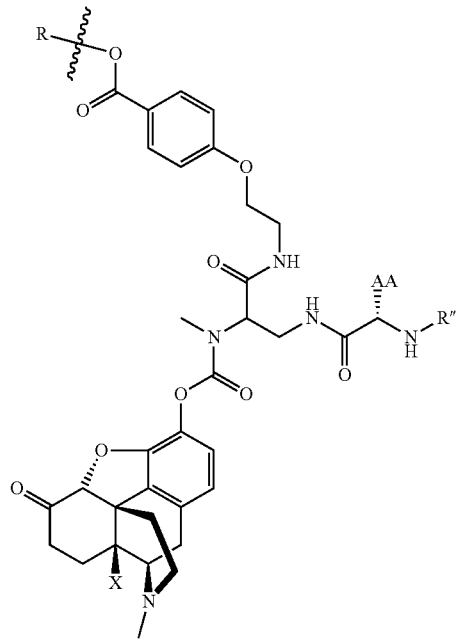
II-I
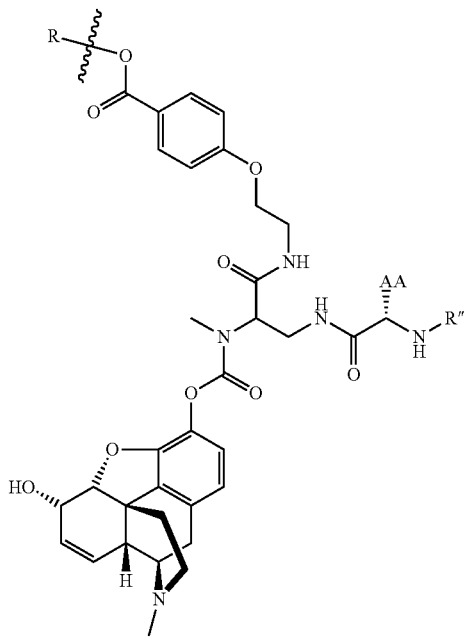
II-J
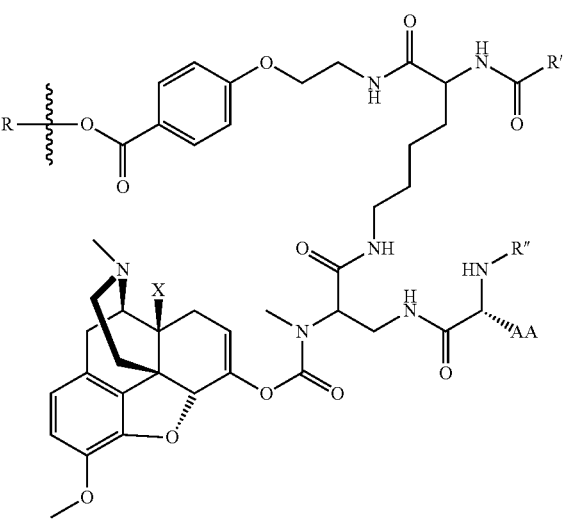

II-K
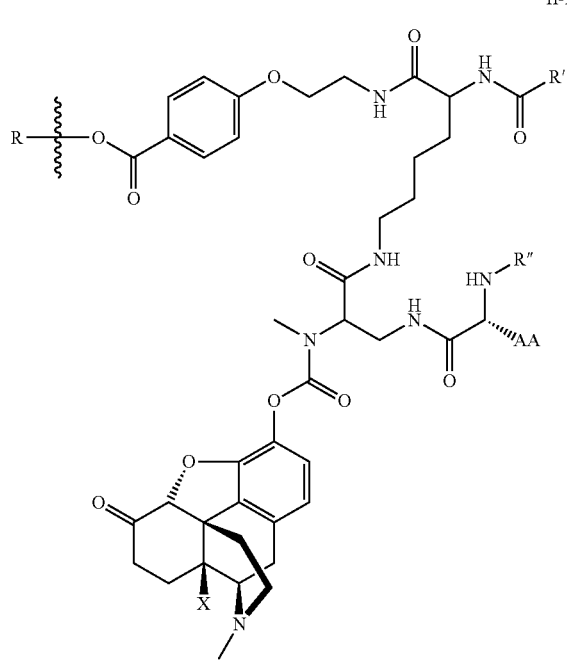
II-M
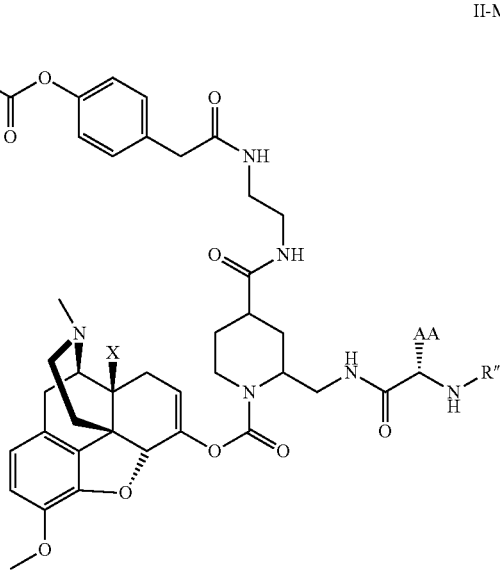
II-L
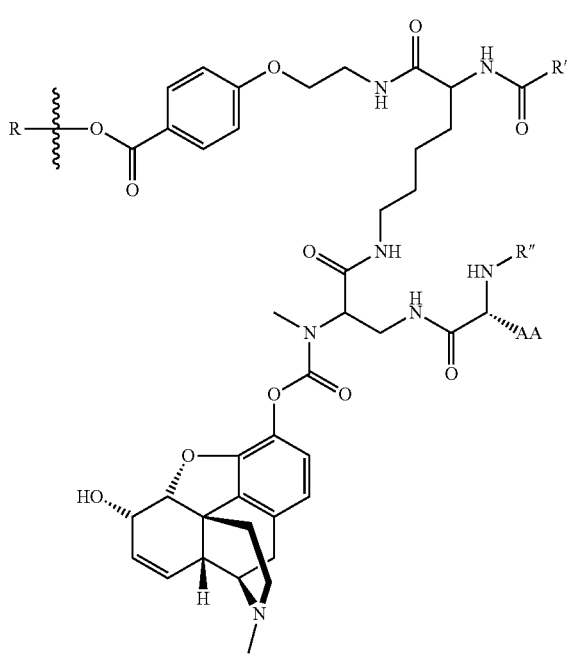
II-N

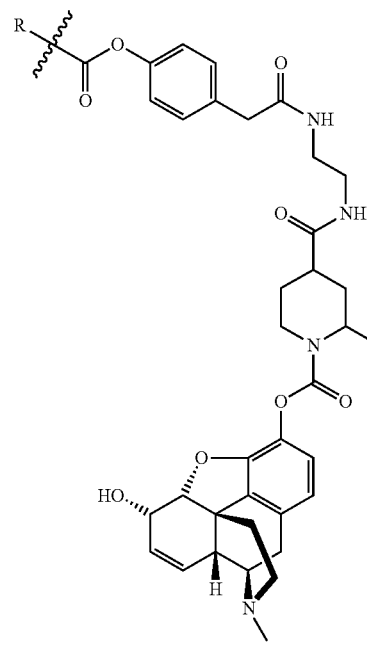
II-O
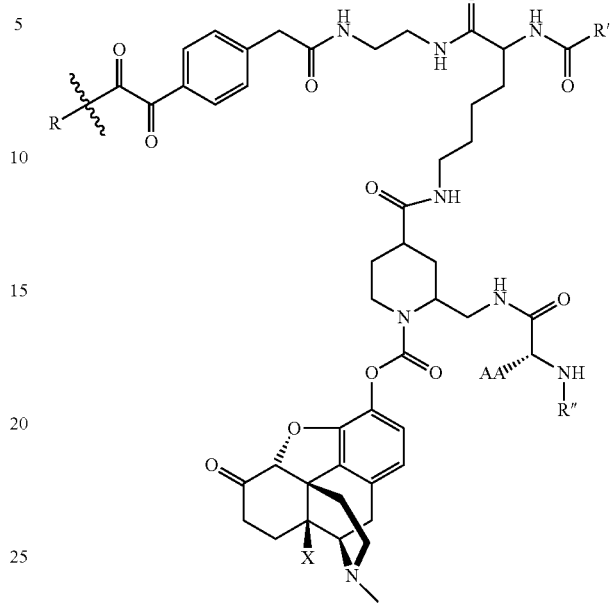
II-Q
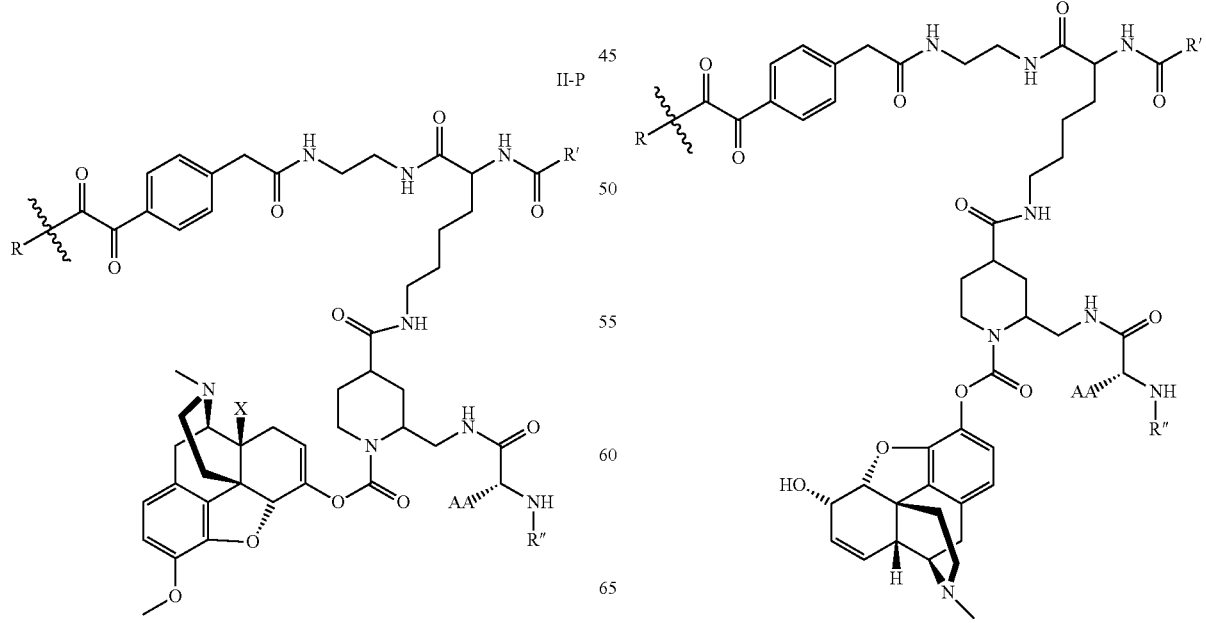
II-P
II-R

151
-continued
II-S
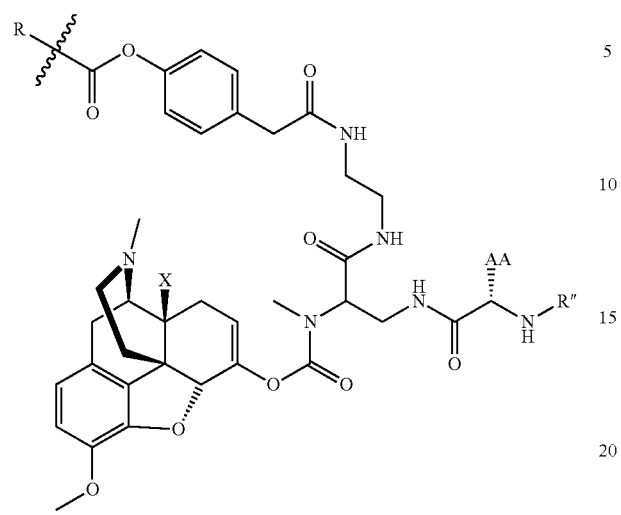
II-T
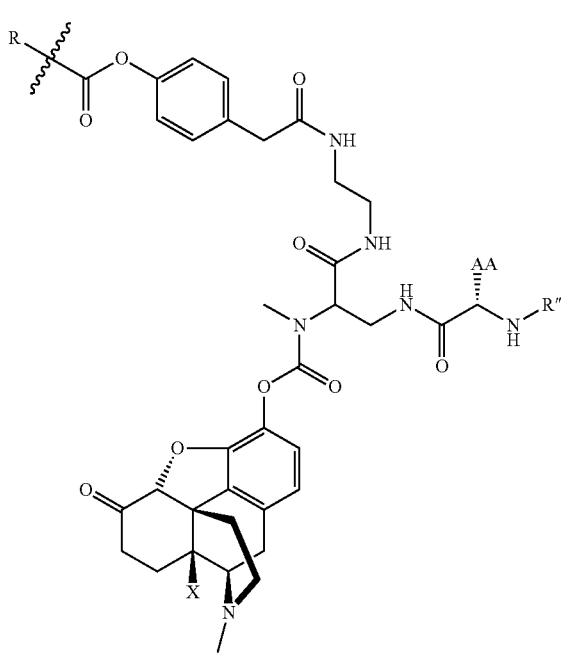
152
-continued
II-U
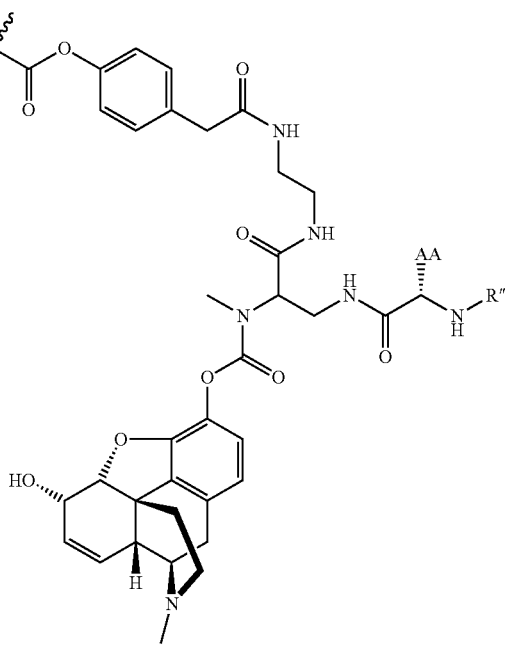
II-V -continued

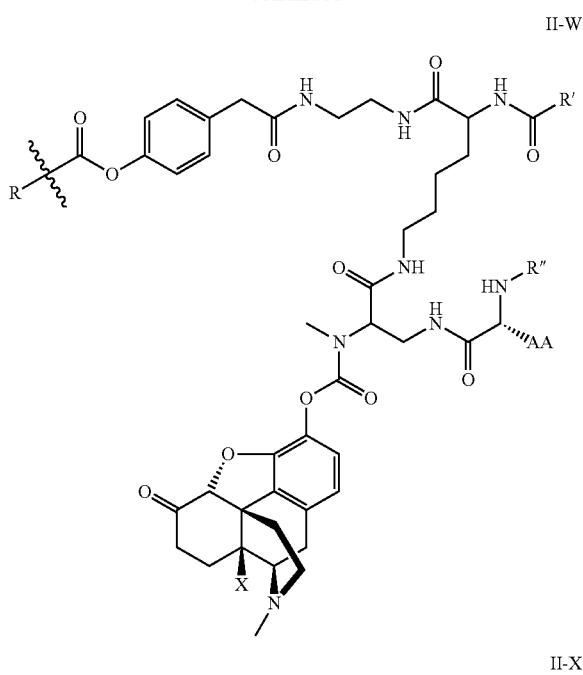

II-W

II-X wherein:
R is selected from the group consisting of:

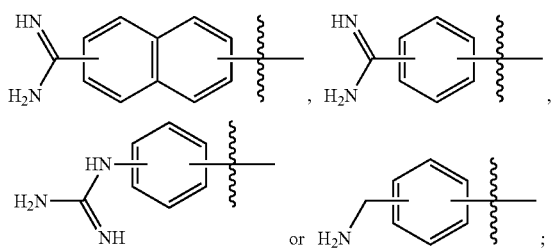

R' can be methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear or branched polyethylene glycol chain up to 5 kDa, benzyloxy, and the like; R" can be an acetyl, substituted acyl, a natural or non-natural amino acid, or a polypeptide chain comprising natural and/or non-natural amino acids up to 10 amino acids in length; AA is a natural or non-natural amino acid side chain capable of being recognized by trypsin; X is hydrogen or OH.

In some embodiments the disclosure provides for compositions comprising two or more of the aforementioned compounds of Formula II wherein:

R can be

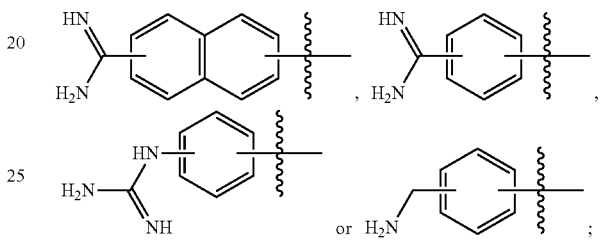

R' can be methyl or benzyloxy; R" can be an acetyl or a substituted acyl, a natural or non-natural amino acid or a di- or tri-peptide comprising natural or non-natural amino acids; AA is a natural or non-natural amino acid side chain capable of being recognized by trypsin; X is hydrogen or OH.

In yet other embodiments the disclosure provides for compositions comprising two or more of the aforementioned compounds of Formula II wherein:

R can be

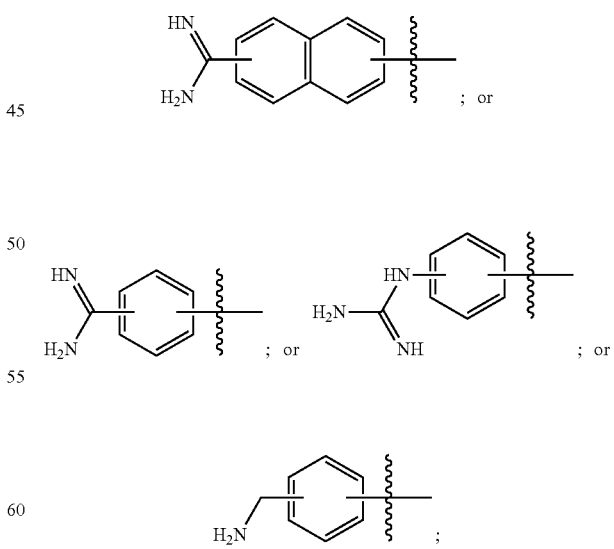

R' can be methyl or benzyloxy; R" can be an acetyl, a natural or non-natural amino acid or a dipeptide comprising natural or non-natural amino acids; AA is the side chain of lysine or arginine; X is hydrogen or OH.

In yet another embodiment the disclosure provides for compositions comprising two or more of the aforementioned compounds of Formula II wherein:
R can be

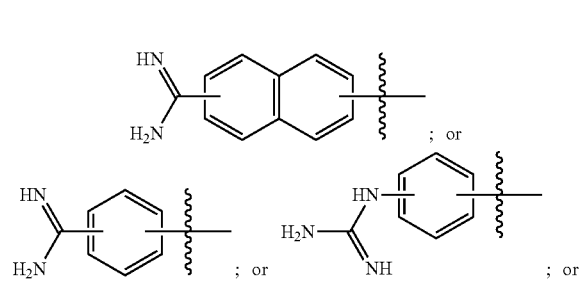

; or

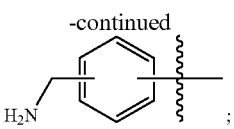

;

R' can be methyl or benzyloxy; R" can be acetyl, -Ala-NAc or -Gly-NAc; AA is the side chain of lysine or arginine; X is hydrogen or OH.

Table 1a illustrates various hydrocodone, hydromorphone, oxycodone, and oxymorphone containing compounds of Formula II-A, II-B, II-G, II-H, II-M, II-N, II-S, and II-T contemplated by the present disclosure.

TABLE 1a

| Compound | R | R" | AA (side chain) | X |
|---|---|---|---|---|
| II-A-1, II-B-1, II-G-1, II-H-1, II-M-1, II-N-1, II-S-1, II-T-1 | naphthalene-amidine | Acetyl | Lysine | Hydrogen |
| II-A-2, II-B-2, II-G-2, II-H-2, II-M-2, II-N-2, II-S-2, II-T-2 | naphthalene-amidine | Acetyl | Lysine | —OH |
| II-A-3, II-B-3, II-G-3, II-H-3, II-M-3, II-N-3, II-S-3, II-T-3 | naphthalene-amidine | Acetyl | Arginine | Hydrogen |
| II-A-4, II-B-4, II-G-4, II-H-4, II-M-4, II-N-4, II-S-4, II-T-4 | naphthalene-amidine | Acetyl | Arginine | —OH |
| II-A-5, II-B-5, II-G-5, II-H-5, II-M-5, II-N-5, II-S-5, II-T-5 | naphthalene-amidine | -Ala-NAc | Lysine | Hydrogen |
| II-A-6, II-B-6, II-G-6, II-H-6, II-M-6, II-N-6, II-S-6, II-T-6 | naphthalene-amidine | -Ala-NAc | Lysine | —OH |

TABLE 1a-continued

| Compound | R | R" | AA (side chain) | X |
|---|---|---|---|---|
| II-A-7, II-B-7, II-G-7, II-H-7, II-M-7, II-N-7, II-S-7, II-T-7 | 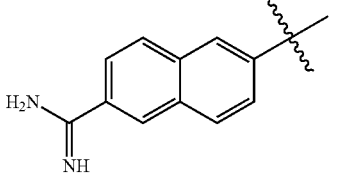 [SMILES: *c1ccc2cc(C(=N)N)ccc2c1] | -Ala-NAc | Arginine | Hydrogen |
| II-A-8, II-B-8, II-C-8, II-G-8, II-H-8, II-I-8, II-M-8, II-N-8, II-O-8, II-S-8, II-T-8, II-U-8 | 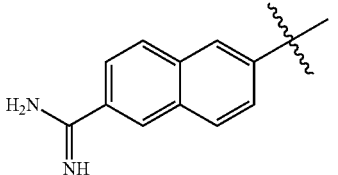 [SMILES: *c1ccc2cc(C(=N)N)ccc2c1] | -Ala-NAc | Arginine | —OH |
| II-A-9, II-B-9, II-G-9, II-H-9, II-M-9, II-N-9, II-S-9, II-T-9 | 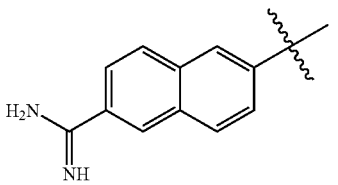 [SMILES: *c1ccc2cc(C(=N)N)ccc2c1] | -Gly-NAc | Lysine | Hydrogen |
| II-A-10, II-B-10, II-G-10, II-H-10, II-M-10, II-N-10, II-S-10, II-T-10 | 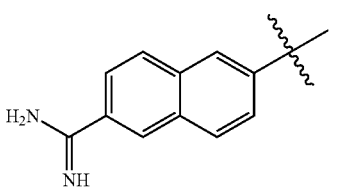 [SMILES: *c1ccc2cc(C(=N)N)ccc2c1] | -Gly-NAc | Lysine | —OH |
| II-A-11, II-B-11, II-G-11, II-H-11, II-M-11, II-N-11, II-S-11, II-T-11 | 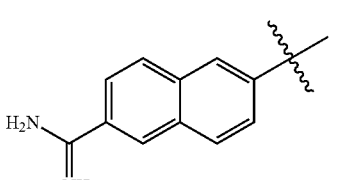 | -Gly-NAc | Arginine | Hydrogen |
| III-A-12, III-B-12, III-G-12, III-H-12, II-M-12, II-N-12, II-S-12, II-T-12 | 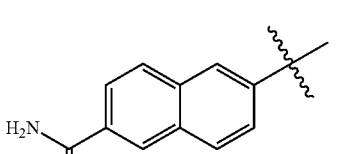 | -Gly-NAc | Arginine | —OH |
| II-A-13(a, b, c), II-B-13(a, b, c), II-G-13(a, b, c), II-H-13(a, b, c), II-M-13(a, b, c), II-N-13(a, b, c), II-S-13(a, b, c), II-T-13(a, b, c) | 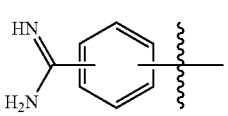<br>a = ortho<br>b = meta<br>c = para | Acetyl | Lysine | Hydrogen |

TABLE 1a-continued

| Compound | R | R'' | AA (side chain) | X |
|---|---|---|---|---|
| II-A-14(a, b, c)<br>II-B-14(a, b, c)<br>II-G-14(a, b, c)<br>II-H-14(a, b, c)<br>II-M-14(a, b, c)<br>II-N-14(a, b, c)<br>II-S-14(a, b, c)<br>II-T-14(a, b, c) | 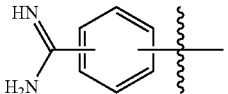<br>a = ortho<br>b = meta<br>c = para | Acetyl | Lysine | —OH |
| II-A-15(a, b, c)<br>II-B-15(a, b, c)<br>II-G-15(a, b, c)<br>II-H-15(a, b, c)<br>II-M-15(a, b, c)<br>II-N-15(a, b, c)<br>II-S-15(a, b, c)<br>II-T-15(a, b, c) | 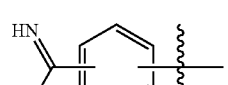<br>a = ortho<br>b = meta<br>c = para | Acetyl | Arginine | Hydrogen |
| II-A-16(a, b, c)<br>II-B-16(a, b, c)<br>II-G-16(a, b, c)<br>II-H-16(a, b, c)<br>II-M-16(a, b, c)<br>II-N-16(a, b, c)<br>II-S-16(a, b, c)<br>II-T-16(a, b, c) | <br>a = ortho<br>b = meta<br>c = para | Acetyl | Arginine | —OH |
| II-A-17(a, b, c)<br>II-B-17(a, b, c)<br>II-G-17(a, b, c)<br>II-H-17(a, b, c)<br>II-M-17(a, b, c)<br>II-N-17(a, b, c)<br>II-S-17(a, b, c)<br>II-T-17(a, b, c) | 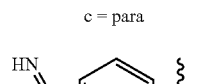<br>a = ortho<br>b = meta<br>c = para | -Ala-NAc | Lysine | Hydrogen |
| II-A-18(a, b, c)<br>II-B-18(a, b, c)<br>II-G-18(a, b, c)<br>II-H-18(a, b, c)<br>II-M-18(a, b, c)<br>II-N-18(a, b, c)<br>II-S-18(a, b, c)<br>II-T-18(a, b, c) | 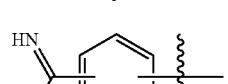<br>a = ortho<br>b = meta<br>c = para | -Ala-NAc | Lysine | —OH |
| II-A-19(a, b, c)<br>II-B-19(a, b, c)<br>II-G-19(a, b, c)<br>II-H-19(a, b, c)<br>II-M-19(a, b, c)<br>II-N-19(a, b, c)<br>II-S-19(a, b, c)<br>II-T-19(a, b, c) | 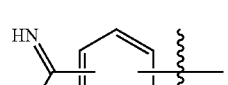<br>a = ortho<br>b = meta<br>c = para | -Ala-NAc | Arginine | Hydrogen |
| II-A-20(a, b, c)<br>II-B-20(a, b, c)<br>II-G-20(a, b, c)<br>II-H-20(a, b, c)<br>II-M-20(a, b, c)<br>II-N-20(a, b, c)<br>II-S-20(a, b, c)<br>II-T-20(a, b, c) | 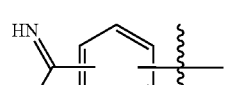<br>a = ortho<br>b = meta<br>c = para | -Ala-NAc | Arginine | —OH |
| II-A-21(a, b, c)<br>II-B-21(a, b, c)<br>II-G-21(a, b, c)<br>II-H-21(a, b, c)<br>II-M-21(a, b, c)<br>II-N-21(a, b, c)<br>II-S-21(a, b, c)<br>II-T-21(a, b, c) | 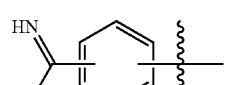<br>a = ortho<br>b = meta<br>c = para | -Gly-NAc | Lysine | Hydrogen |

TABLE 1a-continued

| Compound | R | R" | AA (side chain) | X |
|---|---|---|---|---|
| II-A-22(a, b, c)<br>II-B-22(a, b, c)<br>II-G-22(a, b, c)<br>II-H-22(a, b, c)<br>II-M-22(a, b, c)<br>II-N-22(a, b, c)<br>II-S-22(a, b, c)<br>II-T-22(a, b, c) | HN=C(NH₂)–C₆H₄–<br>a = ortho<br>b = meta<br>c = para | -Gly-NAc | Lysine | —OH |
| II-A-23(a, b, c)<br>II-B-23(a, b, c)<br>II-G-23(a, b, c)<br>II-H-23(a, b, c)<br>II-M-23(a, b, c)<br>II-N-23(a, b, c)<br>II-S-23(a, b, c)<br>II-T-23(a, b, c) | HN=C(NH₂)–C₆H₄–<br>a = ortho<br>b = meta<br>c = para | -Gly-NAc | Arginine | Hydrogen |
| II-A-24(a, b, c)<br>II-B-24(a, b, c)<br>II-G-24(a, b, c)<br>II-H-24(a, b, c)<br>II-M-24(a, b, c)<br>II-N-24(a, b, c)<br>II-S-24(a, b, c)<br>II-T-24(a, b, c) | HN=C(NH₂)–C₆H₄–<br>a = ortho<br>b = meta<br>c = para | -Gly-NAc | Arginine | —OH |
| II-A-25(a, b, c)<br>II-B-25(a, b, c)<br>II-G-25(a, b, c)<br>II-H-25(a, b, c)<br>II-M-25(a, b, c)<br>II-N-25(a, b, c)<br>II-S-25(a, b, c)<br>II-T-25(a, b, c) | H₂N–C(=NH)–NH–C₆H₄–<br>a = ortho<br>b = meta<br>c = para | Acetyl | Lysine | Hydrogen |
| II-A-26(a, b, c)<br>II-B-26(a, b, c)<br>II-G-26(a, b, c)<br>II-H-26(a, b, c)<br>II-M-26(a, b, c)<br>II-N-26(a, b, c)<br>II-S-26(a, b, c)<br>II-T-26(a, b, c) | H₂N–C(=NH)–NH–C₆H₄–<br>a = ortho<br>b = meta<br>c = para | Acetyl | Lysine | —OH |
| II-A-27(a, b, c)<br>II-B-27(a, b, c)<br>II-G-27(a, b, c)<br>II-H-27(a, b, c)<br>II-M-27(a, b, c)<br>II-N-27(a, b, c)<br>II-S-27(a, b, c)<br>II-T-27(a, b, c) | H₂N–C(=NH)–NH–C₆H₄–<br>a = ortho<br>b = meta<br>c = para | Acetyl | Arginine | Hydrogen |
| II-A-28(a, b, c)<br>II-B-28(a, b, c)<br>II-G-28(a, b, c)<br>II-H-28(a, b, c)<br>II-M-28(a, b, c)<br>II-N-28(a, b, c)<br>II-S-28(a, b, c)<br>II-T-28(a, b, c) | H₂N–C(=NH)–NH–C₆H₄–<br>a = ortho<br>b = meta<br>c = para | Acetyl | Arginine | —OH |

TABLE 1a-continued

| Compound | R | R" | AA (side chain) | X |
|---|---|---|---|---|
| II-A-29(a, b, c)<br>II-B-29(a, b, c)<br>II-G-29(a, b, c)<br>II-H-29(a, b, c)<br>II-M-29(a, b, c)<br>II-N-29(a, b, c)<br>II-S-29(a, b, c)<br>II-T-29(a, b, c) | H₂N-C(=NH)-NH-phenyl-<br>a = ortho<br>b = meta<br>c = para | -Ala-NAc | Lysine | Hydrogen |
| II-A-30(a, b, c)<br>II-B-30(a, b, c)<br>II-G-30(a, b, c)<br>II-H-30(a, b, c)<br>II-M-30(a, b, c)<br>II-N-30(a, b, c)<br>II-S-30(a, b, c)<br>II-T-30(a, b, c) | H₂N-C(=NH)-NH-phenyl-<br>a = ortho<br>b = meta<br>c = para | -Ala-NAc | Lysine | —OH |
| II-A-31(a, b, c)<br>II-B-31(a, b, c)<br>II-G-31(a, b, c)<br>II-H-31(a, b, c)<br>II-M-31(a, b, c)<br>II-N-31(a, b, c)<br>II-S-31(a, b, c)<br>II-T-31(a, b, c) | H₂N-C(=NH)-NH-phenyl-<br>a = ortho<br>b = meta<br>c = para | -Ala-NAc | Arginine | Hydrogen |
| II-A-32(a, b, c)<br>II-B-32(a, b, c)<br>II-G-32(a, b, c)<br>II-H-32(a, b, c)<br>II-M-32(a, b, c)<br>II-N-32(a, b, c)<br>II-S-32(a, b, c)<br>II-T-32(a, b, c) | H₂N-C(=NH)-NH-phenyl-<br>a = ortho<br>b = meta<br>c = para | -Ala-NAc | Arginine | —OH |
| II-A-33(a, b, c)<br>II-B-33(a, b, c)<br>II-G-33(a, b, c)<br>II-H-33(a, b, c)<br>II-M-33(a, b, c)<br>II-N-33(a, b, c)<br>II-S-33(a, b, c)<br>II-T-33(a, b, c) | H₂N-C(=NH)-NH-phenyl-<br>a = ortho<br>b = meta<br>c = para | -Gly-NAc | Lysine | Hydrogen |
| II-A-34(a, b, c)<br>II-B-34(a, b, c)<br>II-G-34(a, b, c)<br>II-H-34(a, b, c)<br>II-M-34(a, b, c)<br>II-N-34(a, b, c)<br>II-S-34(a, b, c)<br>II-T-34(a, b, c) | H₂N-C(=NH)-NH-phenyl-<br>a = ortho<br>b = meta<br>c = para | -Gly-NAc | Lysine | —OH |
| II-A-35(a, b, c)<br>II-B-35(a, b, c)<br>II-G-35(a, b, c)<br>II-H-35(a, b, c)<br>II-M-35(a, b, c)<br>II-N-35(a, b, c)<br>II-S-35(a, b, c)<br>II-T-35(a, b, c) | H₂N-C(=NH)-NH-phenyl-<br>a = ortho<br>b = meta<br>c = para | -Gly-NAc | Arginine | Hydrogen |

TABLE 1a-continued

| Compound | R | R" | AA (side chain) | X |
|---|---|---|---|---|
| II-A-36(a, b, c)<br>II-B-36(a, b, c)<br>II-G-36(a, b, c)<br>II-H-36(a, b, c)<br>II-M-36(a, b, c)<br>II-N-36(a, b, c)<br>II-S-36(a, b, c)<br>II-T-36(a, b, c) | guanidino-phenyl<br>a = ortho<br>b = meta<br>c = para | -Gly-NAc | Arginine | —OH |
| II-A-37(a, b, c)<br>II-B-37(a, b, c)<br>II-G-37(a, b, c)<br>II-H-37(a, b, c)<br>II-M-37(a, b, c)<br>II-N-37(a, b, c)<br>II-S-37(a, b, c)<br>II-T-37(a, b, c) | $H_2N$-CH$_2$-phenyl<br>a = ortho<br>b = meta<br>c = para | Acetyl | Lysine | Hydrogen |
| II-A-38(a, b, c)<br>II-B-38(a, b, c)<br>II-G-38(a, b, c)<br>II-H-38(a, b, c)<br>II-M-38(a, b, c)<br>II-N-38(a, b, c)<br>II-S-38(a, b, c)<br>II-T-38(a, b, c) | $H_2N$-CH$_2$-phenyl<br>a = ortho<br>b = meta<br>c = para | Acetyl | Lysine | —OH |
| II-A-39(a, b, c)<br>II-B-39(a, b, c)<br>II-G-39(a, b, c)<br>II-H-39(a, b, c)<br>II-M-39(a, b, c)<br>II-N-39(a, b, c)<br>II-S-39(a, b, c)<br>II-T-39(a, b, c) | $H_2N$-CH$_2$-phenyl<br>a = ortho<br>b = meta<br>c = para | Acetyl | Arginine | Hydrogen |
| II-A-40(a, b, c)<br>II-B-40(a, b, c)<br>II-G-40(a, b, c)<br>II-H-40(a, b, c)<br>II-M-40(a, b, c)<br>II-N-40(a, b, c)<br>II-S-40(a, b, c)<br>II-T-40(a, b, c) | $H_2N$-CH$_2$-phenyl<br>a = ortho<br>b = meta<br>c = para | Acetyl | Arginine | —OH |
| II-A-41(a, b, c)<br>II-B-41(a, b, c)<br>II-G-41(a, b, c)<br>II-H-41(a, b, c)<br>II-M-41(a, b, c)<br>II-N-41(a, b, c)<br>II-S-41(a, b, c)<br>II-T-41(a, b, c) | $H_2N$-CH$_2$-phenyl<br>a = ortho<br>b = meta<br>c = para | -Ala-NAc | Lysine | Hydrogen |
| II-A-42(a, b, c)<br>II-B-42(a, b, c)<br>II-G-42(a, b, c)<br>II-H-42(a, b, c)<br>II-M-42(a, b, c)<br>II-N-42(a, b, c)<br>II-S-42(a, b, c)<br>II-T-42(a, b, c) | $H_2N$-CH$_2$-phenyl<br>a = ortho<br>b = meta<br>c = para | -Ala-NAc | Lysine | —OH |
| II-A-43(a, b, c)<br>II-B-43(a, b, c)<br>II-G-43(a, b, c)<br>II-H-43(a, b, c)<br>II-M-43(a, b, c)<br>II-N-43(a, b, c)<br>II-S-43(a, b, c)<br>II-T-43(a, b, c) | $H_2N$-CH$_2$-phenyl<br>a = ortho<br>b = meta<br>c = para | -Ala-NAc | Arginine | Hydrogen |

TABLE 1a-continued

| Compound | R | R'' | AA (side chain) | X |
|---|---|---|---|---|
| II-A-44(a, b, c) II-B-44(a, b, c) II-G-44(a, b, c) II-H-44(a, b, c) II-M-44(a, b, c) II-N-44(a, b, c) II-S-44(a, b, c) II-T-44(a, b, c) | H₂N-CH₂-C₆H₄- (a = ortho, b = meta, c = para) | -Ala-NAc | Arginine | —OH |
| II-A-45(a, b, c) II-B-45(a, b, c) II-G-45(a, b, c) II-H-45(a, b, c) II-M-45(a, b, c) II-N-45(a, b, c) II-S-45(a, b, c) II-T-45(a, b, c) | H₂N-CH₂-C₆H₄- (a = ortho, b = meta, c = para) | -Gly-NAc | Lysine | Hydrogen |
| II-A-46(a, b, c) II-B-46(a, b, c) II-G-46(a, b, c) II-H-46(a, b, c) II-M-46(a, b, c) II-N-46(a, b, c) II-S-46(a, b, c) II-T-46(a, b, c) | H₂N-CH₂-C₆H₄- (a = ortho, b = meta, c = para) | -Gly-NAc | Lysine | —OH |
| II-A-47(a, b, c) II-B-47(a, b, c) II-G-47(a, b, c) II-H-47(a, b, c) II-M-47(a, b, c) II-N-47(a, b, c) II-S-47(a, b, c) II-T-47(a, b, c) | H₂N-CH₂-C₆H₄- (a = ortho, b = meta, c = para) | -Gly-NAc | Arginine | Hydrogen |
| II-A-48(a, b, c) II-B-48(a, b, c) II-G-48(a, b, c) II-H-48(a, b, c) II-M-48(a, b, c) II-N-48(a, b, c) II-S-48(a, b, c) II-T-48(a, b, c) | H₂N-CH₂-C₆H₄- (a = ortho, b = meta, c = para) | -Gly-NAc | Arginine | —OH |

Table 2a illustrates various morphine containing compounds of Formula II-C, II-O, and II-U contemplated by the present disclosure.

TABLE 2a

| Compound | R | R'' | AA (side chain) |
|---|---|---|---|
| II-C-1 II-I-1 II-O-1 II-U-1 | H₂N-C(=NH)-naphthalen-2,6-diyl- | Acetyl | Lysine |
| II-C-2 II-I-2 II-O-2 II-U-2 | H₂N-C(=NH)-naphthalen-2,6-diyl- | Acetyl | Arginine |

TABLE 2a-continued

| Compound | R | R'' | AA (side chain) |
|---|---|---|---|
| II-C-3<br>II-I-3<br>II-O-3<br>II-U-3 | 6-carbamimidoyl-naphthalen-2-yl | -Ala-NAc | Lysine |
| II-C-4<br>II-I-4<br>II-O-4<br>II-U-4 | 6-carbamimidoyl-naphthalen-2-yl | -Ala-NAc | Arginine |
| II-C-5<br>II-I-5<br>II-O-5<br>II-U-5 | 6-carbamimidoyl-naphthalen-2-yl | -Gly-NAc | Lysine |
| II-C-6<br>II-I-6<br>II-O-6<br>II-U-6 | 6-carbamimidoyl-naphthalen-2-yl | -Gly-NAc | Arginine |
| II-C-7(a, b, c)<br>II-I-7(a, b, c)<br>II-O-7(a, b, c)<br>II-U-7(a, b, c) | carbamimidoyl-phenyl<br>a = ortho<br>b = meta<br>c = para | Acetyl | Lysine |
| II-C-8(a, b, c)<br>II-I-8(a, b, c)<br>II-O-8(a, b, c)<br>II-U-8(a, b, c) | carbamimidoyl-phenyl<br>a = ortho<br>b = meta<br>c = para | Acetyl | Arginine |
| II-C-9(a, b, c)<br>II-I-9(a, b, c)<br>II-O-9(a, b, c)<br>II-U-9(a, b, c) | carbamimidoyl-phenyl<br>a = ortho<br>b = meta<br>c = para | -Ala-NAc | Lysine |
| II-C-10(a, b, c)<br>II-I-10(a, b, c)<br>II-O-10(a, b, c)<br>II-U-10(a, b, c) | carbamimidoyl-phenyl<br>a = ortho<br>b = meta<br>c = para | -Ala-NAc | Arginine |

TABLE 2a-continued

| Compound | R | R" | AA (side chain) |
|---|---|---|---|
| II-C-11(a, b, c)<br>II-I-11(a, b, c)<br>II-O-11(a, b, c)<br>II-U-11(a, b, c) | 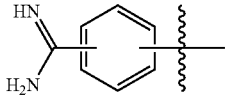<br>a = ortho<br>b = meta<br>c = para | -Gly-NAc | Lysine |
| II-C-12(a, b, c)<br>II-I-12(a, b, c)<br>II-O-12(a, b, c)<br>II-U-12(a, b, c) | 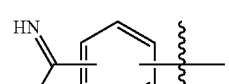<br>a = ortho<br>b = meta<br>c = para | -Gly-NAc | Arginine |
| II-C-13(a, b, c)<br>II-I-13(a, b, c)<br>II-O-13(a, b, c)<br>II-U-13(a, b, c) | 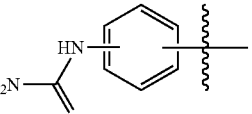<br>a = ortho<br>b = meta<br>c = para | Acetyl | Lysine |
| II-C-14(a, b, c)<br>II-I-14(a, b, c)<br>II-O-14(a, b, c)<br>II-U-14(a, b, c) | 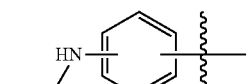<br>a = ortho<br>b = meta<br>c = para | Acetyl | Arginine |
| II-C-15(a, b, c)<br>II-I-15(a, b, c)<br>II-O-15(a, b, c)<br>II-U-15(a, b, c) | 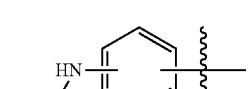<br>a = ortho<br>b = meta<br>c = para | -Ala-NAc | Lysine |
| II-C-16(a, b, c)<br>II-I-16(a, b, c)<br>II-O-16(a, b, c)<br>II-U-16(a, b, c) | 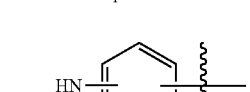<br>a = ortho<br>b = meta<br>c = para | -Ala-NAc | Arginine |
| II-C-17(a, b, c)<br>II-I-17(a, b, c)<br>II-O-17(a, b, c)<br>II-U-17(a, b, c) | 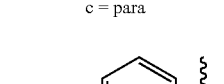<br>a = ortho<br>b = meta<br>c = para | -Gly-NAc | Lysine |

TABLE 2a-continued

| Compound | R | R'' | AA (side chain) |
|---|---|---|---|
| II-C-18(a, b, c)<br>II-I-18(a, b, c)<br>II-O-18(a, b, c)<br>II-U-18(a, b, c) | H₂N-C(=NH)-NH-C₆H₄-<br>a = ortho<br>b = meta<br>c = para | -Gly-NAc | Arginine |
| II-C-19(a, b, c)<br>II-I-19(a, b, c)<br>II-O-19(a, b, c)<br>II-U-19(a, b, c) | H₂N-CH₂-C₆H₄-<br>a = ortho<br>b = meta<br>c = para | Acetyl | Lysine |
| II-C-20(a, b, c)<br>II-I-20(a, b, c)<br>II-O-20(a, b, c)<br>II-U-20(a, b, c) | H₂N-CH₂-C₆H₄-<br>a = ortho<br>b = meta<br>c = para | Acetyl | Arginine |
| II-C-21(a, b, c)<br>II-I-21(a, b, c)<br>II-O-21(a, b, c)<br>II-U-21(a, b, c) | H₂N-CH₂-C₆H₄-<br>a = ortho<br>b = meta<br>c = para | -Ala-NAc | Lysine |
| II-C-22(a, b, c)<br>II-I-22(a, b, c)<br>II-O-22(a, b, c)<br>II-U-22(a, b, c) | H₂N-CH₂-C₆H₄-<br>a = ortho<br>b = meta<br>c = para | -Ala-NAc | Arginine |
| II-C-23(a, b, c)<br>II-I-23(a, b, c)<br>II-O-23(a, b, c)<br>II-U-23(a, b, c) | H₂N-CH₂-C₆H₄-<br>a = ortho<br>b = meta<br>c = para | -Gly-NAc | Lysine |
| II-C-24(a, b, c)<br>II-I-24(a, b, c)<br>II-O-24(a, b, c)<br>II-U-24(a, b, c) | H₂N-CH₂-C₆H₄-<br>a = ortho<br>b = meta<br>c = para | -Gly-NAc | Arginine |

Table 3a illustrates various hydrocodone, hydromorphone, oxycodone, and oxymorphone containing compounds of Formula II-D, II-E, II-J, II-K, II-P, II-Q, II-V, and II-W contemplated by the present disclosure.

TABLE 3a

| Compound | R | R' | R'' | AA (side chain) | X |
|---|---|---|---|---|---|
| II-D-1<br>II-E-1<br>II-J-1<br>II-K-1<br>II-P-1<br>II-Q-1<br>II-V-1<br>II-W-1 | 6-amidino-naphthyl | Methyl | Acetyl | Lysine | Hydrogen |
| II-D-2<br>II-E-2<br>II-J-2<br>II-K-2<br>II-P-2<br>II-Q-2<br>II-V-2<br>II-W-2 | 6-amidino-naphthyl | Methyl | Acetyl | Lysine | —OH |
| II-D-3<br>II-E-3<br>II-J-3<br>II-K-3<br>II-P-3<br>II-Q-3<br>II-V-3<br>II-W-3 | 6-amidino-naphthyl | Methyl | Acetyl | Arginine | Hydrogen |
| II-D-4<br>II-E-4<br>II-J-4<br>II-K-4<br>II-P-4<br>II-Q-4<br>II-V-4<br>II-W-4 | 6-amidino-naphthyl | Methyl | Acetyl | Arginine | —OH |
| II-D-5<br>II-E-5<br>II-J-5<br>II-K-5<br>II-P-5<br>II-Q-5<br>II-V-5<br>II-W-5 | 6-amidino-naphthyl | Methyl | -Ala-NAc | Lysine | Hydrogen |
| II-D-6<br>II-E-6<br>II-J-6<br>II-K-6<br>II-P-6<br>II-Q-6<br>II-V-6<br>II-W-6 | 6-amidino-naphthyl | Methyl | -Ala-NAc | Lysine | —OH |
| II-D-7<br>II-E-7<br>II-J-7<br>II-K-7<br>II-P-7<br>II-Q-7<br>II-V-7<br>II-W-7 | 6-amidino-naphthyl | Methyl | -Ala-NAc | Arginine | Hydrogen |
| II-D-8<br>II-E-8<br>II-J-8<br>II-K-8<br>II-P-8<br>II-Q-8<br>II-V-8<br>II-W-8 | 6-amidino-naphthyl | Methyl | -Ala-NAc | Arginine | —OH |

TABLE 3a-continued

| Compound | R | R' | R" | AA (side chain) | X |
|---|---|---|---|---|---|
| II-D-9<br>II-E-9<br>II-J-9<br>II-K-9<br>II-P-9<br>II-Q-9<br>II-V-9<br>II-W-9 | H₂N-C(=NH)-naphthyl- | Methyl | -Gly-NAc | Lysine | Hydrogen |
| II-D-10<br>II-E-10<br>II-J-10<br>II-K-10<br>II-P-10<br>II-Q-10<br>II-V-10<br>II-W-10 | H₂N-C(=NH)-naphthyl- | Methyl | -Gly-NAc | Lysine | —OH |
| II-D-11<br>II-E-11<br>II-J-11<br>II-K-11<br>II-P-11<br>II-Q-11<br>II-V-11<br>II-W-11 | H₂N-C(=NH)-naphthyl- | Methyl | -Gly-NAc | Arginine | Hydrogen |
| II-D-12<br>II-E-12<br>II-J-12<br>II-K-12<br>II-P-12<br>II-Q-12<br>II-V-12<br>II-W-12 | H₂N-C(=NH)-naphthyl- | Methyl | -Gly-NAc | Arginine | —OH |
| II-D-13<br>II-E-13<br>II-J-13<br>II-K-13<br>II-P-13<br>II-Q-13<br>II-V-13<br>II-W-13 | H₂N-C(=NH)-naphthyl- | Benzyloxy | Acetyl | Lysine | Hydrogen |
| II-D-14<br>II-E-14<br>II-J-14<br>II-K-14<br>II-P-14<br>II-Q-14<br>II-V-14<br>II-W-14 | H₂N-C(=NH)-naphthyl- | Benzyloxy | Acetyl | Lysine | —OH |
| II-D-15<br>II-E-15<br>II-J-15<br>II-K-15<br>II-P-15<br>II-Q-15<br>II-V-15<br>II-W-15 | H₂N-C(=NH)-naphthyl- | Benzyloxy | Acetyl | Arginine | Hydrogen |
| II-D-16<br>II-E-16<br>II-J-16<br>II-K-16<br>II-P-16<br>II-Q-16<br>II-V-16<br>II-W-16 | H₂N-C(=NH)-naphthyl- | Benzyloxy | Acetyl | Arginine | —OH |

TABLE 3a-continued

| Compound | R | R' | R" | AA (side chain) | X |
|---|---|---|---|---|---|
| II-D-17, II-E-17, II-J-17, II-K-17, II-P-17, II-Q-17, II-V-17, II-W-17 | 6-carbamimidoyl-naphthalen-2-yl (H$_2$N-C(=NH)-naphthalene) | Benzyloxy | -Ala-NAc | Lysine | Hydrogen |
| II-D-18, II-E-18, II-J-18, II-K-18, II-P-18, II-Q-18, II-V-18, II-W-18 | 6-carbamimidoyl-naphthalen-2-yl | Benzyloxy | -Ala-NAc | Lysine | —OH |
| II-D-19, II-E-19, II-J-19, II-K-19, II-P-19, II-Q-19, II-V-19, II-W-19 | 6-carbamimidoyl-naphthalen-2-yl | Benzyloxy | -Ala-NAc | Arginine | Hydrogen |
| II-D-20, II-E-20, II-J-20, II-K-20, II-P-20, II-Q-20, II-V-20, II-W-20 | 6-carbamimidoyl-naphthalen-2-yl | Benzyloxy | -Ala-NAc | Arginine | —OH |
| II-D-21, II-E-21, II-J-21, II-K-21, II-P-21, II-Q-21, II-V-21, II-W-21 | 6-carbamimidoyl-naphthalen-2-yl | Benzyloxy | -Gly-NAc | Lysine | Hydrogen |
| II-D-22, II-E-22, II-J-22, II-K-22, II-P-22, II-Q-22, II-V-22, II-W-22 | 6-carbamimidoyl-naphthalen-2-yl | Benzyloxy | -Gly-NAc | Lysine | —OH |
| II-D-23, II-E-23, II-J-23, II-K-23, II-P-23, II-Q-23, II-V-23, II-W-23 | 6-carbamimidoyl-naphthalen-2-yl | Benzyloxy | -Gly-NAc | Arginine | Hydrogen |
| II-D-24, II-E-24, II-J-24, II-K-24, II-P-24, II-Q-24, II-V-24, II-W-24 | 6-carbamimidoyl-naphthalen-2-yl | Benzyloxy | -Gly-NAc | Arginine | —OH |

TABLE 3a-continued

| Compound | R | R' | R" | AA (side chain) | X |
|---|---|---|---|---|---|
| II-D-25(a, b, c)<br>II-E-25(a, b, c)<br>II-J-25(a, b, c)<br>II-K-25(a, b, c)<br>II-P-25(a, b, c)<br>II-Q-25(a, b, c)<br>II-V-25(a, b, c)<br>II-W-25(a, b, c) | HN=C(NH₂)–C₆H₄–<br>a = ortho<br>b = meta<br>c = para | Methyl | Acetyl | Lysine | Hydrogen |
| II-D-26(a, b, c)<br>II-E-26(a, b, c)<br>II-J-26(a, b, c)<br>II-K-26(a, b, c)<br>II-P-26(a, b, c)<br>II-Q-26(a, b, c)<br>II-V-26(a, b, c)<br>II-W-26(a, b, c) | HN=C(NH₂)–C₆H₄–<br>a = ortho<br>b = meta<br>c = para | Methyl | Acetyl | Lysine | —OH |
| II-D-27(a, b, c)<br>II-E-27(a, b, c)<br>II-J-27(a, b, c)<br>II-K-27(a, b, c)<br>II-P-27(a, b, c)<br>II-Q-27(a, b, c)<br>II-V-27(a, b, c)<br>II-W-27(a, b, c) | HN=C(NH₂)–C₆H₄–<br>a = ortho<br>b = meta<br>c = para | Methyl | Acetyl | Arginine | Hydrogen |
| II-D-28(a, b, c)<br>II-E-28(a, b, c)<br>II-J-28(a, b, c)<br>II-K-28(a, b, c)<br>II-P-28(a, b, c)<br>II-Q-28(a, b, c)<br>II-V-28(a, b, c)<br>II-W-28(a, b, c) | HN=C(NH₂)–C₆H₄–<br>a = ortho<br>b = meta<br>c = para | Methyl | Acetyl | Arginine | —OH |
| II-D-29(a, b, c)<br>II-E-29(a, b, c)<br>II-J-29(a, b, c)<br>II-K-29(a, b, c)<br>II-P-29(a, b, c)<br>II-Q-29(a, b, c)<br>II-V-29(a, b, c)<br>II-W-29(a, b, c) | HN=C(NH₂)–C₆H₄–<br>a = ortho<br>b = meta<br>c = para | Methyl | -Ala-NAc | Lysine | Hydrogen |
| II-D-30(a, b, c)<br>II-E-30(a, b, c)<br>II-J-30(a, b, c)<br>II-K-30(a, b, c)<br>II-P-30(a, b, c)<br>II-Q-30(a, b, c)<br>II-V-30(a, b, c)<br>II-W-30(a, b, c) | HN=C(NH₂)–C₆H₄–<br>a = ortho<br>b = meta<br>c = para | Methyl | -Ala-NAc | Lysine | —OH |
| II-D-31(a, b, c)<br>II-E-31(a, b, c)<br>II-J-31(a, b, c)<br>II-K-31(a, b, c)<br>II-P-31(a, b, c)<br>II-Q-31(a, b, c)<br>II-V-31(a, b, c)<br>II-W-31(a, b, c) | HN=C(NH₂)–C₆H₄–<br>a = ortho<br>b = meta<br>c = para | Methyl | -Ala-NAc | Arginine | Hydrogen |
| II-D-32(a, b, c)<br>II-E-32(a, b, c)<br>II-J-32(a, b, c)<br>II-K-32(a, b, c)<br>II-P-32(a, b, c)<br>II-Q-32(a, b, c)<br>II-V-32(a, b, c)<br>II-W-32(a, b, c) | HN=C(NH₂)–C₆H₄–<br>a = ortho<br>b = meta<br>c = para | Methyl | -Ala-NAc | Arginine | —OH |

TABLE 3a-continued

| Compound | R | R' | R" | AA (side chain) | X |
|---|---|---|---|---|---|
| II-D-33(a, b, c)<br>II-E-33(a, b, c)<br>II-J-33(a, b, c)<br>II-K-33(a, b, c)<br>II-P-33(a, b, c)<br>II-Q-33(a, b, c)<br>II-V-33(a, b, c)<br>II-W-33(a, b, c) | 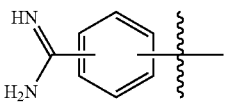<br>a = ortho<br>b = meta<br>c = para | Methyl | -Gly-NAc | Lysine | Hydrogen |
| II-D-34(a, b, c)<br>II-E-34(a, b, c)<br>II-J-34(a, b, c)<br>II-K-34(a, b, c)<br>II-P-34(a, b, c)<br>II-Q-34(a, b, c)<br>II-V-34(a, b, c)<br>II-W-34(a, b, c) | 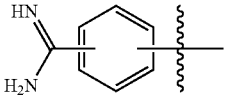<br>a = ortho<br>b = meta<br>c = para | Methyl | -Gly-NAc | Lysine | —OH |
| II-D-35(a, b, c)<br>II-E-35(a, b, c)<br>II-J-35(a, b, c)<br>II-K-35(a, b, c)<br>II-P-35(a, b, c)<br>II-Q-35(a, b, c)<br>II-V-35(a, b, c)<br>II-W-35(a, b, c) | 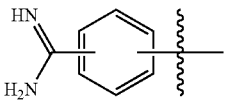<br>a = ortho<br>b = meta<br>c = para | Methyl | -Gly-NAc | Arginine | Hydrogen |
| II-D-36(a, b, c)<br>II-E-36(a, b, c)<br>II-J-36(a, b, c)<br>II-K-36(a, b, c)<br>II-P-36(a, b, c)<br>II-Q-36(a, b, c)<br>II-V-36(a, b, c)<br>II-W-36(a, b, c) | 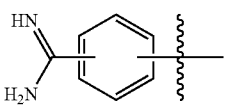<br>a = ortho<br>b = meta<br>c = para | Methyl | -Gly-NAc | Arginine | —OH |
| II-D-37(a, b, c)<br>II-E-37(a, b, c)<br>II-J-37(a, b, c)<br>II-K-37(a, b, c)<br>II-P-37(a, b, c)<br>II-Q-37(a, b, c)<br>II-V-37(a, b, c)<br>II-W-37(a, b, c) | 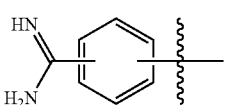<br>a = ortho<br>b = meta<br>c = para | Benzyloxy | Acetyl | Lysine | Hydrogen |
| II-D-38(a, b, c)<br>II-E-38(a, b, c)<br>II-J-38(a, b, c)<br>II-K-38(a, b, c)<br>II-P-38(a, b, c)<br>II-Q-38(a, b, c)<br>II-V-38(a, b, c)<br>II-W-38(a, b, c) | 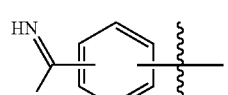<br>a = ortho<br>b = meta<br>c = para | Benzyloxy | Acetyl | Lysine | —OH |
| II-D-39(a, b, c)<br>II-E-39(a, b, c)<br>II-J-39(a, b, c)<br>II-K-39(a, b, c)<br>II-P-39(a, b, c)<br>II-Q-39(a, b, c)<br>II-J-39(a, b, c)<br>II-W-39(a, b, c) | 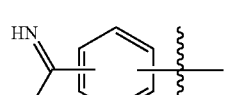<br>a = ortho<br>b = meta<br>c = para | Benzyloxy | Acetyl | Arginine | Hydrogen |
| II-D-40(a, b, c)<br>II-E-40(a, b, c)<br>II-J-40(a, b, c)<br>II-K-40(a, b, c)<br>II-P-40(a, b, c)<br>II-Q-40(a, b, c)<br>II-V-40(a, b, c)<br>II-W-40(a, b, c) | 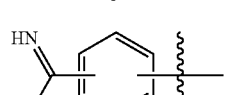<br>a = ortho<br>b = meta<br>c = para | Benzyloxy | Acetyl | Arginine | —OH |

TABLE 3a-continued

| Compound | R | R' | R" | AA (side chain) | X |
|---|---|---|---|---|---|
| II-D-41(a, b, c)<br>II-E-41(a, b, c)<br>II-J-41(a, b, c)<br>II-K-41(a, b, c)<br>II-P-41(a, b, c)<br>II-Q-41(a, b, c)<br>II-V-41(a, b, c)<br>II-W-41(a, b, c) | HN=C(NH$_2$)–C$_6$H$_4$–<br>a = ortho<br>b = meta<br>c = para | Benzyloxy | -Ala-NAc | Lysine | Hydrogen |
| II-D-42(a, b, c)<br>II-E-42(a, b, c)<br>II-J-42(a, b, c)<br>II-K-42(a, b, c)<br>II-P-42(a, b, c)<br>II-Q-42(a, b, c)<br>II-V-42(a, b, c)<br>II-W-42(a, b, c) | HN=C(NH$_2$)–C$_6$H$_4$–<br>a = ortho<br>b = meta<br>c = para | Benzyloxy | -Ala-NAc | Lysine | —OH |
| II-D-43(a, b, c)<br>II-E-43(a, b, c)<br>II-J-43(a, b, c)<br>II-K-43(a, b, c)<br>II-P-43(a, b, c)<br>II-Q-43(a, b, c)<br>II-V-43(a, b, c)<br>II-W-43(a, b, c) | HN=C(NH$_2$)–C$_6$H$_4$–<br>a = ortho<br>b = meta<br>c = para | Benzyloxy | -Ala-NAc | Arginine | Hydrogen |
| II-D-44(a, b, c)<br>II-E-44(a, b, c)<br>II-J-44(a, b, c)<br>II-K-44(a, b, c)<br>II-P-44(a, b, c)<br>II-Q-44(a, b, c)<br>II-V-44(a, b, c)<br>II-W-44(a, b, c) | HN=C(NH$_2$)–C$_6$H$_4$–<br>a = ortho<br>b = meta<br>c = para | Benzyloxy | -Ala-NAc | Arginine | —OH |
| II-D-45(a, b, c)<br>II-E-45(a, b, c)<br>II-J-45(a, b, c)<br>II-K-45(a, b, c)<br>II-P-45(a, b, c)<br>II-Q-45(a, b, c)<br>II-V-45(a, b, c)<br>II-W-45(a, b, c) | HN=C(NH$_2$)–C$_6$H$_4$–<br>a = ortho<br>b = meta<br>c = para | Benzyloxy | -Gly-NAc | Lysine | Hydrogen |
| II-D-46(a, b, c)<br>II-E-46(a, b, c)<br>II-J-46(a, b, c)<br>II-K-46(a, b, c)<br>II-P-46(a, b, c)<br>II-Q-46(a, b, c)<br>II-V-46(a, b, c)<br>II-W-46(a, b, c) | HN=C(NH$_2$)–C$_6$H$_4$–<br>a = ortho<br>b = meta<br>c = para | Benzyloxy | -Gly-NAc | Lysine | —OH |
| II-D-47(a, b, c)<br>II-E-47(a, b, c)<br>II-J-47(a, b, c)<br>II-K-47(a, b, c)<br>II-P-47(a, b, c)<br>II-Q-47(a, b, c)<br>II-V-47(a, b, c)<br>II-W-47(a, b, c) | HN=C(NH$_2$)–C$_6$H$_4$–<br>a = ortho<br>b = meta<br>c = para | Benzyloxy | -Gly-NAc | Arginine | Hydrogen |
| II-D-48(a, b, c)<br>II-E-48(a, b, c)<br>II-J-48(a, b, c)<br>II-K-48(a, b, c)<br>II-P-48(a, b, c)<br>II-Q-48(a, b, c)<br>II-V-48(a, b, c)<br>II-W-48(a, b, c) | HN=C(NH$_2$)–C$_6$H$_4$–<br>a = ortho<br>b = meta<br>c = para | Benzyloxy | -Gly-NAc | Arginine | —OH |

TABLE 3a-continued

| Compound | R | R' | R'' | AA (side chain) | X |
|---|---|---|---|---|---|
| II-D-49(a, b, c)<br>II-E-49(a, b, c)<br>II-J-49(a, b, c)<br>II-K-49(a, b, c)<br>II-P-49(a, b, c)<br>II-Q-49(a, b, c)<br>II-V-49(a, b, c)<br>II-W-49(a, b, c) | guanidino-phenyl<br>a = ortho<br>b = meta<br>c = para | Methyl | Acetyl | Lysine | Hydrogen |
| II-D-50(a, b, c)<br>II-E-50(a, b, c)<br>II-J-50(a, b, c)<br>II-K-50(a, b, c)<br>II-P-50(a, b, c)<br>II-Q-50(a, b, c)<br>II-V-50(a, b, c)<br>II-W-50(a, b, c) | guanidino-phenyl<br>a = ortho<br>b = meta<br>c = para | Methyl | Acetyl | Lysine | —OH |
| II-D-51(a, b, c)<br>II-E-51(a, b, c)<br>II-J-51(a, b, c)<br>II-K-51(a, b, c)<br>II-P-51(a, b, c)<br>II-Q-51(a, b, c)<br>II-V-51(a, b, c)<br>II-W-51(a, b, c) | guanidino-phenyl<br>a = ortho<br>b = meta<br>c = para | Methyl | Acetyl | Arginine | Hydrogen |
| II-D-52(a, b, c)<br>II-E-52(a, b, c)<br>II-J-52(a, b, c)<br>II-K-52(a, b, c)<br>II-P-52(a, b, c)<br>II-Q-52(a, b, c)<br>II-V-52(a, b, c)<br>II-W-52(a, b, c) | guanidino-phenyl<br>a = ortho<br>b = meta<br>c = para | Methyl | Acetyl | Arginine | —OH |
| II-D-53(a, b, c)<br>II-E-53(a, b, c)<br>II-J-53(a, b, c)<br>II-K-53(a, b, c)<br>II-P-53(a, b, c)<br>II-Q-53(a, b, c)<br>II-V-53(a, b, c)<br>II-W-53(a, b, c) | guanidino-phenyl<br>a = ortho<br>b = meta<br>c = para | Methyl | -Ala-NAc | Lysine | Hydrogen |
| II-D-54(a, b, c)<br>II-E-54(a, b, c)<br>II-J-54(a, b, c)<br>II-K-54(a, b, c)<br>II-P-54(a, b, c)<br>II-Q-54(a, b, c)<br>II-V-54(a, b, c)<br>II-W-54(a, b, c) | guanidino-phenyl<br>a = ortho<br>b = meta<br>c = para | Methyl | -Ala-NAc | Lysine | —OH |

TABLE 3a-continued

| Compound | R | R' | R" | AA (side chain) | X |
|---|---|---|---|---|---|
| II-D-55(a, b, c) II-E-55(a, b, c) II-J-55(a, b, c) II-K-55(a, b, c) II-P-55(a, b, c) II-Q-55(a, b, c) II-V-55(a, b, c) II-W-55(a, b, c) | 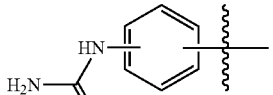 a = ortho b = meta c = para | Methyl | -Ala-NAc | Arginine | Hydrogen |
| II-D-56(a, b, c) II-E-56(a, b, c) II-J-56(a, b, c) II-K-56(a, b, c) II-P-56(a, b, c) II-Q-56(a, b, c) II-V-56(a, b, c) II-W-56(a, b, c) | 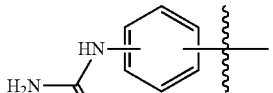 a = ortho b = meta c = para | Methyl | -Ala-NAc | Arginine | —OH |
| II-D-57(a, b, c) II-E-57(a, b, c) II-J-57(a, b, c) II-K-57(a, b, c) II-P-57(a, b, c) II-Q-57(a, b, c) II-V-57(a, b, c) II-W-57(a, b, c) | 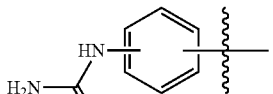 a = ortho b = meta c = para | Methyl | -Gly-NAc | Lysine | Hydrogen |
| II-D-58(a, b, c) II-E-58(a, b, c) II-J-58(a, b, c) II-K-58(a, b, c) II-P-58(a, b, c) II-Q-58(a, b, c) II-V-58(a, b, c) II-W-58(a, b, c) | 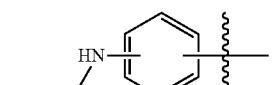 a = ortho b = meta c = para | Methyl | -Gly-NAc | Lysine | —OH |
| II-D-59(a, b, c) II-E-59(a, b, c) II-J-59(a, b, c) II-K-59(a, b, c) II-P-59(a, b, c) II-Q-59(a, b, c) II-V-59(a, b, c) II-W-59(a, b, c) | 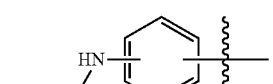 a = ortho b = meta c = para | Methyl | -Gly-NAc | Arginine | Hydrogen |
| II-D-60(a, b, c) II-E-60(a, b, c) II-J-60(a, b, c) II-K-60(a, b, c) II-P-60(a, b, c) II-Q-60(a, b, c) II-V-60(a, b, c) II-W-60(a, b, c) | 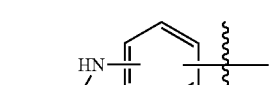 a = ortho b = meta c = para | Methyl | -Gly-NAc | Arginine | —OH |

TABLE 3a-continued

| Compound | R | R' | R" | AA (side chain) | X |
|---|---|---|---|---|---|
| II-D-61(a, b, c)<br>II-E-61(a, b, c)<br>II-J-61(a, b, c)<br>II-K-61(a, b, c)<br>II-P-61(a, b, c)<br>II-Q-61(a, b, c)<br>II-V-61(a, b, c)<br>II-W-61(a, b, c) | guanidino-phenyl<br>a = ortho<br>b = meta<br>c = para | Benzyloxy | Acetyl | Lysine | Hydrogen |
| II-D-62(a, b, c)<br>II-E-62(a, b, c)<br>II-J-62(a, b, c)<br>II-K-62(a, b, c)<br>II-P-62(a, b, c)<br>II-Q-62(a, b, c)<br>II-V-62(a, b, c)<br>II-W-62(a, b, c) | guanidino-phenyl<br>a = ortho<br>b = meta<br>c = para | Benzyloxy | Acetyl | Lysine | —OH |
| II-D-63(a, b, c)<br>II-E-63(a, b, c)<br>II-J-63(a, b, c)<br>II-K-63(a, b, c)<br>II-P-63(a, b, c)<br>II-Q-63(a, b, c)<br>II-V-63(a, b, c)<br>II-W-63(a, b, c) | guanidino-phenyl<br>a = ortho<br>b = meta<br>c = para | Benzyloxy | Acetyl | Arginine | Hydrogen |
| II-D-64(a, b, c)<br>II-E-64(a, b, c)<br>II-J-64(a, b, c)<br>II-K-64(a, b, c)<br>II-P-64(a, b, c)<br>II-Q-64(a, b, c)<br>II-V-64(a, b, c)<br>II-W-64(a, b, c) | guanidino-phenyl<br>a = ortho<br>b = meta<br>c = para | Benzyloxy | Acetyl | Arginine | —OH |
| II-D-65(a, b, c)<br>II-E-65(a, b, c)<br>II-J-65(a, b, c)<br>II-K-65(a, b, c)<br>II-P-65(a, b, c)<br>II-Q-65(a, b, c)<br>II-V-65(a, b, c)<br>II-W-65(a, b, c) | guanidino-phenyl<br>a = ortho<br>b = meta<br>c = para | Benzyloxy | -Ala-NAc | Lysine | Hydrogen |
| II-D-66(a, b, c)<br>II-E-66(a, b, c)<br>II-J-66(a, b, c)<br>II-K-66(a, b, c)<br>II-P-66(a, b, c)<br>II-Q-66(a, b, c)<br>II-V-66(a, b, c)<br>II-W-66(a, b, c) | guanidino-phenyl<br>a = ortho<br>b = meta<br>c = para | Benzyloxy | -Ala-NAc | Lysine | —OH |

TABLE 3a-continued

| Compound | R | R' | R" | AA (side chain) | X |
|---|---|---|---|---|---|
| II-D-67(a, b, c)<br>II-E-67(a, b, c)<br>II-J-67(a, b, c)<br>II-K-67(a, b, c)<br>II-P-67(a, b, c)<br>II-Q-67(a, b, c)<br>II-V-67(a, b, c)<br>II-W-67(a, b, c) | 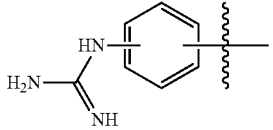<br>a = ortho<br>b = meta<br>c = para | Benzyloxy | -Ala-NAc | Arginine | Hydrogen |
| II-D-68(a, b, c)<br>II-E-68(a, b, c)<br>II-J-68(a, b, c)<br>II-K-68(a, b, c)<br>II-P-68(a, b, c)<br>II-Q-68(a, b, c)<br>II-V-68(a, b, c)<br>II-W-68(a, b, c) | 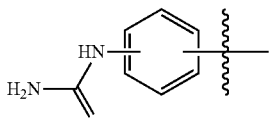<br>a = ortho<br>b = meta<br>c = para | Benzyloxy | -Ala-NAc | Arginine | —OH |
| II-D-69(a, b, c)<br>II-E-69(a, b, c)<br>II-J-69(a, b, c)<br>II-K-69(a, b, c)<br>II-P-69(a, b, c)<br>II-Q-69(a, b, c)<br>II-V-69(a, b, c)<br>II-W-69(a, b, c) | 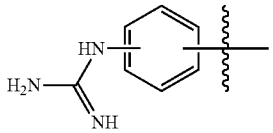<br>a = ortho<br>b = meta<br>c = para | Benzyloxy | -Gly-NAc | Lysine | Hydrogen |
| II-D-70(a, b, c)<br>II-E-70(a, b, c)<br>II-J-70(a, b, c)<br>II-K-70(a, b, c)<br>II-P-70(a, b, c)<br>II-Q-70(a, b, c)<br>II-V-70(a, b, c)<br>II-W-70(a, b, c) | 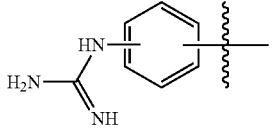<br>a = ortho<br>b = meta<br>c = para | Benzyloxy | -Gly-NAc | Lysine | —OH |
| II-D-71(a, b, c)<br>II-E-71(a, b, c)<br>II-J-71(a, b, c)<br>II-K-71(a, b, c)<br>II-P-71(a, b, c)<br>II-Q-71(a, b, c)<br>II-V-71(a, b, c)<br>II-W-71(a, b, c) | 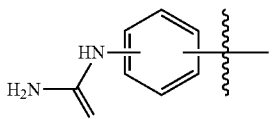<br>a = ortho<br>b = meta<br>c = para | Benzyloxy | -Gly-NAc | Arginine | Hydrogen |
| II-D-72(a, b, c)<br>II-E-72(a, b, c)<br>II-J-72(a, b, c)<br>II-K-72(a, b, c)<br>II-P-72(a, b, c)<br>II-Q-72(a, b, c)<br>II-V-72(a, b, c)<br>II-W-72(a, b, c) | 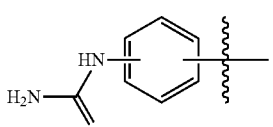<br>a = ortho<br>b = meta<br>c = para | Benzyloxy | -Gly-NAc | Arginine | —OH |
| II-D-73(a, b, c)<br>II-E-73(a, b, c)<br>II-J-73(a, b, c)<br>II-K-73(a, b, c)<br>II-P-73(a, b, c)<br>II-Q-73(a, b, c)<br>II-V-73(a, b, c)<br>II-W-73(a, b, c) | 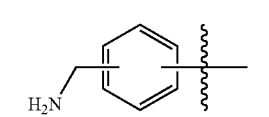<br>a = ortho<br>b = meta<br>c = para | Methyl | Acetyl | Lysine | Hydrogen |

TABLE 3a-continued

| Compound | R | R' | R" | AA (side chain) | X |
|---|---|---|---|---|---|
| II-D-74(a, b, c)<br>II-E-74(a, b, c)<br>II-J-74(a, b, c)<br>II-K-74(a, b, c)<br>II-P-74(a, b, c)<br>II-Q-74(a, b, c)<br>II-V-74(a, b, c)<br>II-W-74(a, b, c) | <br>a = ortho<br>b = meta<br>c = para | Methyl | Acetyl | Lysine | —OH |
| II-D-75(a, b, c)<br>II-E-75(a, b, c)<br>II-J-75(a, b, c)<br>II-K-75(a, b, c)<br>II-P-75(a, b, c)<br>II-Q-75(a, b, c)<br>II-V-75(a, b, c)<br>II-W-75(a, b, c) | 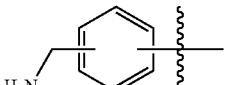<br>a = ortho<br>b = meta<br>c = para | Methyl | Acetyl | Arginine | Hydrogen |
| II-D-76(a, b, c)<br>II-E-76(a, b, c)<br>II-J-76(a, b, c)<br>II-K-76(a, b, c)<br>II-P-76(a, b, c)<br>II-Q-76(a, b, c)<br>II-V-76(a, b, c)<br>II-W-76(a, b, c) | <br>a = ortho<br>b = meta<br>c = para | Methyl | Acetyl | Arginine | —OH |
| II-D-77(a, b, c)<br>II-E-77(a, b, c)<br>II-J-77(a, b, c)<br>II-K-77(a, b, c)<br>II-P-77(a, b, c)<br>II-Q-77(a, b, c)<br>II-V-77(a, b, c)<br>II-W-77(a, b, c) | <br>a = ortho<br>b = meta<br>c = para | Methyl | -Ala-NAc | Lysine | Hydrogen |
| II-D-78(a, b, c)<br>II-E-78(a, b, c)<br>II-J-78(a, b, c)<br>II-K-78(a, b, c)<br>II-P-78(a, b, c)<br>II-Q-78(a, b, c)<br>II-V-78(a, b, c)<br>II-W-78(a, b, c) | <br>a = ortho<br>b = meta<br>c = para | Methyl | -Ala-NAc | Lysine | —OH |
| II-D-79(a, b, c)<br>II-E-79(a, b, c)<br>II-J-79(a, b, c)<br>II-K-79(a, b, c)<br>II-P-79(a, b, c)<br>II-Q-79(a, b, c)<br>II-V-79(a, b, c)<br>II-W-79(a, b, c) | 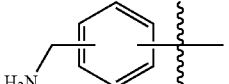<br>a = ortho<br>b = meta<br>c = para | Methyl | -Ala-NAc | Arginine | Hydrogen |
| II-D-80(a, b, c)<br>II-E-80(a, b, c)<br>II-J-80(a, b, c)<br>II-K-80(a, b, c)<br>II-P-80(a, b, c)<br>II-Q-80(a, b, c)<br>II-V-80(a, b, c)<br>II-W-80(a, b, c) | <br>a = ortho<br>b = meta<br>c = para | Methyl | -Ala-NAc | Arginine | —OH |
| II-D-81(a, b, c)<br>II-E-81(a, b, c)<br>II-J-81(a, b, c)<br>II-K-81(a, b, c)<br>II-P-81(a, b, c)<br>II-Q-81(a, b, c)<br>II-V-81(a, b, c)<br>II-W-81(a, b, c) | 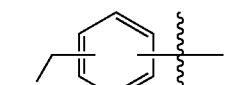<br>a = ortho<br>b = meta<br>c = para | Methyl | -Gly-NAc | Lysine | Hydrogen |

TABLE 3a-continued

| Compound | R | R' | R" | AA (side chain) | X |
|---|---|---|---|---|---|
| II-D-82(a, b, c)<br>II-E-82(a, b, c)<br>II-J-82(a, b, c)<br>II-K-82(a, b, c)<br>II-P-82(a, b, c)<br>II-Q-82(a, b, c)<br>II-V-82(a, b, c)<br>II-W-82(a, b, c) | <br>a = ortho<br>b = meta<br>c = para | Methyl | -Gly-NAc | Lysine | —OH |
| II-D-83(a, b, c)<br>II-E-83(a, b, c)<br>II-J-83(a, b, c)<br>II-K-83(a, b, c)<br>II-P-83(a, b, c)<br>II-Q-83(a, b, c)<br>II-V-83(a, b, c)<br>II-W-83(a, b, c) | 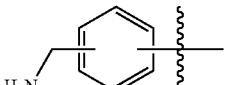<br>a = ortho<br>b = meta<br>c = para | Methyl | -Gly-NAc | Arginine | Hydrogen |
| II-D-84(a, b, c)<br>II-E-84(a, b, c)<br>II-J-84(a, b, c)<br>II-K-84(a, b, c)<br>II-P-84(a, b, c)<br>II-Q-84(a, b, c)<br>II-V-84(a, b, c)<br>II-W-84(a, b, c) | <br>a = ortho<br>b = meta<br>c = para | Methyl | -Gly-NAc | Arginine | —OH |
| II-D-85(a, b, c)<br>II-E-85(a, b, c)<br>II-J-85(a, b, c)<br>II-K-85(a, b, c)<br>II-P-85(a, b, c)<br>II-Q-85(a, b, c)<br>II-V-85(a, b, c)<br>II-W-85(a, b, c) | <br>a = ortho<br>b = meta<br>c = para | Benzyloxy | Acetyl | Lysine | Hydrogen |
| II-D-86(a, b, c)<br>II-E-86(a, b, c)<br>II-J-86(a, b, c)<br>II-K-86(a, b, c)<br>II-P-86(a, b, c)<br>II-Q-86(a, b, c)<br>II-V-86(a, b, c)<br>II-W-86(a, b, c) | <br>a = ortho<br>b = meta<br>c = para | Benzyloxy | Acetyl | Lysine | —OH |
| II-D-87(a, b, c)<br>II-E-87(a, b, c)<br>II-J-87(a, b, c)<br>II-K-87(a, b, c)<br>II-P-87(a, b, c)<br>II-Q-87(a, b, c)<br>II-V-87(a, b, c)<br>II-W-87(a, b, c) | 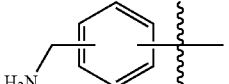<br>a = ortho<br>b = meta<br>c = para | Benzyloxy | Acetyl | Arginine | Hydrogen |
| II-D-88(a, b, c)<br>II-E-88(a, b, c)<br>II-J-88(a, b, c)<br>II-K-88(a, b, c)<br>II-P-88(a, b, c)<br>II-Q-88(a, b, c)<br>II-V-88(a, b, c)<br>II-W-88(a, b, c) | <br>a = ortho<br>b = meta<br>c = para | Benzyloxy | Acetyl | Arginine | —OH |
| II-D-89(a, b, c)<br>II-E-89(a, b, c)<br>II-J-89(a, b, c)<br>II-K-89(a, b, c)<br>II-P-89(a, b, c)<br>II-Q-89(a, b, c)<br>II-V-89(a, b, c)<br>II-W-89(a, b, c) | 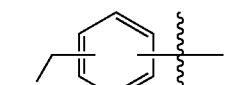<br>a = ortho<br>b = meta<br>c = para | Benzyloxy | -Ala-NAc | Lysine | Hydrogen |

TABLE 3a-continued

| Compound | R | R' | R" | AA (side chain) | X |
|---|---|---|---|---|---|
| II-D-90(a, b, c)<br>II-E-90(a, b, c)<br>II-J-90(a, b, c)<br>II-K-90(a, b, c)<br>II-P-90(a, b, c)<br>II-Q-90(a, b, c)<br>II-V-90(a, b, c)<br>II-W-90(a, b, c) | H₂N–C₆H₄–<br>a = ortho<br>b = meta<br>c = para | Benzyloxy | -Ala-NAc | Lysine | —OH |
| II-D-91(a, b, c)<br>II-E-91(a, b, c)<br>II-J-91(a, b, c)<br>II-K-91(a, b, c)<br>II-P-91(a, b, c)<br>II-Q-91(a, b, c)<br>II-V-91(a, b, c)<br>II-W-91(a, b, c) | H₂N–C₆H₄–<br>a = ortho<br>b = meta<br>c = para | Benzyloxy | -Ala-NAc | Arginine | Hydrogen |
| II-D-92(a, b, c)<br>II-E-92(a, b, c)<br>II-J-92(a, b, c)<br>II-K-92(a, b, c)<br>II-P-92(a, b, c)<br>II-Q-92(a, b, c)<br>II-V-92(a, b, c)<br>II-W-92(a, b, c) | H₂N–C₆H₄–<br>a = ortho<br>b = meta<br>c = para | Benzyloxy | -Ala-NAc | Arginine | —OH |
| II-D-93(a, b, c)<br>II-E-93(a, b, c)<br>II-J-93(a, b, c)<br>II-K-93(a, b, c)<br>II-P-93(a, b, c)<br>II-Q-93(a, b, c)<br>II-V-93(a, b, c)<br>II-W-93(a, b, c) | H₂N–C₆H₄–<br>a = ortho<br>b = meta<br>c = para | Benzyloxy | -Gly-NAc | Lysine | Hydrogen |
| II-D-94(a, b, c)<br>II-E-94(a, b, c)<br>II-J-94(a, b, c)<br>II-K-94(a, b, c)<br>II-P-94(a, b, c)<br>II-Q-94(a, b, c)<br>II-V-94(a, b, c)<br>II-W-94(a, b, c) | H₂N–C₆H₄–<br>a = ortho<br>b = meta<br>c = para | Benzyloxy | -Gly-NAc | Lysine | —OH |
| II-D-95(a, b, c)<br>II-E-95(a, b, c)<br>II-J-95(a, b, c)<br>II-K-95(a, b, c)<br>II-P-95(a, b, c)<br>II-Q-95(a, b, c)<br>II-V-95(a, b, c)<br>II-W-95(a, b, c) | H₂N–C₆H₄–<br>a = ortho<br>b = meta<br>c = para | Benzyloxy | -Gly-NAc | Lysine | Hydrogen |
| II-D-96(a, b, c)<br>II-E-96(a, b, c)<br>II-J-96(a, b, c)<br>II-K-96(a, b, c)<br>II-P-96(a, b, c)<br>II-Q-96(a, b, c)<br>II-V-96(a, b, c)<br>II-W-96(a, b, c) | H₂N–C₆H₄–<br>a = ortho<br>b = meta<br>c = para | Benzyloxy | -Gly-NAc | Arginine | —OH |

Table 4a illustrates various morphine containing compounds of Formula II-F, II-L, II-R, and II-X contemplated by the present disclosure.

TABLE 4a

| Compound | R | R' | R" | AA (side chain) |
| --- | --- | --- | --- | --- |
| II-F-1<br>II-L-1<br>II-R-1<br>II-X-1 | 6-amidino-2-naphthyl (H₂N-C(=NH)-naphthalene-) | Methyl | Acetyl | Lysine |
| II-F-2<br>II-L-2<br>II-R-2<br>II-X-2 | 6-amidino-2-naphthyl | Methyl | Acetyl | Arginine |
| II-F-3<br>II-L-3<br>II-R-3<br>II-X-3 | 6-amidino-2-naphthyl | Methyl | -Ala-NAc | Lysine |
| II-F-4<br>II-L-4<br>II-R-4<br>II-X-4 | 6-amidino-2-naphthyl | Methyl | -Ala-NAc | Arginine |
| II-F-5<br>II-L-5<br>II-R-5<br>II-X-5 | 6-amidino-2-naphthyl | Methyl | -Gly-NAc | Lysine |
| II-F-6<br>II-L-6<br>II-R-6<br>II-X-6 | 6-amidino-2-naphthyl | Methyl | -Gly-NAc | Arginine |
| II-F-7<br>II-L-7<br>II-R-7<br>II-X-7 | 6-amidino-2-naphthyl | Benzyloxy | Acetyl | Lysine |

TABLE 4a-continued

| Compound | R | R' | R" | AA (side chain) |
|---|---|---|---|---|
| II-F-8<br>II-L-8<br>II-R-8<br>II-X-8 | 6-carbamimidoyl-naphthalen-2-yl | Benzyloxy | Acetyl | Arginine |
| II-F-9<br>II-L-9<br>II-R-9<br>II-X-9 | 6-carbamimidoyl-naphthalen-2-yl | Benzyloxy | -Ala-NAc | Lysine |
| II-F-10<br>II-L-10<br>II-R-10<br>II-X-10 | 6-carbamimidoyl-naphthalen-2-yl | Benzyloxy | -Ala-NAc | Arginine |
| II-F-11<br>II-L-11<br>II-R-11<br>II-X-11 | 6-carbamimidoyl-naphthalen-2-yl | Benzyloxy | -Gly-NAc | Lysine |
| II-F-12<br>II-L-12<br>II-R-12<br>II-X-12 | 6-carbamimidoyl-naphthalen-2-yl | Benzyloxy | -Gly-NAc | Arginine |
| II-F-13(a, b, c)<br>II-L-13(a, b, c)<br>II-R-13(a, b, c)<br>II-X-13(a, b, c) | carbamimidoyl-phenyl<br>a = ortho<br>b = meta<br>c = para | Methyl | Acetyl | Lysine |
| II-F-14(a, b, c)<br>II-L-14(a, b, c)<br>II-R-14(a, b, c)<br>II-X-14(a, b, c) | carbamimidoyl-phenyl<br>a = ortho<br>b = meta<br>c = para | Methyl | Acetyl | Arginine |
| II-F-15(a, b, c)<br>II-L-15(a, b, c)<br>II-R-15(a, b, c)<br>II-X-15(a, b, c) | carbamimidoyl-phenyl<br>a = ortho<br>b = meta<br>c = para | Methyl | -Ala-NAc | Lysine |

TABLE 4a-continued

| Compound | R | R' | R" | AA (side chain) |
|---|---|---|---|---|
| II-F-16(a, b, c) II-L-16(a, b, c) II-R-16(a, b, c) II-X-16(a, b, c) | 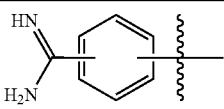 a = ortho b = meta c = para | Methyl | -Ala-NAc | Arginine |
| II-F-17(a, b, c) II-L-17(a, b, c) II-R-17(a, b, c) II-X-17(a, b, c) | 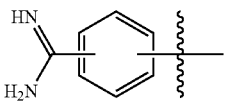 a = ortho b = meta c = para | Methyl | -Gly-NAc | Lysine |
| II-F-18(a, b, c) II-L-18(a, b, c) II-R-18(a, b, c) II-X-18(a, b, c) | 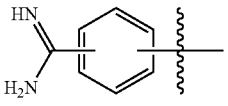 a = ortho b = meta c = para | Methyl | -Gly-NAc | Arginine |
| II-F-19(a, b, c) II-L-19(a, b, c) II-R-19(a, b, c) II-X-19(a, b, c) | 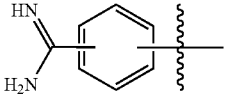 a = ortho b = meta c = para | Benzyloxy | Acetyl | Lysine |
| II-F-20(a, b, c) II-L-20(a, b, c) II-R-20(a, b, c) II-X-20(a, b, c) | 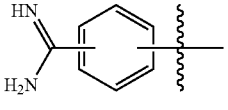 a = ortho b = meta c = para | Benzyloxy | Acetyl | Arginine |
| II-F-21(a, b, c) II-L-21(a, b, c) II-R-21(a, b, c) II-X-21(a, b, c) | 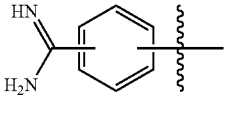 a = ortho b = meta c = para | Benzyloxy | -Ala-NAc | Lysine |
| II-F-22(a, b, c) II-L-22(a, b, c) II-R-22(a, b, c) II-X-22(a, b, c) | 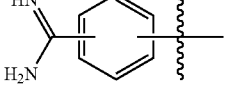 a = ortho b = meta c = para | Benzyloxy | -Ala-NAc | Arginine |
| II-F-23(a, b, c) II-L-23(a, b, c) II-R-23(a, b, c) II-X-23(a, b, c) | 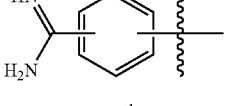 a = ortho b = meta c = para | Benzyloxy | -Gly-NAc | Lysine |

TABLE 4a-continued

| Compound | R | R' | R'' | AA (side chain) |
|---|---|---|---|---|
| II-F-24(a, b, c) II-L-24(a, b, c) II-R-24(a, b, c) II-X-24(a, b, c) | [benzamidine group; a = ortho, b = meta, c = para] | Benzyloxy | -Gly-NAc | Arginine |
| II-F-25(a, b, c) II-L-25(a, b, c) II-R-25(a, b, c) II-X-25(a, b, c) | [phenylguanidine group; a = ortho, b = meta, c = para] | Methyl | Acetyl | Lysine |
| II-F-26(a, b, c) II-L-26(a, b, c) II-R-26(a, b, c) II-X-26(a, b, c) | [phenylguanidine group; a = ortho, b = meta, c = para] | Methyl | Acetyl | Arginine |
| II-F-27(a, b, c) II-L-27(a, b, c) II-R-27(a, b, c) II-X-27(a, b, c) | [phenylguanidine group; a = ortho, b = meta, c = para] | Methyl | -Ala-NAc | Lysine |
| II-F-28(a, b, c) II-L-28(a, b, c) II-R-28(a, b, c) II-X-28(a, b, c) | [phenylguanidine group; a = ortho, b = meta, c = para] | Methyl | -Ala-NAc | Arginine |
| II-F-29(a, b, c) II-L-29(a, b, c) II-R-29(a, b, c) II-X-29(a, b, c) | [phenylguanidine group; a = ortho, b = meta, c = para] | Methyl | -Gly-NAc | Lysine |
| II-F-30(a, b, c) II-L-30(a, b, c) II-R-30(a, b, c) II-X-30(a, b, c) | [phenylguanidine group; a = ortho, b = meta, c = para] | Methyl | -Gly-NAc | Arginine |

TABLE 4a-continued

| Compound | R | R' | R'' | AA (side chain) |
|---|---|---|---|---|
| II-F-31(a, b, c)<br>II-L-31(a, b, c)<br>II-R-31(a, b, c)<br>II-X-31(a, b, c) | 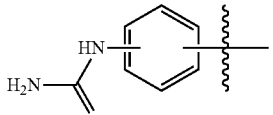<br>a = ortho<br>b = meta<br>c = para | Benzyloxy | Acetyl | Lysine |
| II-F-32(a, b, c)<br>II-L-32(a, b, c)<br>II-R-32(a, b, c)<br>II-X-32(a, b, c) | 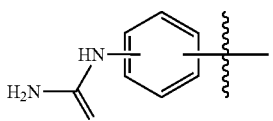<br>a = ortho<br>b = meta<br>c = para | Benzyloxy | Acetyl | Arginine |
| II-F-33(a, b, c)<br>II-L-33(a, b, c)<br>II-R-33(a, b, c)<br>II-X-33(a, b, c) | 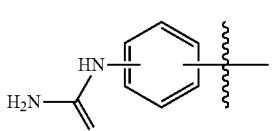<br>a = ortho<br>b = meta<br>c = para | Benzyloxy | -Ala-NAc | Lysine |
| II-F-34(a, b, c)<br>II-L-34(a, b, c)<br>II-R-34(a, b, c)<br>II-X-34(a, b, c) | 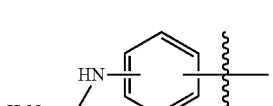<br>a = ortho<br>b = meta<br>c = para | Benzyloxy | -Ala-NAc | Arginine |
| II-F-35(a, b, c)<br>II-L-35(a, b, c)<br>II-R-35(a, b, c)<br>II-X-35(a, b, c) | 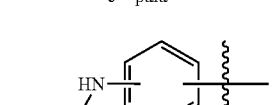<br>a = ortho<br>b = meta<br>c = para | Benzyloxy | -Gly-NAc | Lysine |
| II-F-36(a, b, c)<br>II-L-36(a, b, c)<br>II-R-36(a, b, c)<br>II-X-36(a, b, c) | 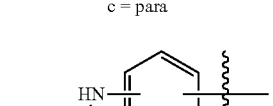<br>a = ortho<br>b = meta<br>c = para | Benzyloxy | -Gly-NAc | Arginine |
| II-F-37(a, b, c)<br>II-L-37(a, b, c)<br>II-R-37(a, b, c)<br>II-X-37(a, b, c) | 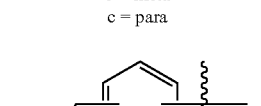<br>a = ortho<br>b = meta<br>c = para | Methyl | Acetyl | Lysine |

TABLE 4a-continued

| Compound | R | R' | R'' | AA (side chain) |
|---|---|---|---|---|
| II-F-38(a, b, c)<br>II-L-38(a, b, c)<br>II-R-38(a, b, c)<br>II-X-38(a, b, c) | H₂N–C₆H₄–<br>a = ortho<br>b = meta<br>c = para | Methyl | Acetyl | Arginine |
| II-F-39(a, b, c)<br>II-L-39(a, b, c)<br>II-R-39(a, b, c)<br>II-X-39(a, b, c) | H₂N–C₆H₄–<br>a = ortho<br>b = meta<br>c = para | Methyl | -Ala-NAc | Lysine |
| II-F-40(a, b, c)<br>II-L-40(a, b, c)<br>II-R-40(a, b, c)<br>II-X-40(a, b, c) | H₂N–C₆H₄–<br>a = ortho<br>b = meta<br>c = para | Methyl | -Ala-NAc | Arginine |
| II-F-41(a, b, c)<br>II-L-41(a, b, c)<br>II-R-41(a, b, c)<br>II-X-41(a, b, c) | H₂N–C₆H₄–<br>a = ortho<br>b = meta<br>c = para | Methyl | -Gly-NAc | Lysine |
| II-F-42(a, b, c)<br>II-L-42(a, b, c)<br>II-R-42(a, b, c)<br>II-X-42(a, b, c) | H₂N–C₆H₄–<br>a = ortho<br>b = meta<br>c = para | Methyl | -Gly-NAc | Arginine |
| II-F-43(a, b, c)<br>II-L-43(a, b, c)<br>II-R-43(a, b, c)<br>II-X-43(a, b, c) | H₂N–C₆H₄–<br>a = ortho<br>b = meta<br>c = para | Benzyloxy | Acetyl | Lysine |
| II-F-44(a, b, c)<br>II-L-44(a, b, c)<br>II-R-44(a, b, c)<br>II-X-44(a, b, c) | H₂N–C₆H₄–<br>a = ortho<br>b = meta<br>c = para | Benzyloxy | Acetyl | Arginine |
| II-F-45(a, b, c)<br>II-L-45(a, b, c)<br>II-R-45(a, b, c)<br>II-X-45(a, b, c) | H₂N–C₆H₄–<br>a = ortho<br>b = meta<br>c = para | Benzyloxy | -Ala-NAc | Lysine |

TABLE 4a-continued

| Compound | R | R' | R" | AA (side chain) |
|---|---|---|---|---|
| II-F-46(a, b, c)<br>II-L-46(a, b, c)<br>II-R-46(a, b, c)<br>II-X-46(a, b, c) | H₂N-CH₂-C₆H₄-<br>a = ortho<br>b = meta<br>c = para | Benzyloxy | -Ala-NAc | Arginine |
| II-F-47(a, b, c)<br>II-L-47(a, b, c)<br>II-R-47(a, b, c)<br>II-X-47(a, b, c) | H₂N-CH₂-C₆H₄-<br>a = ortho<br>b = meta<br>c = para | Benzyloxy | -Gly-NAc | Lysine |
| II-F-48(a, b, c)<br>II-L-48(a, b, c)<br>II-R-48(a, b, c)<br>II-X-48(a, b, c) | H₂N-CH₂-C₆H₄-<br>a = ortho<br>b = meta<br>c = para | Benzyloxy | -Gly-NAc | Arginine |

In one aspect, the present disclosure provides a pharmaceutical composition, the composition comprising:

Two or more polysubunit molecules each comprising GI enzyme labile opioid releasing subunit(s), and gastrointestinal enzyme inhibitor subunit(s) wherein the GI enzyme labile opioid releasing subunit(s) and the GI enzyme inhibitor subunit(s) are covalently linked via a covalent bond, an atom, or a scaffold moiety. In some embodiments the disclosure provides for polysubunit compounds comprising one GI enzyme labile opioid releasing subunit covalently linked to one GI enzyme inhibitor subunit represented by formulae III (A-L) below:

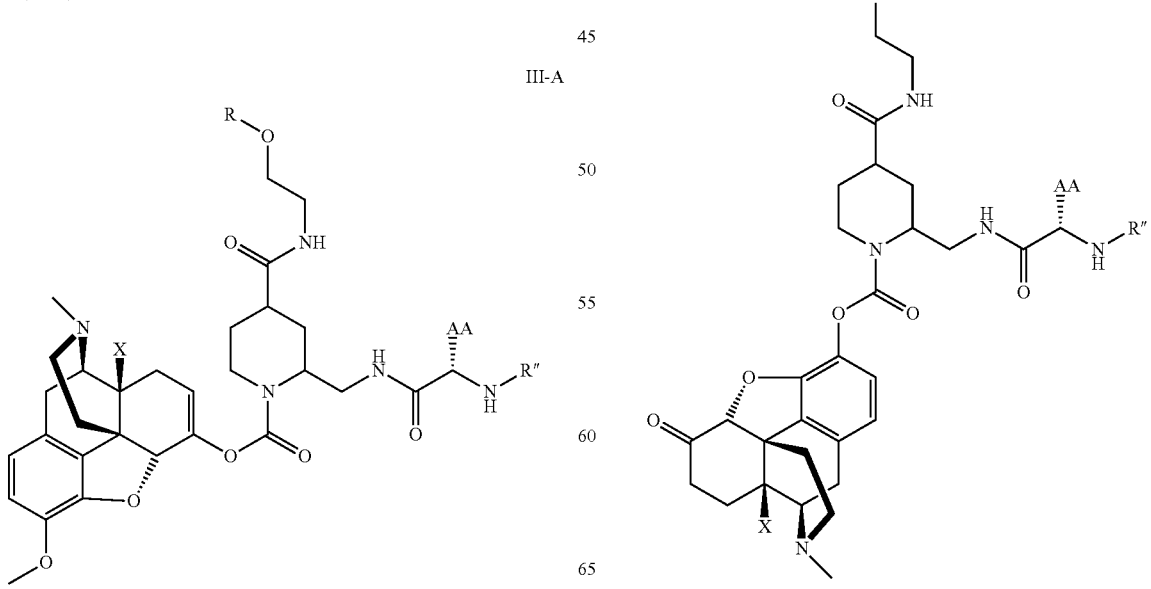

III-C
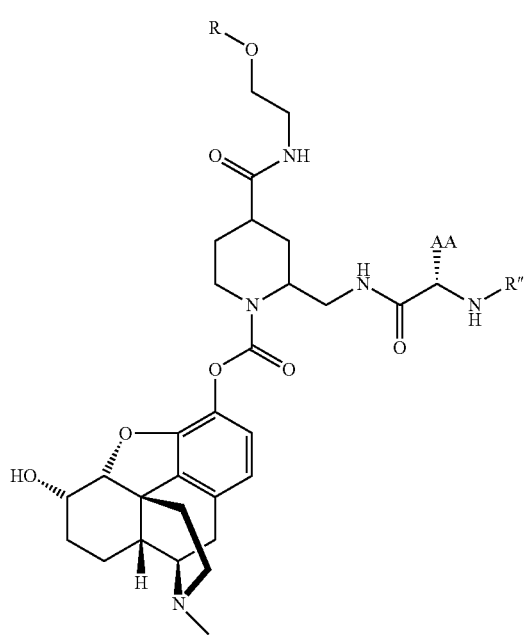
III-E
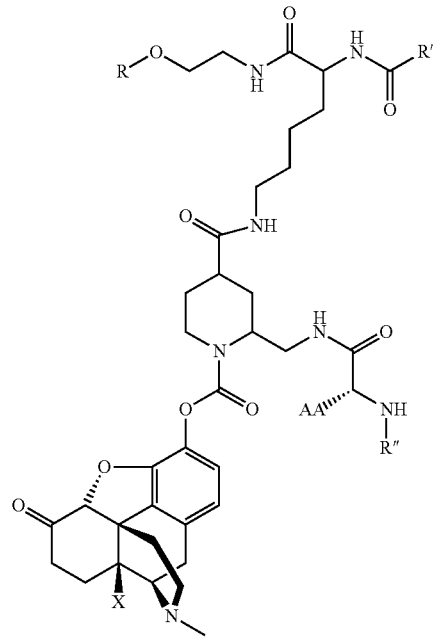
III-D
III-F

III-G
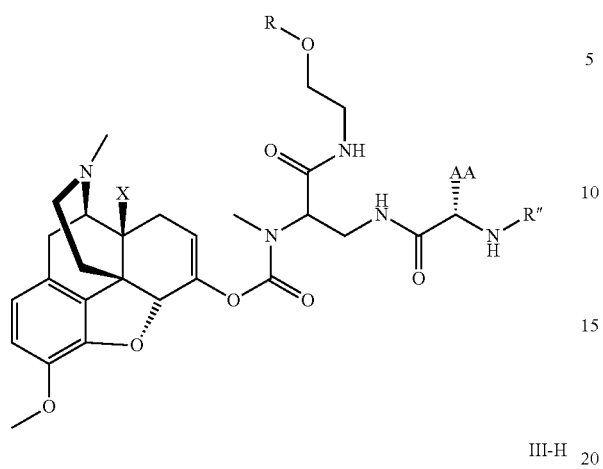
III-H
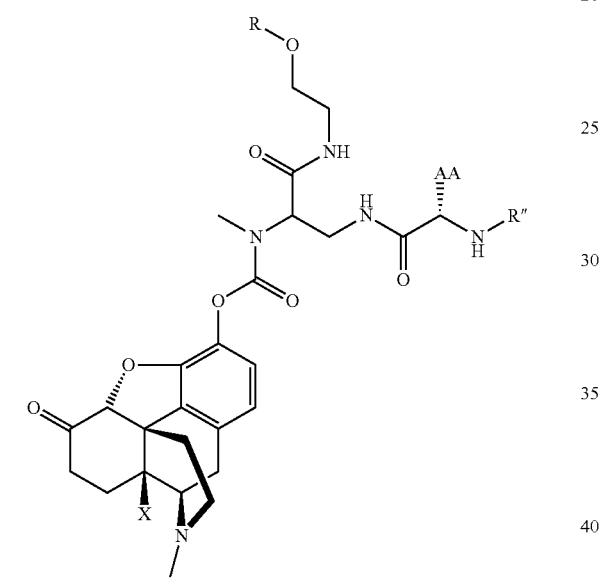
III-I
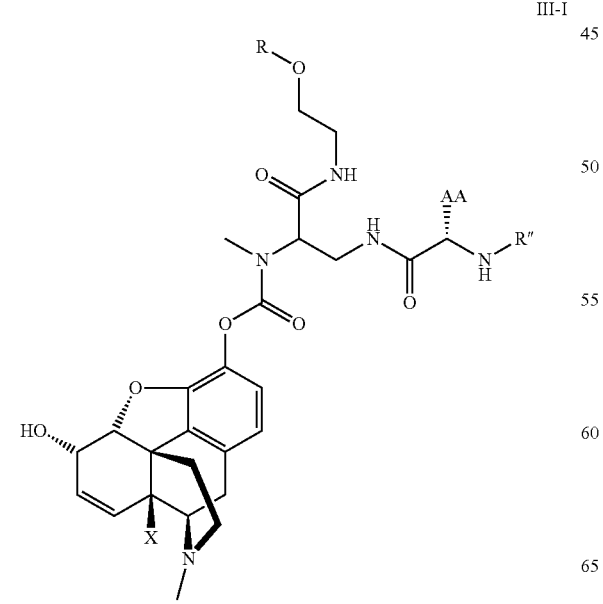
III-J
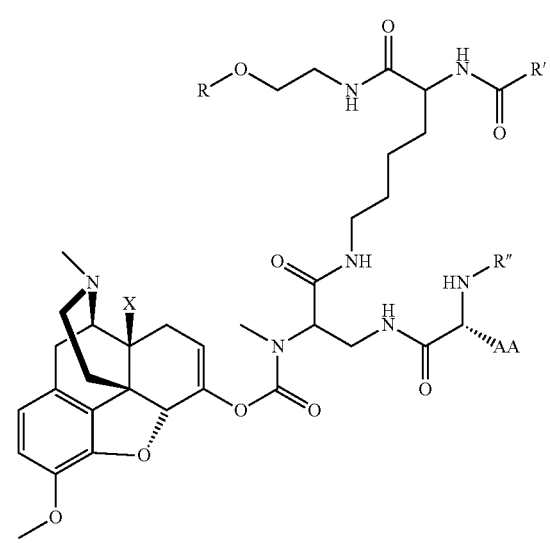
III-K
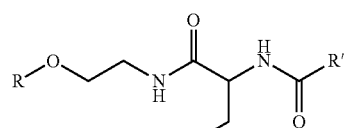
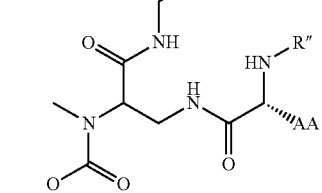
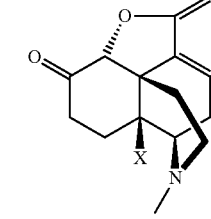

III-L

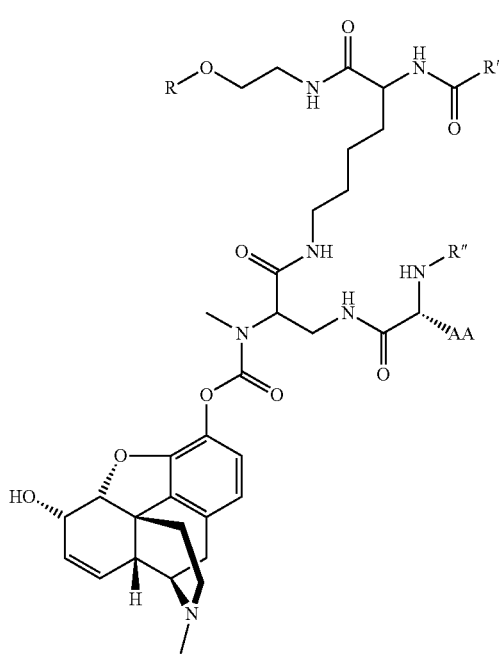

III-L

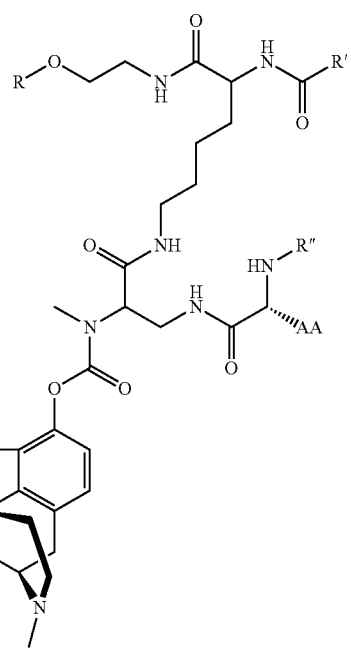

wherein:
R can be

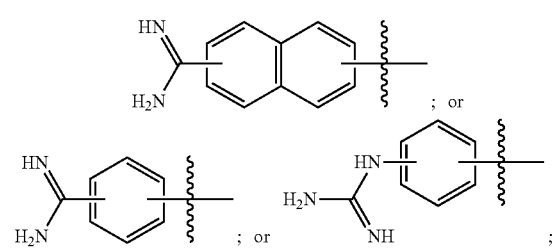

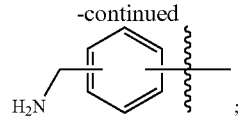

R' can be methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear or branched polyethylene glycol chain up to 5 kDa, benzyloxy, and the like; R" can be an acetyl, substituted acyl, a natural or non-natural amino acid, or a polypeptide chain comprising natural and/or non-natural amino acids up to 10 amino acids in length; AA is a natural or non-natural amino acid side chain recognized by trypsin; X is hydrogen or OH.

In some embodiments the disclosure provides for compositions comprising two or more of the aforementioned compounds of Formula II wherein:
R can be

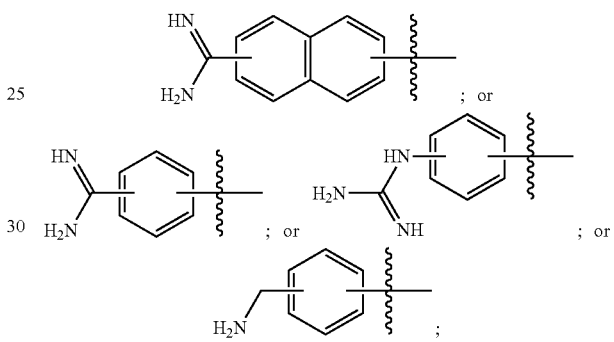

R' can be methyl or benzyloxy; R" can be an acetyl or a substituted acyl, a natural or non-natural amino acid or a di- or tri-peptide comprising natural or non-natural amino acids; AA is a natural or non-natural amino acid side chain recognized by trypsin; X is hydrogen or OH.

In yet other embodiments the disclosure provides one or more of the aforementioned compounds of Formula II wherein:
R can be

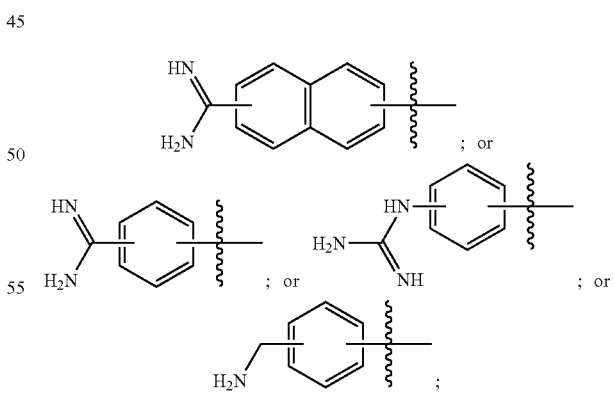

R' can be methyl or benzyloxy; R" can be an acetyl, a natural or non-natural amino acid or a dipeptide comprising natural or non-natural amino acids; AA is the side chain of lysine or arginine; X is hydrogen or OH.

In yet another embodiment the disclosure provides one or more of the aforementioned compounds of Formula II wherein:

R can be

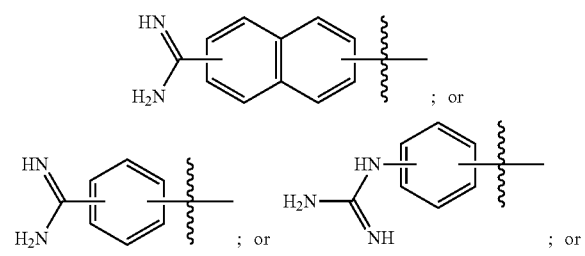
; or

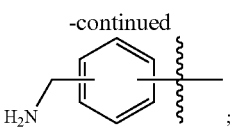
;

R' can be methyl or benzyloxy; R" can be acetyl, -Ala-NAc or -Gly-NAc; AA is the side chain of lysine or arginine; X is hydrogen or OH.

Table 1b illustrates various hydrocodone, hydromorphone, oxycodone, and oxymorphone containing compounds of Formula III-A, III-B, III-G, and III-H contemplated by the present disclosure.

TABLE 1B

| Compound | R | R" | AA (side chain) | X |
|---|---|---|---|---|
| III-A-1<br>III-B-1<br>III-G-1<br>III-H-1 | 6-amidino-2-naphthyl | Acetyl | Lysine | Hydrogen |
| III-A-2<br>III-B-2<br>III-G-2<br>III-H-2 | 6-amidino-2-naphthyl | Acetyl | Lysine | —OH |
| III-A-3<br>III-B-3<br>III-G-3<br>III-H-3 | 6-amidino-2-naphthyl | Acetyl | Arginine | Hydrogen |
| III-A-4<br>III-B-4<br>III-G-4<br>III-H-4 | 6-amidino-2-naphthyl | Acetyl | Arginine | —OH |
| III-A-5<br>III-B-5<br>III-G-5<br>III-H-5 | 6-amidino-2-naphthyl | -Ala-NAc | Lysine | Hydrogen |
| III-A-6<br>III-B-6<br>III-G-6<br>III-H-6 | 6-amidino-2-naphthyl | -Ala-NAc | Lysine | —OH |

TABLE 1B-continued

| Compound | R | R" | AA (side chain) | X |
|---|---|---|---|---|
| III-A-7<br>III-B-7<br>III-G-7<br>III-H-7 | 6-carbamimidoyl-naphthalen-2-yl (H2N-C(=NH)-naphthyl-) | -Ala-NAc | Arginine | Hydrogen |
| III-A-8<br>III-B-8<br>III-C-8<br>III-G-8<br>III-H-8<br>III-I-8 | 6-carbamimidoyl-naphthalen-2-yl | -Ala-NAc | Arginine | —OH |
| III-A-9<br>III-B-9<br>III-G-9<br>III-H-9 | 6-carbamimidoyl-naphthalen-2-yl | -Gly-NAc | Lysine | Hydrogen |
| III-A-10<br>III-B-10<br>III-G-10<br>III-H-10 | 6-carbamimidoyl-naphthalen-2-yl | -Gly-NAc | Lysine | —OH |
| III-A-11<br>III-B-11<br>III-G-11<br>III-H-11 | 6-carbamimidoyl-naphthalen-2-yl | -Gly-NAc | Arginine | Hydrogen |
| III-A-12<br>III-B-12<br>III-G-12<br>III-H-12 | 6-carbamimidoyl-naphthalen-2-yl | -Gly-NAc | Arginine | —OH |
| III-A-13(a, b, c)<br>III-B-13(a, b, c)<br>III-G-13(a, b, c)<br>III-H-13(a, b, c) | carbamimidoyl-phenyl<br>a = ortho<br>b = meta<br>c = para | Acetyl | Lysine | Hydrogen |
| III-A-14(a, b, c)<br>III-B-14(a, b, c)<br>III-G-14(a, b, c)<br>III-H-14(a, b, c) | carbamimidoyl-phenyl<br>a = ortho<br>b = meta<br>c = para | Acetyl | Lysine | —OH |

TABLE 1B-continued

| Compound | R | R" | AA (side chain) | X |
|---|---|---|---|---|
| III-A-15(a, b, c)<br>III-B-15(a, b, c)<br>III-G-15(a, b, c)<br>III-H-15(a, b, c) | 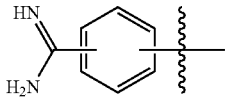<br>a = ortho<br>b = meta<br>c = para | Acetyl | Arginine | Hydrogen |
| III-A-16(a, b, c)<br>III-B-16(a, b, c)<br>III-G-16(a, b, c)<br>III-H-16(a, b, c) | 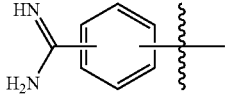<br>a = ortho<br>b = meta<br>c = para | Acetyl | Arginine | —OH |
| III-A-17(a, b, c)<br>III-B-17(a, b, c)<br>III-G-17(a, b, c)<br>III-H-17(a, b, c) | 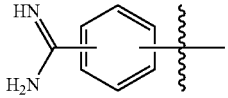<br>a = ortho<br>b = meta<br>c = para | -Ala-NAc | Lysine | Hydrogen |
| III-A-18(a, b, c)<br>III-B-18(a, b, c)<br>III-G-18(a, b, c)<br>III-H-18(a, b, c) | 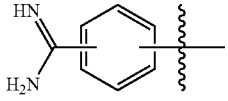<br>a = ortho<br>b = meta<br>c = para | -Ala-NAc | Lysine | —OH |
| III-A-19(a, b, c)<br>III-B-19(a, b, c)<br>III-G-19(a, b, c)<br>III-H-19(a, b, c) | 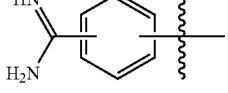<br>a = ortho<br>b = meta<br>c = para | -Ala-NAc | Arginine | Hydrogen |
| III-A-20(a, b, c)<br>III-B-20(a, b, c)<br>III-G-20(a, b, c)<br>III-H-20(a, b, c) | 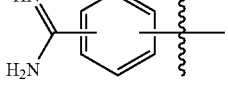<br>a = ortho<br>b = meta<br>c = para | -Ala-NAc | Arginine | —OH |
| III-A-21(a, b, c)<br>III-B-21(a, b, c)<br>III-G-21(a, b, c)<br>III-H-21(a, b, c) | 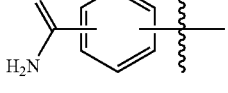<br>a = ortho<br>b = meta<br>c = para | -Gly-NAc | Lysine | Hydrogen |
| III-A-22(a, b, c)<br>III-B-22(a, b, c)<br>III-G-22(a, b, c)<br>III-H-22(a, b, c) | 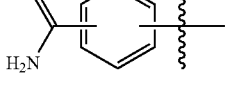<br>a = ortho<br>b = meta<br>c = para | -Gly-NAc | Lysine | —OH |

TABLE 1B-continued

| Compound | R | R" | AA (side chain) | X |
|---|---|---|---|---|
| III-A-23(a, b, c)<br>III-B-23(a, b, c)<br>III-G-23(a, b, c)<br>III-H-23(a, b, c) | 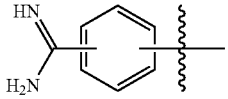<br>a = ortho<br>b = meta<br>c = para | -Gly-NAc | Arginine | Hydrogen |
| III-A-24(a, b, c)<br>III-B-24(a, b, c)<br>III-G-24(a, b, c)<br>III-H-24(a, b, c) | 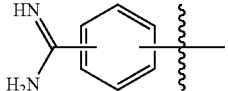<br>a = ortho<br>b = meta<br>c = para | -Gly-NAc | Arginine | —OH |
| III-A-25(a, b, c)<br>III-B-25(a, b, c)<br>III-G-25(a, b, c)<br>III-H-25(a, b, c) | 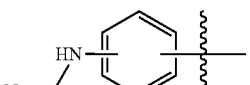<br>a = ortho<br>b = meta<br>c = para | Acetyl | Lysine | Hydrogen |
| III-A-26(a, b, c)<br>III-B-26(a, b, c)<br>III-G-26(a, b, c)<br>III-H-26(a, b, c) | 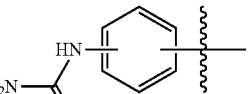<br>a = ortho<br>b = meta<br>c = para | Acetyl | Lysine | —OH |
| III-A-27(a, b, c)<br>III-B-27(a, b, c)<br>III-G-27(a, b, c)<br>III-H-27(a, b, c) | 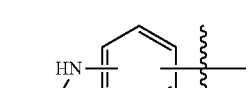<br>a = ortho<br>b = meta<br>c = para | Acetyl | Arginine | Hydrogen |
| III-A-28(a, b, c)<br>III-B-28(a, b, c)<br>III-G-28(a, b, c)<br>III-H-28(a, b, c) | 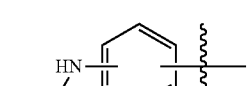<br>a = ortho<br>b = meta<br>c = para | Acetyl | Arginine | —OH |
| III-A-29(a, b, c)<br>III-B-29(a, b, c)<br>III-G-29(a, b, c)<br>III-H-29(a, b, c) | a = ortho<br>b = meta<br>c = para | -Ala-NAc | Lysine | Hydrogen |

TABLE 1B-continued

| Compound | R | R" | AA (side chain) | X |
|---|---|---|---|---|
| III-A-30(a, b, c)<br>III-B-30(a, b, c)<br>III-G-30(a, b, c)<br>III-H-30(a, b, c) | (a, b, c)<br>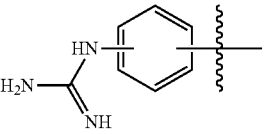<br>a = ortho<br>b = meta<br>c = para | -Ala-NAc | Lysine | —OH |
| III-A-31(a, b, c)<br>III-B-31(a, b, c)<br>III-G-31(a, b, c)<br>III-H-31(a, b, c) | 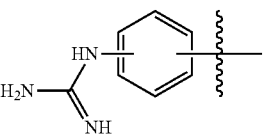<br>a = ortho<br>b = meta<br>c = para | -Ala-NAc | Arginine | Hydrogen |
| III-A-32(a, b, c)<br>III-B-32(a, b, c)<br>III-G-32(a, b, c)<br>III-H-32(a, b, c) | 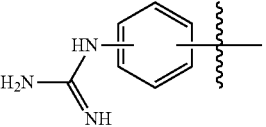<br>a = ortho<br>b = meta<br>c = para | -Ala-NAc | Arginine | —OH |
| III-A-33(a, b, c)<br>III-B-33(a, b, c)<br>III-G-33(a, b, c)<br>III-H-33(a, b, c) | 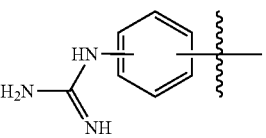<br>a = ortho<br>b = meta<br>c = para | -Gly-NAc | Lysine | Hydrogen |
| III-A-34(a, b, c)<br>III-B-34(a, b, c)<br>III-G-34(a, b, c)<br>III-H-34(a, b, c) | 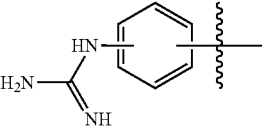<br>a = ortho<br>b = meta<br>c = para | -Gly-NAc | Lysine | —OH |
| III-A-35(a, b, c)<br>III-B-35(a, b, c)<br>III-G-35(a, b, c)<br>III-H-35(a, b, c) | 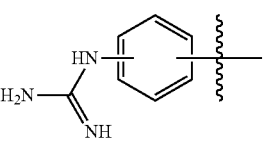<br>a = ortho<br>b = meta<br>c = para | -Gly-NAc | Arginine | Hydrogen |

TABLE 1B-continued

| Compound | R | R" | AA (side chain) | X |
|---|---|---|---|---|
| III-A-36(a, b, c)<br>III-B-36(a, b, c)<br>III-G-36(a, b, c)<br>III-H-36(a, b, c) | H₂N-C(=NH)-NH-C₆H₄-<br>a = ortho<br>b = meta<br>c = para | -Gly-NAc | Arginine | —OH |
| III-A-37(a, b, c)<br>III-B-37(a, b, c)<br>III-G-37(a, b, c)<br>III-H-37(a, b, c) | H₂N-CH₂-C₆H₄-<br>a = ortho<br>b = meta<br>c = para | Acetyl | Lysine | Hydrogen |
| III-A-38(a, b, c)<br>III-B-38(a, b, c)<br>III-G-38(a, b, c)<br>III-H-38(a, b, c) | H₂N-CH₂-C₆H₄-<br>a = ortho<br>b = meta<br>c = para | Acetyl | Lysine | —OH |
| III-A-39(a, b, c)<br>III-B-39(a, b, c)<br>III-G-39(a, b, c)<br>III-H-39(a, b, c) | H₂N-CH₂-C₆H₄-<br>a = ortho<br>b = meta<br>c = para | Acetyl | Arginine | Hydrogen |
| III-A-40(a, b, c)<br>III-B-40(a, b, c)<br>III-G-40(a, b, c)<br>III-H-40(a, b, c) | H₂N-CH₂-C₆H₄-<br>a = ortho<br>b = meta<br>c = para | Acetyl | Arginine | —OH |
| III-A-41(a, b, c)<br>III-B-41(a, b, c)<br>III-G-41(a, b, c)<br>III-H-41(a, b, c) | H₂N-CH₂-C₆H₄-<br>a = ortho<br>b = meta<br>c = para | -Ala-NAc | Lysine | Hydrogen |
| III-A-42(a, b, c)<br>III-B-42(a, b, c)<br>III-G-42(a, b, c)<br>III-H-42(a, b, c) | H₂N-CH₂-C₆H₄-<br>a = ortho<br>b = meta<br>c = para | -Ala-NAc | Lysine | —OH |
| III-A-43(a, b, c)<br>III-B-43(a, b, c)<br>III-G-43(a, b, c)<br>III-H-43(a, b, c) | H₂N-CH₂-C₆H₄-<br>a = ortho<br>b = meta<br>c = para | -Ala-NAc | Arginine | Hydrogen |

TABLE 1B-continued

| Compound | R | R" | AA (side chain) | X |
|---|---|---|---|---|
| III-A-44(a, b, c)<br>III-B-44(a, b, c)<br>III-G-44(a, b, c)<br>III-H-44(a, b, c) | 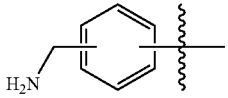<br>a = ortho<br>b = meta<br>c = para | -Ala-NAc | Arginine | —OH |
| III-A-45(a, b, c)<br>III-B-45(a, b, c)<br>III-G-45(a, b, c)<br>III-H-45(a, b, c) | 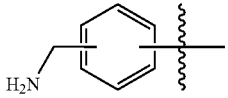<br>a = ortho<br>b = meta<br>c = para | -Gly-NAc | Lysine | Hydrogen |
| III-A-46(a, b, c)<br>III-B-46(a, b, c)<br>III-G-46(a, b, c)<br>III-H-46(a, b, c) | 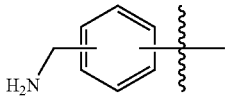<br>a = ortho<br>b = meta<br>c = para | -Gly-NAc | Lysine | —OH |
| III-A-47(a, b, c)<br>III-B-47(a, b, c)<br>III-G-47(a, b, c)<br>III-H-47(a, b, c) | 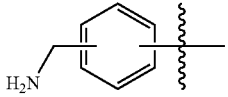<br>a = ortho<br>b = meta<br>c = para | -Gly-NAc | Arginine | Hydrogen |
| III-A-48(a, b, c)<br>III-B-48(a, b, c)<br>III-G-48(a, b, c)<br>III-H-48(a, b, c) | 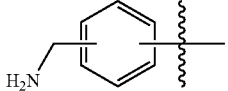<br>a = ortho<br>b = meta<br>c = para | -Gly-NAc | Arginine | —OH |

Table 2b illustrates various morphine containing compounds of Formula III-C and III-I contemplated by the present disclosure.

TABLE 2b

| Compound | R | R" | AA (side chain) |
|---|---|---|---|
| III-C-1<br>III-I-1 | 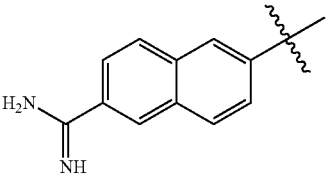 [SMILES: *c1ccc2cc(C(=N)N)ccc2c1] | Acetyl | Lysine |

TABLE 2b-continued
| Compound | R | R" | AA (side chain) |
|---|---|---|---|
| III-C-2<br>III-I-2 | 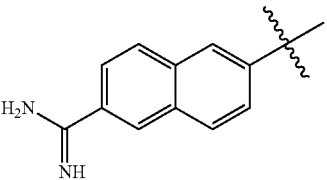 [SMILES: *c1ccc2cc(C(=N)N)ccc2c1] | Acetyl | Arginine |
| III-C-3<br>III-I-3 | 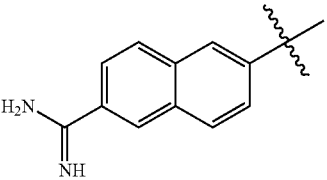 [SMILES: *c1ccc2cc(C(=N)N)ccc2c1] | -Ala-NAc | Lysine |
| III-C-4<br>III-I-4 | 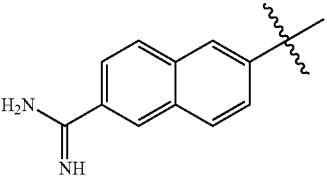 | -Ala-NAc | Arginine |
| III-C-5<br>III-I-5 | 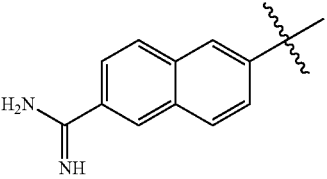 [SMILES: *c1ccc2cc(C(=N)N)ccc2c1] | -Gly-NAc | Lysine |
| III-C-6<br>III-I-6 | 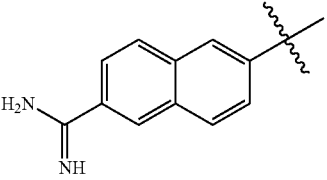 [SMILES: *c1ccc2cc(C(=N)N)ccc2c1] | -Gly-NAc | Arginine |
| III-C-7(a, b, c)<br>III-I-7(a, b, c) | 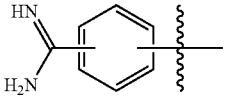<br>a = ortho<br>b = meta<br>c = para | Acetyl | Lysine |
| III-C-8(a, b, c)<br>III-I-8(a, b, c) | 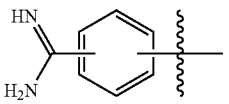<br>a = ortho<br>b = meta<br>c = para | Acetyl | Arginine |

TABLE 2b-continued

| Compound | R | R" | AA (side chain) |
|---|---|---|---|
| III-C-9(a, b, c)<br>III-I-9(a, b, c) | 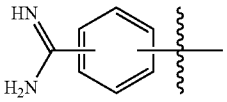<br>a = ortho<br>b = meta<br>c = para | -Ala-NAc | Lysine |
| III-C-10(a, b, c)<br>III-I-10(a, b, c) | 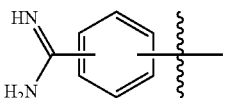<br>a = ortho<br>b = meta<br>c = para | -Ala-NAc | Arginine |
| III-C-11(a, b, c)<br>III-I-11(a, b, c) | <br>a = ortho<br>b = meta<br>c = para | -Gly-NAc | Lysine |
| III-C-12(a, b, c)<br>III-I-12(a, b, c) | 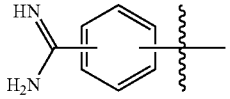<br>a = ortho<br>b = meta<br>c = para | -Gly-NAc | Arginine |
| III-C-13(a, b, c)<br>III-I-13(a, b, c) | 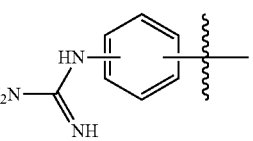<br>a = ortho<br>b = meta<br>c = para | Acetyl | Lysine |
| III-C-14(a, b, c)<br>III-I-14(a, b, c) | 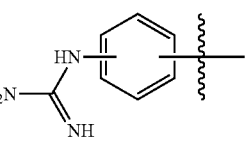<br>a = ortho<br>b = meta<br>c = para | Acetyl | Arginine |
| III-C-15(a, b, c)<br>III-I-15(a, b, c) | 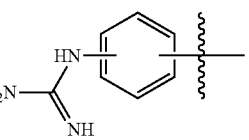<br>a = ortho<br>b = meta<br>c = para | -Ala-NAc | Lysine |

TABLE 2b-continued

| Compound | R | R" | AA (side chain) |
|---|---|---|---|
| III-C-16(a, b, c)<br>III-I-16(a, b,c) | guanidinyl-phenyl (a = ortho, b = meta, c = para) | -Ala-NAc | Arginine |
| III-C-17(a, b, c)<br>III-I-17(a, b, c) | guanidinyl-phenyl (a = ortho, b = meta, c = para) | -Gly-NAc | Lysine |
| III-C-18(a, b, c)<br>III-I-18(a, b, c) | guanidinyl-phenyl (a = ortho, b = meta, c = para) | -Gly-NAc | Arginine |
| III-C-19(a, b, c)<br>III-I-19(a, b, c) | aminomethyl-phenyl (a = ortho, b = meta, c = para) | Acetyl | Lysine |
| III-C-20(a, b, c)<br>III-I-20(a, b, c) | aminomethyl-phenyl (a = ortho, b = meta, c = para) | Acetyl | Arginine |
| III-C-21(a, b, c)<br>III-I-21(a, b, c) | aminomethyl-phenyl (a = ortho, b = meta, c = para) | -Ala-NAc | Lysine |
| III-C-22(a, b, c)<br>III-I-22(a, b, c) | aminomethyl-phenyl (a = ortho, b = meta, c = para) | -Ala-NAc | Arginine |

TABLE 2b-continued

| Compound | R | R" | AA (side chain) |
|---|---|---|---|
| III-C-23(a, b, c)<br>III-I-23(a, b, c) | H₂N–C₆H₄–CH₂– (a = ortho, b = meta, c = para) | -Gly-NAc | Lysine |
| III-C-24(a, b, c)<br>III-I-24(a, b, c) | H₂N–C₆H₄–CH₂– (a = ortho, b = meta, c = para) | -Gly-NAc | Arginine |

Table 3b illustrates various hydrocodone, hydromorphone, oxycodone, and oxymorphone containing compounds of Formula III-D, III-J, and III-K contemplated by the present disclosure.

TABLE 3b

| Compound | R | R' | R" | AA (side chain) | X |
|---|---|---|---|---|---|
| III-D-1<br>III-E-1<br>III-J-1<br>III-K-1 | 6-amidinonaphthalen-2-yl | Methyl | Acetyl | Lysine | Hydrogen |
| III-D-2<br>III-E-2<br>III-J-2<br>III-K-2 | 6-amidinonaphthalen-2-yl | Methyl | Acetyl | Lysine | —OH |
| III-D-3<br>III-E-3<br>III-J-3<br>III-K-3 | 6-amidinonaphthalen-2-yl | Methyl | Acetyl | Arginine | Hydrogen |
| III-D-4<br>III-E-4<br>III-J-4<br>III-K-4 | 6-amidinonaphthalen-2-yl | Methyl | Acetyl | Arginine | —OH |

TABLE 3b-continued

| Compound | R | R' | R" | AA (side chain) | X |
|---|---|---|---|---|---|
| III-D-5<br>III-E-5<br>III-J-5<br>III-K-5 | H₂N-C(=NH)-naphthyl- | Methyl | -Ala-NAc | Lysine | Hydrogen |
| III-D-6<br>III-E-6<br>III-J-6<br>III-K-6 | H₂N-C(=NH)-naphthyl- | Methyl | -Ala-NAc | Lysine | —OH |
| III-D-7<br>III-E-7<br>III-J-7<br>III-K-7 | H₂N-C(=NH)-naphthyl- | Methyl | -Ala-NAc | Arginine | Hydrogen |
| III-D-8<br>III-E-8<br>III-J-8<br>III-K-8 | H₂N-C(=NH)-naphthyl- | Methyl | -Ala-NAc | Arginine | —OH |
| III-D-9<br>III-E-9<br>III-J-9<br>III-K-9 | H₂N-C(=NH)-naphthyl- | Methyl | -Gly-NAc | Lysine | Hydrogen |
| III-D-10<br>III-E-10<br>III-J-10<br>III-K-10 | H₂N-C(=NH)-naphthyl- | Methyl | -Gly-NAc | Lysine | —OH |
| III-D-11<br>III-E-11<br>III-J-11<br>III-K-11 | H₂N-C(=NH)-naphthyl- | Methyl | -Gly-NAc | Arginine | Hydrogen |

TABLE 3b-continued

| Compound | R | R' | R" | AA (side chain) | X |
|---|---|---|---|---|---|
| III-D-12<br>III-E-12<br>III-J-12<br>III-K-12 | 6-carbamimidoyl-naphthalen-2-yl | Methyl | -Gly-NAc | Arginine | —OH |
| III-D-13<br>III-E-13<br>III-J-13<br>III-K-13 | 6-carbamimidoyl-naphthalen-2-yl | Benzyloxy | Acetyl | Lysine | Hydrogen |
| III-D-14<br>III-E-14<br>III-J-14<br>III-K-14 | 6-carbamimidoyl-naphthalen-2-yl | Benzyloxy | Acetyl | Lysine | —OH |
| III-D-15<br>III-E-15<br>III-J-15<br>III-K-15 | 6-carbamimidoyl-naphthalen-2-yl | Benzyloxy | Acetyl | Arginine | Hydrogen |
| III-D-16<br>III-E-16<br>III-J-16<br>III-K-16 | 6-carbamimidoyl-naphthalen-2-yl | Benzyloxy | Acetyl | Arginine | —OH |
| III-D-17<br>III-E-17<br>III-J-17<br>III-K-17 | 6-carbamimidoyl-naphthalen-2-yl | Benzyloxy | -Ala-NAc | Lysine | Hydrogen |
| III-D-18<br>III-E-18<br>III-J-18<br>III-K-18 | 6-carbamimidoyl-naphthalen-2-yl | Benzyloxy | -Ala-NAc | Lysine | —OH |

TABLE 3b-continued

| Compound | R | R' | R" | AA (side chain) | X |
|---|---|---|---|---|---|
| III-D-19<br>III-E-19<br>III-J-19<br>III-K-19 | 6-amidino-2-naphthyl (H₂N-C(=NH)- at 6, attachment at 2) | Benzyloxy | -Ala-NAc | Arginine | Hydrogen |
| III-D-20<br>III-E-20<br>III-J-20<br>III-K-20 | 6-amidino-2-naphthyl | Benzyloxy | -Ala-NAc | Arginine | —OH |
| III-D-21<br>III-E-21<br>III-J-21<br>III-K-21 | 6-amidino-2-naphthyl | Benzyloxy | -Gly-NAc | Lysine | Hydrogen |
| III-D-22<br>III-E-22<br>III-J-22<br>III-K-22 | 6-amidino-2-naphthyl | Benzyloxy | -Gly-NAc | Lysine | —OH |
| III-D-23<br>III-E-23<br>III-J-23<br>III-K-23 | 6-amidino-2-naphthyl | Benzyloxy | -Gly-NAc | Arginine | Hydrogen |
| III-D-24<br>III-E-24<br>III-J-24<br>III-K-24 | 6-amidino-2-naphthyl | Benzyloxy | -Gly-NAc | Arginine | —OH |
| III-D-25(a, b, c)<br>III-E-25(a, b, c)<br>III-J-25(a, b, c)<br>III-K-25(a, b, c) | amidino-phenyl (a = ortho, b = meta, c = para) | Methyl | Acetyl | Lysine | Hydrogen |

TABLE 3b-continued

| Compound | R | R' | R" | AA (side chain) | X |
|---|---|---|---|---|---|
| III-D-26(a, b, c) III-E-26(a, b, c) III-J-26(a, b, c) III-K-26(a, b, c) | HN=C(NH₂)-C₆H₄- a = ortho b = meta c = para | Methyl | Acetyl | Lysine | —OH |
| III-D-27(a, b, c) III-E-27(a, b, c) III-J-27(a, b, c) III-K-27(a, b, c) | HN=C(NH₂)-C₆H₄- a = ortho b = meta c = para | Methyl | Acetyl | Arginine | Hydrogen |
| III-D-28(a, b, c) III-E-28(a, b, c) III-J-28(a, b, c) III-K-28(a, b, c) | HN=C(NH₂)-C₆H₄- a = ortho b = meta c = para | Methyl | Acetyl | Arginnine | —OH |
| III-D-29(a, b, c) III-E-29(a, b, c) III-J-29(a, b, c) III-K-29(a, b, c) | HN=C(NH₂)-C₆H₄- a = ortho b = meta c = para | Methyl | -Ala-NAc | Lysine | Hydrogen |
| III-D-30(a, b, c) III-E-30(a, b, c) III-J-30(a, b, c) III-K-30(a, b, c) | HN=C(NH₂)-C₆H₄- a = ortho b = meta c = para | Methyl | -Ala-NAc | Lysine | —OH |
| III-D-31(a, b, c) III-E-31(a, b, c) III-J-31(a, b, c) III-K-31(a, b, c) | HN=C(NH₂)-C₆H₄- a = ortho b = meta c = para | Methyl | -Ala-NAc | Arginine | Hydrogen |
| III-D-32(a, b, c) III-E-32(a, b, c) III-J-32(a, b, c) III-K-32(a, b, c) | HN=C(NH₂)-C₆H₄- a = ortho b = meta c = para | Methyl | -Ala-NAc | Arginine | —OH |

TABLE 3b-continued

| Compound | R | R' | R" | AA (side chain) | X |
|---|---|---|---|---|---|
| III-D-33(a, b, c) III-E-33(a, b, c) III-J-33(a, b, c) III-K-33(a, b, c) | HN=C(NH₂)–C₆H₄– a = ortho b = meta c = para | Methyl | -Gly-NAc | Lysine | Hydrogen |
| III-D-34(a, b, c) III-E-34(a, b, c) III-J-34(a, b, c) III-K-34(a, b, c) | HN=C(NH₂)–C₆H₄– a = ortho b = meta c = para | Methyl | -Gly-NAc | Lysine | —OH |
| III-D-35(a, b, c) III-E-35(a, b, c) III-J-35(a, b, c) III-K-35(a, b, c) | HN=C(NH₂)–C₆H₄– a = ortho b = meta c = para | Methyl | -Gly-NAc | Arginine | Hydrogen |
| III-D-36(a, b, c) III-E-36(a, b, c) III-J-36(a, b, c) III-K-36(a, b, c) | HN=C(NH₂)–C₆H₄– a = ortho b = meta c = para | Methyl | -Gly-NAc | Arginine | —OH |
| III-D-37(a, b, c) III-E-37(a, b, c) III-J-37(a, b, c) III-K-37(a, b, c) | HN=C(NH₂)–C₆H₄– a = ortho b = meta c = para | Benzyloxy | Acetyl | Lysine | Hydrogen |
| III-D-38(a, b, c) III-E-38(a, b, c) III-J-38(a, b, c) III-K-38(a, b, c) | HN=C(NH₂)–C₆H₄– a = ortho b = meta c = para | Benzyloxy | Acetyl | Lysine | —OH |
| III-D-39(a, b, c) III-E-39(a, b, c) III-J-39(a, b, c) III-K-39(a, b, c) | HN=C(NH₂)–C₆H₄– a = ortho b = meta c = para | Benzyloxy | Acetyl | Arginine | Hydrogen |

TABLE 3b-continued

| Compound | R | R' | R" | AA (side chain) | X |
|---|---|---|---|---|---|
| III-D-40(a, b, c)<br>III-E-40(a, b, c)<br>III-J-40(a, b, c)<br>III-K-40(a, b, c) | HN=C(NH₂)-C₆H₄-<br>a = ortho<br>b = meta<br>c = para | Benzyloxy | Acetyl | Arginine | —OH |
| III-D-41(a, b, c)<br>III-E-41(a, b, c)<br>III-J-41(a, b, c)<br>III-K-41(a, b, c) | HN=C(NH₂)-C₆H₄-<br>a = ortho<br>b = meta<br>c = para | Benzyloxy | -Ala-NAc | Lysine | Hydrogen |
| III-D-42(a, b, c)<br>III-E-42(a, b, c)<br>III-J-42(a, b, c)<br>III-K-42(a, b, c) | HN=C(NH₂)-C₆H₄-<br>a = ortho<br>b = meta<br>c = para | Benzyloxy | -Ala-NAc | Lysine | —OH |
| III-D-43(a, b, c)<br>II-E-43(a, b, c)<br>III-J-43(a, b, c)<br>III-K-43(a, b, c) | HN=C(NH₂)-C₆H₄-<br>a = ortho<br>b = meta<br>c = para | Benzyloxy | -Ala-NAc | Arginine | Hydrogen |
| III-D-44(a, b, c)<br>III-E-44(a, b, c)<br>III-J-44(a, b, c)<br>III-K-44(a, b, c) | HN=C(NH₂)-C₆H₄-<br>a = ortho<br>b = meta<br>c = para | Benzyloxy | -Ala-NAc | Arginine | —OH |
| III-D-45(a, b, c)<br>III-E-45(a, b, c)<br>III-J-45(a, b, c)<br>III-K-45(a, b, c) | HN=C(NH₂)-C₆H₄-<br>a = ortho<br>b = meta<br>c = para | Benzyloxy | -Gly-NAc | Lysine | Hydrogen |
| III-D-46(a, b, c)<br>III-E-46(a, b, c)<br>III-J-46(a, b, c)<br>III-K-46(a, b, c) | HN=C(NH₂)-C₆H₄-<br>a = ortho<br>b = meta<br>c = para | Benzyloxy | -Gly-NAc | Lysine | —OH |

TABLE 3b-continued

| Compound | R | R' | R" | AA (side chain) | X |
|---|---|---|---|---|---|
| III-D-47(a, b, c)<br>III-E-47(a, b, c)<br>III-J-47(a, b, c)<br>III-K-47(a, b, c) | HN=C(NH₂)–C₆H₄–<br>a = ortho<br>b = meta<br>c = para | Benzyloxy | -Gly-NAc | Arginine | Hydrogen |
| III-D-48(a, b, c)<br>III-E-48(a, b, c)<br>III-J-48(a, b, c)<br>III-K-48(a, b, c) | HN=C(NH₂)–C₆H₄–<br>a = ortho<br>b = meta<br>c = para | Benzyloxy | -Gly-NAc | Arginine | —OH |
| III-D-49(a, b, c)<br>III-E-49(a, b, c)<br>III-J-49(a, b, c)<br>III-K-49(a, b, c) | H₂N–C(=NH)–NH–C₆H₄–<br>a = ortho<br>b = meta<br>c = para | Methyl | Acetyl | Lysine | Hydrogen |
| III-D-50(a, b, c)<br>III-E-50(a, b, c)<br>III-J-50(a, b, c)<br>III-K-50(a, b, c) | H₂N–C(=NH)–NH–C₆H₄–<br>a = ortho<br>b = meta<br>c = para | Methyl | Acetyl | Lysine | —OH |
| III-D-51(a, b, c)<br>III-E-51(a, b, c)<br>III-J-51(a, b, c)<br>III-K-51(a, b, c) | H₂N–C(=NH)–NH–C₆H₄–<br>a = ortho<br>b = meta<br>c = para | Methyl | Acetyl | Arginine | Hydrogen |
| III-D-52(a, b, c)<br>III-E-52(a, b, c)<br>III-J-52(a, b, c)<br>III-K-52(a, b, c) | H₂N–C(=NH)–NH–C₆H₄–<br>a = ortho<br>b = meta<br>c = para | Methyl | Acetyl | Arginine | —OH |

TABLE 3b-continued

| Compound | R | R' | R" | AA (side chain) | X |
|---|---|---|---|---|---|
| III-D-53(a, b, c)<br>III-E-53(a, b, c)<br>III-J-53(a, b, c)<br>III-K-53(a, b, c) | guanidino-phenyl<br>a = ortho<br>b = meta<br>c = para | Methyl | -Ala-NAc | Lysine | Hydrogen |
| III-D-54(a, b, c)<br>III-E-54(a, b, c)<br>III-J-54(a, b, c)<br>III-K-54(a, b, c) | guanidino-phenyl<br>a = ortho<br>b = meta<br>c = para | Methyl | -Ala-NAc | Lysine | —OH |
| III-D-55(a, b, c)<br>III-E-55(a, b, c)<br>III-J-55(a, b, c)<br>III-K-55(a, b, c) | guanidino-phenyl<br>a = ortho<br>b = meta<br>c = para | Methyl | -Ala-NAc | Arginine | Hydrogen |
| III-D-56(a, b, c)<br>III-E-56(a, b, c)<br>III-J-56(a, b, c)<br>III-K-56(a, b, c) | guanidino-phenyl<br>a = ortho<br>b = meta<br>c = para | Methyl | -Ala-NAc | Arginine | —OH |
| III-D-57(a, b, c)<br>III-E-57(a, b, c)<br>III-J-57(a, b, c)<br>III-K-57(a, b, c) | guanidino-phenyl<br>a = ortho<br>b = meta<br>c = para | Methyl | -Gly-NAc | Lysine | Hydrogen |
| III-D-58(a, b, c)<br>III-E-58(a, b, c)<br>III-J-58(a, b, c)<br>III-K-58(a, b, c) | guanidino-phenyl<br>a = ortho<br>b = meta<br>c = para | Methyl | -Gly-NAc | Lysine | —OH |

TABLE 3b-continued

| Compound | R | R' | R" | AA (side chain) | X |
|---|---|---|---|---|---|
| III-D-59(a, b, c) III-E-59(a, b, c) III-J-59(a, b, c) III-K-59(a, b, c) | H₂N-C(=NH)-NH-C₆H₄- a = ortho b = meta c = para | Methyl | -Gly-NAc | Arginine | Hydrogen |
| III-D-60(a, b, c) III-E-60(a, b, c) III-J-60(a, b, c) III-K-60(a, b, c) | H₂N-C(=NH)-NH-C₆H₄- a = ortho b = meta c = para | Methyl | -Gly-NAc | Arginine | —OH |
| III-D-61(a, b, c) III-E-61(a, b, c) III-J-61(a, b, c) III-K-61(a, b, c) | H₂N-C(=NH)-NH-C₆H₄- a = ortho b = meta c = para | Benzyloxy | Acetyl | Lysine | Hydrogen |
| III-D-62(a, b, c) III-E-62(a, b, c) III-J-62(a, b, c) III-K-62(a, b, c) | H₂N-C(=NH)-NH-C₆H₄- a = ortho b = meta c = para | Benzyloxy | Acetyl | Lysine | —OH |
| III-D-63(a, b, c) III-E-63(a, b, c) III-J-63(a, b, c) III-K-63(a, b, c) | H₂N-C(=NH)-NH-C₆H₄- a = ortho b = meta c = para | Benzyloxy | Acetyl | Arginine | Hydrogen |
| III-D-64(a, b, c) III-E-64(a, b, c) III-J-64(a, b, c) III-K-64(a, b, c) | H₂N-C(=NH)-NH-C₆H₄- a = ortho b = meta c = para | Benzyloxy | Acetyl | Arginine | —OH |

TABLE 3b-continued

| Compound | R | R' | R" | AA (side chain) | X |
|---|---|---|---|---|---|
| III-D-65(a, b, c) III-E-65(a, b, c) III-J-65(a, b, c) III-K-65(a, b, c) | guanidino-phenyl (a = ortho, b = meta, c = para) | Benzyloxy | -Ala-NAc | Lysine | Hydrogen |
| III-D-66(a, b, c) III-E-66(a, b, c) III-J-66(a, b, c) III-K-66(a, b, c) | guanidino-phenyl (a = ortho, b = meta, c = para) | Benzyloxy | -Ala-NAc | Lysine | —OH |
| III-D-67(a, b, c) III-E-67(a, b, c) III-J-67(a, b, c) III-K-67(a, b, c) | guanidino-phenyl (a = ortho, b = meta, c = para) | Benzyloxy | -Ala-NAc | Arginine | Hydrogen |
| III-D-68(a, b, c) III-E-68(a, b, c) III-J-68(a, b, c) III-K-68(a, b, c) | guanidino-phenyl (a = ortho, b = meta, c = para) | Benzyloxy | -Ala-NAc | Arginine | —OH |
| III-D-69(a, b, c) III-E-69(a, b, c) III-J-69(a, b, c) III-K-69(a, b, c) | guanidino-phenyl (a = ortho, b = meta, c = para) | Benzyloxy | -Gly-NAc | Lysine | Hydrogen |
| III-D-70(a, b, c) III-E-70(a, b, c) III-J-70(a, b, c) III-K-70(a, b, c) | guanidino-phenyl (a = ortho, b = meta, c = para) | Benzyloxy | -Gly-NAc | Lysine | —OH |

TABLE 3b-continued

| Compound | R | R' | R'' | AA (side chain) | X |
|---|---|---|---|---|---|
| III-D-71(a, b, c)<br>III-E-71(a, b, c)<br>III-J-71(a, b, c)<br>III-K-71(a, b, c) | guanidino-phenyl<br>a = ortho<br>b = meta<br>c = para | Benzyloxy | -Gly-NAc | Arginine | Hydrogen |
| III-D-72(a, b, c)<br>III-E-72(a, b, c)<br>III-J-72(a, b, c)<br>III-K-72(a, b, c) | guanidino-phenyl<br>a = ortho<br>b = meta<br>c = para | Benzylxoy | -Gly-NAc | Arginine | —OH |
| III-D-73(a, b, c)<br>III-E-73(a, b, c)<br>III-J-73(a, b, c)<br>III-K-73(a, b, c) | aminomethyl-phenyl<br>a = ortho<br>b = meta<br>c = para | Methyl | Acetyl | Lysine | Hydrogen |
| III-D-74(a, b, c)<br>III-E-74(a, b, c)<br>III-J-74(a, b, c)<br>III-K-74(a, b, c) | aminomethyl-phenyl<br>a = ortho<br>b = meta<br>c = para | Methyl | Acetyl | Lysine | —OH |
| III-D-75(a, b, c)<br>III-E-75(a, b, c)<br>III-J-75(a, b, c0)<br>III-K-75(a, b, c) | aminomethyl-phenyl<br>a = ortho<br>b = meta<br>c = para | Methyl | Acetyl | Arginine | Hydrogen |
| III-D-76(a, b, c)<br>III-E-76(a, b, c)<br>III-J-76(a, b, c)<br>III-K-76(a, b, c) | aminomethyl-phenyl<br>a = ortho<br>b = meta<br>c = para | Methyl | Acetyl | Arginine | —OH |
| III-D-77(a, b, c)<br>III-E-77(a, b, c)<br>III-J-77(a, b, c)<br>III-K-77(a, b, c) | aminomethyl-phenyl<br>a = ortho<br>b = meta<br>c = para | Methyl | -Ala-NAc | Lysine | Hydrogen |

TABLE 3b-continued

| Compound | R | R' | R" | AA (side chain) | X |
|---|---|---|---|---|---|
| III-D-78(a, b, c) III-E-78(a, b, c) III-J-78(a, b, c) III-K-78(a, b, c) | 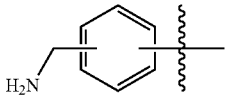 a = ortho b = meta c = para | Methyl | -Ala-NAc | Lysine | —OH |
| III-D-79(a, b, c) III-E-79(a, b, c) III-J-79(a, b, c) III-K-79(a, b, c) | 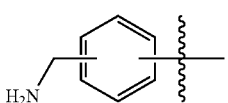 a = ortho b = meta c = para | Methyl | -Ala-NAc | Arginine | Hydrogen |
| III-D-80(a, b, c) III-E-80(a, b, c) III-J-80(a, b, c) III-K-80(a, b, c) | 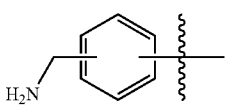 a = ortho b = meta c = para | Methyl | -Ala-NAc | Arginine | —OH |
| III-D-81(a, b, c) III-E-81(a, b, c) III-J-81(a, b, c) III-K-81(a, b, c) | 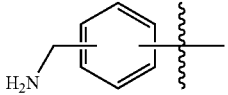 a = ortho b = meta c = para | Methyl | -Gly-NAc | Lysine | Hydrogen |
| III-D-82(a, b, c) III-E-82(a, b, c) III-J-82(a, b, c) III-K-82(a, b, c) | 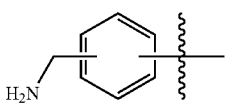 a = ortho b = meta c = para | Methyl | -Gly-NAc | Lysine | —OH |
| III-D-83(a, b, c) III-E-83(a, b, c) III-J-83(a, b, c) III-K-83(a, b, c) | 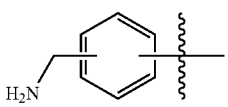 a = ortho b = meta c = para | Methyl | -Gly-NAc | Arginine | Hydrogen |
| III-D-84(a, b, c) III-E-84(a, b, c) III-J-84(a, b, c) III-K-84(a, b, c) |  a = ortho b = meta c = para | Methyl | -Gly-NAc | Arginine | —OH |

TABLE 3b-continued

| Compound | R | R' | R" | AA (side chain) | X |
|---|---|---|---|---|---|
| III-D-85(a, b, c)<br>III-E-85(a, b, c)<br>III-J-85(a, b, c)<br>III-K-85(a, b, c) | 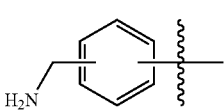<br>a = ortho<br>b = meta<br>c = para | Benzyloxy | Acetyl | Lysine | Hydrogen |
| III-D-86(a, b, c)<br>III-E-86(a, b, c)<br>III-J-86(a, b, c)<br>III-K-86(a, b, c) | 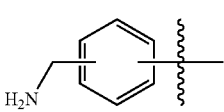<br>a = ortho<br>b = meta<br>c = para | Benzyloxy | Acetyl | Lysine | —OH |
| III-D-87(a, b, c)<br>III-E-87(a, b, c)<br>III-J-87(a, b, c)<br>III-K-87(a, b, c) | 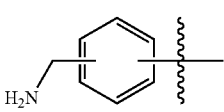<br>a = ortho<br>b = meta<br>c = para | Benzyloxy | Acetyl | Arginine | Hydrogen |
| III-D-88(a, b, c)<br>III-E-88(a, b, c)<br>III-J-88(a, b, c)<br>III-K-88(a, b, c) | 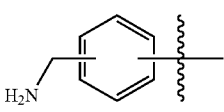<br>a = ortho<br>b = meta<br>c = para | Benzyloxy | Acetyl | Arginine | —OH |
| III-D-89(a, b, c)<br>III-E-89(a, b, c)<br>III-J-89(a, b, c)<br>III-K-89(a, b, c) | 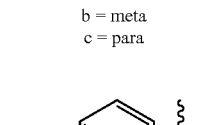<br>a = ortho<br>b = meta<br>c = para | Benzyloxy | -Ala-NAc | Lysine | Hydrogen |
| III-D-90(a, b, c)<br>III-E-90(a, b, c)<br>III-J-90(a, b, c)<br>III-K-90(a, b, c) | 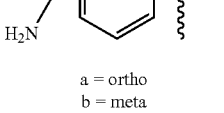<br>a = ortho<br>b = meta<br>c = para | Benzyloxy | -Ala-NAc | Lysine | —OH |
| III-D-91(a, b, c)<br>III-E-91(a, b, c)<br>III-J-91(a, b, c)<br>III-K-91(a, b, c) | 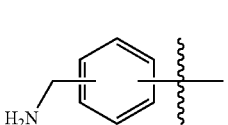<br>a = ortho<br>b = meta<br>c = para | Benzyloxy | -Ala-NAc | Arginine | Hydrogen |

TABLE 3b-continued

| Compound | R | R' | R" | AA (side chain) | X |
|---|---|---|---|---|---|
| III-D-92(a, b, c)<br>III-E-92(a, b, c)<br>III-J-92(a, b, c)<br>III-K-92(a, b, c) | 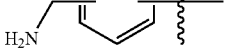<br>a = ortho<br>b = meta<br>c = para | Benzyloxy | -Ala-NAc | Arginine | —OH |
| III-D-93(a, b, c)<br>III-E-93(a, b, c)<br>III-J-93(a, b, c)<br>III-K-93(a, b, c) | 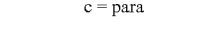<br>a = ortho<br>b = meta<br>c = para | Benzyloxy | -Gly-NAc | Lysine | Hydrogen |
| III-D-94(a, b, c)<br>III-E-94(a, b, c)<br>III-J-94(a, b, c)<br>III-K-94(a, b, c) | 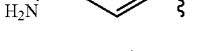<br>a = ortho<br>b = meta<br>c = para | Benzyloxy | -Gly-NAc | Lysine | —OH |
| III-D-95(a, b, c)<br>II-E-95(a, b, c)<br>III-J-95(a, b, c)<br>III-K-95(a, b,c ) | 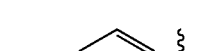<br>a = ortho<br>b = meta<br>c = para | Benzyloxy | -Gly-NAc | Arginine | Hydrogen |
| III-D-96(a, b, c)<br>III-E-96(a, b, c)<br>III-J-96(a, b, c)<br>III-K-96(a, b, c) | 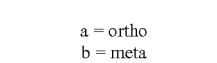<br>a = ortho<br>b = meta<br>c = para | Benzyloxy | -Gly-NAc | Arginine | —OH |

Table 4b illustrates various morphine containing compounds of Formula and III-L contemplated by the present disclosure.

TABLE 4b

| Compound | R | R' | R" | AA (side chain) |
|---|---|---|---|---|
| III-F-1<br>III-L-1 |  | Methyl | Acetyl | Lysine |

TABLE 4b-continued
| Compound | R | R' | R" | AA (side chain) |
|---|---|---|---|---|
| III-F-2<br>III-L-2 | 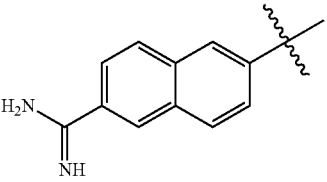 [SMILES: *c1ccc2cc(C(=N)N)ccc2c1] | Methyl | Acetyl | Arginine |
| III-F-3<br>III-L-3 | 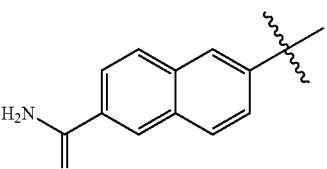 | Methyl | -Ala-NAc | Lysine |
| III-F-4<br>III-L-4 | 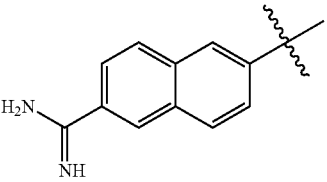 [SMILES: *c1ccc2cc(C(=N)N)ccc2c1] | Methyl | -Ala-NAc | Arginine |
| III-F-5<br>III-L-5 | 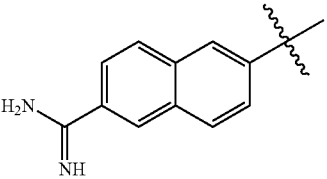 [SMILES: *c1ccc2cc(C(=N)N)ccc2c1] | Methyl | -Gly-NAc | Lysine |
| III-F-6<br>III-L-6 | 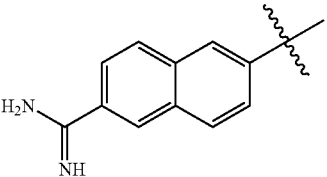 [SMILES: *c1ccc2cc(C(=N)N)ccc2c1] | Methyl | -Gly-NAc | Arginine |
| III-F-7<br>III-L-7 | 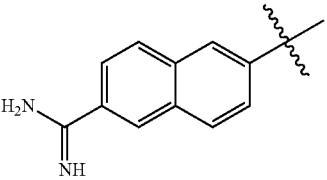 [SMILES: *c1ccc2cc(C(=N)N)ccc2c1] | Benzyloxy | Acetyl | Lysine |
| III-F-8<br>III-L-8 | 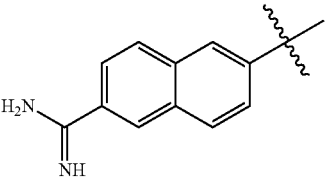 [SMILES: *c1ccc2cc(C(=N)N)ccc2c1] | Benzyloxy | Acetyl | Arginine |

TABLE 4b-continued

| Compound | R | R' | R'' | AA (side chain) |
|---|---|---|---|---|
| III-F-9<br>III-L-9 | 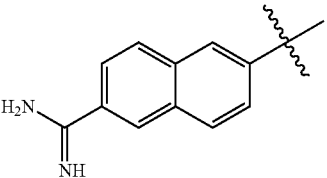 [SMILES: *c1ccc2cc(C(=N)N)ccc2c1] | Benzyloxy | -Ala-NAc | Lysine |
| III-F-10<br>III-L-10 | 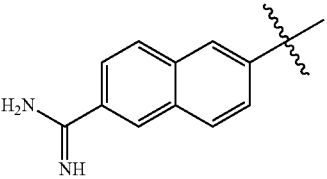 [SMILES: *c1ccc2cc(C(=N)N)ccc2c1] | Benzyloxy | -Ala-NAc | Arginine |
| III-F-11<br>III-L-11 | 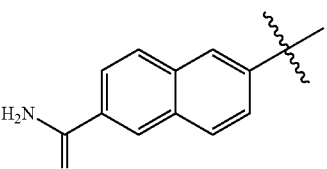 | Benzyloxy | -Gly-NAc | Lysine |
| III-F-12<br>III-L-12 | 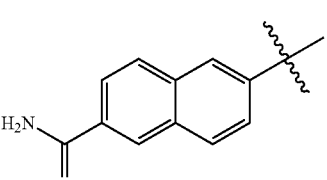 | Benzyloxy | -Gly-NAc | Arginine |
| III-F-13(a, b, c)<br>III-L-13(a, b, c) | 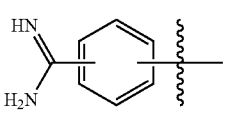<br>a = ortho<br>b = meta<br>c = para | Methyl | Acetyl | Lysine |
| III-F-14(a, b, c)<br>III-L-14(a, b, c) | 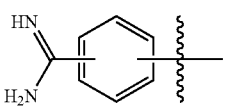<br>a = ortho<br>b = meta<br>c = para | Methyl | Acetyl | Arginine |
| III-F-15(a, b, c)<br>III-L-15(a, b, c) | 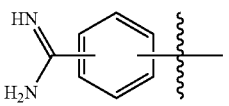<br>a = ortho<br>b = meta<br>c = para | Methyl | -Ala-NAc | Lysine |

TABLE 4b-continued

| Compound | R | R' | R" | AA (side chain) |
|---|---|---|---|---|
| III-F-16(a, b, c)<br>III-L-16(a, b, c) | 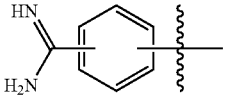<br>a = ortho<br>b = meta<br>c = para | Methyl | -Ala-NAc | Arginine |
| III-F-17(a, b, c)<br>III-L-17(a, b, c) | 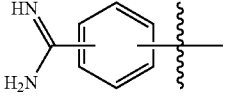<br>a = ortho<br>b = meta<br>c = para | Methyl | -Gly-NAc | Lysine |
| III-F-18(a, b, c)<br>III-L-18(a, b, c) | 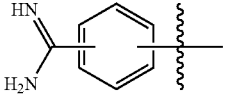<br>a = ortho<br>b = meta<br>c = para | Methyl | -Gly-NAc | Arginine |
| III-F-19(a, b, c)<br>III-L-19(a, b, c) | 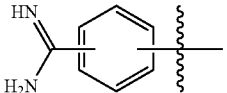<br>a = ortho<br>b = meta<br>c = para | Benzyloxy | Acetyl | Lysine |
| III-F-20(a, b, c)<br>III-L-20(a, b, c) | 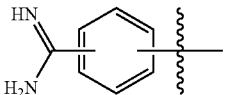<br>a = ortho<br>b = meta<br>c = para | Benzyloxy | Acetyl | Arginine |
| III-F-21(a, b, c)<br>III-L-21(a, b, c) | 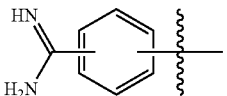<br>a = ortho<br>b = meta<br>c = para | Benzyloxy | -Ala-NAc | Lysine |
| III-F-22(a, b, c)<br>III-L-22(a, b, c) | 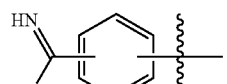<br>a = ortho<br>b = meta<br>c = para | Benzyloxy | -Ala-NAc | Arginine |

TABLE 4b-continued

| Compound | R | R' | R" | AA (side chain) |
|---|---|---|---|---|
| III-F-23(a, b, c)<br>III-L-23(a, b, c) | 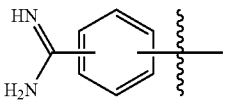<br>a = ortho<br>b = meta<br>c = para | Benzyloxy | -Gly-NAc | Lysine |
| III-F-24(a, b, c)<br>III-L-24(a, b, c) | 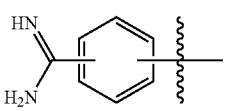<br>a = ortho<br>b = meta<br>c = para | Benzyloxy | -Gly-NAc | Arginine |
| III-F-25(a, b, c)<br>III-L-25(a, b, c) | 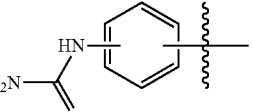<br>a = ortho<br>b = meta<br>c = para | Methyl | Acetyl | Lysine |
| III-F-26(a, b, c)<br>III-L-26(a, b, c) | 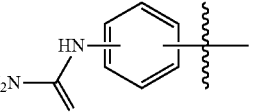<br>a = ortho<br>b = meta<br>c = para | Methyl | Acetyl | Arginnine |
| III-F-27(a, b, c)<br>III-L-27(a, b, c) | 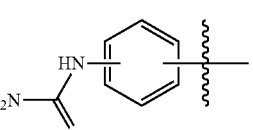<br>a = ortho<br>b = meta<br>c = para | Methyl | -Ala-NAc | Lysine |
| III-F-28(a, b, c)<br>III-L-28(a, b, c) | 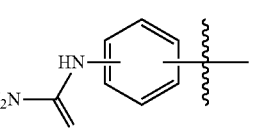<br>a = ortho<br>b = meta<br>c = para | Methyl | -Ala-NAc | Arginine |

TABLE 4b-continued

| Compound | R | R' | R'' | AA (side chain) |
|---|---|---|---|---|
| III-F-29(a, b, c)<br>III-L-29(a, b, c) | 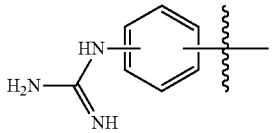<br>a = ortho<br>b = meta<br>c = para | Methyl | -Gly-NAc | Lysine |
| III-F-30(a, b, c)<br>III-L-30(a, b, c) | 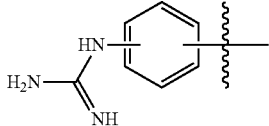<br>a = ortho<br>b = meta<br>c = para | Methyl | -Gly-NAc | Arginine |
| III-F-31(a, b, c)<br>III-L-31(a, b, c) | 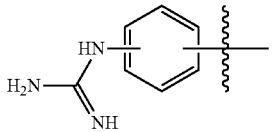<br>a = ortho<br>b = meta<br>c = para | Benzyloxy | Acetyl | Lysine |
| III-F-32(a, b, c)<br>III-L-32(a, b, c) | 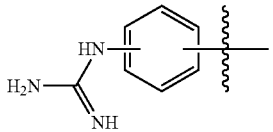<br>a = ortho<br>b = meta<br>c = para | Benzyloxy | Acetyl | Arginine |
| III-F-33(a, b, c)<br>III-L-33(a, b, c) | 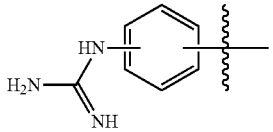<br>a = ortho<br>b = meta<br>c = para | Benzyloxy | -Ala-NAc | Lysine |
| III-F-34(a, b, c)<br>III-L-34(a, b, c) | 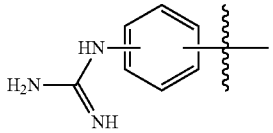<br>a = ortho<br>b = meta<br>c = para | Benzyloxy | -Ala-NAc | Arginine |

TABLE 4b-continued

| Compound | R | R' | R" | AA (side chain) |
|---|---|---|---|---|
| III-F-35(a, b, c)<br>III-L-35(a, b, c) | H₂N–C(=NH)–NH–C₆H₄–<br>a = ortho<br>b = meta<br>c = para | Benzyloxy | -Gly-NAc | Lysine |
| III-F-36(a, b, c)<br>III-L-36(a, b, c) | H₂N–C(=NH)–NH–C₆H₄–<br>a = ortho<br>b = meta<br>c = para | Benzyloxy | -Gly-NAc | Arginine |
| III-F-37(a, b, c)<br>III-L-37(a, b, c) | H₂N–CH₂–C₆H₄–<br>a = ortho<br>b = meta<br>c = para | Methyl | Acetyl | Lysine |
| III-F-38(a, b, c)<br>III-L-38(a, b, c) | H₂N–CH₂–C₆H₄–<br>a = ortho<br>b = meta<br>c = para | Methyl | Acetyl | Arginine |
| III-F-39(a, b, c)<br>III-L-39(a, b, c) | H₂N–CH₂–C₆H₄–<br>a = ortho<br>b = meta<br>c = para | Methyl | -Ala-NAc | Lysine |
| III-F-40(a, b, c)<br>III-L-40(a, b, c) | H₂N–CH₂–C₆H₄–<br>a = ortho<br>b = meta<br>c = para | Methyl | -Ala-NAc | Arginine |
| III-F-41(a, b, c)<br>III-L-41(a, b, c) | H₂N–CH₂–C₆H₄–<br>a = ortho<br>b = meta<br>c = para | Methyl | -Gly-NAc | Lysine |

TABLE 4b-continued

| Compound | R | R' | R" | AA (side chain) |
|---|---|---|---|---|
| III-F-42(a, b, c) III-L-42(a, b, c) |  a = ortho b = meta c = para | Methyl | -Gly-NAc | Arginine |
| III-F-43(a, b, c) III-L-43(a, b, c) | 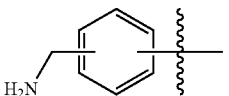 a = ortho b = meta c = para | Benzyloxy | Acetyl | Lysine |
| III-F-44(a, b, c) III-L-44(a, b, c) | 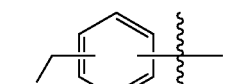 a = ortho b = meta c = para | Benzyloxy | Acetyl | Arginine |
| III-F-45(a, b, c) III-L-45(a, b, c) |  a = ortho b = meta c = para | Benzyloxy | -Ala-NAc | Lysine |
| III-F-46(a, b, c) III-L-46(a, b, c) |  a = ortho b = meta c = para | Benzyloxy | -Ala-NAc | Arginine |
| III-F-47(a, b, c) III-L-47(a, b,c ) |  a = ortho b = meta c = para | Benzyloxy | -Gly-NAc | Lysine |
| III-F-48(a, b, c) III-L-48(a, b, c) |  a = ortho b = meta c = para | Benzyloxy | -Gly-NAc | Arginine |

Preparation of Compounds of the Invention

Compounds of the invention can be synthesized using techniques and materials known to those of skill in the art, such as described, for example, in Smith and March, MARCH'S ADVANCED ORGANIC CHEMISTRY: Reactions, Mechanisms, and Structure, Fifth Edition, (Wiley-Interscience, 2001), Vogel, A TEXTBOOK OF PRACTICAL ORGANIC CHEMISTRY, Including Qualitative Organic Analysis, Fourth Edition, New York, (Longman, 1978), Carey and Sundberg, ADVANCED ORGANIC CHEMISTRY 3rd Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention can be obtained using standard techniques and commercially available precursor materials, such as those available from Aldrich Chemical Co. (Milwaukee, Wis.), Sigma Chemical Co. (St. Louis, Mo.), Lancaster Synthesis (Ward Hill, Mass.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention can include one or more steps of protection and deprotection (e.g., the formation and removal of suitable protecting groups). In addition, the synthetic procedures disclosed below can include various purifications, such as column chromatography, flash chromatography, thin-layer chromatography (TLC), recrystallization, distillation, high-pressure liquid chromatography (HPLC), dialysis, size-exclusion chromatography, and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS), and multi-angle light scattering (MALS) can be used as well. Methods of protection and deprotection, purification and identification and quantification are well known in the chemical arts.

In some embodiments, the synthetic methods use polymeric scaffolds having multiple repeating functional groups, where the functional groups can react with a complementary functional $Z^{1, 2 \text{ or } 3}$ groups on the enzyme inhibiting, opioid agonist releasing, or opioid antagonist releasing substrate subunits, respectively; thereby providing a covalently-bonded unimolecular polysubstrate construct. The functional groups of the polymer scaffold can be, for example, a carboxylic acid, an activated ester, an aldehyde, an alcohol, an amine, an isocyanate, an epoxide, and the like.

Compounds of the invention can be collected and purified using methods known in the art. In general, compound of the invention as described herein can be purified by any of the means known in the art, including chromatographic means, such as high performance liquid chromatography (HPLC), preparative thin layer chromatography, flash column chromatography and ion exchange chromatography, size exclusion chromatography. Any suitable stationary phase can be used, including normal and reversed phases as well as ionic resins. See, e.g., Introduction to Modem Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

Compound of the invention described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of compound of the invention including the stereoisomerically pure forms (e.g., geometrically pure, enantiomerically pure or diastereomerically pure) and enantiomeric or stereoisomeric mixtures are included in the description of compound of the invention described herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or solid or liquid forms. Furthermore, in some embodiments, compounds of the invention are present as salts, and compositions of the invention comprise salts of the indicated compounds or molecules. In general, all physical forms are equivalent for the uses contemplated herein and are intended to be within the scope of the present disclosure.

Representative synthetic routes useful for the preparation of exemplary compounds of the invention are depicted below in the following schemes.

Synthesis of II-D-71c

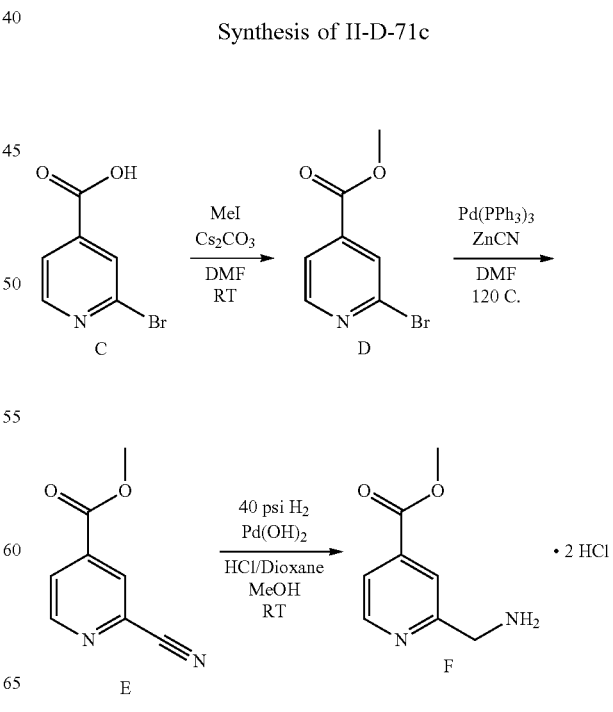

Synthesis of 2-bromo-4-carbomethoxypyridine (Intermediate D

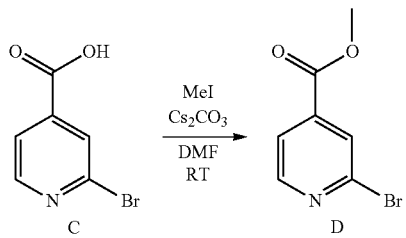

2-bromo-4-carboxypyridine (40.0 g) was dissolved in ~200 mL anhydrous DMF; CsCO₃ (1 eq.) was then added (caution vigorous $CO_2$ evolution occurs); MeI (1 eq.) was then added and the reaction was stirred at RT overnight. Reaction was confirmed to be complete by LC/MS, then diluted with ~500 mL of ethyl acetate and transferred to a 1 L separatory funnel and the remaining salts were dissolved in ~100 mL water and also transferred to the separatory funnel. The resulting aqueous layer was extracted with EtOAc (3×100 mL); the combined organic layers were washed with water (2×100 mL); saturated sodium bicarbonate solution (2×100 mL); and brine (1×100 mL); the organic phase was then dried over $MgSO_4$; filtered and concentrated to afford 39.0 g of Intermediate D as an off-white solid which was used in the next step without further purification.

Synthesis of 2-cyano-4-carbomethoxypyridine (Intermediate E

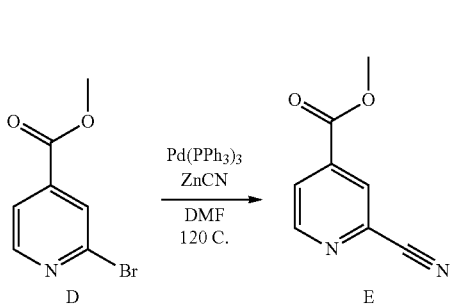

Intermediate D (2-bromo-4-carbomethoxypyridine, 20 g) was dissolved in anhydrous DMF (150 mL) followed by the addition of $Zn(CN)_2$ (0.6 eq.) in a single portion. To the resulting slurry was added $Pd(PPh_3)_4$ (4.5 g). The mixture was then heated on an oil bath to 120° C. for 3 h. The reaction mixture was allowed to cool to RT and then the reaction mixture was added slowly to a well-stirred flask containing 800 mL of water at room temperature. The resulting thick, off-white precipitate was stirred for ~15 min, then collected via filtration and washed with water (5×100 mL). The isolated solid was dried under vacuum to produce Intermediate E (18.8 g) that was used in the next step without further purification.

Synthesis of 2-aminomethyl-4-carbomethoxypyridine (Intermediate F

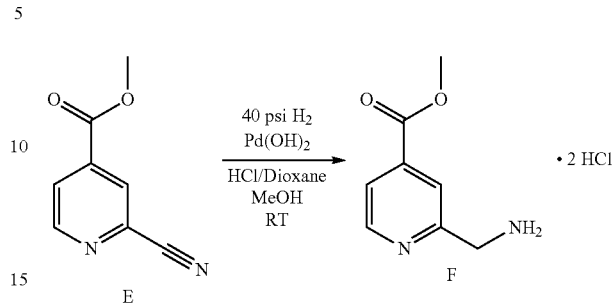

Intermediate E (2-cyano-4-carbomethoxypyridine, 10 g) was dissolved in methanol (100 mL) and transferred to a 250 mL Parr bottle containing 20% $Pd(OH)_2$—C w/~50% water (200 mg). Dry HCl (4M in dioxane/3 eq.) was added. The parr bottle was equipped with a metal safety shield, affixed to a Parr shaker and pressurized to 35 psi with Hz. The reaction was shaken for 3 h at RT, then vented and removed from the Parr shaker. The reaction was determined to be complete by LC/MS, then filtered through paper filter to remove catalyst. The catalyst and Parr bottle were rinsed with methanol (3×25 mL). The resulting methanol solution was concentrated under vacuum, to produce Intermediate F (9.2 g) as a white solid after drying under high vacuum for several hours that was used without further purification.

Synthesis of 2-(aminomethyl-Arg(Pbf)-Gly-NAc)-4-carbomethoxypyridine (Intermediate I

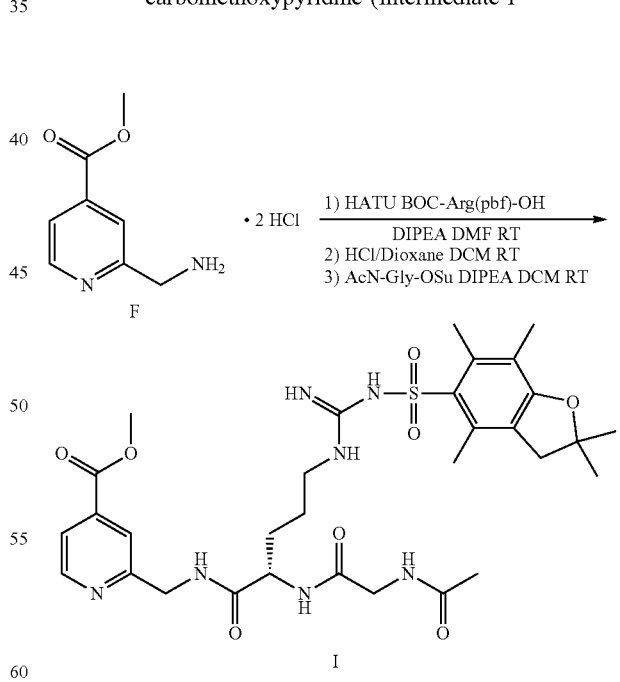

Intermediate F (2-aminomethyl-4-carbomethoxypyridine·2HCl, 2.0 g) was dissolved in anhydrous DMF (80 mL). To the solution was added BOC-Arg (Pbf)-OH (1 eq.) and HATU (1.2 eq.) and the resulting solution was stirred at RT until all solids dissolved. The reaction was then cooled to −78° C. (dry ice/acetone) and DIPEA (4 eq.) was added slowly dropwise. The reaction was stirred for an additional 10 min at −78° C. and then allowed to warm slowly to RT. The reaction was determined to be complete by LC/MS after stirring for 30 min at RT. The reaction was transferred to a 1 L separatory funnel, diluted with water (100 mL) and extracted with ethyl acetate (1×300 mL; then 3×100 mL). The combined organic extracts were washed with 1 M $HCl_{aq}$ (1×100 mL), saturated $NaHCO_3$ solution (1×100 mL), brine (1×100 mL) and then dried over $MgSO_4$, filtered and concentrated. The resulting residue was dried under high vacuum then dissolved in DCM (300 mL). 4N HCl in dioxane (10 mL) was then added and the reaction stirred at RT until LC/MS analysis indicated complete removal of the BOC protecting group. The reaction was then concentrated on a rotary evaporator and the resulting residue dissolved in a minimal amount of anhydrous methanol. The methanol solution was added slowly dropwise to a well-stirred 500 mL RB flask containing MTBE (300 mL) at RT, resulting in the formation of a thick white precipitate. The stirring was ceased, and the precipitate was allowed to settle to the bottom of the flask. The supernatant liquid was carefully poured off (~90% removed) and replaced with fresh MTBE (300 mL) and stirred vigorously. The stirring was ceased, and the precipitate was allowed to settle to the bottom of the flask. The supernatant was carefully poured off (~90% removed) and the resulting solid was dried under vacuum. The resulting solid was diluted with DCM (150 mL), then AcN-Gly-OSu (1.0 eq.) and DIPEA (2.0 eq.) were added successively to the solution at RT. The reaction was determined to be complete by LC/MS after being stirred at RT for 4 h. The reaction was transferred to a 1 L separatory funnel and water (100 mL) and ethyl acetate (200 mL) were then added. The water layer was extracted with ethyl acetate (3×100 mL) and the combined organic layers were washed with water (3×100 mL) then brine (1×100 mL). The combined organic phase was then dried over $MgSO_4$, filtered, concentrated, and then dried under vacuum to produce Intermediate I (2.7 g) of the desired product as an amorphous white solid that was used without further purification.

Synthesis of 2-(aminomethyl-Arg(Pbf)-Gly-NAc)-4-carboxypiperidine (Intermediate L

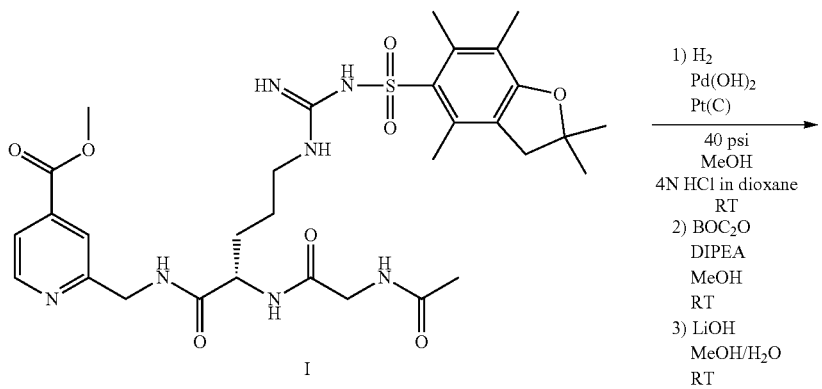

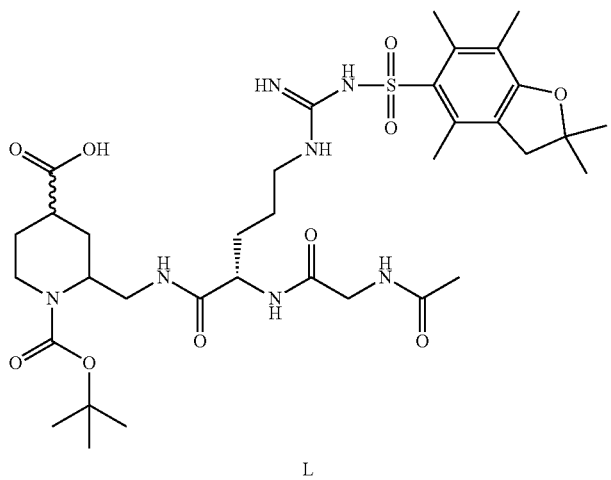

Intermediate I (2-(aminomethyl-Arg(Pbf)-Gly-NAc)-4-carbomethoxypyridine, 2.4 g) was dissolved in methanol (100 mL) and transferred to a 250 mL Parr bottle containing a methanolic solution of 20% Pd(OH)$_2$.C w/~50% water (100 mg), 10% Pt·C (100 mg that was pre-wetted with an equal mass of water to prevent undesired ignition of methanol vapors), and 4N HCl in dioxane (2 eq.). The parr bottle was equipped with a metal safety shield, affixed to a Parr shaker and pressurized to 40 psi H$_2$. The reaction was shaken overnight at RT, then vented and removed from the Parr shaker. The reaction was determined to be complete by LC/MS, then filtered through a paper filter to remove catalyst. The collected catalyst and the Parr bottle were rinsed with methanol (3×25 mL). The resulting methanol solution was concentrated on a rotovap, and then the resulting white solid was further dried under high vacuum for several hours. The resulting solid was dissolved in methanol (~50 mls) and then (BOC)$_2$O (1.1 eq.) and DIPEA (1.2 eq) were then added. The reaction was determined to be complete by LC/MS after being stirred for 8 h at RT. The reaction was transferred to a 500 mL separatory funnel containing 0.5 M HCl aq (100 mL) and ethyl acetate (250 mL). The aqueous layer was extracted with ethyl acetate (2×100 mL), then the combined organic layers were washed with water (2×100 mL) and brine (1×100 mL), dried over MgSO$_4$, filtered, concentrated, and then dried under vacuum. The resulting residue was dissolved in 9:1 methanol:water (100 mL) and then LiOH (4 eq.) was added to the reaction with vigorous stirring at RT. The reaction was monitored by LC/MS and determined to be complete after stirring for 4 h at RT. The reaction was neutralized to pH 4-5 via the addition of aqueous 1N HCl (~4 eq.). The resulting solution was concentrated on a rotary evaporator. The resulting residue was dissolved in 1:1 ACN/H$_2$O (100 mL), frozen at −78° C., and then placed on a lyophilizer overnight to afford the desired acid Intermediate L (2.2 g) as a dry white solid that was used without further purification.

Synthesis of 2-(aminomethyl-Arg(pbf)-Gly-NAc)-4-(Z-Lys-H) piperidine amide (Intermediate A

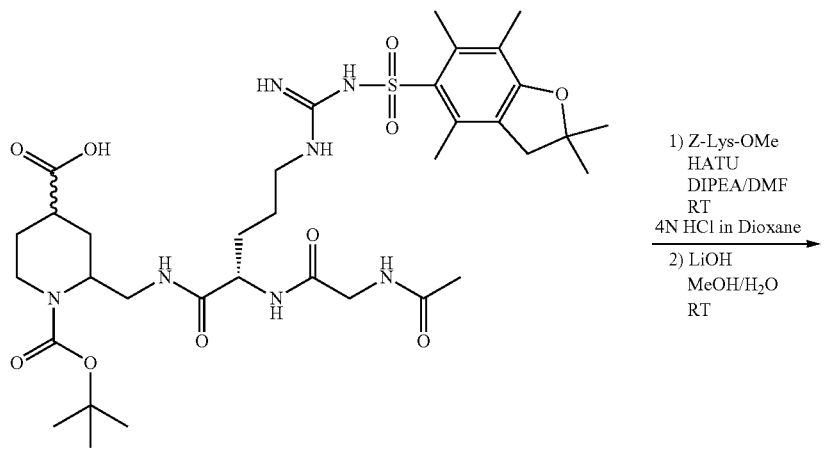

L

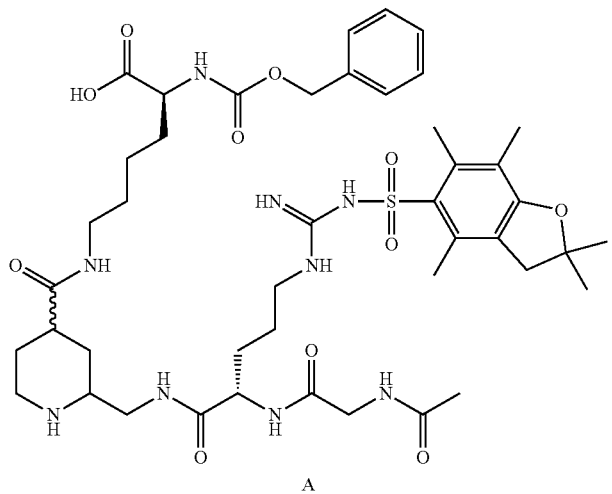

A

Intermediate L (2.0 g), Z-Lys-OMe (1 eq.), and HATU (1.1 eq.) were dissolved in anhydrous DMF (50 mL). The mixture was stirred at ambient temperature until all observable solids were fully dissolved. The solution was cooled to −10° C. (wet ice/acetone) then DIPEA (3 eq.) was added dropwise. Once the addition of DIPEA was completed, the reaction was allowed to warm slowly to room temperature. The reaction was observed to be complete by LC/MS after stirring for ~20 minutes at room temperature. The reaction was transferred to a separatory funnel and diluted with DCM (200 mL). The organic layer was washed with water (2×50 mL) then saturated NaCl solution (50 mL). The organic layer was then dried with MgSO$_4$ and filtered. To the resulting organic layer, at ambient temperature, was added 4N HCl in dioxane (5 mL) with vigorous stirring. The reaction was stirred at room temperature and monitored with LC/MS. The reaction was complete after ~45 mins. Upon completion, the reaction was concentrated on a rotary evaporator to yield a white solid. The resulting solid was dissolved in 2:1 MeOH/water (100 mL) and stirred at room temperature. The pH of the reaction mixture was slowly elevated to ~12 via the addition of 1M LiOH solution. The reaction was monitored by LC/MS and was complete after stirring for 1.5 hours at room temperature. The reaction was acidified to pH 4-6 via the addition of 1M aqueous HCl. The resulting solution was condensed under vacuum and next the concentrated solution was then frozen at −78° C. (dry ice/acetone) and dried on a lyophilizer overnight to produce a white solid. The resulting solid was triturated with water (to remove inorganic salts), filtered, washed with water, and then dried under vacuum. The resulting solid, Intermediate A (1.9 g), was used without further purification.

Synthesis of 4-Bis-boc guanidinophenol (Intermediate 4-M

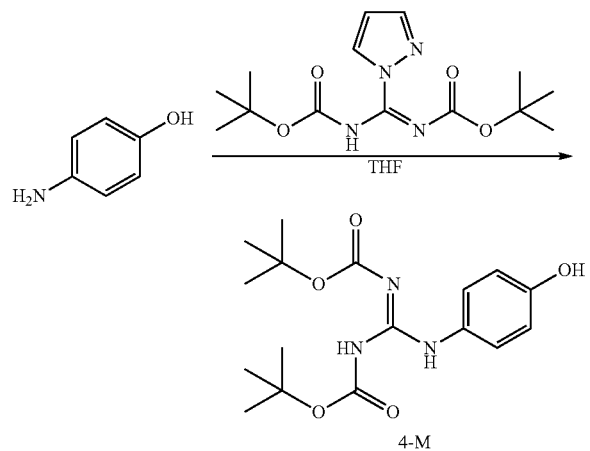

4-aminophenol (25 g) was dissolved in anhydrous THF (200 mL). The solution was stirred at room temperature and bisBoc-pyrazole reagent (1.1 eq.) was added in one portion. The reaction was stirred at room temperature and monitored with LC/MS. The reaction was complete after stirring at room temperature for 6 hours. The reaction was concentrated on a rotary evaporator to remove approximately 50% of the initial volume of THF, then transferred to a separatory funnel and diluted with ethyl acetate (200 mL). The resulting organic solution was washed several times with water (50 mL), then once with saturated sodium chloride solution (~50 mL). The organic layer was dried with MgSO$_4$, filtered, and concentrated to a pasty beige crystalline solid on a rotary evaporator. The resulting beige solid was dissolved in a minimum volume of refluxing anhydrous ethanol, cooled to ambient temperature, then placed in a −10° C. freezer overnight to crystallize. The crystals were collected via filtration using a Buchner funnel fitted with a paper filter, rinsed with cold ethanol (−10° C.), then placed under high vacuum to dry. This resulted in the isolation of Intermediate 4-M (~36.0 g) of crystalline white solid that was used without further purification.

Synthesis of 4-(2-(((benzyloxy)carbonyl)amino)ethoxy)benzoic acid (Intermediate N

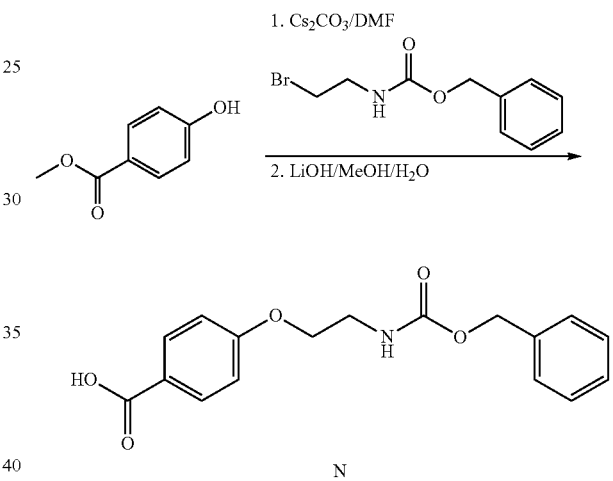

Cesium carbonate (1 eq.) was slurried in anhydrous DMF (200 mL) at room temperature. Methyl paraben (20 g) was then added to the slurry followed by N-(2-bromethyl)benzyl carbamate (1 eq.). The reaction was stirred overnight at room temperature. The reaction was then transferred to a separatory funnel and diluted with ethyl acetate (400 mL) and water (100 mL). The organic layer was subsequently washed with water (2×50 mL), then washed with saturated NaCl solution (50 mL). The organic layer was dried with MgSO$_4$, filtered, and concentrated on a rotary evaporator to a white solid. The resulting material was dissolved in 2:1 methanol:water, and the pH of the solution was then brought to ~12 via the addition of 1 M LiOH solution. The reaction was stirred at room temperature overnight. The reaction was then placed on a rotary evaporator to remove most of the methanol, then diluted with water (300 mL), then adjusted to pH ~2 via the addition of concentrated HCl solution resulting in formation of a thick white precipitate. The solid was isolated via filtration through a Buchner funnel fitted with a paper filter and washed with water (3×100 mL). The solid was then dried under vacuum to produce Intermediate N (25 g) that was used without further purification.

Synthesis of Intermediate O

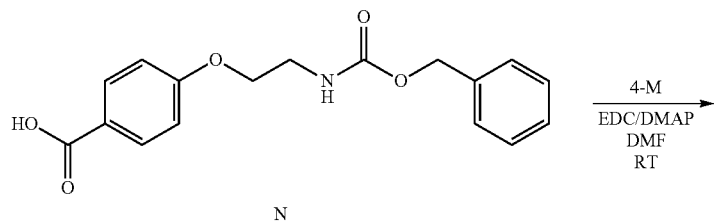

N

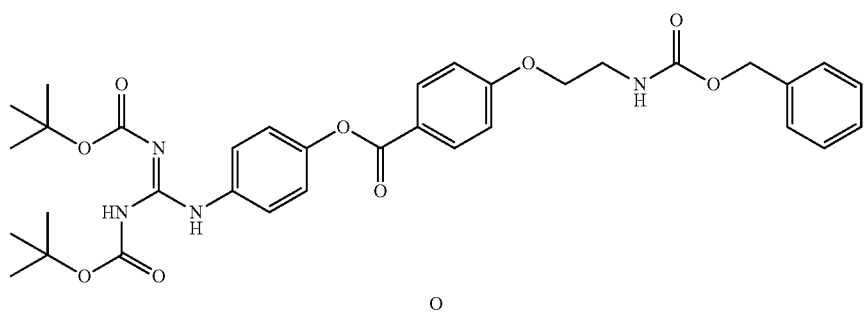

O

Intermediate N (5.0 g), Intermediate 4-M (1 eq.), DMAP (1 eq.), and EDC (1.2 eq.) were dissolved in anhydrous DMF (100 mL). The reaction was stirred at room temperature and monitored with LC/MS. The coupling was observed to be complete after stirring at room temperature overnight. The reaction was diluted with ethylacetate (300 mL), then transferred to a separator), funnel. The organic solution was washed with water (2×50 mL), 0.1 M HCl solution (50 mL), then saturated sodium chloride solution (50 mL). The reaction was then dried with MgSO$_4$, filtered, and concentrated on a rotary evaporator until a white solid is obtained. The white solid is dried under vacuum to produce of Intermediate O (6.6 g) that was used without further purification.

Synthesis of Intermediate 4-B

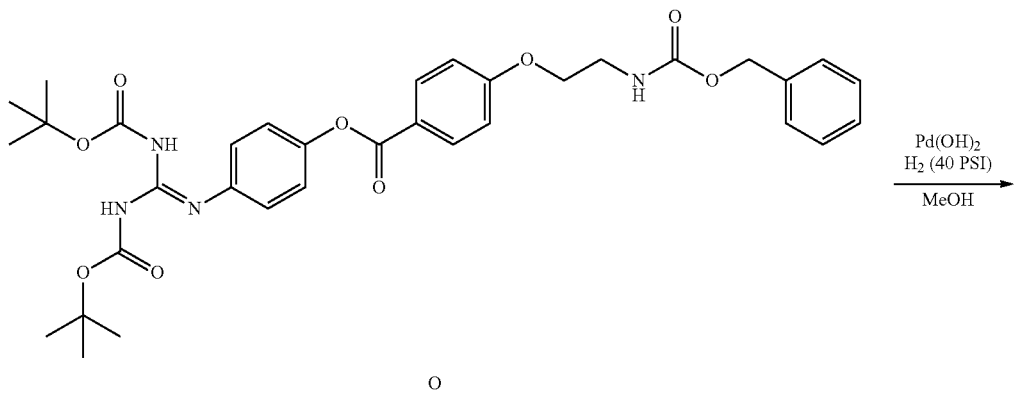

O

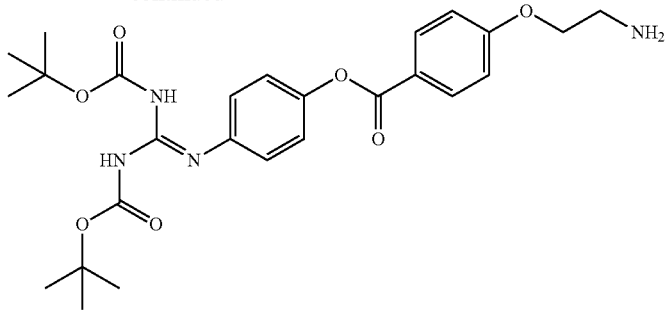

4-B

Pd(OH)$_2$ (100 mg) and Intermediate O (3.0 g) were placed in a 500 mL Parr bottle followed by the addition of a 1:1 solution of methanol:THF (~100 mL). The bottle was attached to a Parr shaker and pressurized to ~40 psi with H$_2$. The reaction was shaken at room temperature for 2 hours. The bottle was then depressurized and removed from the Parr shaker. The reaction was filtered using a Buchner funnel fitted with a paper filter to remove catalyst. The catalyst was washed with methanol (2×50 mL). The filtered solution was then concentrated using a rotary evaporator resulting in an amorphous white solid that was dried under vacuum to produce Intermediate 4-B (2.25 g) as a white solid that was used without further purification.

Synthesis of Activated Hydrocodone (HC*.HCl)

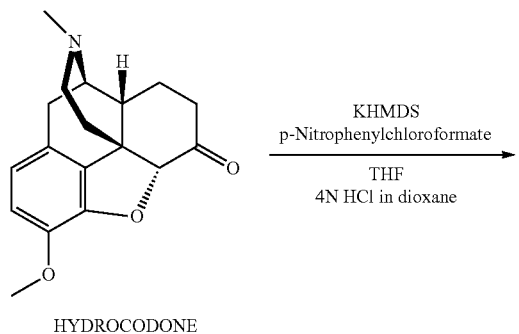

HYDROCODONE

KHMDS
p-Nitrophenylchloroformate
THF
4N HCl in dioxane

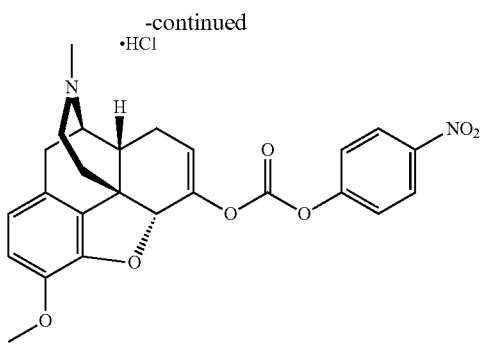

Hydrocodone freebase (5.0 g) was dissolved in anhydrous THF (150 mL) in an oven-dried, round-bottom flask then cooled to −10° C. 1M KHMDS in THF (1.05 eq.) was then added rapidly dropwise to the cold solution. The resulting enolate solution was maintained at −10° C. for 30 minutes, then cooled to −78° C. In a separate flask p-nitrophenylchloroformate (1.10 eq.) was dissolved in anhydrous THF (100 mL) and cooled to −78° C. The enolate solution was transferred slowly via cannula to the vigorously stirred solution of p-nitrophenylchloroformate while maintaining the temp below −60° C. Upon completion of the addition, the reaction mixture was stirred for 1 h at −78 C. The reaction was then quenched into a stirring biphasic 1:2 mixture of water:DCM (200 mL total). The quenched mixture was partitioned, and the organic layer was separated and washed with water (100 mL). The organic layer was then dried over MgSO$_4$ and filtered, concentrated close to dryness (~95% removal), then THF (100 mL) was added. Diethyl ether (100 mL) is the added to effect complete precipitation and washing of the desired product which was filtered, washed with diethyl ether, then dried under vacuum to produce Activated Hydrocodone (HC*.HCl, 6.23 g).

Synthesis of Intermediate P

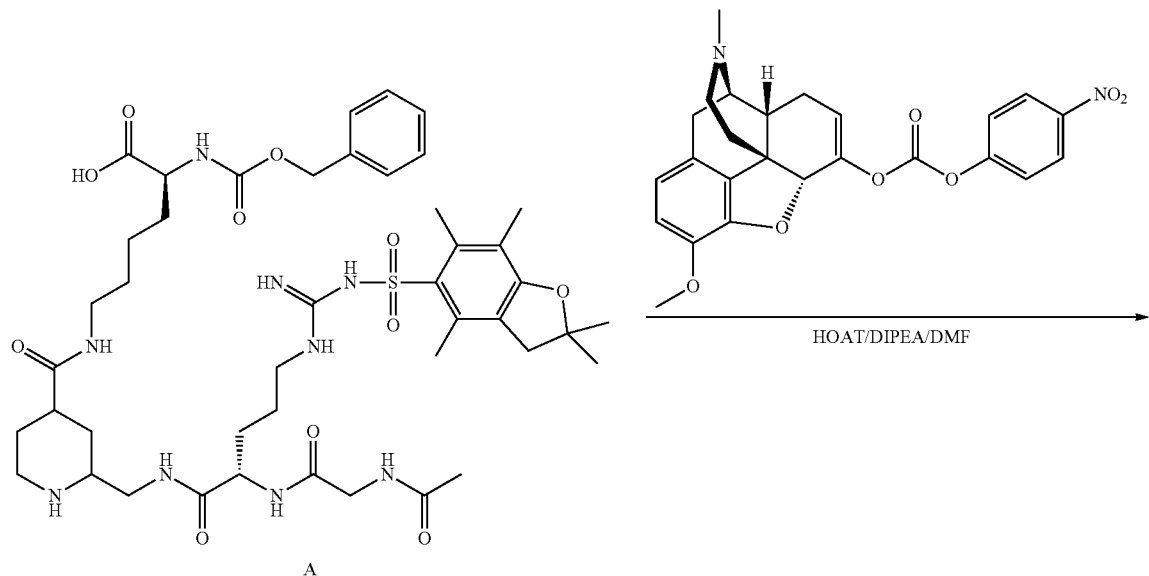

A

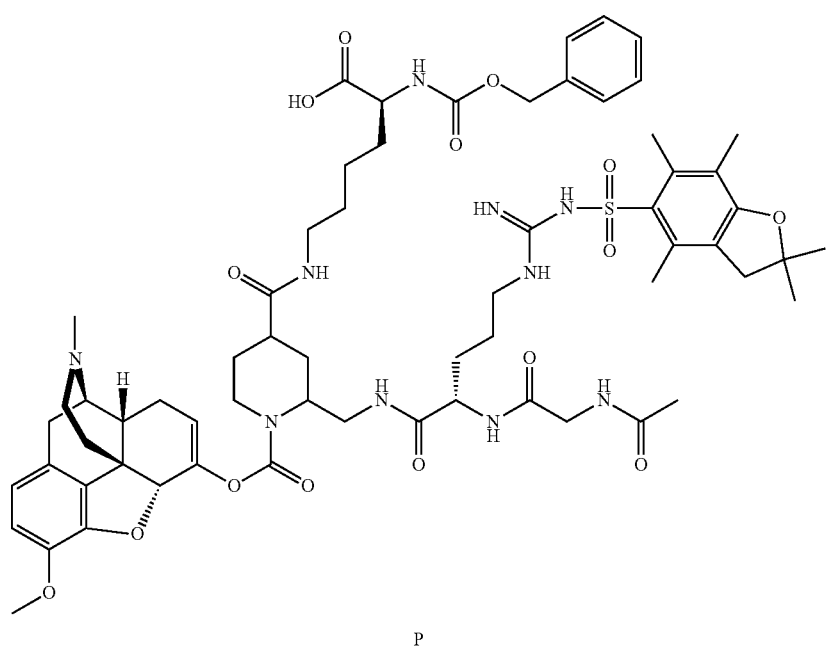

P

Intermediate A (2-(aminomethyl-Arg(Pbf)-Gly-NAc)-4-(Z-Lys-)H) piperidine amide, 500 mg), Activated hydrocodone·HCl (1.0 eq.), and HOAt (1.0 eq.) are dissolved in anhydrous DMF (15 mL). The solution is stirred at room temperature until all solids have dissolved. DIPEA (3 eq.) is then added to the reaction mixture. The stirred reaction was heated to ~45° C. and monitored with LC/MS. The reaction was determined to be complete after stirring at ~45° C. for an additional 4 hours. The reaction mixture was then transferred to a separatory funnel and diluted with DCM (~200 mL) and washed twice with aqueous 0.1N HCl solution (50 mL). The combined acidic aqueous extracts were extracted with DCM (2×50 mL). The combined organic phases were then washed with saturated NaCl solution, dried with MgSO$_4$, filtered and concentrated on a rotary evaporator produce Intermediate P that was subsequently dried under high vacuum to yield 541 mg (amorphous white solid) that was used without further purification.

Synthesis of Intermediate 4-Q

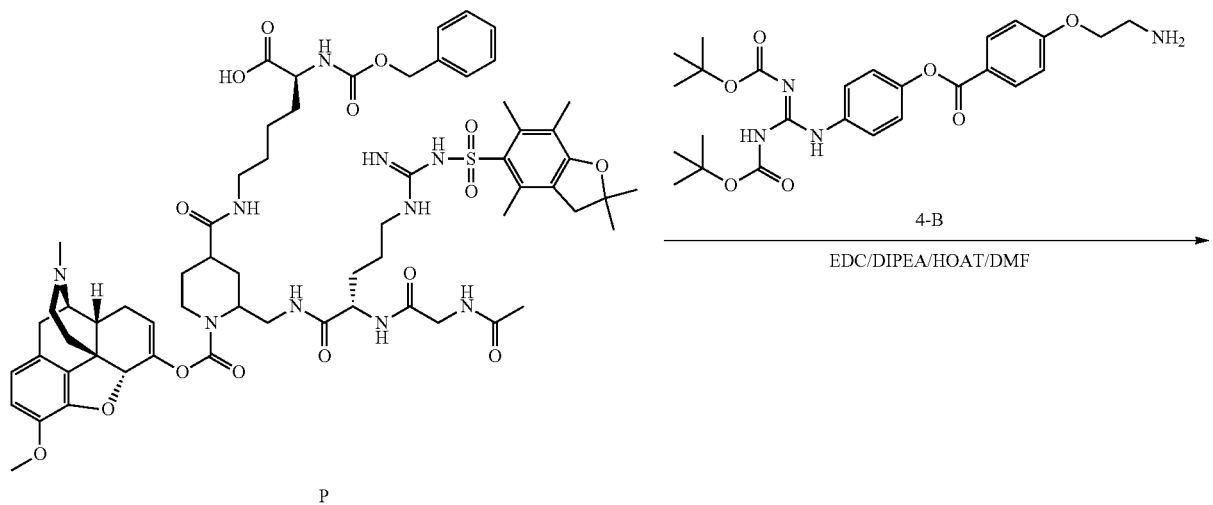

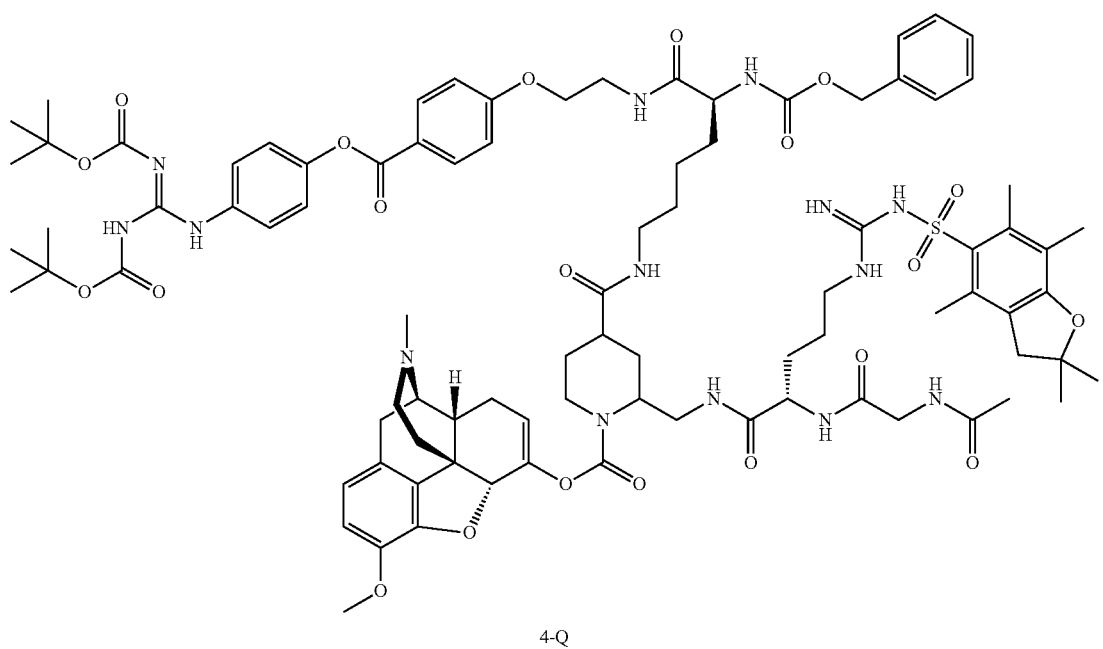

To Intermediate P (250 mg), amine 4-B (1 eq.), HOAT (1 eq.), and EDC (1.2 eq.) were added anhydrous DMF (3 mL) and DIPEA (2 eq.). The reaction was monitored with LC/MS. After stirring overnight at room temperature, the reaction was confirmed to be complete by LC/MS. The reaction was transferred to a separatory funnel and diluted with ethyl acetate (100 mL), washed with aqueous 0.1M HCl solution (2×25 mL), and then with saturated NaCl solution (25 mL). The resulting organic phase was dried with MgSO$_4$, filtered, and concentrated 4847-6967-2954 on a rotary evaporator to yield a viscous, colorless oil that solidified following drying under high-vacuum for several hours. The resulting product, Intermediate 4-Q (263 mg) was used without further purification.

Synthesis of II-D-71c

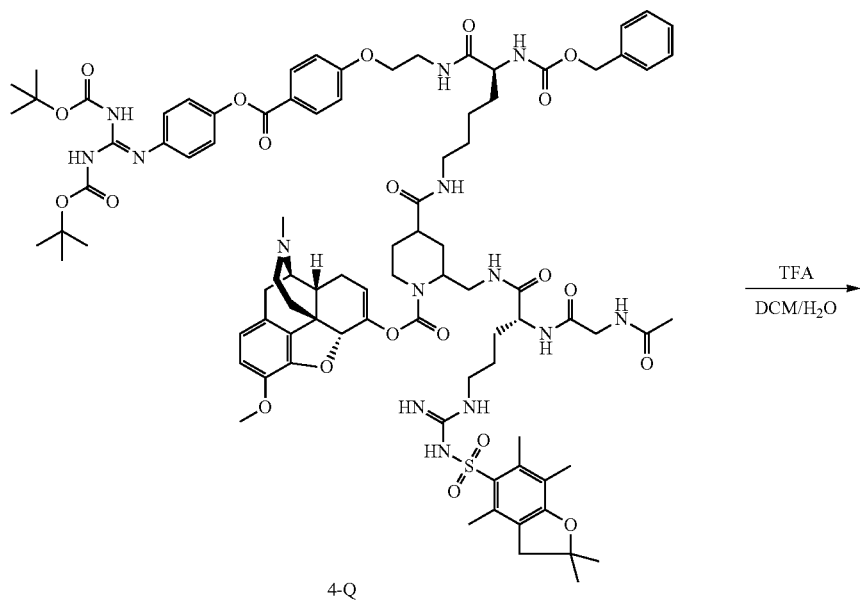

4-Q

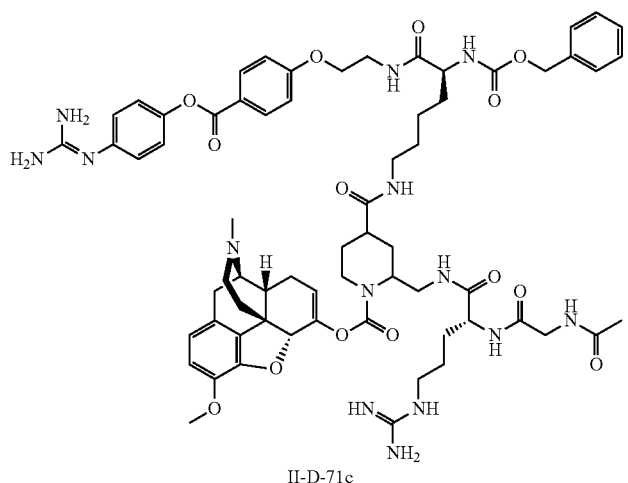

II-D-71c

Intermediate 4-Q (100 mg) is dissolved in 10 mL of a 3:1:0.1 mixture of TFA:DCM:Water. The resulting solution was stirred at room temperature and monitored with LC/MS. The reaction was demonstrated to be complete by LC/MS after 6 hours. The reaction mixture was added slowly dropwise to a stirring solution of MTBE resulting in the formation of a white precipitate. The white precipitate was washed several times with MTBE via decantation then dried under vacuum to produce II-D-71c as a white solid (56 mg, white solid).

305
Synthesis of II-D-71b

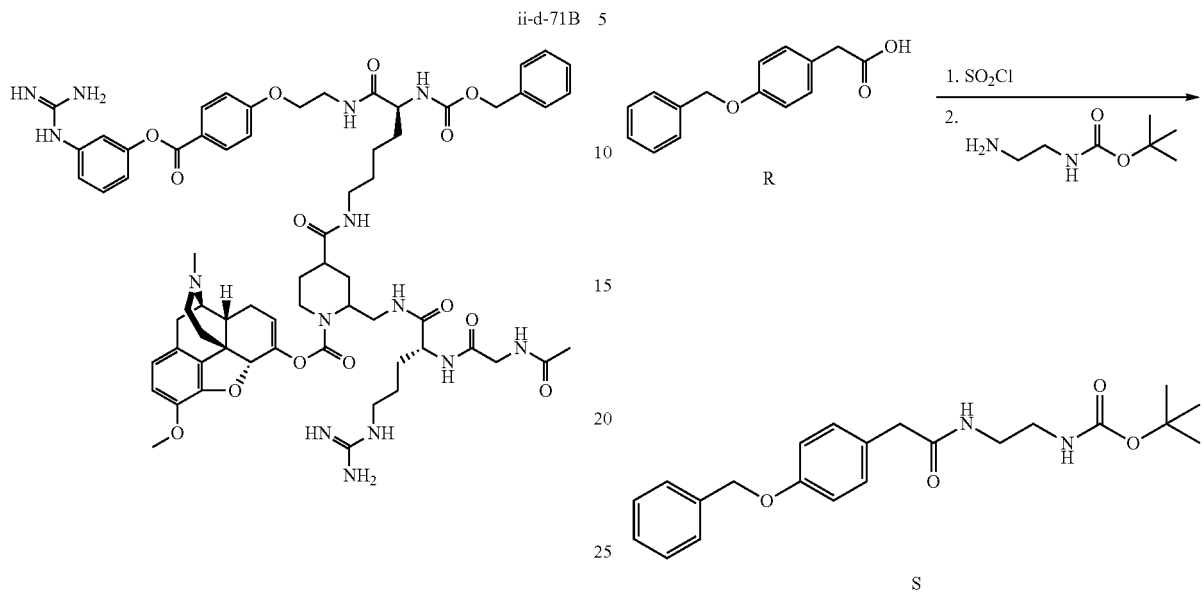

Compound H-D-71b was prepared according to the procedure listed for II-D-71b, however 4-aminophenol was replaced with 3-aminophenol.

Synthesis of II-P-47b

306
Synthesis of tert-butyl (2-(2-(4-(benzyloxy)phenyl)acetamido)ethyl)carbamate (Intermediate S A solution of Intermediate R (10.0 g) in thionyl chloride (50 mL) [Caution: reaction involves gasses being generated and will pressurize the system] was heated to 60° C. for 2 hours. Upon completion, the reaction was condensed under vacuum and the mixture was further processed via addition of toluene (2×25 mL), followed by further condensing under vacuum to afford the acid chloride of Intermediate R. Next, the acid chloride was dissolved in DCM (100 mL) and the resulting solution was added slowly to a solution of tert-butyl (2-aminoethyl)carbamate (6.61 g), DIPEA (8.70 mL) in DCM (100 mL). The reaction was stirred at RT for 30 min. The reaction mixture was then transferred to a separatory funnel and diluted with DCM (200 mL) and washed twice with aqueous 0.1N HCl solution (250 mL), sat NaHCO$_3$ (250 ml), brine (250 ml). Next, the combined organic phases were dried with MgSO$_4$, filtered and concentrated on a rotary evaporator produce Intermediate S as a white solid that was subsequently dried under vacuum to yield 14.8 g that was used without further purification.

Synthesis of 4-(2-((2-((tert-butoxycarbonyl)amino)ethyl)amino)-2-oxoethyl)phenyl 4-nitrobenzoate (Intermediate T

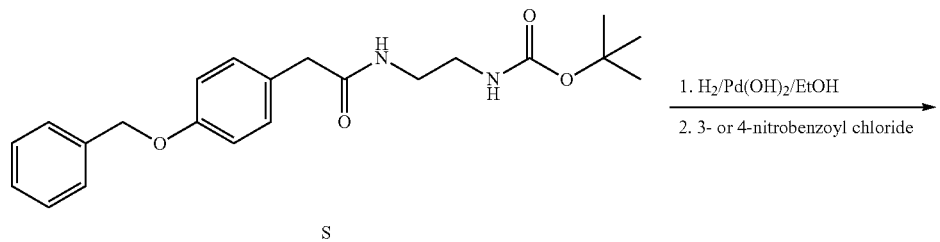

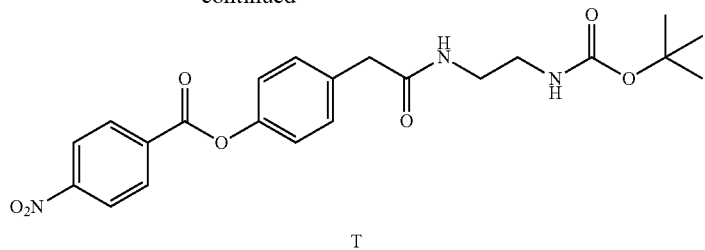

T

Pd(OH)$_2$ (~700 mg) and Intermediate S (7.38 g) were placed in a 500 mL Parr bottle followed by the addition of ethanol (~200 mL). The bottle was attached to a Parr shaker and pressurized to ~40 psi with H$_2$. The reaction was shaken at room temperature for 3 hours. The bottle was then depressurized and removed from the Parr shaker. The reaction was filtered using a Buchner funnel fitted with a paper filter to remove catalyst. The catalyst was washed with ethanol (2×50 mL). The filtered solution was then concentrated using a rotary evaporator resulting in an amorphous off-white solid that was dried under vacuum to produce the de-benzylated phenol as an off-white solid. The resulting phenol (6.6 g) was dissolved in DCM (200 mL) and then further treated with DIPEA (5.2 mL) and 4-nitrobenzoyl chloride (4.65 g) at RT. The reaction was stirred for 30 min and then diluted with 10:1 DCM:MeOH (200 mL), followed by transferred to a separatory funnel and washed twice with aqueous 0.1N HCl solution (200 mL), sat NaHCO$_3$ (200 ml), brine (200 ml). Next, the organic phase was dried with MgSO$_4$, filtered and concentrated on a rotary evaporator produce Intermediate T as a white solid that was subsequently dried under vacuum to yield 6.71 g that was used without further purification.

Synthesis of 4-(2-((2-((tert-butoxycarbonyl)amino) ethyl)amino)-2-oxoethyl)phenyl 4-guanidinobenzoate (Intermediate U

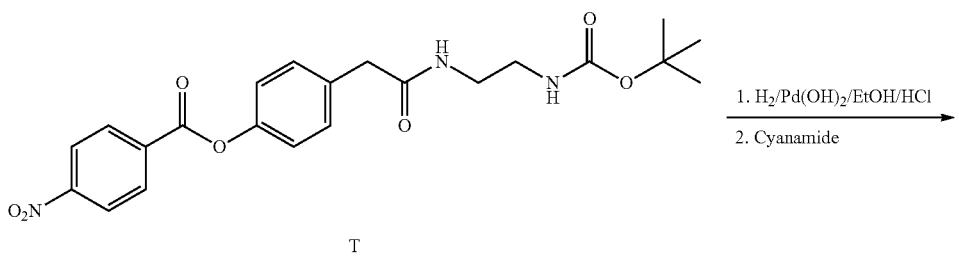

T

1. H$_2$/Pd(OH)$_2$/EtOH/HCl
2. Cyanamide

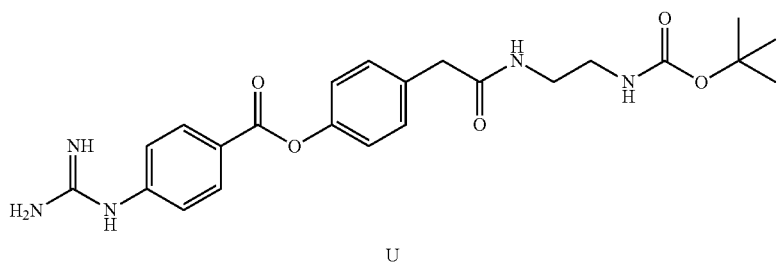

U

Pd(OH)$_2$ (~600 mg) and Intermediate T (6.0 g) were placed in a 500 mL Parr bottle followed by the addition of THF (~200 mL). The bottle was attached to a Parr shaker and pressurized to ~30 psi with H$_2$. The reaction was shaken at room temperature for 2 hours. The bottle was then depressurized and removed from the Parr shaker and demonstrated to be complete by LC/MS. The reaction was filtered using a Buchner funnel fitted with a paper filter to remove catalyst. The catalyst was washed with THF (2×50 mL). The filtered solution was then concentrated using a rotary evaporator resulting in an amorphous off-white solid that was dried under vacuum to produce the de-benzylated phenol as an off-white solid. The resulting phenol (6.6 g) was dissolved in DCM (200 mL) and then further treated with DIPEA (5.2 mL) and 4-nitrobenzoyl chloride (4.65 g) at RT. The reaction was stirred for 30 min and then diluted with 10:1 DCM:MeOH (200 mL), followed by transferred to a separatory funnel and washed twice with aqueous 0.1N HCl solution (200 mL), sat NaHCO$_3$ (200 ml), brine (200 ml). Next, the organic phase was dried with MgSO$_4$, filtered and concentrated on a rotary evaporator produce Intermediate U (6.71 g) as a white solid that was subsequently dried under vacuum that was used without further purification.

Synthesis of 4-(2-((2-aminoethyl)amino)-2-oxoethyl)phenyl 4-guanidinobenzoate (Intermediate V

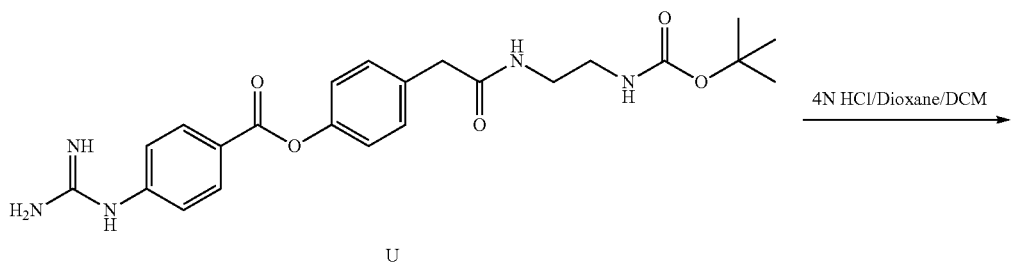

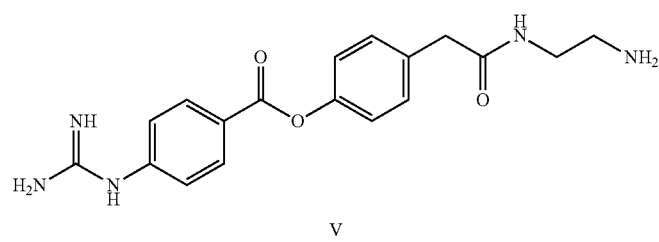

To a flask containing Intermediate U (1.40 g) in DCM (50 mL) was added 4N HCl in dioxane (10 mL) and the reaction stirred at RT until LC/MS analysis indicated complete removal of the BOC protecting group. The reaction was then concentrated and the resulting residue dissolved in a minimal amount of anhydrous methanol (~5 mL). The methanol solution was added slowly dropwise to a well-stirred 500 mL RB flask containing Et$_2$O (300 mL) at RT, resulting in the formation of a thick white precipitate. The stirring was halted and the precipitate was allowed to settle to the bottom of the flask. The supernatant was carefully poured off (~90% removed) and replaced with fresh Et$_2$O (300 mL) and stirred vigorously. The stirring was ceased and the precipitate was allowed to settle to the bottom of the flask. The supernatant was carefully poured off (~90% removed) and the resulting solid was dried under vacuum to afford intermediate V (1.01 g). The product was used without further purification.

Synthesis of II-P-47b

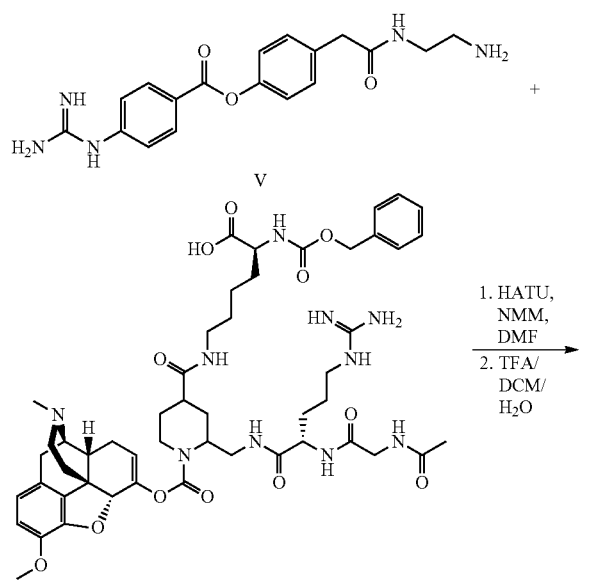

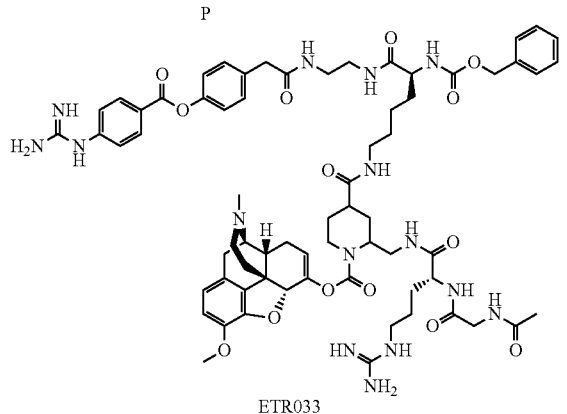

Intermediate V (900 mg) was added to anhydrous DMF (10 mL), Intermediate P (1.20 g) and HATU (750 mg) were added and the resulting solution was stirred at RT until all solids dissolved. The reaction was then cooled to −78° C. (dry ice/acetone) and DIPEA (4 eq.) was added slowly dropwise. The reaction was stirred for an additional 10 min at −78° C. and then allowed to warm slowly to RT. The reaction was determined to be complete by LC/MS after stirring for 30 min at RT. The reaction was transferred to a 100 mL separatory funnel, diluted with water (200 mL) and extracted with ethyl acetate (1×300 mL; then 3×100 mL). The combined organic extracts were washed with 1 M HCl$_{aq}$ (1×100 mL), saturated NaHCO$_3$ solution (1×100 mL), brine (1×100 mL) and then dried over MgSO$_4$, filtered and concentrated. The resulting residue was dried under high vacuum then dissolved in 50 mL of a 3:1:0.1 mixture of TFA:DCM:Water. The resulting solution was stirred at room temperature and monitored with LC/MS. The reaction was demonstrated to be complete by LC/MS after 5 hours. The reaction mixture was added slowly dropwise to a stirring solution of MTBE resulting in the formation of a white precipitate. The white precipitate was washed several times with MTBE via decantation then dried under vacuum to produce II-P-47b as a white solid (1.66 g).

Synthesis of II-P-47c

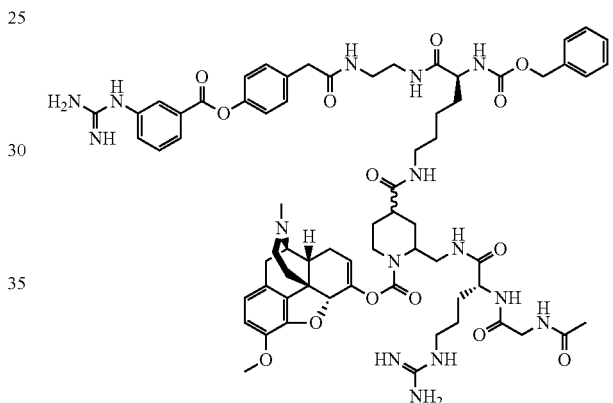

Compound II-P-47c was prepared according to the procedure listed for II-P-47b, however 4-aminobenzoic acid was replaced with 3-aminobenzoic acid.

Synthesis of II-D-71c-NTX

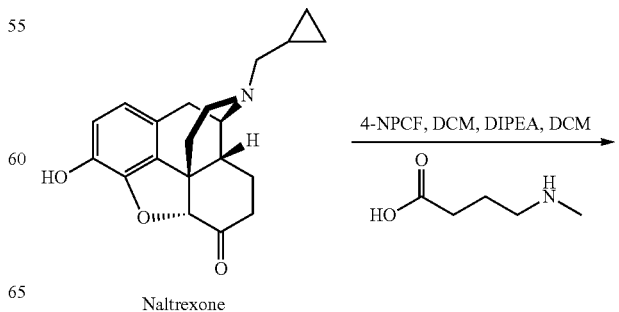

313
-continued

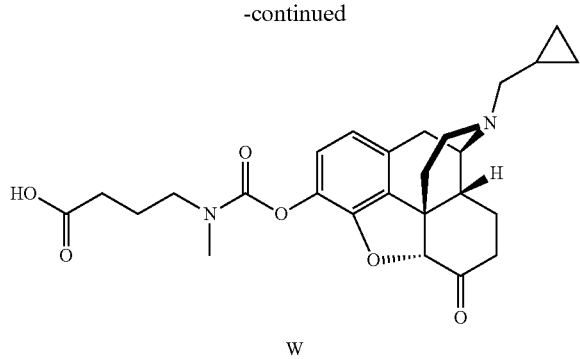

W

314

Naltrexone freebase (100 mg) was dissolved in anhydrous DCM (1 mL) in an oven-dried, round-bottom flask then cooled to −10° C. DIPEA (0.14 mL) and was then added to the cold solution, followed by transfer of the resulting solution to a pre-prepared solution of 4-nitrophenylchloroformate (60.5 mg). The resulting solution was maintained at −10° C. for 30 minutes. Next, to the solution was added 4-(methylamino)butanoic acid (40 mg) and the reaction was stirred for 1 hour at −10° C. The reaction was then warmed to RT, condensed and the resulting crude residue was then purified via prep-HPLC to afford Intermediate W (78 mg) as an off-white solid.

Synthesis of II-D-71c-NTX

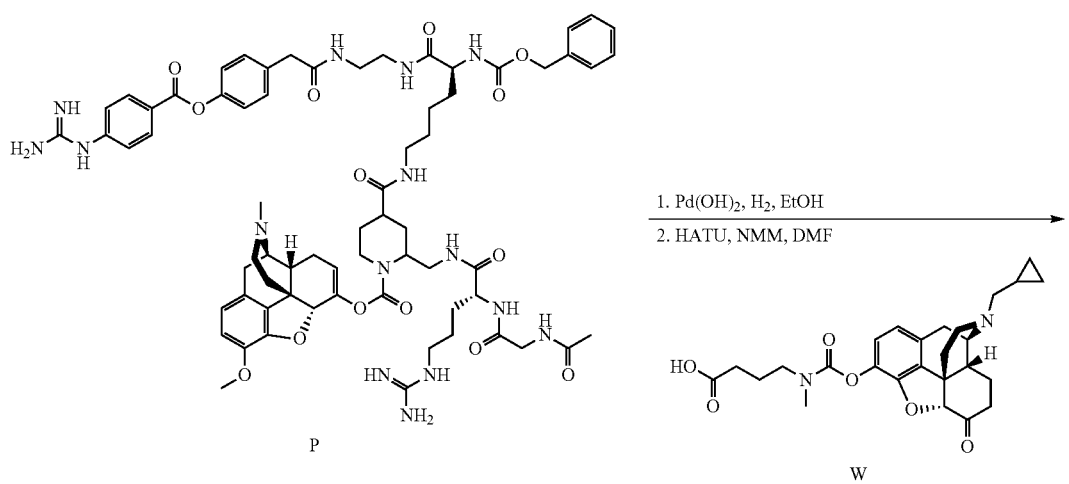

1. Pd(OH)$_2$, H$_2$, EtOH
2. HATU, NMM, DMF

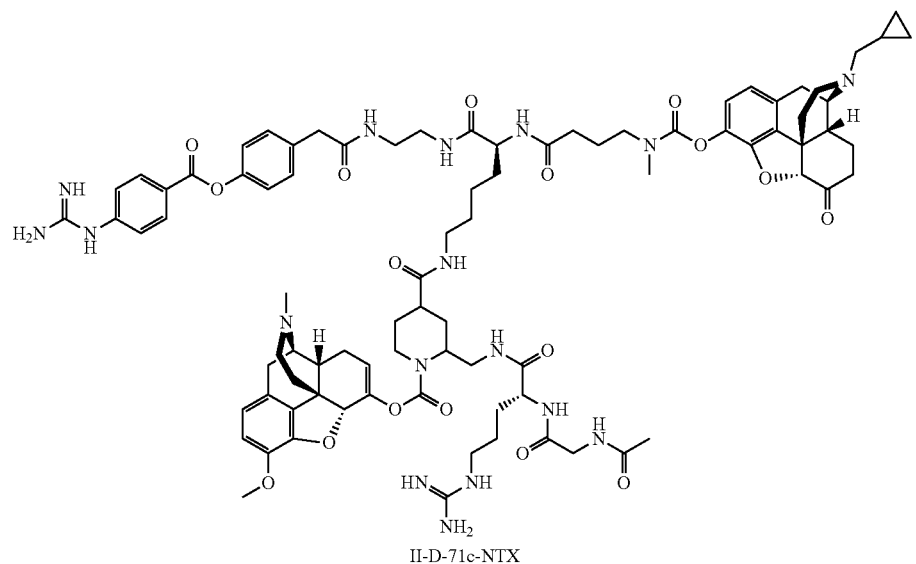

II-D-71c-NTX

Pd(OH)₂ (~0.10 mg) and Intermediate P (78 mg) were placed in a 500 mL Parr bottle followed by the addition of EtOH (~20 mL). The bottle was attached to a Parr shaker and pressurized to ~30 psi with H₂. The reaction was shaken at room temperature for 2 hours. The bottle was then depressurized and removed from the Parr shaker and demonstrated to be complete by LC/MS. The reaction was filtered using a Buchner funnel fitted with a paper filter to remove catalyst. The catalyst was washed with EtOH (2×50 mL). The filtered solution was then concentrated using a rotary evaporator resulting in an amorphous off-white solid that was dried under vacuum to produce the de-benzoylated amine as an off-white solid. The resulting amine was then dissolved in DMF (5 mL). To the resulting mixture was added Intermediate W (29 mg) and NMM (0.012 mL). Next, the solution was cooled to 0° C. and HATU (14 mg) was added. The reaction was slowly allowed to warm to RT, followed by stirring at RT for 30 min. Next, the mixture was condensed and the crude reaction mixture was purified by preparative HPLC to afford compound II-D-71c-NTX·4TFA (30 mg) as an off-white solid.

Synthesis of II-G-35b and II-G-35c

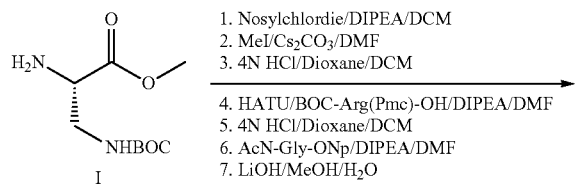

1. Nosylchlordie/DIPEA/DCM
2. MeI/Cs₂CO₃/DMF
3. 4N HCl/Dioxane/DCM
4. HATU/BOC-Arg(Pmc)-OH/DIPEA/DMF
5. 4N HCl/Dioxane/DCM
6. AcN-Gly-ONp/DIPEA/DMF
7. LiOH/MeOH/H₂O

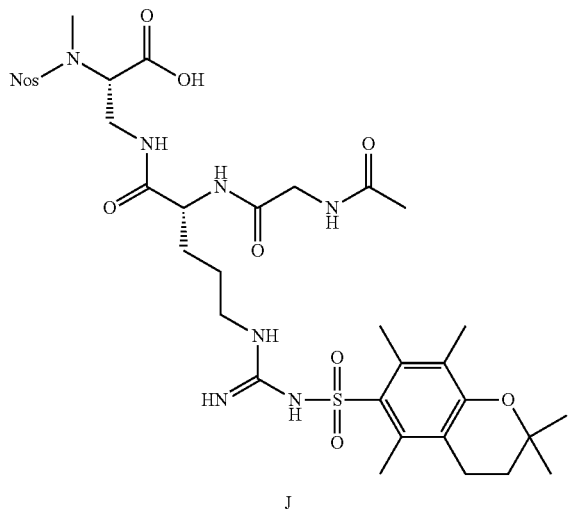

Compound I (3.5 g, 22.4 mmol, 1.0 eq) and diisopropylethylamine (11.7 mL, 67.2 mmol, 3.0 eq) were dissolved in DCM (70 mL) and cooled to 0° C. A solution of nosylchloride (4.95 g, 22.4 mmol, 1.0 eq), dissolved in DCM (30 mL), was then added dropwise to the solution. The reaction was stirred for 30 minutes, then transferred to a separatory funnel and diluted with DCM (~100 mL). The DCM solution was then washed with 1 M HCl(aq), saturated NaHCO₃ solution, water, then brine. The organic layer was then dried over MgSO₄, filtered, then concentrated to produce light yellow crystals. The light yellow crystals were dissolved in DMF (~75 mL). Cs₂CO₃ (21.84 g, 67.2 mmol, 3.0 eq) was added followed by iodomethane (1.39 mL, 22.4 mmol, 1.0 eq). The reaction was stirred at room temperature for 3 hours, water was added to dissolve remaining Cs₂CO₃ salts, then the mixture was transferred to a separatory funnel and diluted with EtOAc (~200 mL). The EtOAc solution was washed with 1 M HCl (100 mL), saturated NaHCO₃ solution (100 mL), water (100 mL), then brine (100 mL). The organic layer was dried over MgSO₄, filtered, then concentrated to produce a light yellow crystalline solid. The resulting solid was dissolved in DCM (150 mL) and treated with 4N HCl in dioxane (10 mL) and stirred at RT for 3 hours. The reaction was concentrated and placed under high vacuum to remove any residual solvents resulting in the isolation of a viscous light yellow residue. The resulting residue was dissolved in DMF (50 mL) followed by the addition of HATU (9.36 g, 22.4 mmol, 1.1 eq) and Boc-Arg(Pmc)-OH (12.7 g, 22.4 mmol, 1.0 eq). The solution was cooled to −78° C. and DIPEA (11.7 mL, 67.2 mmol, 3.0 eq) was added dropwise with vigorous stirring. The reaction was allowed to warm to RT and stirred for an additional 2 hours. The concentrated reaction was diluted with EtOAc (100 mL) and transferred to a separatory funnel. The EtOAc solution was washed with 1 M HCl (100 mL), saturated NaHCO₃ solution (100 mL), water (100 mL), then brine (100 mL). The organic layer was dried over MgSO₄, filtered, then concentrated to produce a light yellow crystalline solid. The resulting solid was dissolved in DCM (150 mL) and treated with 4N HCl in dioxane (15 mL) and stirred at RT for 3 hours. The reaction was concentrated and placed under high vacuum to remove any residual solvents resulting in the isolation of a viscous light yellow residue. The resulting residue was dissolved in DCM (150 mL) and diisopropylethylamine (11.7 mL, 67.2 mmol, 3.0 eq) was added followed by the addition of solid AcN-Gly-ONp (0.53 g, 22.4 mmol, 1.0 eq) in one portion. The reaction was stirred at RT for 2 hours, concentrated on a rotary evaporator, then purified using preparative HPLC (C-18 column employing a method of 20-100% acetonitrile (ACN) with a 20 minute ramp) to afford 8.30 g (10 mmol, 47% overall yield) of the methyl ester form of Intermediate J as a white solid following lyophilization of the collected fractions. The methyl ester form of Intermediate J was dissolved in 5:1 methanol (MeOH):water. Next, LiOH (0.24 g, 100 mmol, 10 eq) was added and the reaction was stirred at RT for several hours. The reaction was neutralized to pH ~4-5 with acetic acid (AcOH) and concentrated on a rotary evaporator. The resulting Intermediate J was used without further purification. LC-MS [M+H]: 825.1 (C₃₄H₄₈N₈O₁₂S₂+H, calc: 824.3).

Synthesis of II-G-35c

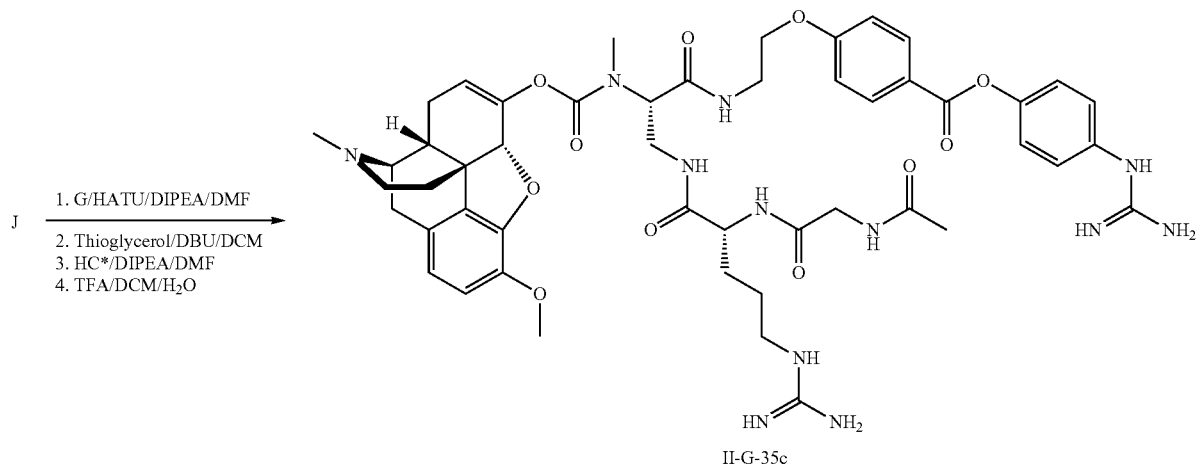

Intermediate J (0.50 g, 0.78 mmol, 1.0 eq) and Intermediate G (0.303 g, 0.78 mmol, 1.0 eq) were dissolved in DMF (15 ml) followed by the addition of HATU (0.296 g, 0.78 mmol, 1.0 eq). The solution was cooled to −78° C. and diisopropylethylamine (0.41 mL, 2.3 mmol, 3.0 eq) was added dropwise to the vigorously stirred solution. The reaction was allowed to warm to RT and stirred for an additional 2 hours. The reaction was then concentrated under high vacuum to a viscous amber residue. The resulting residue was dissolved in THF (20 mL) and to this solution was added thioglycerol (0.84 g, 7.8 mmol, 10.0 eq) and DBU (1.17 mL, 7.8 mmol, 10.0 eq) at RT. The reaction was stirred at RT for 3 hours then concentrated on a rotary evaporator to afford a viscous yellow oil. The resulting oil was then purified using preparative HPLC (C-18 column employing a method of 20-100% acetonitrile (ACN) with a 20 minute ramp) to afford 0.418 g (0.66 mmol, 84% overall yield) of the desired amine precursor to compound II-G-35c as a white solid following lyophilization of the collected fractions. The amine precursor to compound II-G-35c was dissolved in DMF (15 mL) followed by the addition of DIPEA (0.344 mL, 1.98 mmol, 3.0 eq) and Activated HC—HCl (0.315 g, 0.66 mmol, 1.0 eq). The reaction was stirred overnight then concentrated to a viscous yellow residue under vacuum. The resulting residue was then purified using preparative HPLC (C-18 column employing a method of 20-100% ACN with a 20 minute ramp) to afford 0.716 g (0.57 mmol, 87% yield) of the PMC protected II-G-35c as a white solid following lyophilization of the collected fractions. The resulting white solid was dissolved in a 3:1:0.1 mixture of TFA:DCM:water and stirred at RT for 1 hour. The solution was concentrated under vacuum and the resulting residue was purified using preparative HPLC (C-18 column employing a method of 10-50% acetonitrile (ACN) with a 20 minute ramp) to afford 0.694 g (0.52 mmol, 91% yield) of the tris-TFA salt of compound II-G-35c as a white solid. LC-MS [M+H]: 995.3 ($C_{49}H_{62}N_{12}O_{11}$+H, calc: 994.5).

Synthesis of II-J-71b and II-J-71c

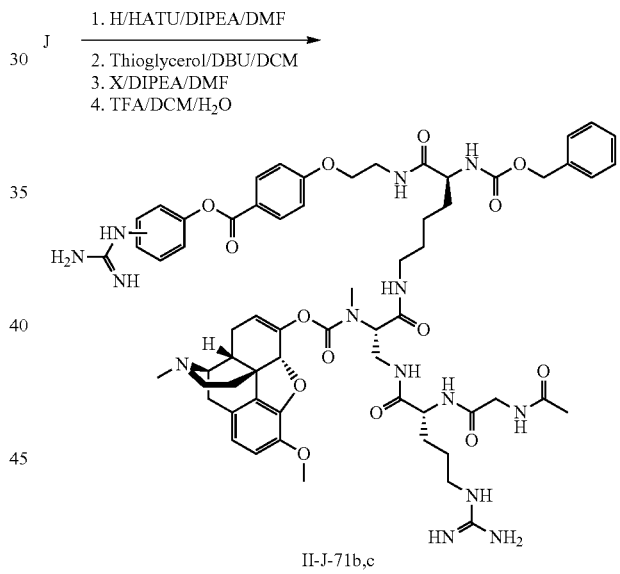

Compound II-J-71b and II-J-71c were prepared in 61% and 58% yield, respectively using the procedure described above by employing the meta- and para-isomers of Intermediate H instead of Intermediate J. LC-MS [M+H]: 1257.4 ($C_{63}H_{80}N_{14}O_{14}$+H, calc: 1256.6).

Oxycodone containing compounds II-A-36b, II-A-36c, II-D-72b, II-D-72c, II-G-36b, II-G-36c, II-J-72b, and II-J-72c were also synthesized in 18.9%, 21.3%, 8.9%, 14.7%, 22.5%, 13.9%, 11.9%, 17.7% overall yields respectively, using the methods described above employing Activated OC.HCl instead of Activated HC.HCl.

Pharmaceutical Compositions

Also embraced within this invention are pharmaceutical compositions comprising two or more polysubunit molecules described above in association with one or more non-toxic, pharmaceutically acceptable carriers and/or diluents and/or adjuvants (collectively referred to herein as "carrier" materials) and, if desired, other active ingredients. In other embodiments, the composition comprises at least 2, at least 3, at least 4, at least 5, or at least 6 different polysubunit molecules.

The compounds and compositions of the present invention can be administered orally, preferably in the form of a pharmaceutical composition adapted to oral administration, and in a dose effective for the prevention or treatment of pain.

For oral administration, the pharmaceutical composition can be in the form of, for example, a tablet, capsule, a soft gelatin (softgel) capsule, a hard gelatin capsule, suspension or liquid.

The amount of each therapeutically active compound that is administered and the dosage regimen for treating or preventing of pain with the compounds and/or compositions of this invention depends on a variety of factors, including the age, weight, sex and medical condition of the subject, the severity of pain, the route and frequency of administration, and the particular compound employed, and thus may vary widely. The pharmaceutical compositions may contain two or more compounds of the invention in the range of about 0.1 to 2000 mg each, preferably in the range of about 0.5 to 1000 mg each, and most preferably between about 1 and 500 mg each. A daily dose of about 0.01 to 100 mg/kg body weight, preferably between about 0.1 and about 50 mg/kg body weight and most preferably from about 0.5 to about 20 mg/kg body weight, may be appropriate. The daily dose can be administered in one to four to six to eight or more doses per day.

As mentioned previously, a wide range of targeted oral pharmacokinetic profiles can be achieved by administering pharmaceutical compositions containing specific combinations of different polysubunit molecules to subjects. For example, the different polysubunit molecules contained in the composition may differ with regard to (i) the specific opioid agonists delivered, (ii) the rates at which the opioid agonist is delivered in vivo (i.e. to modify the oral pharmacokinetic profile of the delivered opioid), and (iii) the combined inhibitory potency of the GI enzyme inhibiting subunits [i.e. to modify the overdose protection profile and/or the prescribed dose strengths of the delivered opioid agonist(s)]. Table 5 below provides non-limiting examples of compounds of the invention with their key differentiating attributes. Table 6 discusses scenarios and rationales for using the compounds presented in Table 5 in combination with each other, in useful pharmaceutical formulations of the invention.

TABLE 5 illustrates examples of compounds of the disclosure.

| Compound | Molecular Structure | Trypsin Inhibitory Potency | Rate of Release of Opioid Against |
|---|---|---|---|
| II-D-71c | 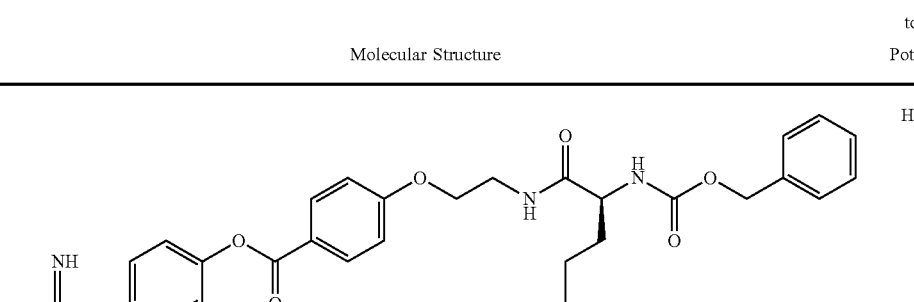 | High | Fast ($T_{1/2}$~10 mins) |

TABLE 5-continued
illustrates examples of compounds of the disclosure.
| Compound | Molecular Structure | Trypsin Inhibitory Potency | Rate of Release of Opioid Against |
|---|---|---|---|
| II-D-71b | 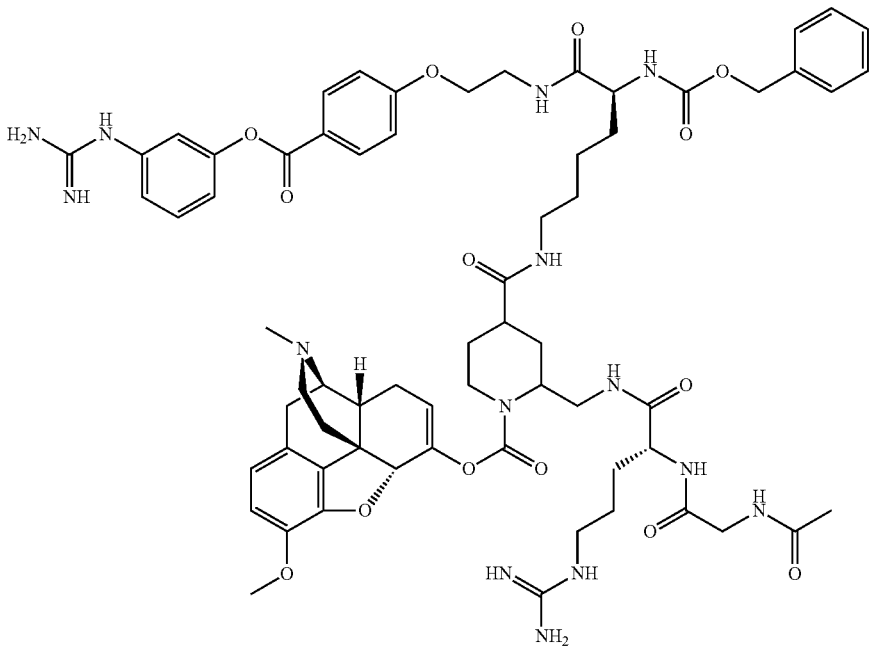 | Low | Fast ($T_{1/2}$~10 mins) |
| II-J-71c | 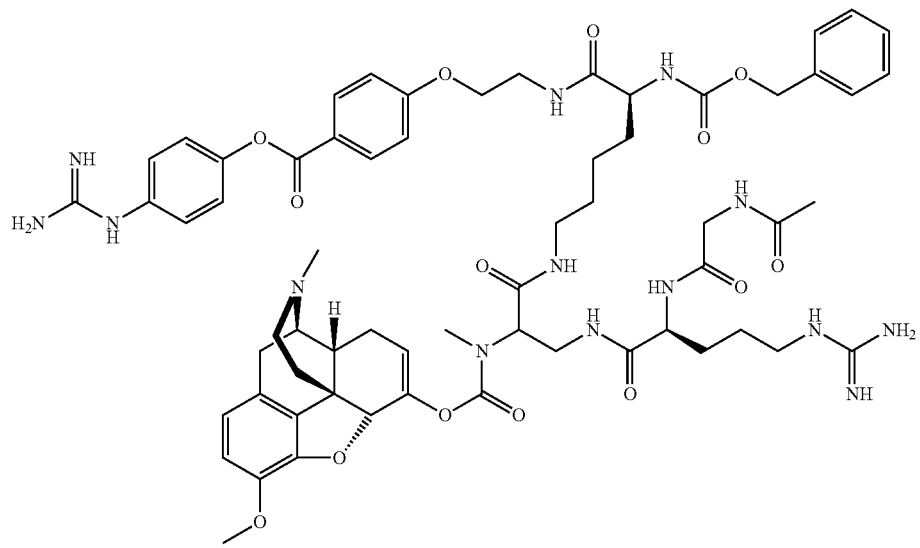 | High | Slow ($T_{1/2}$~3 hours) |

TABLE 5-continued illustrates examples of compounds of the disclosure.

| Compound | Molecular Structure | Trypsin Inhibitory Potency | Rate of Release of Opioid Against |
|---|---|---|---|
| II-J-71b | 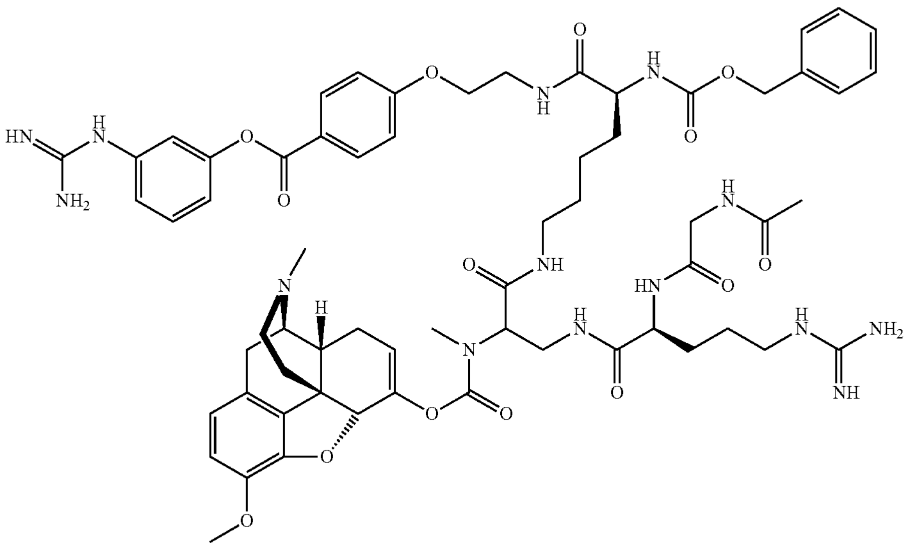 | Low | Slow ($T_{1/2}$~3 hours) |

TABLE 6

Examples of target pharmacokinetic profiles, combinations of compounds according to the present disclosure, and rationales for combining them to achieve various target pharmacokinetic profiles.

| Target Pharmacokinetic Profile | | | | Compound(s) in Formulation | Rationale |
|---|---|---|---|---|---|
| Onset of action | Duration of action | Dose Strength | Overdose Protection Profile | | |
| Rapid | Short | Low | Opioid agonist exposure can only be titrated within a targeted therapeutic range via co-ingestion of 2-3 pills | II-D-71c or II-D-71c combined with II-D-71b or II-D-71b | The short half-life of opioid delivery from II-D-71c and II-D-71b results in rapid onset of action The high inhibitory potency of the enzyme inhibiting subunit in II-D-71c can be leveraged to limit dose titratability and effect overdose protection at lower prescribed dose strengths The lower inhibitory potency of the enzyme inhibiting subunit in II-D-71b can be leveraged to enable or "tune" dose titratability at low, medium and high prescribed dose strengths, and also to effect overdose protection while maintaining high opioid delivery efficiency at high prescribed dose strengths |
| Rapid | Short | Low | Opioid agonist exposure can not be titrated beyond recommended single dose via co-ingestion of multiple pills | | |
| Rapid | Short | Medium | Opioid agonist exposure can only be titrated within a targeted therapeutic range via co-ingestion of 2-3 pills | | |
| Rapid | Short | Medium | Opioid agonist exposure can not be titrated beyond recommended single dose via co-ingestion of multiple pills | | |
| Rapid | Short | High | Opioid agonist exposure can only be titrated within a targeted therapeutic range via co-ingestion of 2-3 pills | | |

TABLE 6-continued

Examples of target pharmacokinetic profiles, combinations of compounds according to the present disclosure, and rationales for combining them to achieve various target pharmacokinetic profiles.

| Target Pharmacokinetic Profile | | | | Compound(s) in Formulation | Rationale |
|---|---|---|---|---|---|
| Onset of action | Duration of action | Dose Strength | Overdose Protection Profile | | |
| Rapid | Short | High | Opioid agonist exposure can not be titrated beyond recommended single dose via co-ingestion of multiple pills | | |
| Rapid | Long | Low | Opioid agonist exposure can only be titrated within a targeted therapeutic range via co-ingestion of 2-3 pills | II-D-71c or II-D-71b combined with II-J-71c or II-J-71b | The short half-life of opioid delivery from II-D-71c and II-D-71cb results in rapid onset of action |
| Rapid | Long | Low | Opioid agonist exposure can not be titrated beyond recommended single dose via co-ingestion of multiple pills | | The long half-life of opioid delivery from II-J-71c and II-J-71b results in long duration of action |
| Rapid | Long | Medium | Opioid agonist exposure can only be titrated within a targeted therapeutic range via co-ingestion of 2-3 pills | | The high inhibitory potency of the enzyme inhibiting subunits in II-D-71c and II-J-71c can be leveraged to limit dose titratability and effect overdose protection at lower prescribed dose strengths |
| Rapid | Long | Medium | Opioid agonist exposure can not be titrated beyond recommended single dose via co-ingestion of multiple pills | | The lower inhibitory potency of the enzyme inhibiting subunits in II-D-71b and II-J-71b can be leveraged to enable or "tune" dose titratability at low, medium and high prescribed dose strengths, and also to effect overdose protection while maintaining high opioid delivery efficiency at high prescribed dose strengths |
| Rapid | Long | High | Opioid agonist exposure can only be titrated within a targeted therapeutic range via co-ingestion of 2-3 pills | | |
| Rapid | Long | High | Opioid agonist exposure can not be titrated beyond recommended single dose via co-ingestion of multiple pills | | |
| Slow | Long | Low | Opioid agonist exposure can only be titrated within a targeted therapeutic range via co-ingestion of 2-3 pills | II-J-71c or II-J-71c combined with II-J-71b or II-J-71b | The long half-life of opioid deliver from II-J-71b and II-J-71c results in a delayed onset or action |
| Slow | Long | Low | Opioid agonist exposure can not be titrated beyond recommended single dose via co-ingestion of multiple pills | | The high inhibitory potency of the enzyme inhibiting subunit in II-J-71c can be leveraged to limit dose titratability and effect overdose protection at lower prescribed dose strengths |
| Slow | Long | Medium | Opioid agonist exposure can only be titrated within a targeted therapeutic range via co-ingestion of 2-3 pills | | The lower inhibitory potency of the enzyme inhibiting subunit in II-J-71b can be leveraged to enable or "tune" dose titratability at low, medium and high prescribed dose strengths, and also to effect overdose protection while maintaining high opioid delivery efficiency at high prescribed dose strengths |
| Slow | Long | Medium | Opioid agonist exposure can not be titrated beyond recommended single dose via co-ingestion of multiple pills | | |
| Slow | Long | High | Opioid agonist exposure can only be titrated within a targeted therapeutic range via co-ingestion of 2-3 pills | | |

TABLE 6-continued

Examples of target pharmacokinetic profiles, combinations of compounds according to the present disclosure, and rationales for combining them to achieve various target pharmacokinetic profiles.

| Target Pharmacokinetic Profile | | | | Compound(s) | |
|---|---|---|---|---|---|
| Onset of action | Duration of action | Dose Strength | Overdose Protection Profile | in Formulation | Rationale |
| Slow | Long | High | Opioid agonist exposure can not be titrated beyond recommended single dose via co-ingestion of multiple pills | | |

When used in combination, two compounds of the invention can be present in either weight or molar ratios of 20:1, 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.75:1, 1.5:1, 1.25:1, 1.2:1, 1.15:1, 1.1:1, 1:1, 1:1.1, 1:1.15, 1:1.2, 1:1.25, 1:1.5, 1:1.75, 1:2, 1:2.5, 1:3, 1:3.5, 1:4, 1:4.5, 1:5, 1:5.5, 1:6, 1:6.5; 1:7, 1:7.5, 1:8, 1:8.5, 1:9, 1:9.5, 1:10, 1:11, 1:12, 1:13, 1:14, 1:15, 1:16, 1:17, 1:18, 1:19, or 1:20.

For therapeutic purposes, the compounds of this invention are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The pharmaceutical composition of this invention may be prepared by uniformly mixing predetermined amounts of the active ingredient(s), the absorption aid and optionally the base, etc. in a stirrer or a grinding mill, if required.

The pharmaceutical compositions disclosed herein comprise a compound, or compounds of the invention disclosed herein with a suitable amount of a pharmaceutically acceptable vehicle, so as to provide a form for proper administration to a subject.

Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, gelling, lubricating and coloring, and/or agents designed to deter oral and non-oral abuse (e.g. gelling and or irritant agents) may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate processing of compositions and compounds disclosed herein into preparations that can be used pharmaceutically.

The present pharmaceutical compositions can take the form of solutions, suspensions, emulsion, tablets, pills, pellets, capsules, capsules containing liquids, powders, sustained-release formulations, emulsions, suspensions or any other form suitable for use known to the skilled artisan. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995).

Pharmaceutical compositions for oral delivery may be in the form of tablets, lozenges, aqueous or oily suspensions, granules, powders, emulsions, capsules, syrups, slurries, suspensions or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation.

Moreover, when in tablet or pill form, the compositions may be coated or formulated in a controlled release matrix to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, sucrose, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), granulating agents, binding agents and disintegrating agents such as the cross-linked polyvinylpyrrolidone, agar, or alginic acid or a salt thereof such as sodium alginate etc.

The methods that involve oral administration of compounds disclosed herein of can also be practiced with a number of different dosage forms, which provide sustained release.

In some embodiments, the dosage form is comprised of beads that on dissolution or diffusion release compositions and/or compounds disclosed herein over an extended period of hours, preferably, over a period of at least 6 hours, more preferably, over a period of at least 8 hours and even more preferably, over a period of at least 12 hours and most preferably, over a period of at least 24 hours. The beads may have a central composition or core comprising compounds disclosed herein and pharmaceutically acceptable vehicles, including optional lubricants, antioxidants and buffers. The beads may be medical preparations with a diameter of about 1 to about 2 mm. Individual beads may comprise doses of the compounds disclosed herein. The beads, in some embodiments, are formed of non-cross-linked materials to enhance their discharge from the gastrointestinal tract. The beads may be coated with a release rate-controlling polymer that gives a timed-release profile.

The time-release beads may be manufactured into a tablet for therapeutically effective administration. The beads can be made into matrix tablets by direct compression of a plurality of beads coated with, for example, an acrylic resin and blended with excipients such as hydroxypropylmethyl cellulose. The manufacture of beads has been disclosed in the art (Lu, Int. J. Pharm. 1994, 112, 117-124; Pharmaceutical Sciences by Remington, 14$^{th}$ ed, pp 1626-1628 (1970); Fincher, J. Pharm. Sci. 1968, 57, 1825-1835; Benedikt, U.S. Pat. No. 4,083,949) as has the manufacture of tablets (Pharmaceutical Sciences, by Remington, 17$^{th}$ Ed, Ch. 90, pp 1603-1625 (1985).

In other embodiments, an oral sustained release pump may be used (Langer, supra; Sefton, 1987, CRC Crit Ref Biomed. Eng. 14:201; Saudek et al., 1989, N. Engl. J Med. 321:574).

In still other embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., 1983, J Macromol. Sci. Rev. Macromol Chem. 23:61; Levy et al., 1985, Science 228: 190; During et al., 1989, Ann. Neurol. 25:351; Howard et al., 1989, J. Neurosurg. 71:105). In some embodiments, polymeric materials are used for oral sustained release delivery. Such polymers include, for example, sodium carboxymethylcellulose, hydroxypropylcellulose, hydroxypropylmethylcellulose and hydroxyethylcellulose (most preferred, hydroxypropylmethylcellulose). Other cellulose ethers have been described (Alderman, Int. J. Pharm. Tech. & Prod. Mfr. 1984, 5(3) 1-9). Factors affecting drug release are well known to the skilled artisan and have been described in the art (Bamba et al., Int. J. Pharm. 1979, 2, 307).

In still other embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. For example, solid microparticles of compositions and/or compounds disclosed herein may be coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, waxes can be used for oral sustained release administration. Examples of suitable sustained releasing waxes are disclosed in Cain et al., U.S. Pat. No. 3,402,240 (carnauba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., Drug Dev. Ind. Pharm. 2000, 26:695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In still other embodiments, the dosage form comprises compounds disclosed herein coated on a polymer substrate. The polymer can be an erodible or a nonerodible polymer. The coated substrate may be folded onto itself to provide a bilayer polymer drug dosage form. For example, compounds disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the compounds over a sustained release period. Representative biodegradable polymers comprise a member selected from the group consisting of biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dihydropyrans), and poly(dioxinones) which are known in the art (Rosoff, Controlled Release of Drugs, Chap. 2, pp. 53-95 (1989); Heller et al., U.S. Pat. No. 3,811,444; Michaels, U.S. Pat. No. 3,962,414; Capozza, U.S. Pat. No. 4,066,747; Schmitt, U.S. Pat. No. 4,070,347; Choi et al., U.S. Pat. No. 4,079,038; Choi et al., U.S. Pat. No. 4,093,709).

In other embodiments, the dosage form comprises one or more compound(s) disclosed herein loaded into a polymer that releases the drug(s) by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of the drug(s). The dosage form may be manufactured by procedures known in the art. An example of providing a dosage form comprises blending a pharmaceutically acceptable carrier like polyethylene glycol, with a known dose of compositions and/or compounds disclosed herein at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form comprise a member selected from the group consisting of olefin, and vinyl polymers, addition polymers, condensation polymers, carbohydrate polymers, and silicone polymers as represented by polyethylene, polypropylene, polyvinyl acetate, polymethylacrylate, polyisobutylmethacrylate, poly alginate, polyamide and polysilicone. The polymers and procedures for manufacturing them have been described in the art (Coleman et al., Polymers 1990, 31, 1187-1231; Roerdink et al., Drug Carrier Systems 1989, 9, 57-10; Leong et al., Adv. Drug Delivery Rev. 1987, 1, 199-233; Roff et al., Handbook of Common Polymers 1971, CRC Press; Chien et al., U.S. Pat. No. 3,992,518).

In other embodiments, the dosage form comprises a plurality of tiny pills. The tiny time-release pills provide a number of individual doses for providing various time doses for achieving a sustained-release drug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic matrix comprises a plurality of 4 to 50 tiny pills, each tiny pill comprises a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of drug(s). Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in Urquhart et al., U.S. Pat. No. 4,434,153; Urquhart et al., U.S. Pat. No. 4,721,613; Theeuwes, U.S. Pat. No. 4,853,229; Barry, U.S. Pat. No. 2,996,431; Neville, U.S. Pat. No. 3,139,383; Mehta, U.S. Pat. No. 4,752,470.

In other embodiments, the dosage form comprises an osmotic dosage form, which comprises a semipermeable wall that surrounds a therapeutic composition comprising one or more compounds disclosed herein. In use within a subject, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained release. These delivery platforms can provide an essentially zero order delivery profile as opposed to the spiked profiles of immediate release formulations.

In other embodiments, the dosage form comprises another osmotic dosage form comprising a wall surrounding a compartment, the wall comprising a semipermeable polymeric composition permeable to the passage of fluid and substantially impermeable to the passage of compounds disclosed herein present in the compartment, a drug-containing layer composition in the compartment, a hydrogel push layer composition in the compartment comprising an osmotic formulation for imbibing and absorbing fluid for expanding in size for pushing the drug composition layer from the dosage form, and at least one passageway in the wall for releasing the composition. The method delivers compounds disclosed herein by imbibing fluid through the semipermeable wall at a fluid imbibing rate determined by the permeability of the semipermeable wall and the osmotic pressure across the semipermeable wall causing the push layer to expand, thereby delivering the compounds disclosed herein from the dosage form through the exit passageway to a subject over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,000 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisole, hydroxycoumarin, butylated hydroxytoluene, cephalm, ethyl gallate, propyl gallate, octyl gallate, lauryl gallate, propyl-hydroxybenzoate, trihydroxybutyrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid and a fatty, alicyclic or aromatic acid.

In the osmotic dosage forms, the semipermeable wall comprises a composition that is permeable to the passage of fluid and impermeable to the passage of compounds disclosed herein. The wall is non-toxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkylcellulose such as hydroxypropylmethylcellulose. The total weight percent of all components comprising the wall is equal to 100 wt %. The internal compartment comprises the drug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of compounds disclosed herein to a subject over time. The dosage form comprises a passageway in the wall that connects the exterior of the dosage form with the internal compartment. The osmotic powered dosage form can be made to deliver drug from the dosage form to the subject at a zero order rate of release over a period of up to about 24 hours.

The expression "passageway" as used herein comprises means and methods suitable for the metered release of the compounds disclosed herein from the compartment of the dosage form. The exit means comprises at least one passageway, including orifice, bore, aperture, pore, porous element, hollow fiber, capillary tube, channel, porous overlay, or porous element that provides for the osmotic controlled release of the compounds disclosed herein. The passageway includes a material that erodes or is leached from the wall in a fluid environment of use to produce at least one controlled-release dimensioned passageway. Representative materials suitable for forming a passageway, or a multiplicity of passageway's comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of compositions and/or drugs from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in Theeuwes et al., U.S. Pat. No. 3,845,770; Theeuwes et al., U.S. Pat. No. 3,916,899; Saunders et al., U.S. Pat. No. 4,063,064; Theeuwes et al., U.S. Pat. No. 4,088,864 and Ayer et al., U.S. Pat. No. 4,816,263. Passageways formed by leaching are disclosed in Ayer et al., U.S. Pat. No. 4,200,098 and Ayer et al., U.S. Pat. No. 4,285,987.

In order to decrease dosing frequency and augment the convenience to the subject and increase subject compliance, the sustained release oral dosage form (regardless of the specific form of the sustained release dosage form) preferably, provides therapeutic concentrations of the compounds disclosed herein in the patient's blood over a period of at least about 6 hours, more preferably, over a period of at least about 8 hours, even preferably, over a period of at least about 12 hours and most preferably, over a period of at least 24 hours.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

When used to treat and/or prevent diseases the compounds disclosed herein and/or pharmaceutical compositions thereof may be administered alone or in combination with other pharmaceutical agents including compounds disclosed herein and/or pharmaceutical compositions thereof. The compounds disclosed herein may be administered or applied per se or as pharmaceutical compositions.

The amount of compounds disclosed herein and/or pharmaceutical compositions thereof that will be effective in the treatment or prevention of diseases in a patient will depend on the specific nature of the condition and can be determined by standard clinical techniques known in the art. The amount of compounds disclosed herein and/or pharmaceutical compositions thereof administered will, of course, be dependent on, among other factors, the subject being treated, the weight of the subject, the severity of the affliction, and the judgment of the prescribing physician.

In certain embodiments, compounds disclosed herein and/or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent (e.g. including, but not limited to, peripheral opioid antagonists, laxatives, non-opioid analgesics, anti-emetic agents, and the like). In other embodiments, compounds disclosed herein and/or pharmaceutical compositions thereof are administered prior or subsequent to administration of other therapeutic agents.

Thus, in one aspect of the invention, the oral dosage form can contain two or more compounds of the invention and one or more non-opioid drugs. Such non-opioid drugs would preferably provide additional analgesia and/or anti-inflammatory effects, and include, for example, aspirin, acetaminophen, non-steroidal anti-inflammatory drugs ("NSAIDS") such as, for example, naproxen, ibuprofen, ketoprofen, N-methyl-D-aspartate (NMDA) receptor antagonists, such as, for example, a morphinan such as dextromethorphan or dextrorphan, or ketamine, a cycooxygenase-II inhibitors ("COX-II inhibitors"); an anti-emetic agent such as, for example, promethazine, and/or glycine receptor antagonists.

All printed patents and publications referred to in this application are hereby incorporated herein in their entirety by this reference. While the preferred embodiment of the invention has been illustrated and described, it will be appreciated that various changes can be made therein without departing from the spirit and scope of the invention.

Pharmacokinetic and Pharmacodynamic Measurements

Pharmacokinetic and pharmacodynamic data can be obtained by various experimental techniques. Appropriate pharmacokinetic and pharmacodynamic profile components describing a particular composition can vary due to variations in drug metabolism in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A dose can be modulated to achieve a desired pharmacokinetic or pharmacodynamic profile, such as a desired or effective blood profile, as described herein. A compound of the invention can be present in a composition in a range of from about 1 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

The outcome of treating a human subject with a combination therapy can be measured by calculating pharmacodynamic and pharmacokinetic parameters. Non-limiting examples of pharmacodynamic and pharmacokinetic parameters that can be used to determine the effect of treatment of a subject with a composition of the disclosure include: a) the amount of opioid agonist drug delivered, which can be represented as a dose D; b) the dosing interval, which can be represented as $\tau$; c) the apparent volume in which a drug is distributed, which can be represented as a volume of distribution $V_d$, where $V_d = D/C_0$; d) the amount of drug in a given volume of plasma, which can be represented as concentration $C_0$ or $C_{ss}$, where $C_0$ or $C_{ss} = D/Vd$; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss} \cdot CL$; h) the integral of the concentration-time curve after administration of a single dose, which can be represented as $AUC_{0-\infty}$, wherein $\int_0^\infty C \, dt$, or in steady-state, which can be represented as $AUC_{\tau, ss}$, wherein $\int_t^{t+\tau} C \, dt$; i) the volume of plasma cleared of the drug per unit time, which can be represented as CL (clearance), wherein $CL = V_d \cdot k_e = D/AUC$; j) the P systemically available fraction of a drug, which can be represented as $f$, where $$f = \frac{AUC_{po} \cdot Div}{AUC_{iv} \cdot Dpo}; k)$$

the peak plasma concentration of a drug after administration $C_{max}$; l) the time taken by a drug to reach $C_{max}$, $T_{max}$; m) the lowest concentration that a drug reaches before the next dose is administered $C_{min}$; and n) the peak trough fluctuation within one dosing interval at steady state, which can be represented as $$\% \, PTF = 100 \cdot \frac{(C_{max,ss} - C_{min,ss})}{C_{av,ss}} \text{ where } C_{av,ss} = \frac{AUC_{\tau,ss}}{\tau}.$$

The pharmacokinetics parameters can be any parameters suitable for describing the plasma profiles of the opioid agonist delivered by a compound of the invention. For example, the pharmacokinetic profile of an opioid agonist delivered by a compound of the invention can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing an opioid agonist, or agonists, delivered from compounds of the invention. The Cmax can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; or any other Cmax appropriate for describing a pharmacokinetic profile of an opioid agonist described herein. The Cmax can be, for example, about 1 ng/mL to about 5 ng/mL; about 1 ng/mL to about 10 ng/mL; about 1 ng/mL to about 30 ng/mL; about 1 ng/mL to about 50 ng/mL; about 1 ng/mL to about 75 ng/mL; about 1 µg/mL to about 100 ng/mL; about 1 ng/mL to about 150 ng/mL; about 1 ng/mL to about 200 ng/mL; or about 1 ng/mL to about 300 ng/mL.

The $AUC_{(0-inf)}$ or $AUC_{(0-t)}$ of a compound of the invention, or opioid agonist, or agonists, delivered therefrom as described herein can be, for example, not less than about 10 ng·hr/mL, not less than about 25 ng·hr/mL, not less than about 50 ng·hr/mL, not less than about 100 ng·hr/mL, not less than about 150 ng·hr/mL, not less than about 200 ng·hr/mL, not less than about 300 ng·hr/mL, not less than about 350 ng·hr/mL, not less than about 400 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 2000 ng·hr/mL, not less than about 3000 ng·hr/mL, not less than about 4000 ng·hr/mL, or any other $AUC_{(0-t)}$ appropriate for describing a pharmacokinetic profile of a unimolecular polysubstrate entity or opioid agonist, or agonists, delivered therefrom as described herein.

EXAMPLES

Example 1: In Vitro Characterization of an Overdose Protection Mechanism with Compounds of the Disclosure This example describes in vitro experiments with a compound of the disclosure to provide a mechanism of overdose protection. Specifically, this study was designed to assess the ability of increasing concentrations of compounds II-D-11, II-D-23, II-D-71c and II-D-71b to progressively inhibit trypsin activity.

The effect of increasing concentrations of compounds II-D-11, II-D-23, II-D-71c and II-D-71b on the rate and extent of the trypsin-catalyzed hydrolysis of a commercially available trypsin substrate $N_\alpha$-Benzoyl-L-arginine 4-nitroanilide hydrochloride (BANA) was evaluated in the presence of trypsin (2,000 BAEE activity) in a pH 7.4 phosphate buffer at 37° C. in vitro. Both buffer solution alone (i.e. no trypsin) and trypsin containing buffer solution (i.e. no test compounds) controls were run contemporaneously. The data are presented below in the Tables below, and clearly demonstrate the ability of compounds II-D-11, II-D-23, II-D-71c and II-D-71b to progressively inhibit trypsin in a concentration dependent manner with a steep concentration vs. inhibition relationship. Based on these data, it is reasonable to assume that compounds II-D-11, II-D-23, II-D-71c and II-D-71b are capable of rapidly auto-attenuating the trypsin-mediated release of their appended opioid agonists in vivo as multiple doses are co-ingested.

TABLE 7

Percent $N_\alpha$-Benzoyl-L-arginine 4-nitroanilide hydrochloride remaining vs. Time

| Compound | Concentration | \multicolumn{7}{c}{Time (Minutes)} |
|---|---|---|---|---|---|---|---|---|
|  |  | 2 | 13 | 24 | 80 | 102 | 119 | 234 |
|  |  | \multicolumn{7}{c}{Percent BANA remaining} |
| II-D-11 | 1 mM | 100 | 100 | 99 | 100 | 100 | 100 | 100 |
|  | 100 uM | 100 | 98 | 100 | 99 | 99 | 99 | 99 |
|  | 10 uM | 100 | 98 | 96 | 94 | 93 | 94 | 87 |
|  | 1 uM | 100 | 39 | 0 | 0 | 0 | 0 | 0 |
| Trypsin Control |  | 100 | 0 | 0 | 0 | 0 | 0 | 0 |
| Buffer control (no Trypsin) |  | 100 | 100 | 99 | 99 | 99 | 99 | 98 |

TABLE 8

Percent $N_\alpha$-Benzoyl-L-arginine 4-nitroanilide hydrochloride remaining vs. Time

| Compound | Concentration | \multicolumn{9}{c}{Time (Minutes)} |
|---|---|---|---|---|---|---|---|---|---|---|
|  |  | 2 | 14 | 24 | 32 | 70 | 100 | 145 | 156 | 247 |
|  |  | \multicolumn{9}{c}{Percent BANA remaining} |
| II-D-23 | 1 mM | 100 | 99 | 98 | 99 | 99 | 98 | 98 | 97 | 96 |
|  | 100 uM | 100 | 99 | 100 | 100 | 100 | 100 | 100 | 100 | 100 |
|  | 10 uM | 100 | 98 | 96 | 98 | 97 | 95 | 96 | 96 | 93 |
|  | 1 uM | 100 | 20 | 11 | 0 | 0 | 0 | 0 | 0 | 0 |
| Trypsin Control |  | 100 | 0 | 0 | 0 | 0 | 0 | 0 | 0 | 0 |
| Buffer control (no Trypsin) |  | 100 | 100 | 100 | 100 | 100 | 99 | 99 | 98 | 98 |

TABLE 9

Percent $N_\alpha$-Benzoyl-L-arginine 4-nitroanilide hydrochloride remaining vs. Time

| Compound | Concentration | \multicolumn{6}{c}{Time (Minutes)} |
|---|---|---|---|---|---|---|---|
|  |  | 2 | 13 | 24 | 35 | 46 | 57 | 68 |
|  |  | \multicolumn{6}{c}{Percent BANA remaining} |
| II-D-71c | 1 mM | 100 | 100 | 99 | 100 | 100 | 100 | 100 |
|  | 100 uM | 100 | 100 | 99 | 100 | 100 | 100 | 100 |
|  | 10 uM | 76.5 | 58.5 | 42.5 | 26.0 | 13.0 | 4.7 | 0 |
|  | 1 uM | 81.5 | 0 | 0 | 0 | 0 | 0 | 0 |
| Trypsin Control |  | 30 | 0 | 0 | 0 | 0 | 0 | 0 |
| Buffer control (no Trypsin) |  | 100 | 100 | 100 | 100 | 100 | 100 | 100 |

TABLE 10

Percent N$_\alpha$-Benzoyl-L-arginine 4-nitroanilide hydrochloride remaining vs. Time

| Compound | Concentration | 2 | 13 | 24 | 35 | 46 | 57 | 68 |
|---|---|---|---|---|---|---|---|---|
| | | | | Percent BANA remaining | | | | |
| II-D-71b | 1 mM | 100 | 76.1 | 66.6 | 59.6 | 56.3 | 55.7 | 53.7 |
| | 100 uM | 93.1 | 15.1 | 2.4 | 2.3 | 1.4 | 0 | 0 |
| | 10 uM | 87.9 | 0 | 0 | 0 | 0 | 0 | 0 |
| Trypsin Control | | 30 | 0 | 0 | 0 | 0 | 0 | 0 |
| Buffer control (no Trypsin) | | 100 | 100 | 100 | 100 | 100 | 100 | 100 |

Time (Minutes) header spans columns 2–68.

Example 2: Evaluation of Hydrocodone (HC) and Naltrexone (NTX) Release from II-D-71c-NTX Following Incubation in a Highly Basic Solution at 60° C.

Figure 2:
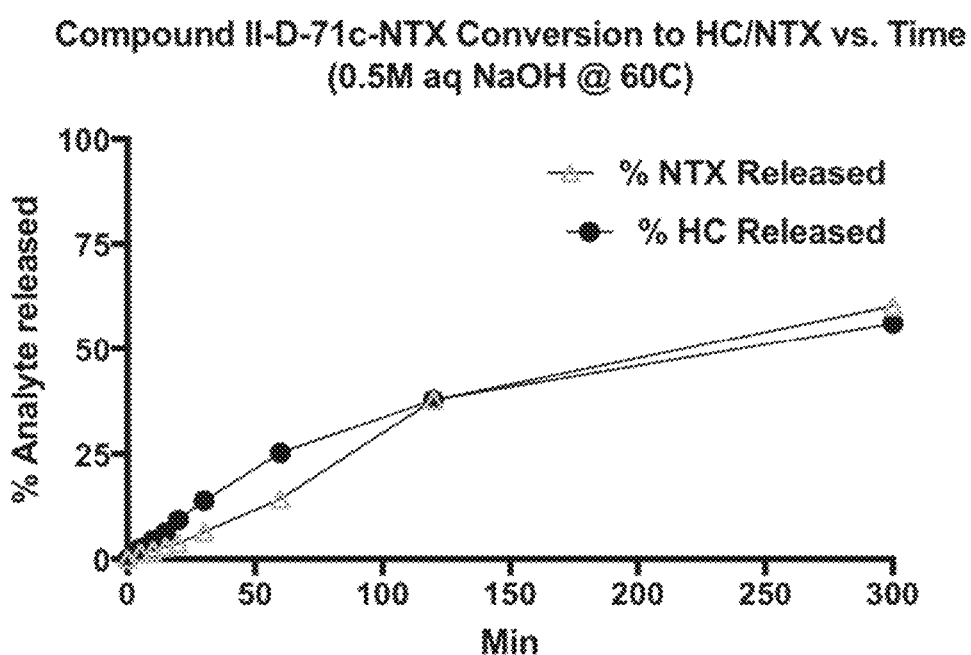
FIG. 2 depicts the % release of Naltrexone (NTX) and Hydrocodone (HC) from compound II-D-71c-NTX when exposed to 0.5M aqueous NaOH at 60° C. over time.
Figure 3:
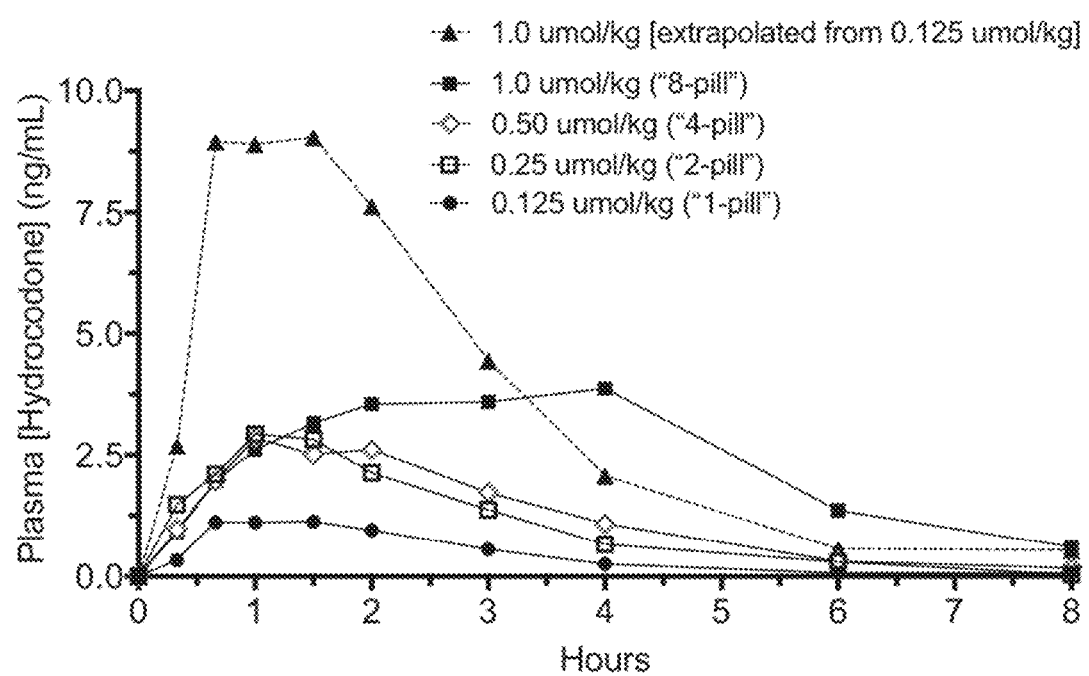
FIGS. 3 AND 4 show mean plasma hydrocodone concentrations vs. time curves for escalating doses of compounds II-D-11 and II-D-23, respectively. Extrapolated curves (based on a linear dose-proportional extrapolation of the respective single pill doses) for the 8-pill dose for II-D-11, and the 7-pill dose for II-D-23, are included for comparison (dotted lines).
Figure 4:
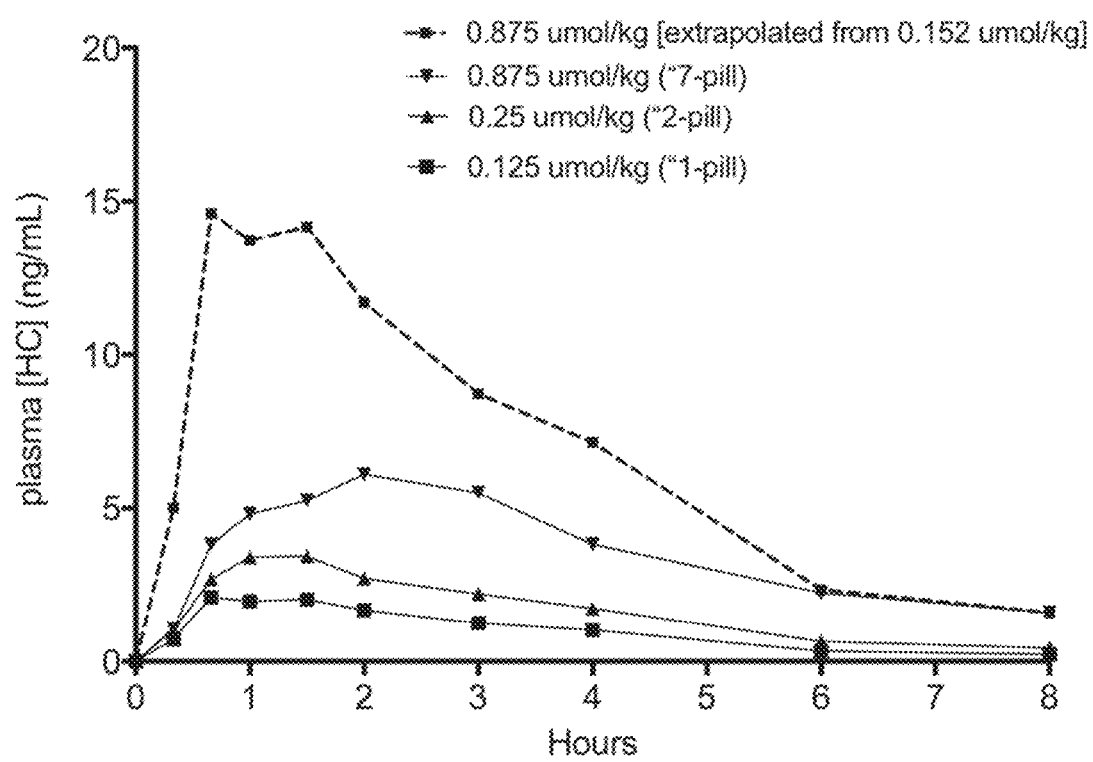
Figure 5:
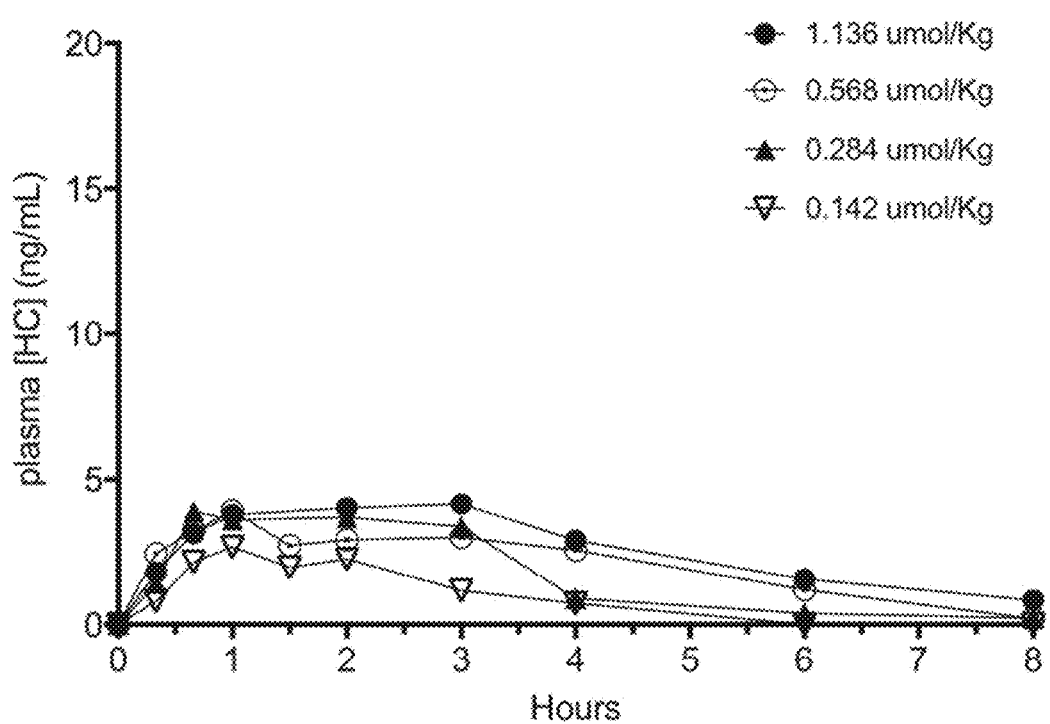
FIGS. 5 AND 6 show mean plasma hydrocodone concentrations vs. time curves for escalating doses of compounds II-D-71c and II-D-71b, respectively.
Figure 6:
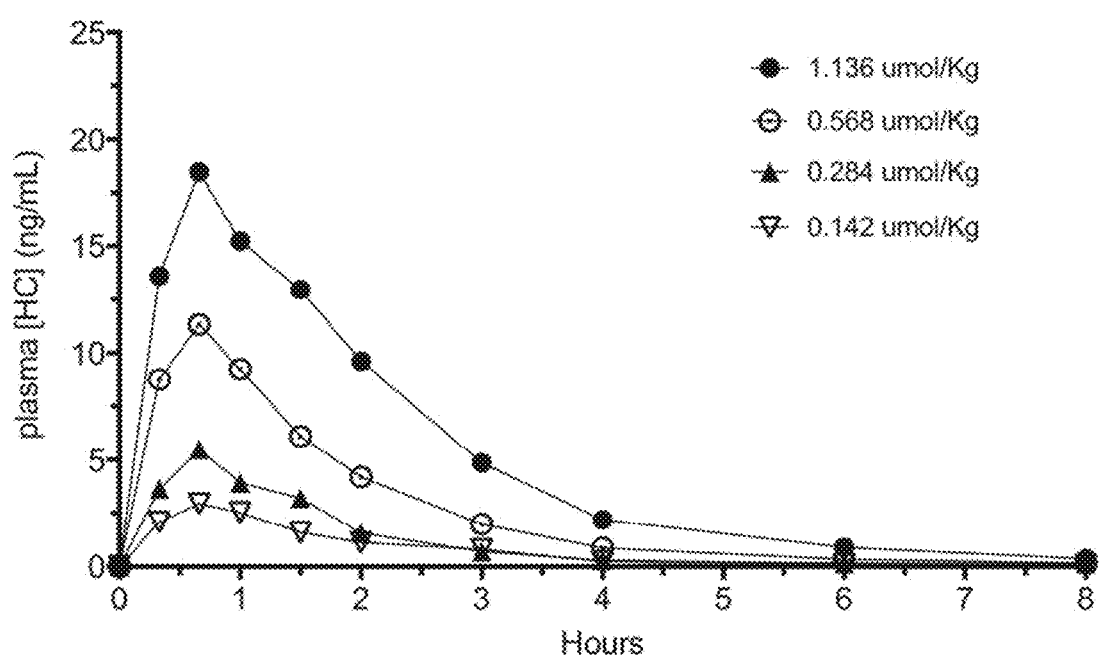
Figure 7:
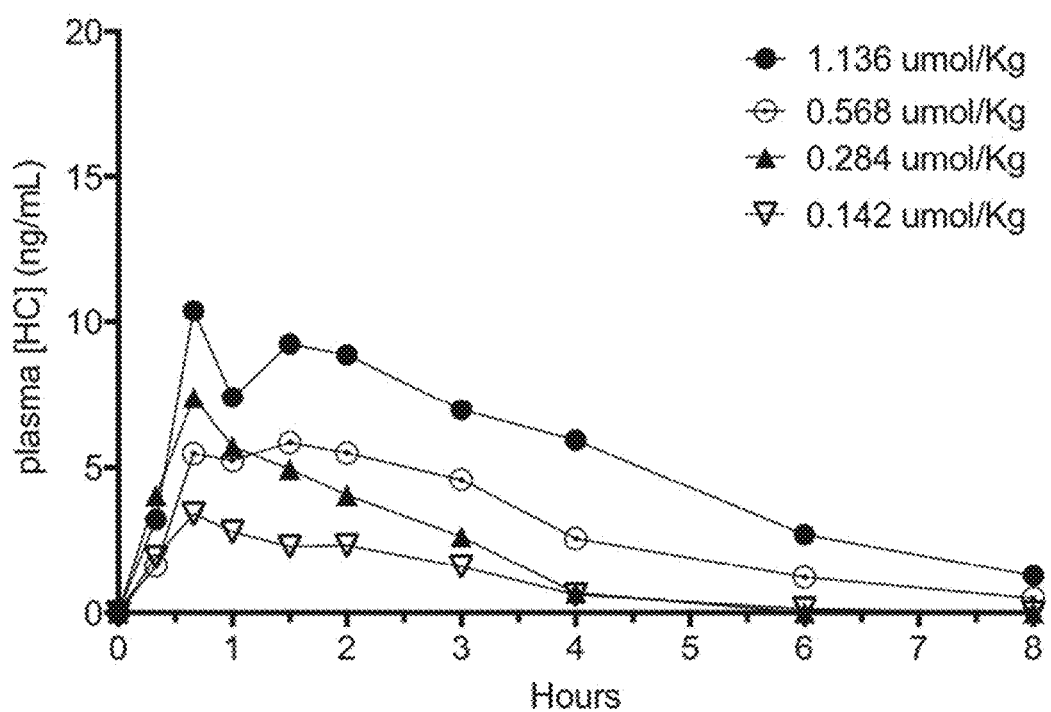
FIGS. 7 AND 8 show mean plasma hydrocodone concentration vs. time plots for escalating doses of mixtures of compounds including a 1:4 ratio of II-D-71c and II-D-71b and a 1:1 ratio of II-D-71c and II-D-71b, respectively.
Figure 8:
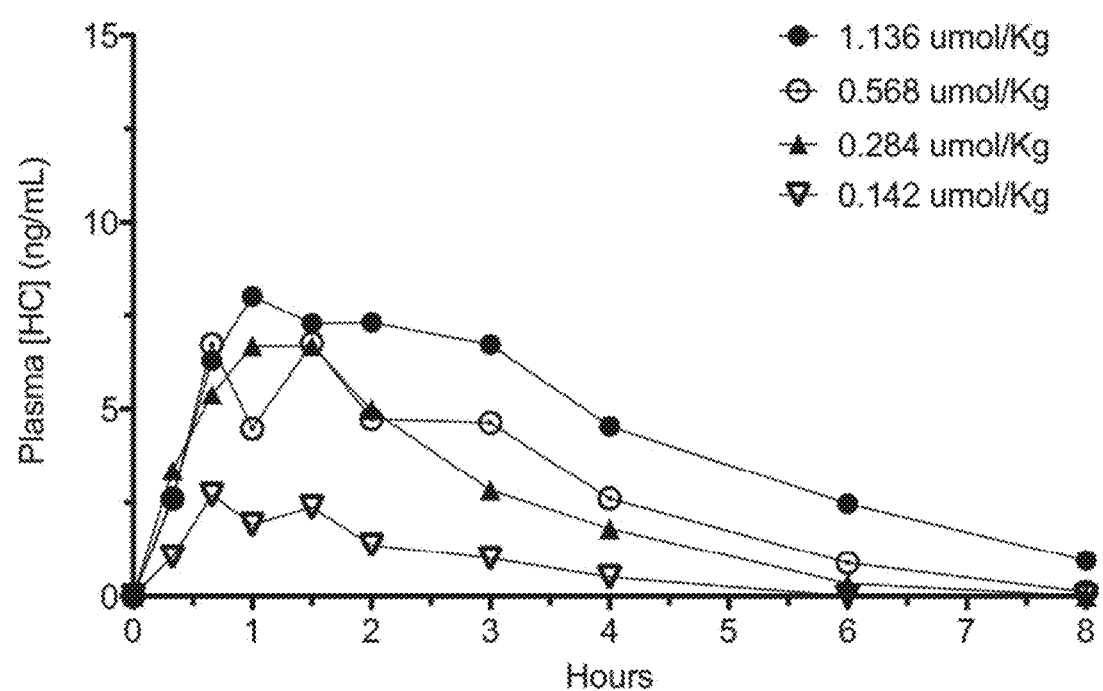
Figure 9:
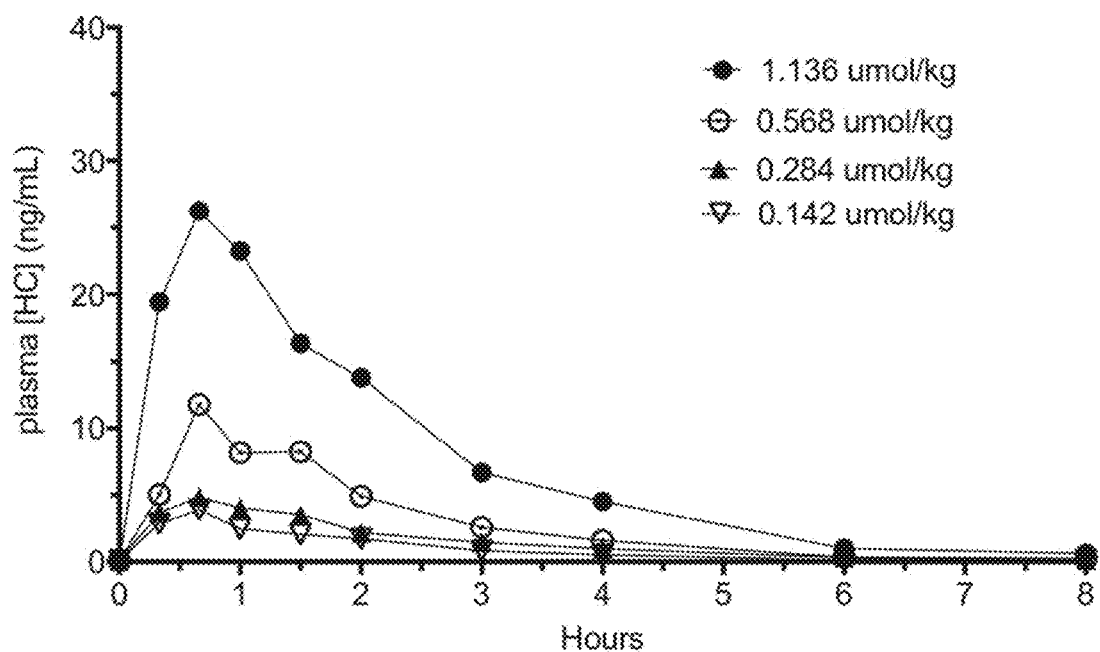
FIGS. 9 AND 10 show mean plasma hydrocodone concentration vs. time plots for escalating doses of mixtures of compounds including a 1:49 ratio of II-P-47c and 11-P-47b and a 1:4 ratio of II-P-47c and II-P-47b, respectively.
Figure 10:
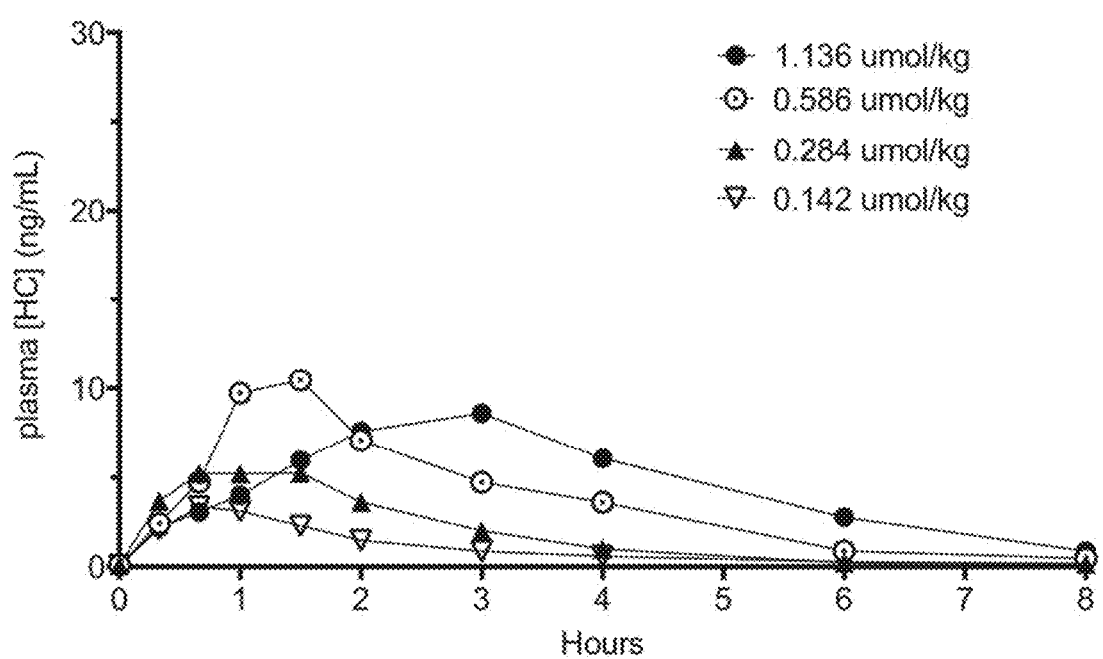
Figure 11:
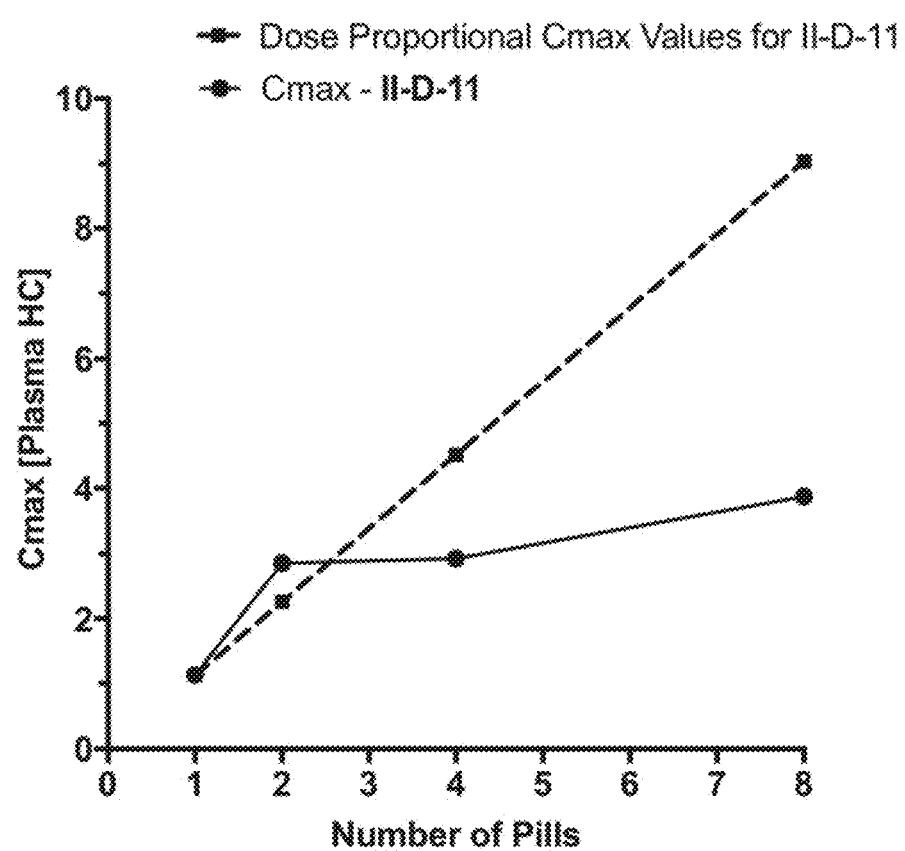
FIGS. 11 AND 12 show the relationship of Cmax vs. escalating doses (i.e. number of pills co-ingested) for compounds II-D-11 and II-D-23, respectively as compared to an extrapolated dose-linear relationship of Cmax based on their respective single-pill doses (dotted lines).
Figure 12:
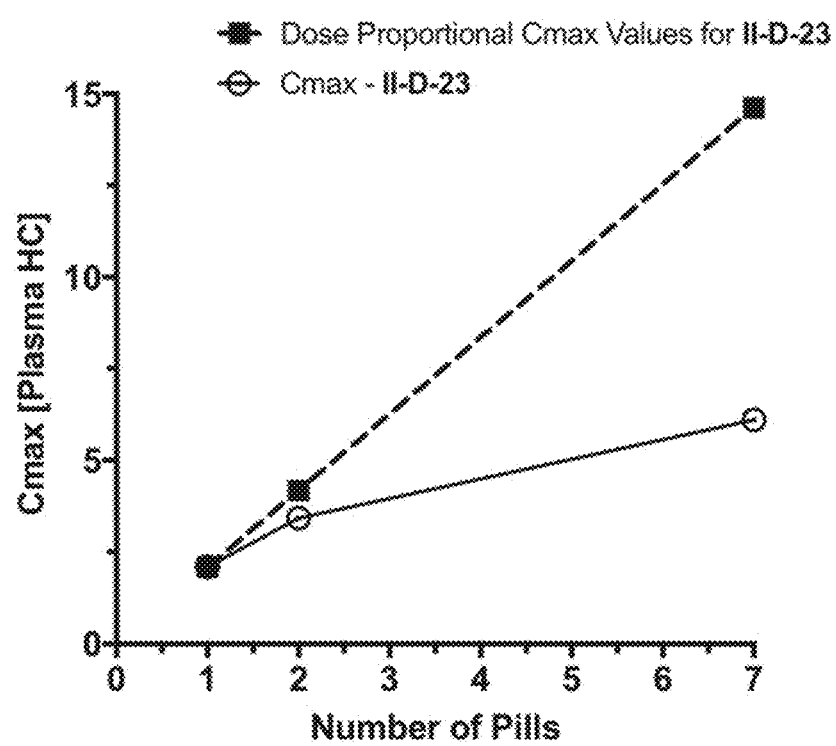
Figure 13:
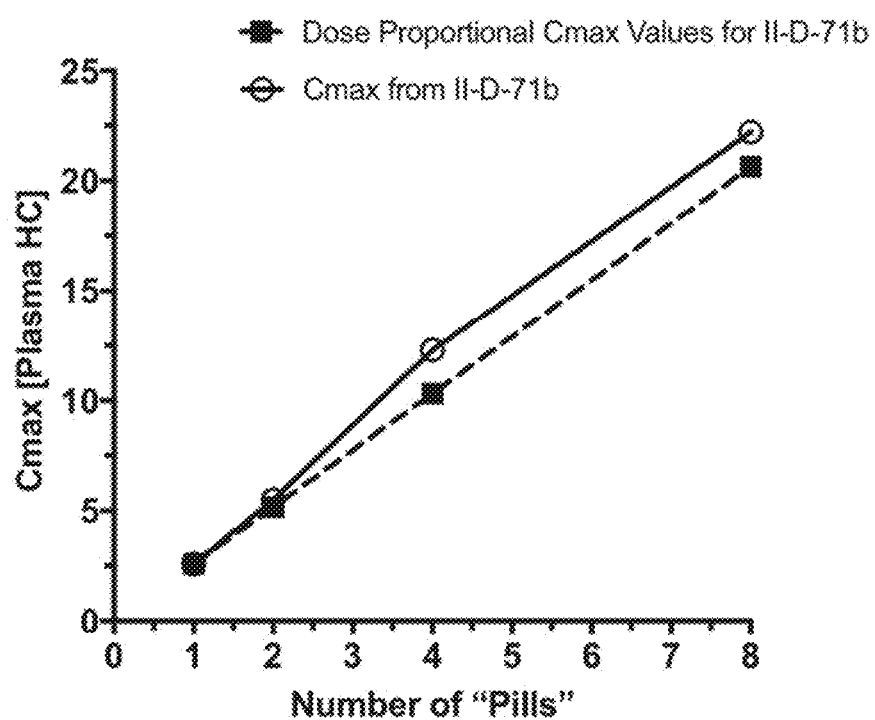
FIGS. 13 AND 14 show the relationship of Cmax vs. escalating doses (i.e. number of pills co-ingested) for compounds II-D-71b and II-D-71c, respectively as compared to an extrapolated dose-linear relationship of Cmax based on their respective single-pill doses (dotted lines).
Figure 14:
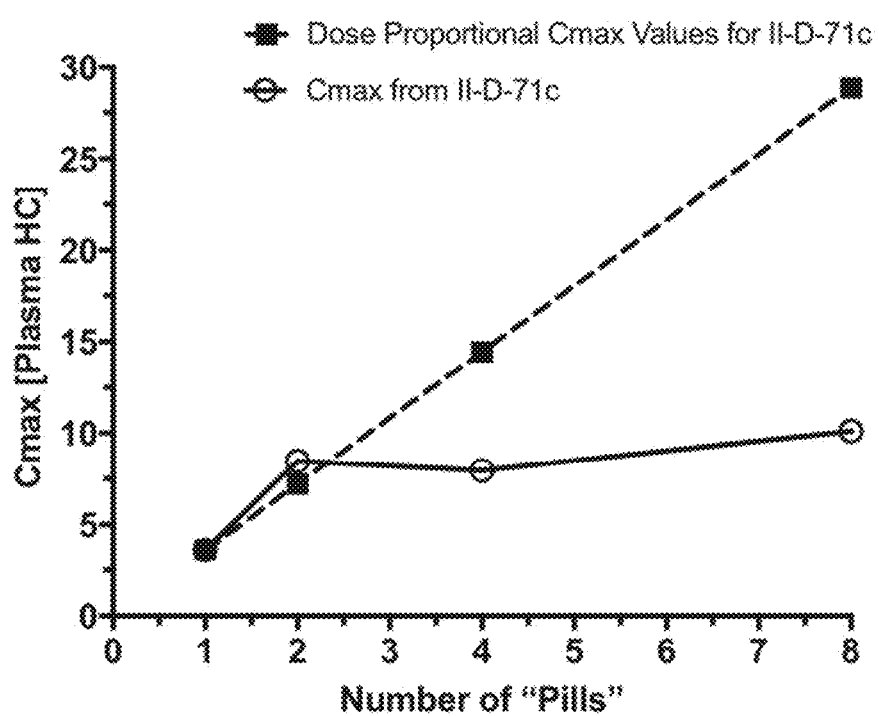
Figure 15:
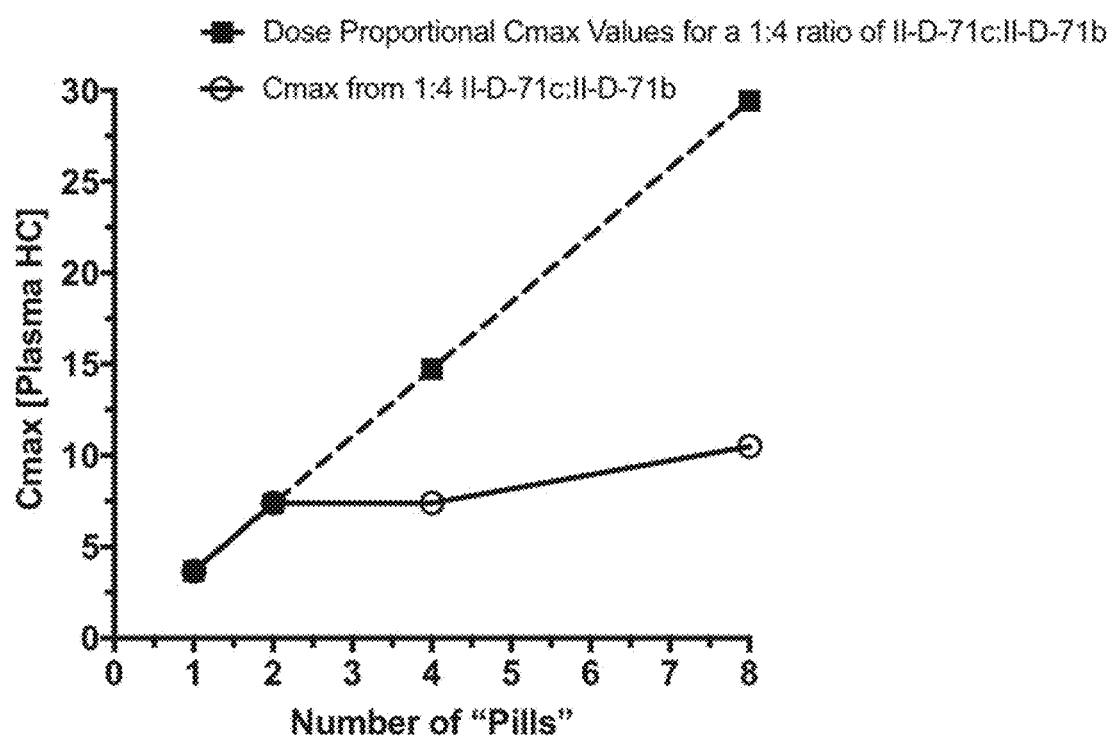
FIGS. 15 AND 16 show the relationship of Cmax vs. escalating doses (i.e. number of pills co-ingested) for mixtures of compounds including a1:4 ratio of II-D-71c and II-D-71b and a 1:1 ratio of II-D-71c and II-D-71b, respectively as compared to an extrapolated dose-linear relationship of Cmax based on their respective single-pill doses (dotted lines).
Figure 16:
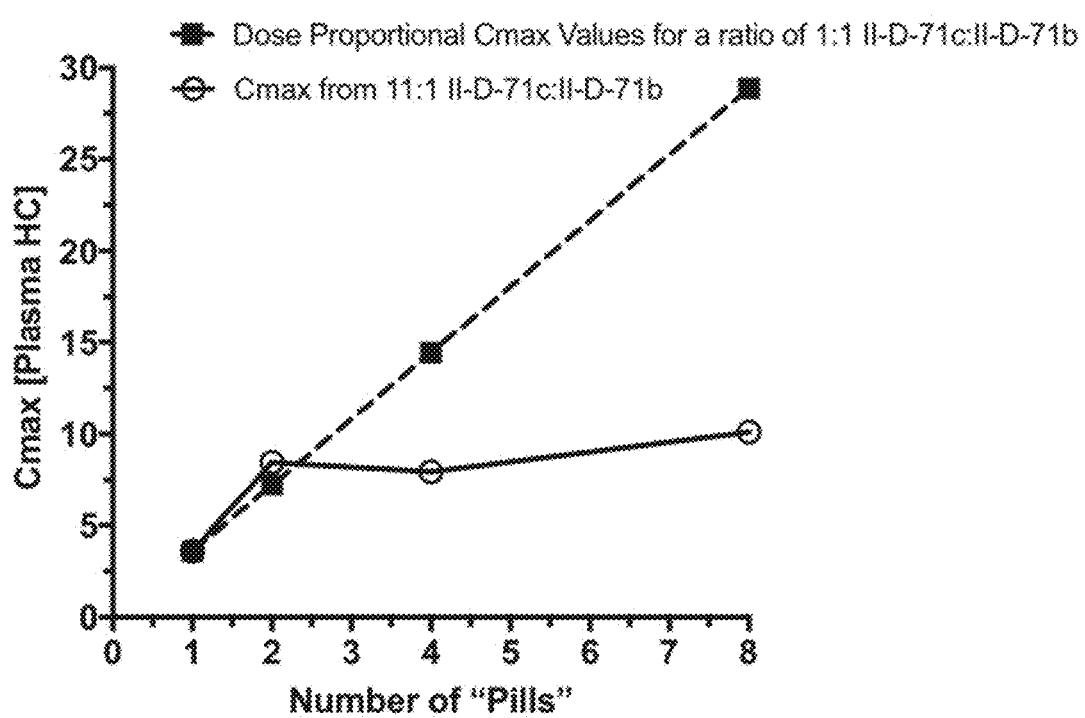
Figure 17:
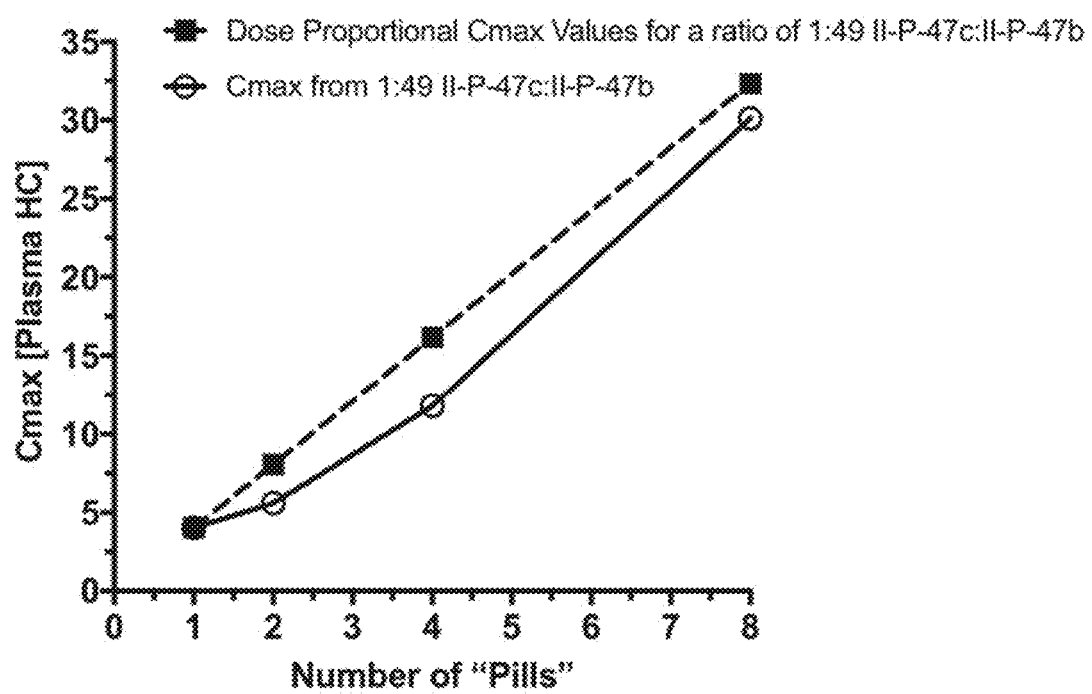
FIGS. 17 AND 18 show the relationship of Cmax vs. escalating doses (i.e. number of pills co-ingested) for mixtures of compounds including a 1:49 ratio of II-P-47c and II-P-47b and a 1:4 ratio of II-P-47c and II-P-47b, respectively as compared to an extrapolated dose-linear relationship of Cmax based on their respective single-pill doses (dotted lines).
Figure 18:
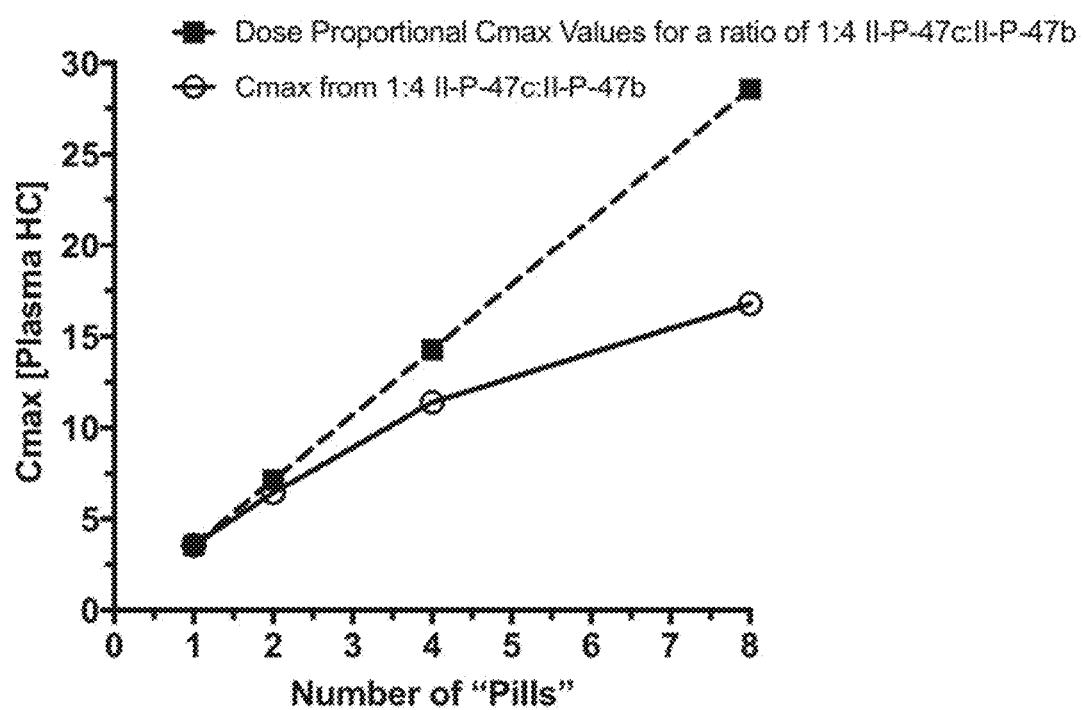

This example describes the release profiles (i.e. rate and extent) of both hydrocodone and naltrexone from Compound II-D-71c-NTX when subjected to tampering by potential abusers. H-D-71c-NTX was incubated in a strongly basic solution of 0.5M aqueous sodium hydroxide at 60° C. for 300 minutes. The solution was analyzed for the presence of both hydrocodone and naltrexone at specified time points using LC/MS analysis. The percentage of released hydrocodone and naltrexone were determined based on comparative peak area analyses to reference standards based on 100% molar release of the specific analytes. The peak areas for the analytes measured at the specified time points for the solution are presented in the Tables below. This data demonstrates that the release of the opioid agonist (e.g. hydrocodone) occurs concomitantly with the release of the opioid antagonist as designed, effectively thwarting abuse via tampering. The data from this study is presented graphically in FIG. 2.

TABLE 11

Reference standard peak areas for 100% release of analytes

| NTX (RT = 18.2 min) | HC (RT = 19.0 min) |
|---|---|
| 2705 (avg of 3 runs) | 2965 (avg of 3 runs) |

TABLE 12

60° C. incubation in 0.5M aqueous NaOH

| Time | NTX Peak Area | Percent NTX Released | HC Peak Area | Percent HC Released |
|---|---|---|---|---|
| 0 | ND | 0 | ND | 0 |
| 5 | 39 | 1.44 | 75 | 2.52 |
| 10 | 54 | 2.0 | 132 | 4.45 |
| 15 | 80 | 2.95 | 186 | 6.27 |
| 20 | 100 | 3.69 | 275 | 9.27 |
| 30 | 175 | 6.47 | 415 | 13.99 |
| 60 | 390 | 14.41 | 751 | 25.32 |
| 120 | 1023 | 37.81 | 1124 | 37.9 |
| 300 | 1630 | 60.25 | 1665 | 56.1 |

Example 3: In Vivo Demonstration of Non-Linear Pharmacokinetics (i.e. Overdose Protection) with Compounds of the Disclosure This example describes in vivo experiments with a compound of the disclosure to demonstrate overdose protection (i.e. non-linear pharmacokinetics of delivered hydrocodone). The effect of increasing oral doses of compounds II-D-23, II-D-11, II-D-71c, II-D-71b, II-P-47b, II-P47c and mixtures thereof on the pharmacokinetics of delivered hydrocodone (i.e. measured plasma hydrocodone concentrations vs. time) was evaluated in dogs. Calculated PK Parameters for Hydrocodone resulting from the oral dosing of reference compounds and compositions of the invention to dogs (N=4/dose group) are presented below and in FIGS. 3-18.

TABLE 13

Calculated PK Parameters

| Dose | $C_{max\ ng}$ (Mean ± SD) | $T_{max\ h}$ (Mean ± SD) | $AUC_{0-8\ h\ ng*h/mL}$ (Mean ± SD) |
|---|---|---|---|
| Hydrocodone | | | |
| 0.142 mg/kg | 4.89 ± 1.2 | 0.333 ± 0 | 8.92 ± 1.03 |
| A 1:49 ratio of II-P-47c:II-P-47b | | | |
| 0.270 mg/kg | 4.04 ± 0.06 | 0.584 ± 0.167 | 7.40 ± 0.99 |
| 0.539 mg/kg | 5.61 ± 1.99 | 0.667 ± 0.272 | 11.6 ± 2.8 |
| 1.079 mg/kg | 11.8 ± 3.3 | 0.667 ± 0 | 22.7 ± 4.6 |
| 2.157 mg/kg | 30.1 ± 4.4 | 0.750 ± 0.167 | 59.6 ± 12.1 |
| A 1:4 ratio of II-P-47c:II-P-47b | | | |
| 0.270 mg/kg | 3.57 ± 1.41 | 0.750 ± 0.167 | 7.79 ± 3.43 |
| 0.539 mg/kg | 6.45 ± 2.98 | 1.21 ± 0.66 | 14.5 ± 8.3 |
| 1.079 mg/kg | 11.4 ± 6.6 | 2.0 ± 1.35 | 29.5 ± 14.5 |
| 2.157 mg/kg | 16.8 ± 13.3 | 2.75 ± 0.50 | 61.1 ± 48.9 |
| II-D-71b | | | |
| 0.142 mg/kg | 2.58 ± 0.88 | 0.500 ± 0.193 | 5.12 ± 2.67 |
| 0.284 mg/kg | 5.49 ± 1.79 | 0.667 ± 0 | 8.77 ± 2.7 |
| 0.568 mg/kg | 12.3 ± 2.2 | 0.500 ± 0.193 | 20.8 ± 7.0 |
| 1.136 mg/kg | 22.2 ± 5.3 | 0.667 ± 0.272 | 40.6 ± 8.3 |
| II-D-71c | | | |
| 0.142 mg/kg | 3.15 ± 0.74 | 0.959 ± 0.394 | 6.7 ± 2.42 |
| A 1:4 ratio of II-D-71c:II-D-71b | | | |
| 0.270 mg/kg | 3.68 ± 1.94 | 1.25 ± 1.17 | 8.56 ± 2.32 |
| 0.539 mg/kg | 7.40 ± 3.15 | 0.667 ± 0 | 15.3 ± 5.6 |
| 1.079 mg/kg | 7.39 ± 4.30 | 1.67 ± 1.05 | 22.9 ± 9.7 |
| 2.157 mg/kg | 10.5 ± 6.4 | 1.10 ± 0.62 | 36.7 ± 25.3 |

TABLE 13-continued

Calculated PK Parameters

| Dose | $C_{max\ ng}$ (Mean ± SD) | $T_{max\ h}$ (Mean ± SD) | $AUC_{0-8\ h\ ng*h/mL}$ (Mean ± SD) |
|---|---|---|---|
| A 1:1 ratio of II-D-71c:II-D-71b | | | |
| 0.142 mg/kg | 3.61 ± 0.20 | 0.667 ± 0 | 6.48 ± 1.19 |
| 0.284 mg/kg | 8.47 ± 1.99 | 0.875 ± 0.498 | 19.0 ± 6.6 |
| 0.568 mg/kg | 7.96 ± 2.96 | 1.46 ± 1.10 | 22.4 ± 4.2 |
| 1.136 mg/kg | 10.1 ± 4.6 | 2.04 ± 1.16 | 34.9 ± 16.8 |

Noncompartmental pharmacokinetic parameters were calculated using Phoenix WinNonlin 8.0 using the concentrations for the individual dogs. WinNonlin was also used for calculation of the mean concentrations. Plasma concentrations reported as below the limit of quantitation were assumed to be 0 ng/mL for the calculations. The maximum concentration, Cmax, and time of maximum concentration, $T_{max}$, were determined as the maximum measured concentration and its associated time. The areas under the plasma concentration curve from 0 to 8 hours, $AUC_{0-8}$ was calculated using trapezoidal estimation.

What is claimed is:

1. A composition comprising two or more different molecules, wherein each different molecule comprises at least one GI enzyme-labile opioid agonist releasing subunit comprising an opioid agonist, wherein the at least one GI enzyme-labile opioid agonist releasing subunit is covalently linked to at least one GI enzyme inhibitor subunit.

2. The composition of claim 1, wherein the two or more different molecules comprise different GI enzyme inhibitor subunits.

3. The composition of claim 2, wherein the different GI enzyme inhibitor subunits have different inhibitory potencies.

4. The composition of claim 1, wherein the two or more different molecules have different GI enzyme-labile opioid agonist releasing subunits comprising an opioid agonist.

5. The composition of claim 4, wherein the different GI enzyme-labile opioid agonist releasing subunits comprise different opioid agonists.

6. The composition of claim 5, wherein the different opioid agonists are selected from the group consisting of morphine, hydromorphone, hydrocodone, oxycodone, codeine, levorphanol, meperidine, methadone, oxymorphone, dihydrocodeine, tramadol, tapentadol, buprenorphine, and pharmaceutically acceptable salts, prodrugs, and mixtures thereof.

7. The composition of claim 4, wherein at least one of the GI enzyme-labile opioid agonist releasing subunits comprises oxycodone.

8. The composition of claim 4, wherein at least one of the GI enzyme-labile opioid agonist releasing subunits comprises hydrocodone.

9. The composition of claim 4, wherein at least one of the GI enzyme-labile opioid agonist releasing subunits comprises morphine.

10. The composition of claim 4, wherein the GI enzyme-labile opioid agonist releasing subunits release the opioid agonist in vivo or in vitro at different rates.

11. The composition of claim 1, wherein the composition comprises at least three, at least four, at least five, or at least six different molecules.

12. The composition of claim 1, wherein the at least one GI enzyme-labile opioid agonist releasing subunit comprising an opioid agonist and the at least one GI enzyme inhibitor subunit of each different molecule are covalently linked via a scaffold moiety.

13. The composition of claim 12, wherein the scaffold moiety comprises an atom, a functional group, a natural or non-natural amino acid, a peptide, a polypeptide, a polymer, or a polysaccharide.

14. The composition of claim 13, wherein the scaffold moiety comprises a polypeptide or a polysaccharide.

15. The composition of claim 1, wherein the GI enzyme is trypsin.

16. The composition of claim 1, wherein the GI enzyme is chymotrypsin.

17. The composition of claim 1, wherein the at least one GI enzyme-labile opioid agonist releasing subunit comprising an opioid agonist releases the opioid agonist in the presence of the GI enzyme.

18. The composition of claim 1, wherein the two or more different molecules are independently selected from the group consisting of a structure of Formula (IF), (IG), (IH), (II), and salts thereof:

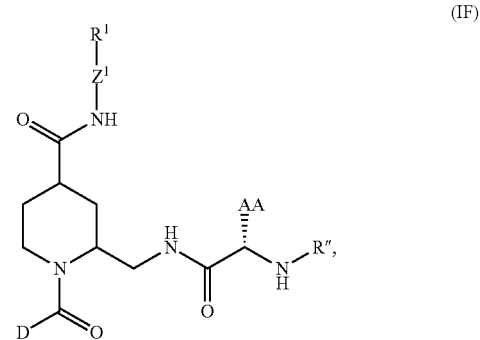

(IF)

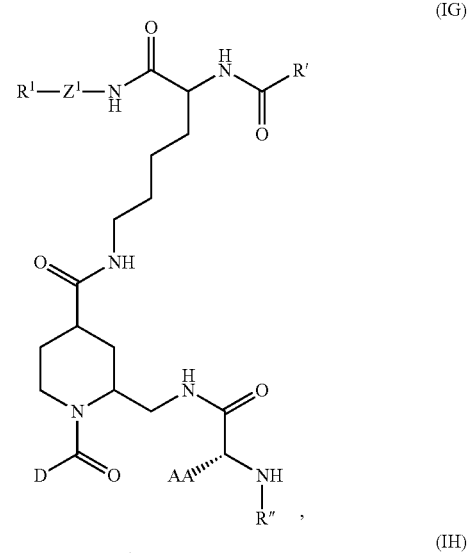

(IG)

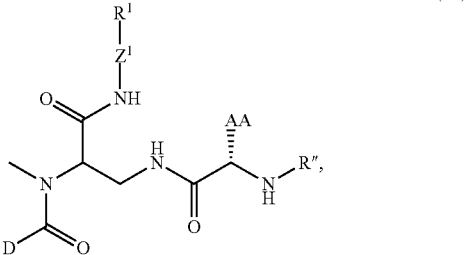

(IH)

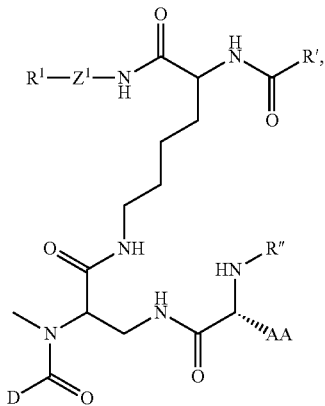

(II)

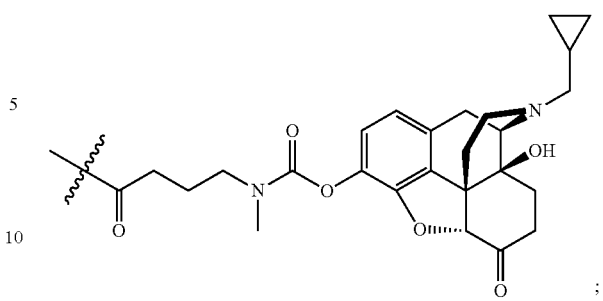

R″ is selected from the group consisting of acetyl, substituted acyl, a natural or a non-natural amino acid, and a polypeptide chain comprising natural or non-natural amino acids up to 10 amino acids in length;

AA is a natural or a non-natural amino acid side chain that is recognized by trypsin; and $Z^1$ of $R^1$—$Z^1$— is independently selected from the group consisting of $R^1$—O—$CH_2$—$CH_2$— and $R^1$—$CH_2$—C(O)—NH—$CH_2$—$CH_2$—.

19. The composition of claim 18, or salts thereof, wherein Y is amidine, aminomethyl, or guanidine.

20. The composition of claim 18, or salts thereof, wherein $R^1$ of $R^1$—$Z^1$— is independently selected from the group consisting of:

and salts thereof;
wherein:
D is an opioid agonist;
$R^1$ of $R^1$—$Z^1$ is independently selected from the group consisting of

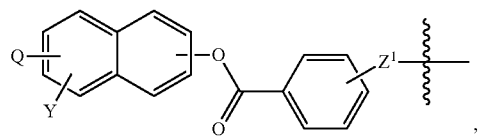

,

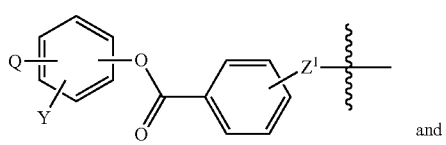

and

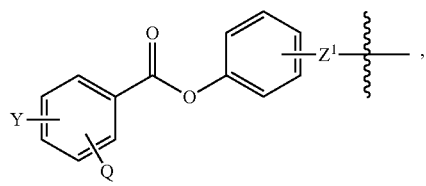

, wherein Y is amidine, guanidine, aminomethyl, substituted amidine, substituted guanidine, substituted aminomethyl, amidinomethyl, guanidinomethyl, substituted amidinomethyl, or substituted guanidinomethyl, and Q is hydrogen;

R′ is selected from the group consisting of methyl, lower alkyl, substituted alkyl, aryl, substituted aryl, heteroalkyl, a natural or a non-natural amino acid, a polypeptide chain comprising natural or non-natural amino acids up to 10 amino acids in length, a linear or a branched polyethylene glycol chain up to 5 kDa, benzyloxy, and

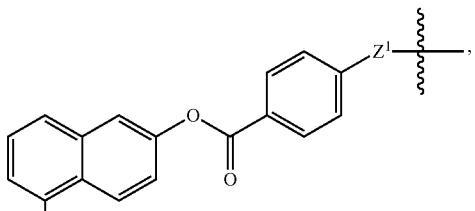

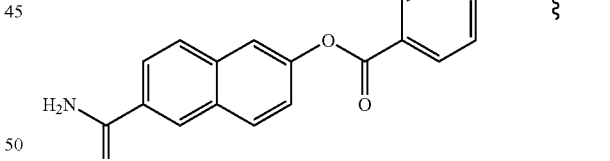

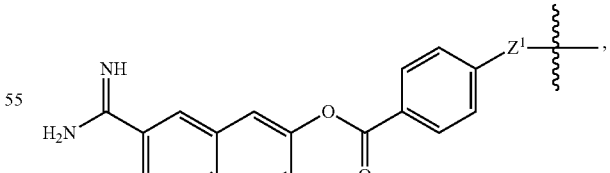

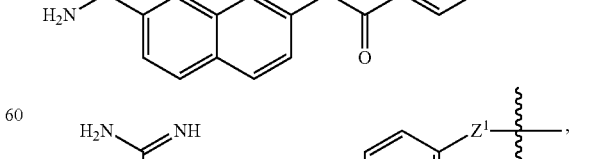

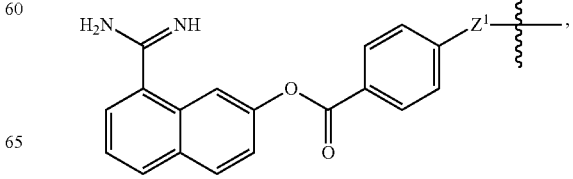

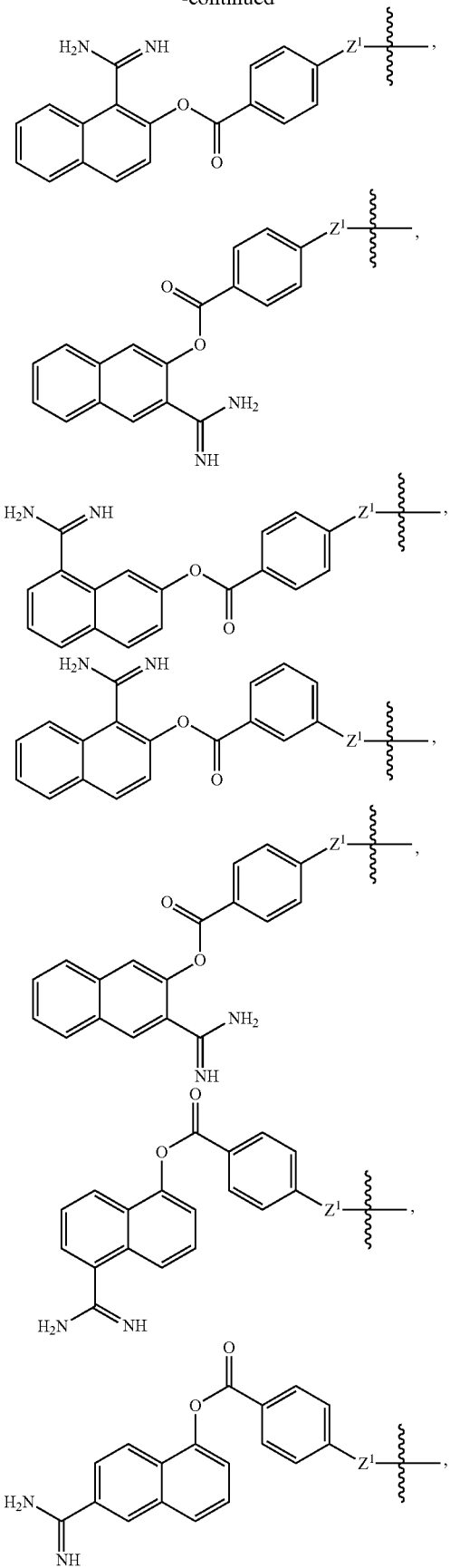
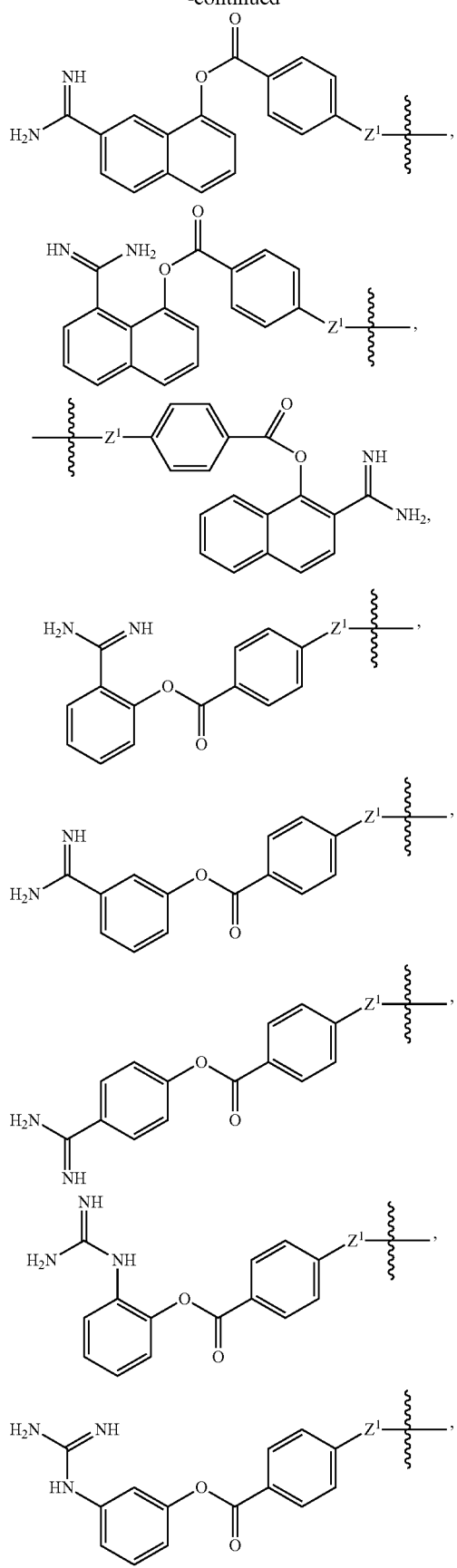

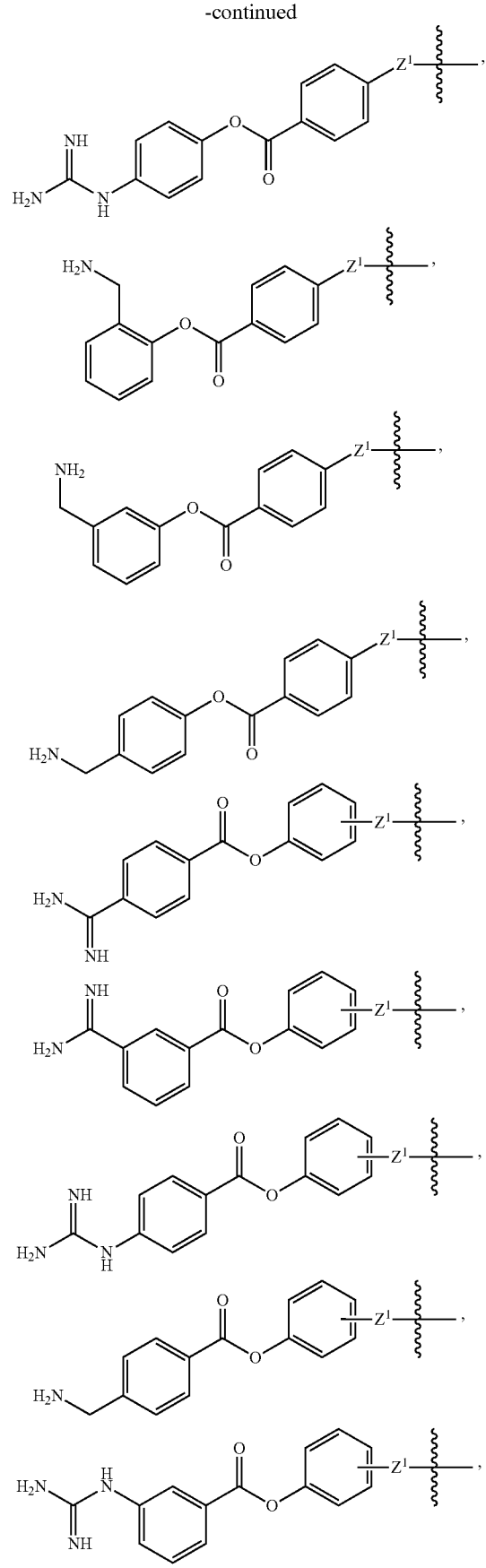
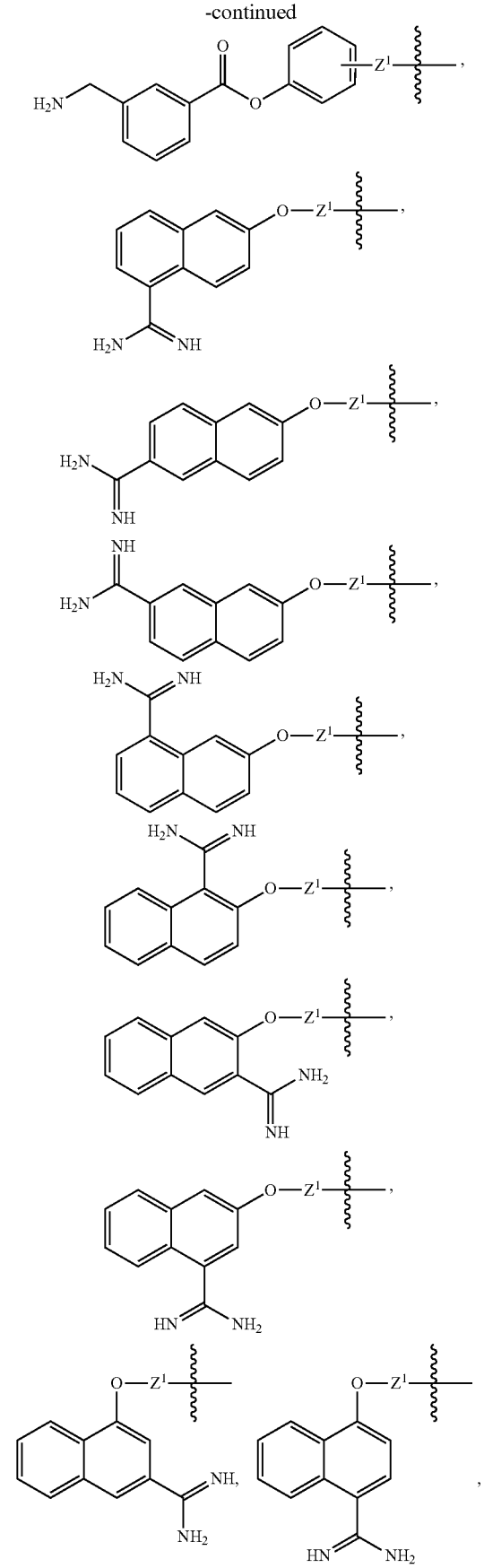

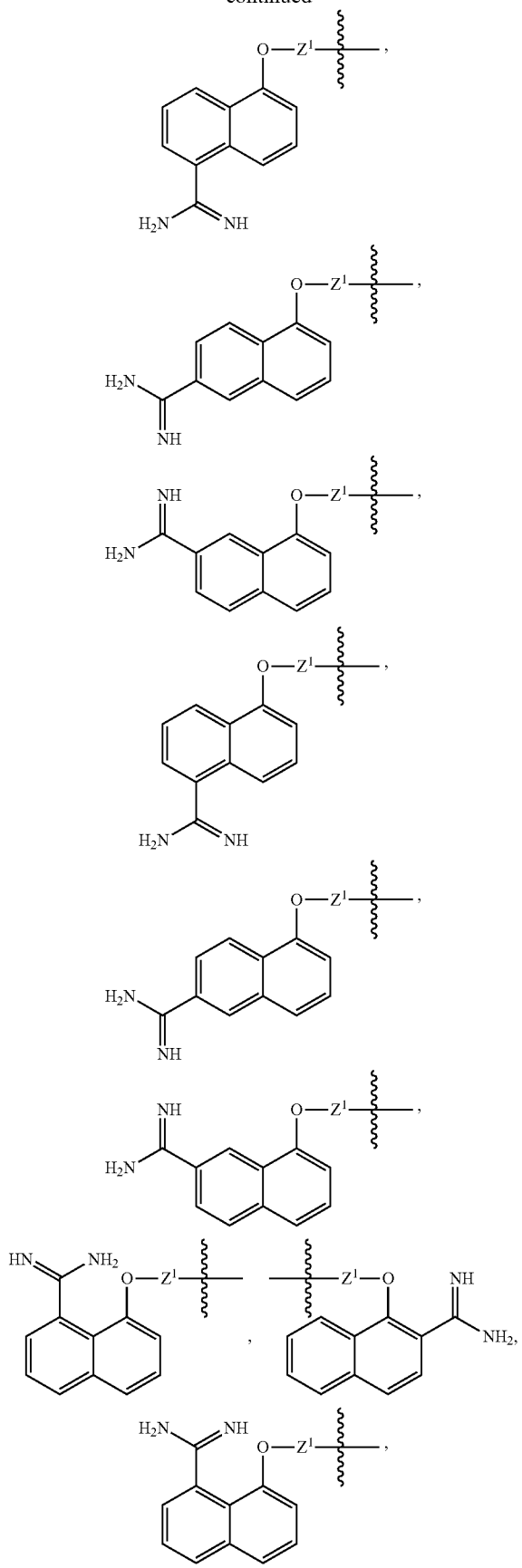
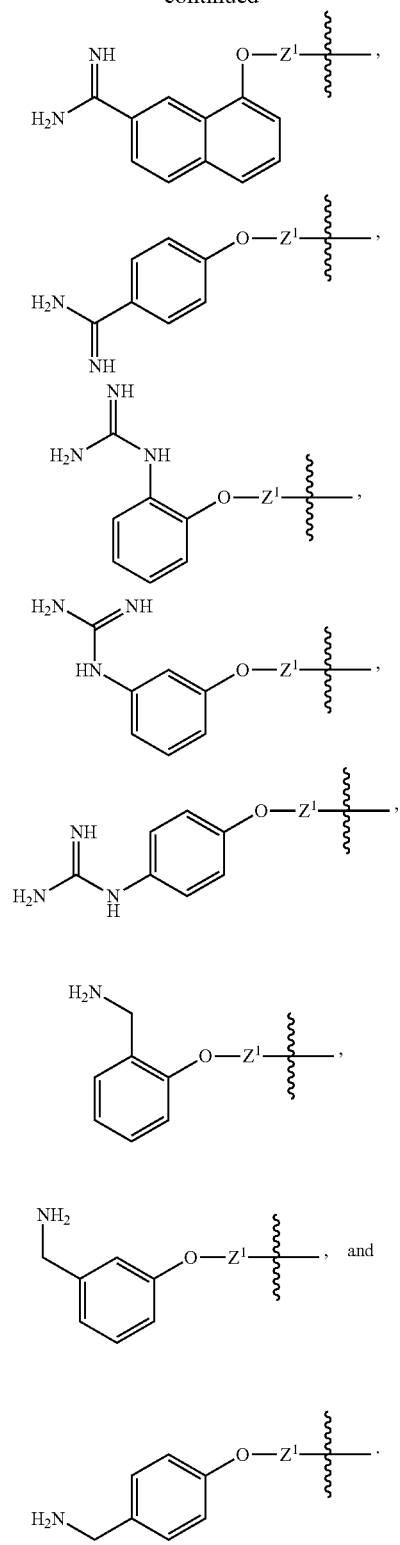
21. The composition of claim 18, wherein the two or more different molecules are independently selected from the group consisting of a structure of Formula (II-A), (II-B), (II-C), (II-D), (II-E), (II-F), (II-G), (II-H), (II-I), (II-J), (II-K), (II-L), (II-M), (II-N), (II-O), (II-P), (II-Q), (II-R), (II-S), (II-T), (II-U), (II-V), (II-W), (II-X), and salts thereof:

II-A
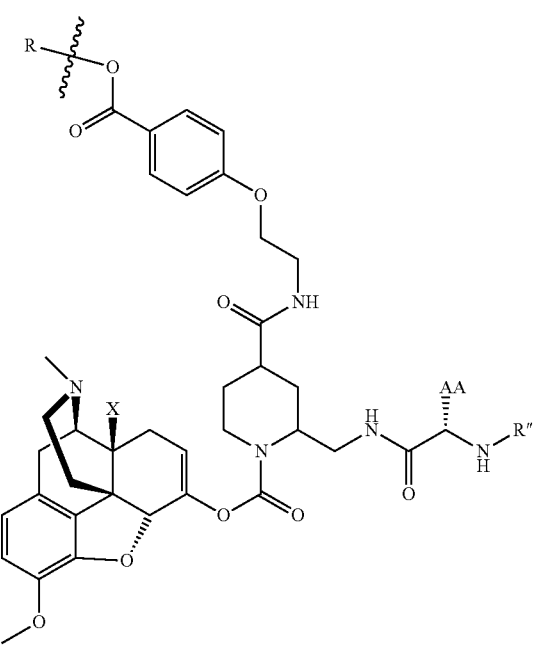
II-B
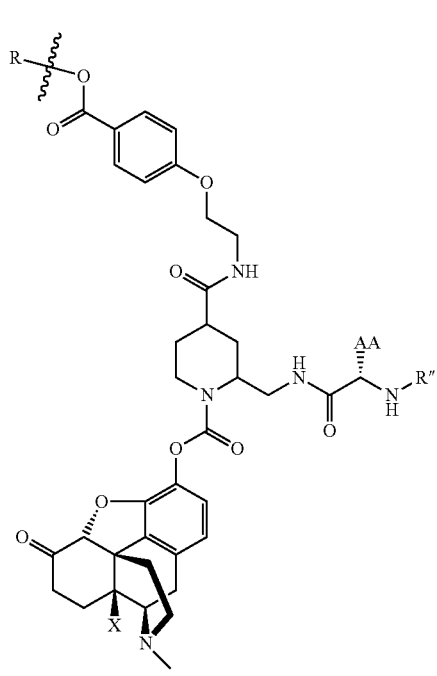
II-C
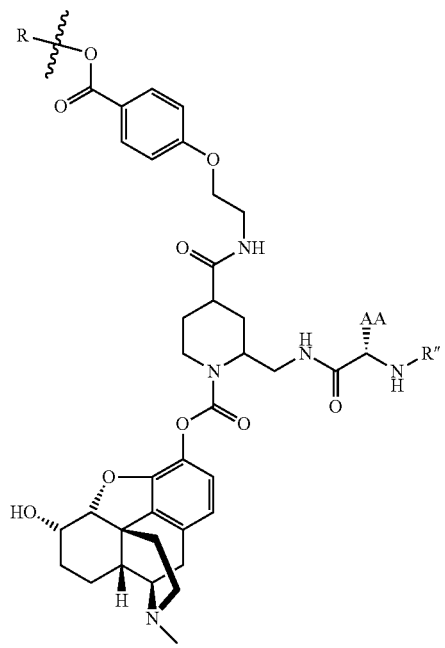
II-D
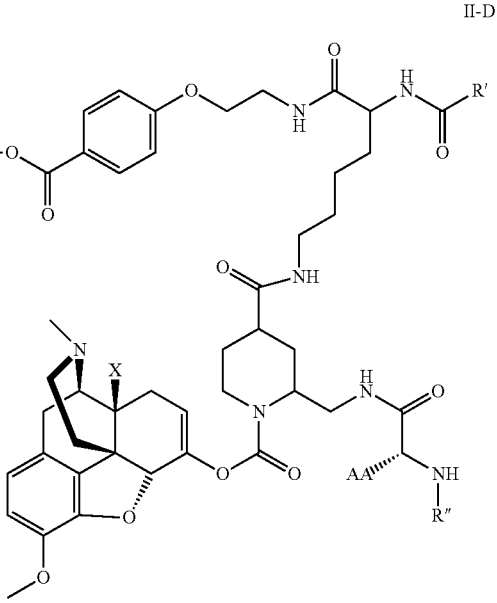

II-E
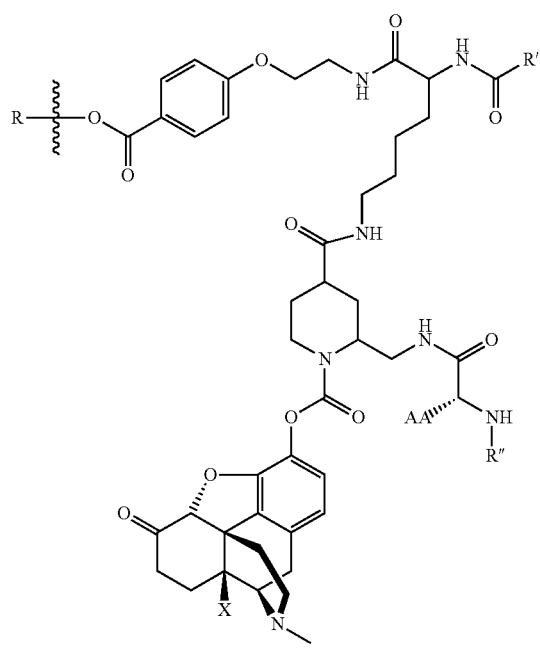
II-G
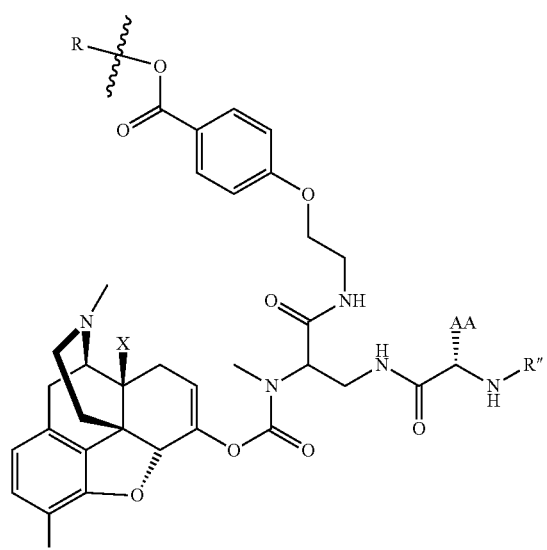
II-F
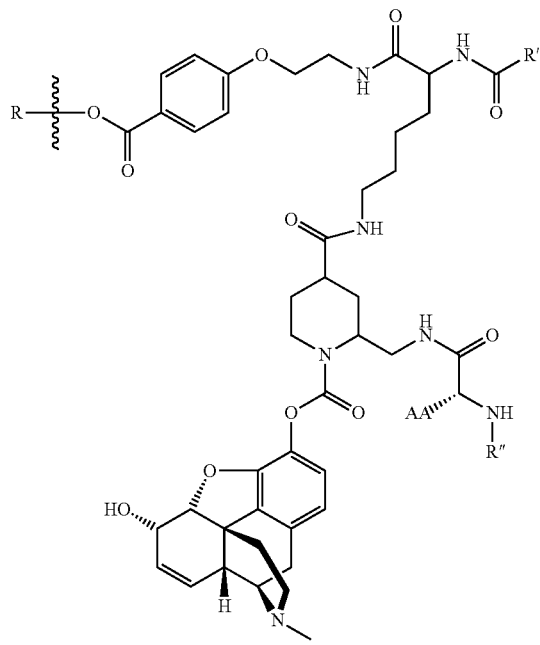
II-H
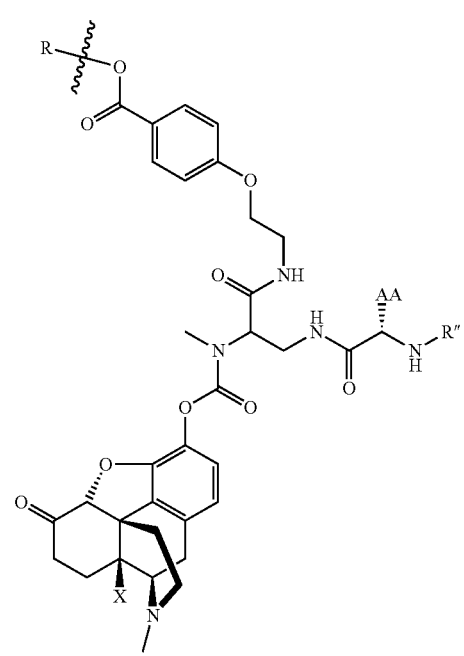

355
-continued

II-I

356
-continued

II-K

II-J

II-L

II-M
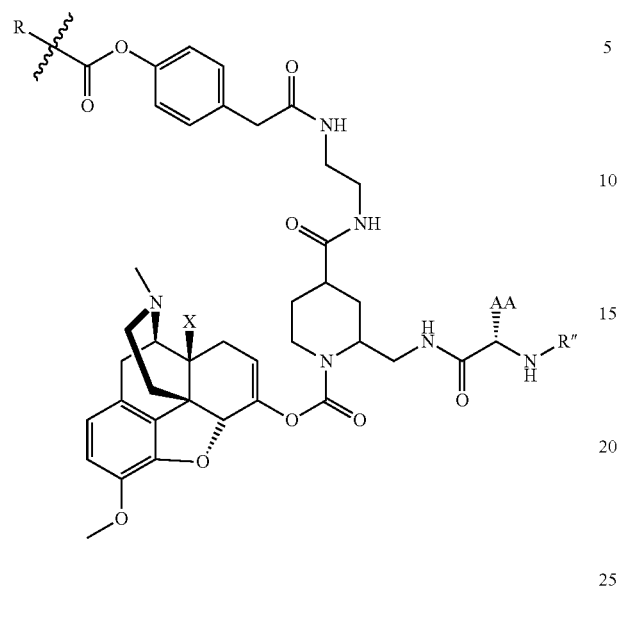
II-O
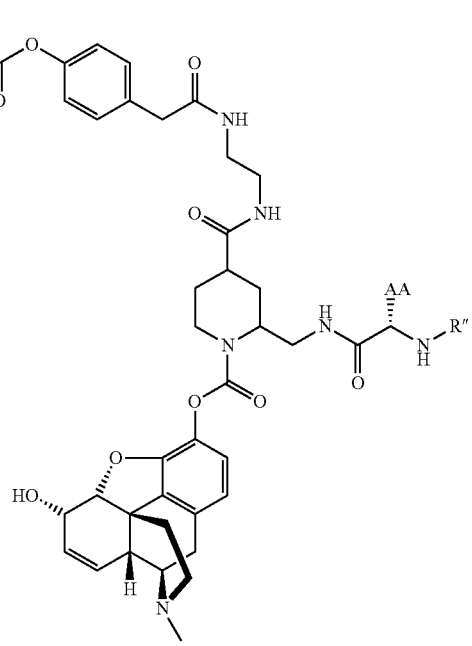
II-N
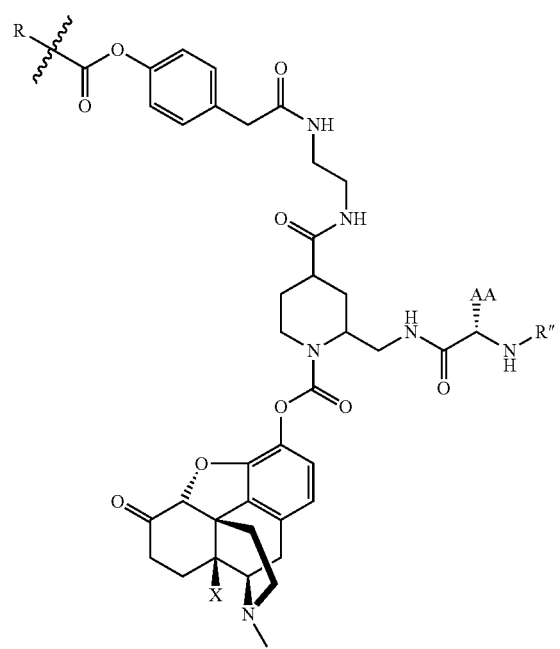
II-P
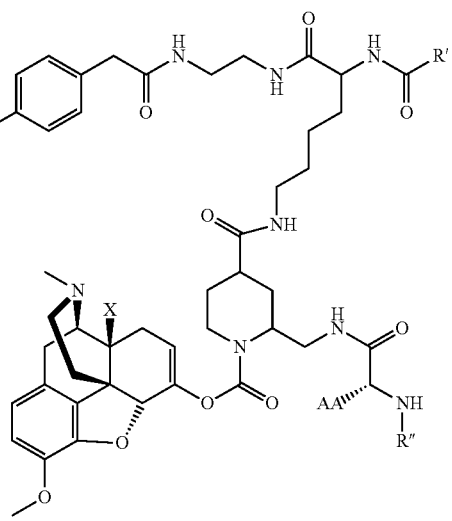

II-Q
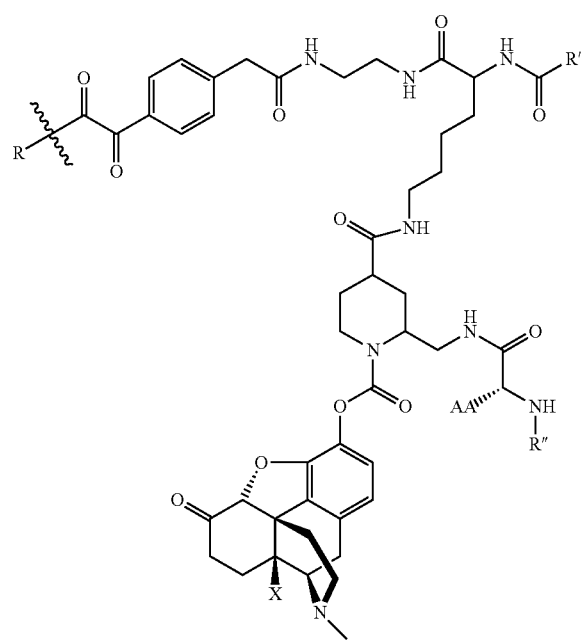
II-S
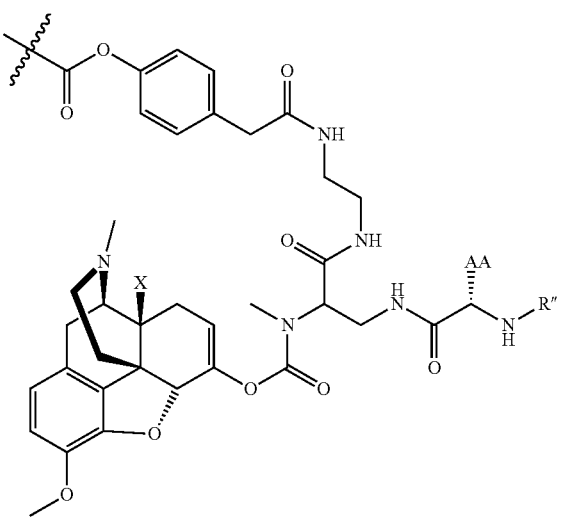
II-R
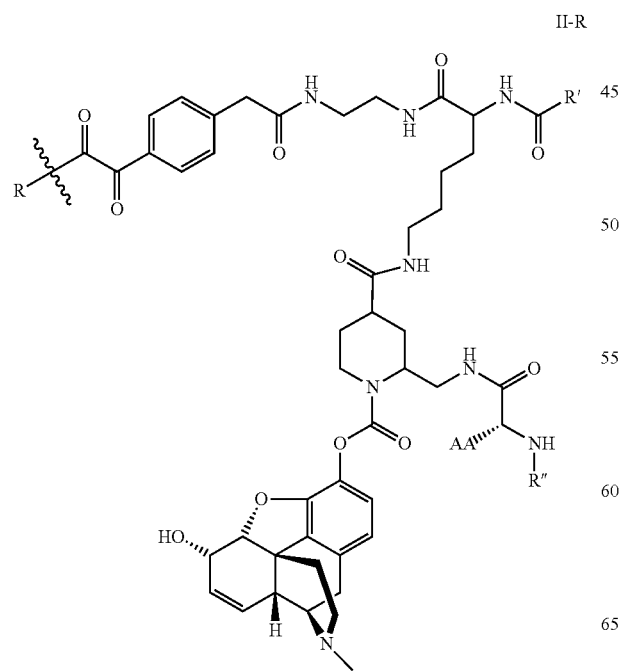
II-T
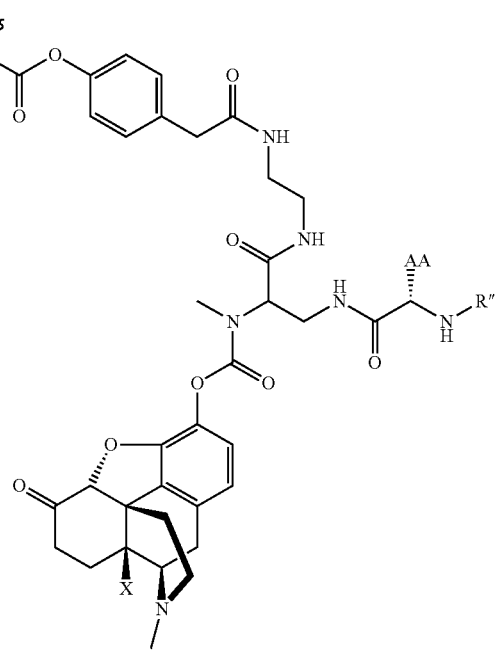

II-U
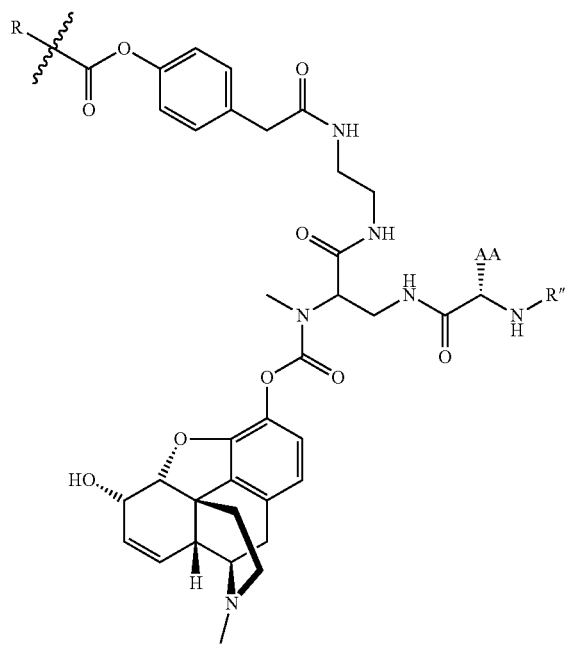
II-V
II-W
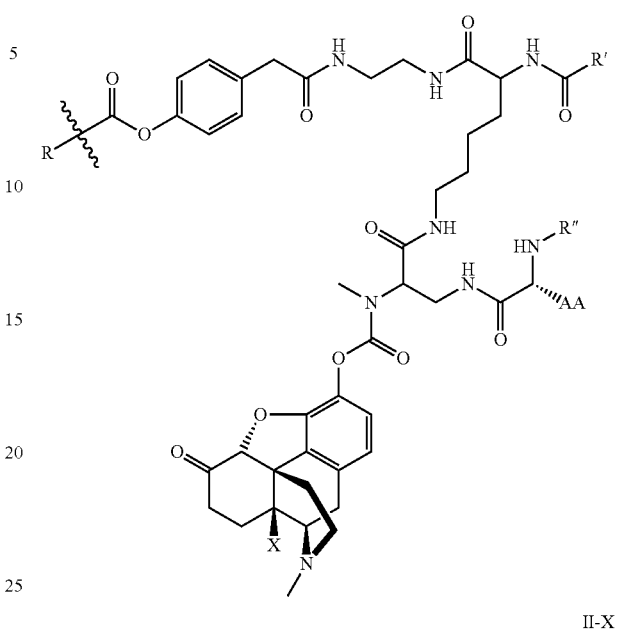
II-X
wherein:
R is selected from the group consisting of
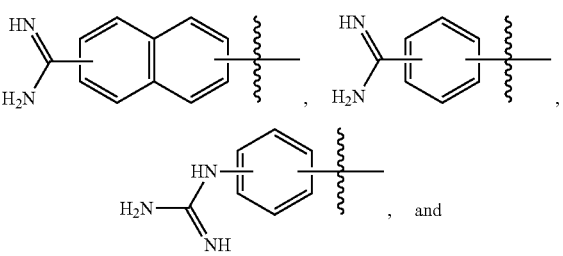
, and -continued

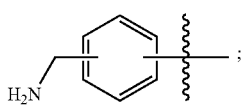

and

X is hydrogen or —OH.

22. The composition of claim 21, or salts thereof, wherein AA is the side chain of lysine or arginine.

23. The composition of claim 21, or salts thereof, wherein R' is methyl, benzyloxy, or

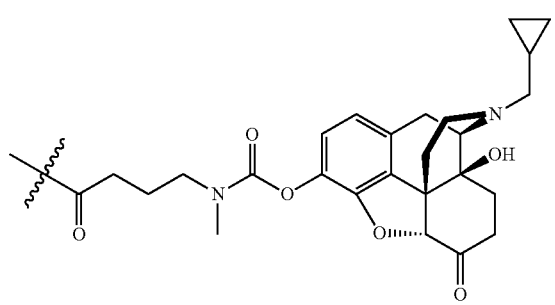

24. The composition of claim 21, or salts thereof, wherein R" is acetyl, -Gly-NAc, or -Ala-NAc.

25. A composition comprising two or more different molecules selected from the group consisting of III-A, III-B, III-H, III-I, III-J, III-L, and salts thereof:

III-A

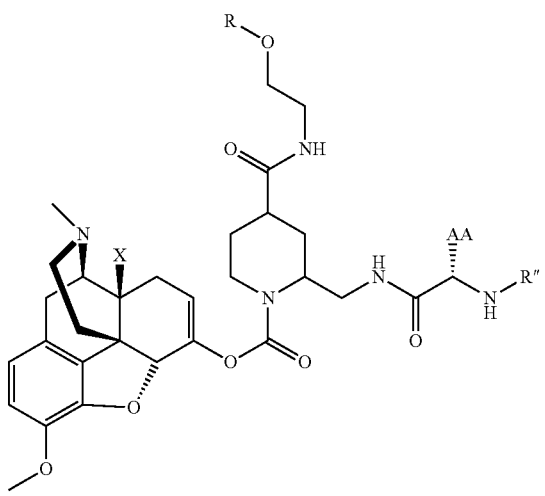

-continued

III-B

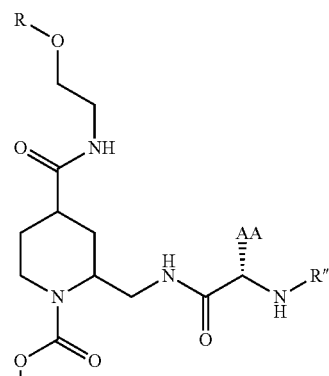

III-C

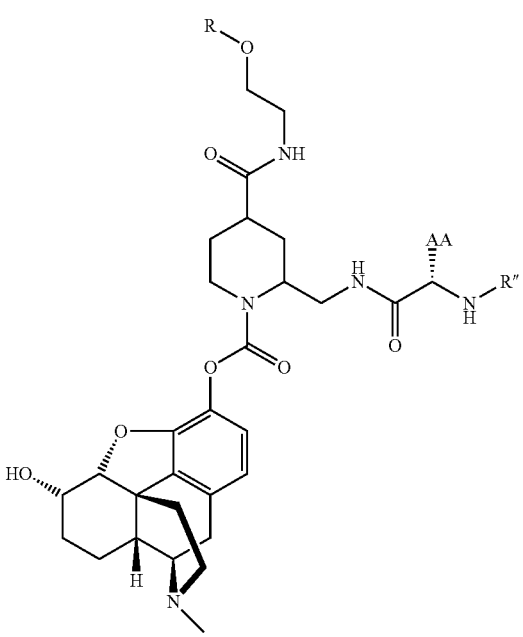

-continued
III-D
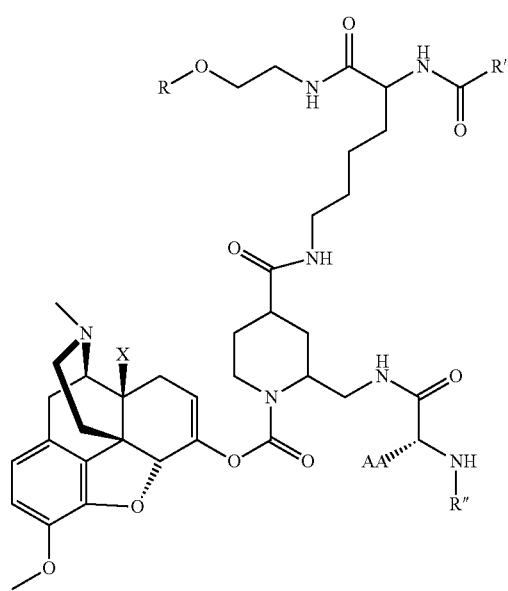
III-E
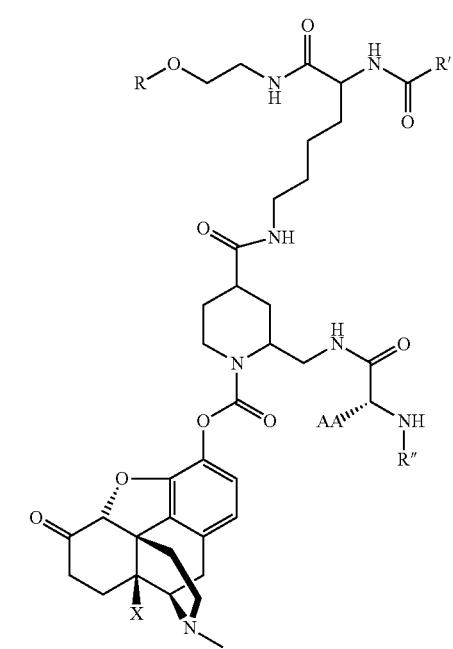
-continued
III-F
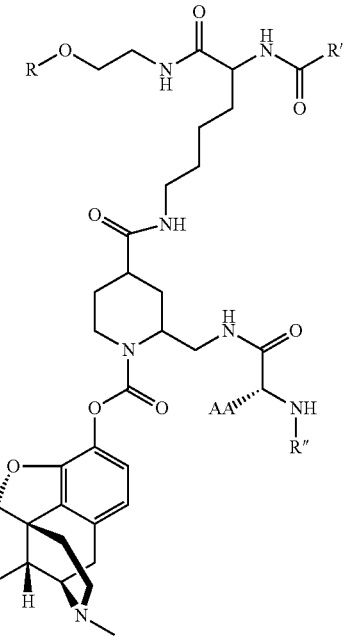
III-G
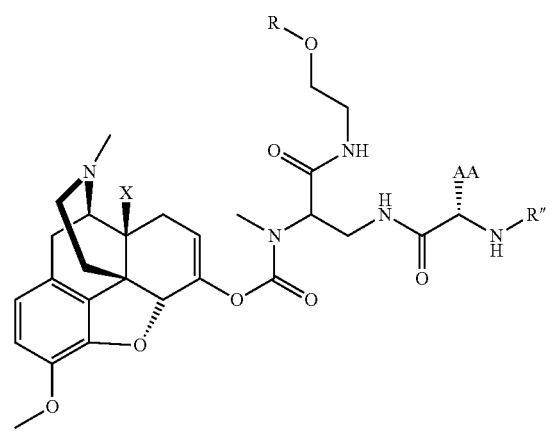
III-H
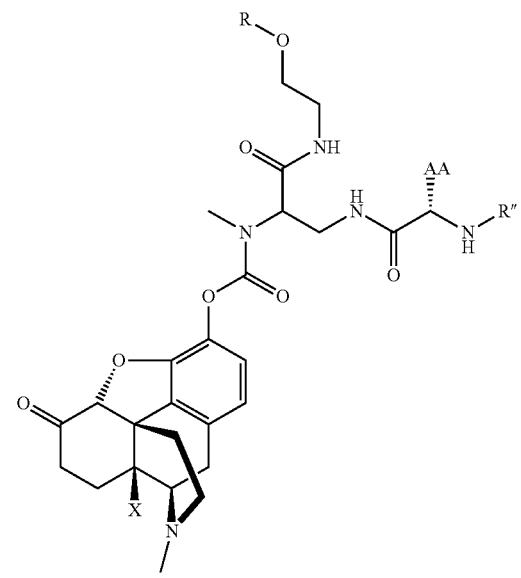

III-I
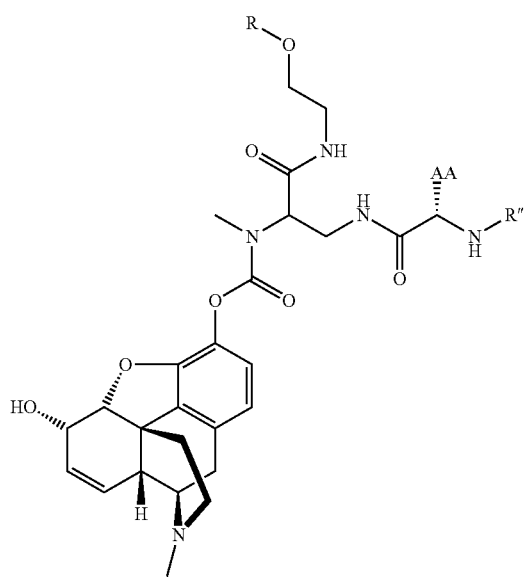
III-J
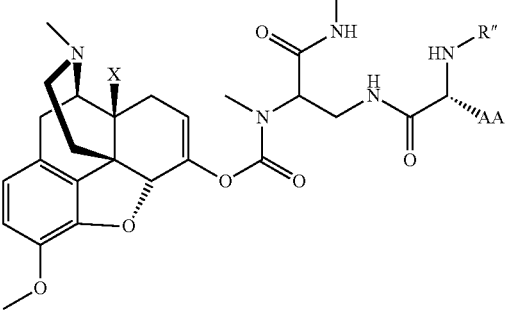
III-K
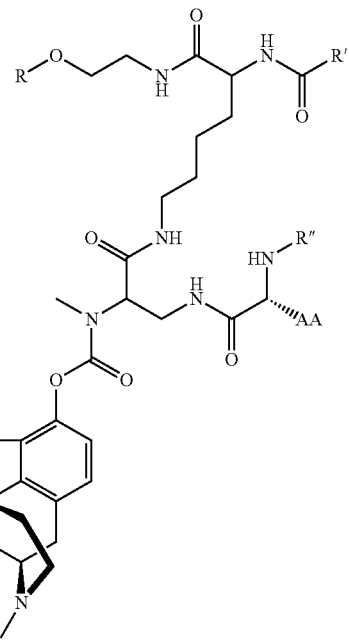
III-L
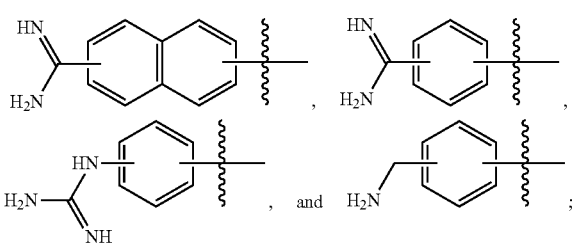
wherein:
R is selected from the group consisting of
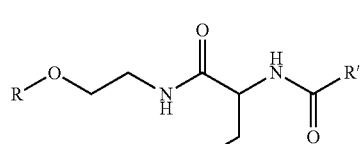

R' is selected from the group consisting of methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear or branched polyethylene glycol chain up to 5 kDa, benzyloxy, and

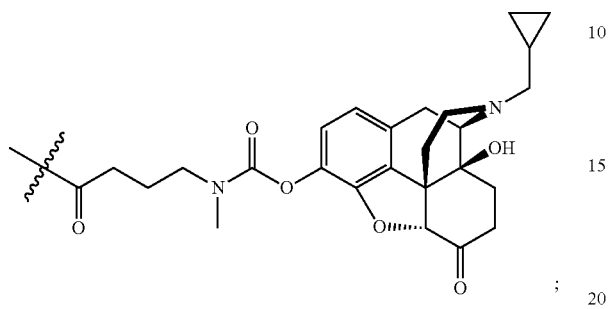

R" is selected from the group consisting of an acetyl, substituted acyl, a natural or non-natural amino acid, and a polypeptide chain comprising natural and/or non-natural amino acids up to 10 amino acids in length;

AA is a natural or non-natural amino acid side chain recognized by trypsin; and

X is hydrogen or OH.

26. The composition of claim 25, or salts thereof, wherein AA is the side chain of lysine or arginine.

27. The composition of claim 25, or salts thereof, wherein R' is methyl, benzyloxy, or

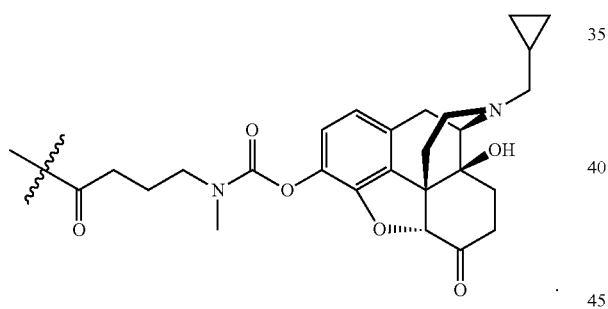

28. The composition of claim 25, or salts thereof, wherein R" is acetyl, -Gly-NAc, or -Ala-NAc.

29. The composition of claim 19, comprising:

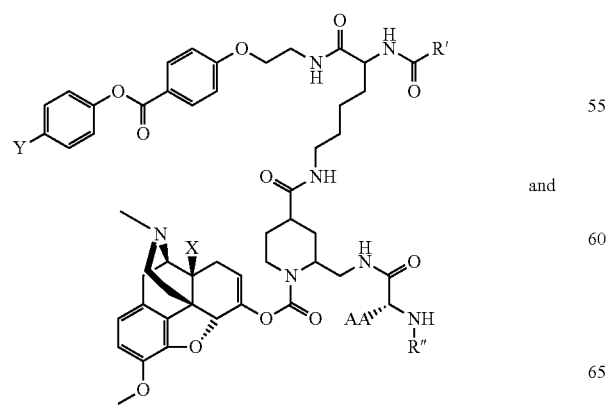

and

-continued

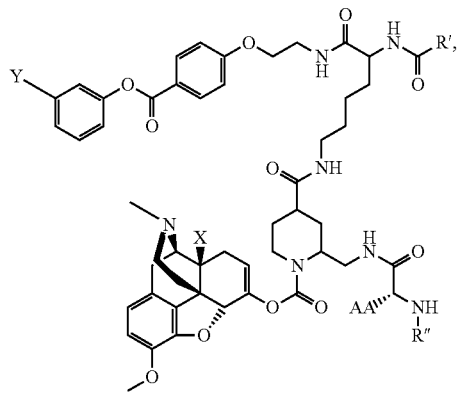

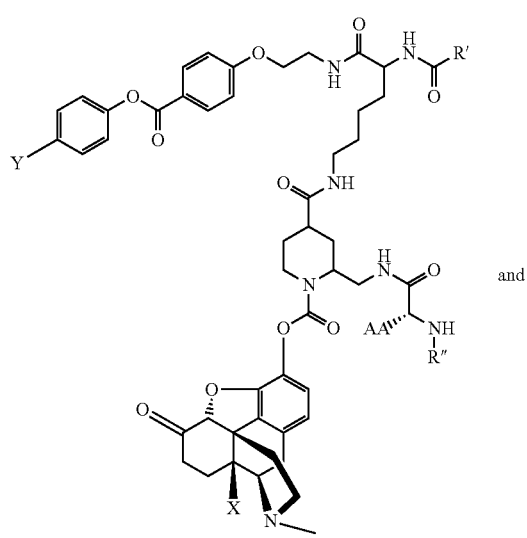

and

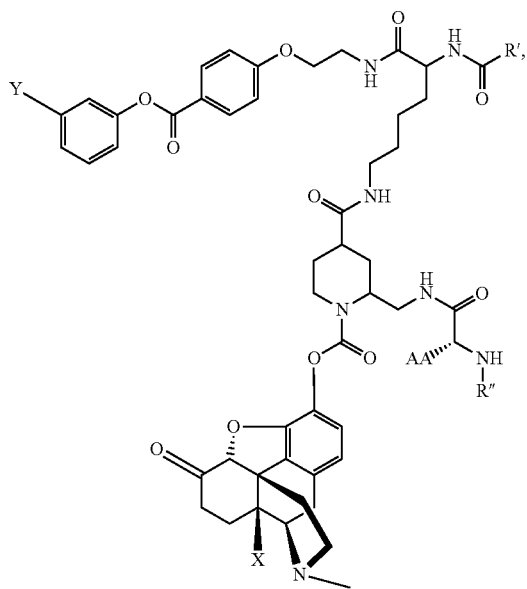

371
-continued

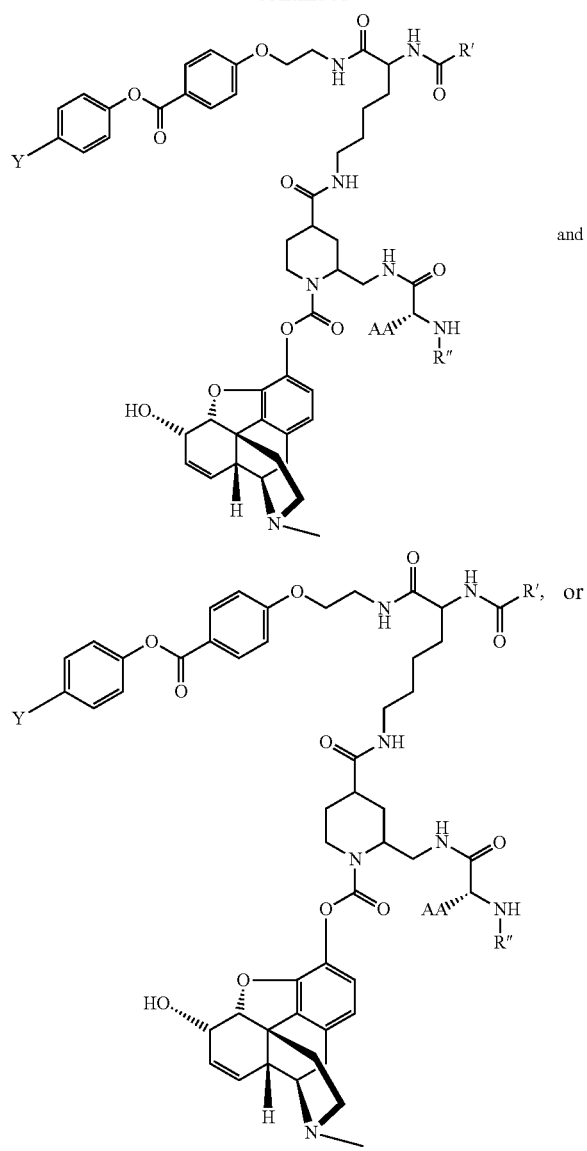

372
-continued
and or salts thereof;
wherein:
R' is independently, methyl, benzyloxy, or AA is independently, the side chain of lysine or arginine;
R" is independently, acetyl, -Gly-NAc, or -Ala-NAc; and
X is independently, hydrogen or —OH.

30. The composition of claim 1, wherein the composition comprises two different molecules and the two different molecules are present in the composition in a molar ratio of 20:1, 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.75:1, 1.5:1, 1.25:1, 1.2:1, 1.15:1, 1.1:1, 1:1, 1:1.1, 1:1.15, 1:1.2, 1:1.25, 1:1.5, 1:1.75, 1:2, 1:2.5, 1:3, 1:3.5, 1:4, 1:4.5, 1:5, 1:5.5, 1:6, 1:6.5; 1:7, 1:7.5, 1:8, 1:8.5, 1:9, 1:9.5, 1:10, 1:11, 1:12, 1:13, 1:14, 1:15, 1:16, 1:17, 1:18, 1:19, or 1:20.

31. The composition of claim 1, wherein the composition comprises two different molecules and the two different molecules are present in the composition in a weight ratio of 20:1, 19:1, 18:1, 17:1, 16:1, 15:1, 14:1, 13:1, 12:1, 11:1, 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.75:1, 1.5:1, 1.25:1, 1.2:1, 1.15:1, 1.1:1, 1:1, 1:1.1, 1:1.15, 1:1.2, 1:1.25, 1:1.5, 1:1.75, 1:2, 1:2.5, 1:3, 1:3.5, 1:4, 1:4.5, 1:5, 1:5.5, 1:6, 1:6.5; 1:7, 1:7.5, 1:8, 1:8.5, 1:9, 1:9.5, 1:10, 1:11, 1:12, 1:13, 1:14, 1:15, 1:16, 1:17, 1:18, 1:19, or 1:20.

32. A pharmaceutical formulation comprising a composition according to claim 18, and one or more pharmaceutically acceptable excipients.

33. The pharmaceutical formulation of claim 32, further formulated as an oral dose unit, wherein the two or more different molecules are each present in the dose unit in amounts effective to provide for a defined pharmacokinetic (PK) profile of the opioid agonist following ingestion of a prescribed dose.

34. The pharmaceutical formulation of claim 33, wherein the PK profile of the opioid agonist comprises at least one PK parameter value that does not demonstrate linear dose proportionality when a dose in excess of the prescribed dose is ingested.

35. The pharmaceutical formulation of claim 34, wherein the PK parameter value is a Cmax value, an AUC exposure value, or a Tmax value.

\* \* \* \* \*